US012655142B2

(12) United States Patent
Dorsch et al.

(10) Patent No.: US 12,655,142 B2
(45) Date of Patent: Jun. 16, 2026

(54) 4-(IMIDAZO[1,2-A]PYRIDIN-3-YL)-PYRIMIDINE

(71) Applicant: Merck Patent GmbH, Darmstadt (DE)

(72) Inventors: Dieter Dorsch, Ober-Ramstadt (DE); Andreas Blum, Bensheim (DE); Hans-Peter Buchstaller, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 1181 days.

(21) Appl. No.: 17/597,729

(22) PCT Filed: Jul. 22, 2020

(86) PCT No.: PCT/EP2020/070616
§ 371 (c)(1),
(2) Date: Jan. 20, 2022

(87) PCT Pub. No.: WO2021/013864
PCT Pub. Date: Jan. 28, 2021

(65) Prior Publication Data

US 2022/0267320 A1 Aug. 25, 2022

(30) Foreign Application Priority Data

Jul. 24, 2019 (EP) .................................... 19188031

(51) Int. Cl.

| | |
|---|---|
| ***A61K 31/506*** | (2006.01) |
| ***A61K 31/5377*** | (2006.01) |
| ***A61K 31/541*** | (2006.01) |
| ***A61K 45/06*** | (2006.01) |
| ***C07D 239/42*** | (2006.01) |
| ***C07D 403/12*** | (2006.01) |
| ***C07D 471/04*** | (2006.01) |
| ***C07D 519/00*** | (2006.01) |

(52) U.S. Cl.
CPC .......... *C07D 471/04* (2013.01); *A61K 31/506* (2013.01); *A61K 31/5377* (2013.01); *A61K 31/541* (2013.01); *A61K 45/06* (2013.01); *C07D 239/42* (2013.01); *C07D 403/12* (2013.01); *C07D 519/00* (2013.01)

(58) Field of Classification Search
None
See application file for complete search history.

(56) References Cited

U.S. PATENT DOCUMENTS 7,718,801 B2 5/2010 Kawamura et al.

FOREIGN PATENT DOCUMENTS

| | | | |
|---|---|---|---|
| CN | 105683166 | | 6/2016 |
| EP | 2116543 | A1 | 12/2007 |
| JP | 2006-522143 | A | 9/2006 |
| JP | WO2008-081914 | A1 | 7/2008 |
| JP | 2011-528040 | A | 11/2011 |
| JP | 2016-529292 | A | 9/2016 |
| RU | 2 612 972 | | 3/2017 |
| WO | 2004/089286 | A2 | 10/2004 |
| WO | 2006/025567 | | 3/2006 |

(Continued)

OTHER PUBLICATIONS

Danziger, Automated site-directed drug design: a general algorithm for knowledge acquisition about hydrogen-bonding regions at protein surfaces, Proc. R. Soc. Lond., 1989, 236, pp. 101-113 (Year: 1989).*
Simone, Oncology: Introduction, Textbook of Medicine, 1997, 14, pp. 1004-1010 (Year: 1997).*
English translation of Chinese Search Report dated Sep. 11, 2023, in Chinese Application No. 202080052946.6, 2 pages.
I. L. Knunânc, Himiëeskij enciklopedičeskij slovar [Encyclopedia of Chemistry], Moscow: Sovetskaâ Enciklopediâ, 1983, pp. 559-560, with English translation.
M. D. Maškovskij, "Lekarstvennye sredstva [Medicaments], Moscow, New wave", vol. 1, 2005, pp. 10-11, with English translation.
V.G. Belikov, "Pharmacevtiĉeskaă himiă [Pharmaceutical Chemistry]", Moscow "MEDpress-inform", Chapter 2.6, 2007, pp. 27-29, with English translation.
Wikipedia, "Malignant tumor", available at link https://ru.wikipedia.org/wiki/3[illegible], Jan. 10, 2024, with English translation, 39 pages.

(Continued)

*Primary Examiner* — Renee Claytor
*Assistant Examiner* — Andrew P Lee
(74) *Attorney, Agent, or Firm* — Grüneberg Global IP, PLLC

(57) ABSTRACT

Compounds of the formula I

I

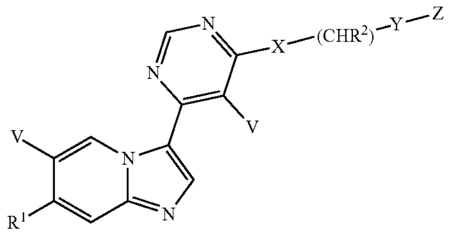

are inhibitors of c-Kit kinase, and can be employed for the treatment of cancer. $R^1$ denotes H, Hal, $CF_3$, $NO_2$, A, $[C(R^3)_2]_nN(R^3)_2$, $[C(R^3)_2]_nHet^1$, $OR^3$, $O[C(R^3)_2]_nN(R^3)_2$, $O[C(R^3)_2]_nS(O)_mR^3$, $O[C(R^3)_2]_nCOOR^3$, $O[C(R^3)_2]_nCOON(R^3)_2$, $O[C(R^3)_2]_nHet^1$, $O[C(R^3)_2]_nN(R^3)Het^1$, $O[C(R^3)_2]_nPh$, or $O[C(R^3)_2]_nCyc$. $R^2$ denotes H or $CH_3$. $R^3$ denotes H or A. V denotes H or Hal. X denotes O or $N(R^3)$. Y denotes phenylene, pyridin-diyl, thiophen-diyl, 1,3-thiazol-diyl or pyrazol-diyl, each of which is unsubstituted or mono-, di- or trisubstituted by Hal and/or A. Z denotes $CON(R^3)_2$, phenyl, $Het^4$ or —O-A.

8 Claims, No Drawings

(56) References Cited

FOREIGN PATENT DOCUMENTS

| | | |
|---|---|---|
| WO | 2010/009155 | 1/2010 |
| WO | 2010/132598 | 11/2010 |
| WO | 2011/076419 | 6/2011 |
| WO | 2013/014170 | 1/2013 |
| WO | 2015/030847 | 3/2015 |
| WO | 2017/040993 | 3/2017 |
| WO | 2018/136634 | 7/2018 |

OTHER PUBLICATIONS

Allan B. Foster, "*Deuterium Isotope Effects in the Metabolism of Drugs and Xenobiotics: Implications for Drug Design*", Advances in Drug Research, vol. 14, 1985, pp. 1-40.

Ashman et al., "*Therapeutic targeting of c-KIT in cancer*", Expert Opinion on Investigational Drugs, vol. 22, 2013, pp. 103-115.

Barder et al., "*Catalysts for Suzuki-Miyaura Coupling Processes: Scope and Studies of the Effect of Ligand Structure*", Journal of American Chemical Society, vol. 127, 2005, pp. 4685-4696.

Chen et al., "*A Missense Mutation in KIT Kinase Domain 1 Correlates with Imatinib Resistance in Gastrointestinal Stromal Tumors*", Cancer Research, vol. 64, Sep. 1, 2004, pp. 5913-5919.

Gillette et al., "*Theory for the Observed Isotope Effects on the Formation of Multiple Products by Different Kinetic Mechanisms of Cytochrome P450 Enzymes*", Biochemistry, vol. 33, 1994, pp. 2927-2937.

Hanzlik et al., "*Active Site Dynamics of Toluene Hydroxylation by Cytochrome P-450*[1]", Journal of Org. Chem., vol. 55, No. 13, 1990, pp. 3992-3997.

Hirota et al., "*Gain-of-Function Mutations of Platelet-Derived Growth Factor Receptor a Gene in Gastrointestinal Stromal Tumors*", Gastroenterology, vol. 125, No. 3, 2003, pp. 660-667.

International Search Report issued Nov. 20, 2020 in PCT/EP2020/070616, 3 pages.

Jarman et al., "*The deuterium isotope effect for the α-hydroxylation of tamoxifen by rat liver microsomes accounts for the reduced genotoxicity of* [*$D_5$-ethyl*] *tamoxifen*", Carcinogenesis, vol. 16, No. 4, 1995, pp. 683-688.

Kotha et al., "*Recent applications of the Suzuki-Miyaura cross-coupling reaction in organic synthesis*", Tetrahedron, vol. 58, 2002, pp. 9633-9695.

Praveen Tyle, "*Iontophoretic Devices for Drug Delivery*", Pharmaceutical Research, vol. 3, No. 6, 1986, pp. 318-326.

Reider et al., "*Synthesis of (R)-Serine-2-d and Its Conversion to the Broad Spectrum Antibiotic Fludalanine*", Journal of Org. Chem., vol. 52, No. 15, 1987, pp. 3326-3334.

Roberts et al., "*Resistance to c-KIT kinase inhibitors conferred by V654A mutation*", Mol. Cancer Theory, vol. 6, No. 3, Mar. 2007, pp. 1159-1166.

Written Opinion issued Nov. 20, 2020 in PCT/EP2020/070616, 4 pages.

Patric Schöffski, et al. "StrateGIST 1: A first-in-human (FIH), phase 1 study of IDRX-42 in patients with metastatic gastrointestinal stromal tumors resistant to prior treatment with tyrosine kinase inhibitors (TKIs)", Sarcoma, Journal of Clinical Oncology, American Society of Clinical Oncology, May 29, 2024, 1 page.

Japanese Office Action issued in Japanese Patent Application No. 2022-504198, issued Jul. 3, 2024 (with English machine translation), 5 pages.

Japanese Office Action issued in Japanese Patent Application No. 2024-212157, issued Jun. 17, 2025 (with English machine translation), 7 pages.

Office Action issued in Korean Patent Application No. 10-2022-7005802, issued Aug. 28, 2025 (with English machine translation), 10 pages.

Hearing Notice issued in Indian Patent Application No. 202217007918 on Mar. 23, 2026, with English translation, 3 pages.

* cited by examiner

4-(IMIDAZO[1,2-A]PYRIDIN-3-YL)-PYRIMIDINE

CROSS-REFERENCE TO RELATED APPLICATIONS

This application is the National Stage entry under § 371 of International Application No. PCT/EP2020/070616, filed on Jul. 22, 2020, and which claims the benefit of European Application No. 19188031.9, filed on Jul. 24, 2019. The content of each of these applications is hereby incorporated by reference in its entirety.

BACKGROUND OF THE INVENTION

Field of the Invention

The invention had the object of finding novel compounds having valuable properties, in particular those which can be used for the preparation of medicaments.

The present invention relates to 4-(imidazo[1,2-a]pyridin-3-yl)-pyrimidine derivatives which inhibit c-KIT kinase across a wide range of c-KIT mutations and secondary mutations (V654A secondary resistance mutation in Exon 13) that may arise in GIST (gastrointestinal stromal tumor) patients. The compounds of this invention are therefore useful in treating diseases such as cancer. The present invention also provides methods for preparing these compounds, pharmaceutical compositions comprising these compounds, the compounds for use for the treatment of diseases and methods of treating diseases utilizing pharmaceutical compositions comprising these compounds. Gastrointestinal stromal tumors (GISTs) are the most common mesenchymal tumors of the gastrointestinal (GI) tract.

Description of the Related Art

C-KIT is a type III receptor tyrosine kinase and plays an important role in the occurrence of cancer. Mutated forms of the receptor tyrosine kinase c-KIT are drivers in several cancers, such as GIST, SM (Systemic Mastocytosis), certain kinds of AML and melanoma, and are therefore attractive targets for therapy. KIT gain of function mutations play an important role in the pathogenesis of gastrointestinal tumors (GISTs).

GISTs are defined as c-KIT (CD117, stem cell factor receptor)-positive mesenchymal spindle cell or epitheloid neoplasms. GISTs have commonly primary activating mutations of the KIT gene (90%) leading to ligand-independent activation of the receptor tyrosine kinase c-KIT rendering the tumor dependent on oncogenic KIT activity.

While benefits have been obtained from use of inhibitors of KIT kinase activity such as imatinib, especially in GIST, primary resistance occurs with certain oncogenic mutations. Furthermore, resistance frequently develops due to secondary mutations (L. K. Ashman & R. Griffith (2013) Expert Opinion on Investigational Drugs, 22:1, 103-115). It has been reported that, Imatinib treatment of GISTs with primary mutation has an initial response rate of ~70% but that acquired resistance develops in 40-50% of cases with an average of two years. The secondary mutation V654A in exon13 is the most frequent resistance mutation post Imatinib.

L. L. Chen et al. describe "A Missense Mutation in KIT kinase domain 1 correlates with imatinib resistance in gastrointestinal stromal tumors" in Cancer res. 2004; 64:5913-5919. K. G. Roberts et al. describe "Resistance to c-KIT kinase inhibitors conferred by V654A mutation" in Mol. Cancer Ther. 2007; 6:1159-1166.

There is a high unmet medical need for development of a safe and specific inhibitor against KIT V654A resistance mutation.

SUMMARY OF THE INVENTION

It has been found that the compounds according to the invention and salts thereof have very valuable pharmacological properties while being well tolerated.

The present invention specifically relates to compounds of the formula I which inhibit c-KIT kinase, preferably the mutant V654A of c-KIT kinase.

Moreover, compounds of the formula I inhibit PDGFRα (V651D). The gain-of-function mutations of PDGFRα appear to play an important role in development of GISTs without KIT mutations (S. Hirota et al., Gastroenterology 2003; 125:660-667).

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

WO 2010/009155 discloses other fused heterocyclic compounds as inhibitors of histone deacylase and/or cyclin dependent kinase. WO 2011/076419 discloses imidazopyridines as inhibitors of JAK kinases.

DETAILED DESCRIPTION OF THE INVENTION

The invention relates to compounds of the formula I

I

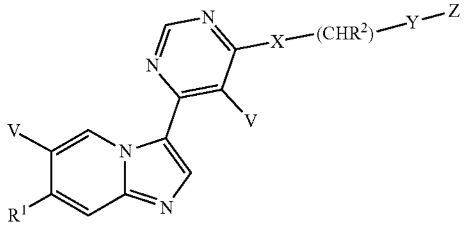

in which $R^1$ denotes H, Hal, $CF_3$, $NO_2$, A, $[C(R^3)_2]_nN(R^3)_2$, $[C(R^3)_2]_nHet^1$, $OR^3$, $O[C(R^3)_2]_nN(R^3)_2$, $O[C(R^3)_2]_nS(O)_mR^3$, $O[C(R^3)_2]_nCOOR^3$, $O[C(R^3)_2]_nCOON(R^3)_2$, $O[C(R^3)_2]_nHet^1$, $O[C(R^3)_2]_nN(R^3)Het^1$, $O[C(R^3)_2]_nPh$ or $O[C(R^3)_2]_nCyc$, $R^2$ denotes H or $CH_3$, $R^3$ denotes H or A, V denotes H or Hal, X denotes O or $N(R^3)$, Y denotes phenylene, pyridin-diyl, thiophen-diyl, 1,3-thiazol-diyl or pyrazol-diyl, each of which is unsubstituted or mono-, di- or trisubstituted by Hal and/or A, Z denotes $CON(R^3)_2$, phenyl,$Het^4$ or —O-A, $Het^1$ denotes a 4-, 5-, 6- or 7-membered monocyclic aromatic, unsaturated or saturated heterocycle having 1, 2, 3 or 4 N, O and/or S atoms, which may be unsubstituted or mono-, di- or trisubstituted by A, Hal, CN, $OR^3$, $[C(R^3)_2]_nN(R^3)_2$, $[C(R^3)_2]_nSO_2R^3$, $Het^2$, oxetanyl, $=NR^3$ and/or =O, and wherein a N atom may be oxidized, or denotes a 6-, 7-, 8-, 9- or 10-membered bicyclic or spirocyclic aromatic, unsaturated or saturated heterocycle having 1, 2, 3 or 4 N, O and/or S atoms, which may be unsubstituted or mono-, di- or trisubstituted by A, Hal, CN, $OR^3$, $[C(R^3)_2]_nN(R^3)_2$, $[C(R^3)_2]_nSO_2R^3$, $Het^2$, oxetanyl, $=NR^3$ and/or =O, and wherein a N atom may be oxidized, $Het^2$ denotes a 5- to 6-membered monocyclic aromatic or unsaturated heterocycle having 1, 2, 3 or 4 N, O and/or S atoms, which may be unsubstituted or mono- or disubstituted by A and/or Hal, or denotes a 7-, 8-, 9- or 10-membered bicyclic aromatic or unsaturated heterocycle having 1, 2, 3 or 4 N, O and/or S atoms, which may be unsubstituted or mono- or disubstituted by A and/or Hal, $Het^3$ denotes a 4-, 5-, 6- or 7-membered monocyclic saturated heterocycle having 1, 2, 3 or 4 N and/or O atoms, which may be unsubstituted or mono- or disubstituted by A, Hal, $OR^3$ and/or =O, $Het^4$ denotes a 4-, 5-, 6- or 7-membered monocyclic aromatic, unsaturated or saturated heterocycle having 1, 2, 3 or 4 N and/or O atoms, which may be unsubstituted or mono-, di- or trisubstituted by A, Hal, $OR^3$, $[C(R^3)_2]_nHet^3$, $—N(R^3)_2$ and/or =O, or denotes a 6-, 7-, 8-, 9- or 10-membered bicyclic aromatic, unsaturated or saturated heterocycle having 1, 2, 3 or 4 N and/or O atoms, which may be unsubstituted or mono-, di- or trisubstituted by A, Hal, $OR^3$, $[C(R^3)_2]_nHet^3$ and/or =O, A denotes unbranched or branched alkyl with 1, 2, 3, 4, 5, 6, 7, 8, 9 or 10 C-atoms, wherein 1, 2 or 3 non-adjacent CH- and/or $CH_2$-groups may be replaced by O-atoms or NH and wherein 1, 2, 3, 4, 5, 6 or 7H-atoms may be replaced by $R^5$, or denotes $(CH_2)_nCyc$, Cyc denotes cyclic alkyl having 3, 4, 5, 6 or 7 C atoms, $R^5$ denotes F, Cl, CN or OH, Ph denotes phenyl, which may be unsubstituted or mono-, di- or trisubstituted by A, $OR^3$ and/or Hal Hal denotes F, Cl, Br or I, m denotes 0, 1 or 2, n denotes 0, 1, 2, 3 or 4, and/or pharmaceutically acceptable salt, tautomer and/or stereoisomer thereof.

In one embodiment, the present invention relates to compounds of the formula I

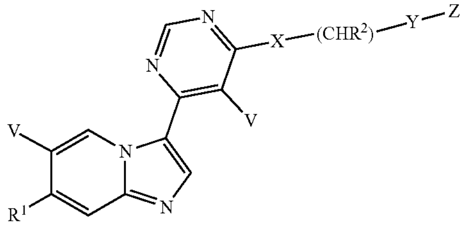

I in which $R^1$ denotes H, Hal, $CF_3$, $NO_2$, A, $[C(R^3)_2]_nN(R^3)_2$, $[C(R^3)_2]_nHet^1$, $OR^3$, $O[C(R^3)_2]_nN(R^3)_2$, $O[C(R^3)_2]_nS(O)_mR^3$, $O[C(R^3)_2]_nCOOR^3$, $O[C(R^3)_2]_nCOON(R^3)_2$, $O[C(R^3)_2]_nHet^1$, $O[C(R^3)_2]_nPh$ or $O[C(R^3)_2]_nCyc$, $R^2$ denotes H or $CH_3$, $R^3$ denotes H or A, V denotes H or Hal, X denotes O or $N(R^3)$, Y denotes phenylene, pyridin-diyl, thiophen-diyl, 1,3-thiazol-diyl or pyrazol-diyl, each of which is unsubstituted or mono-, di- or trisubstituted by Hal and/or A, Z denotes $CON(R^3)_2$, phenyl or $Het^4$, $Het^1$ denotes a 4- to 7-membered monocyclic aromatic, unsaturated or saturated heterocycle having 1 to 4 N, O and/or S atoms, which may be unsubstituted or mono-, di- or trisubstituted by A, Hal, CN, $OR^3$, $[C(R^3)_2]_nN(R^3)_2$, $[C(R^3)_2]_nSO_2R^3$, $Het^2$, oxetanyl, $=NR^3$ and/or =O, and wherein a N atom may be oxidized, or denotes a 7- to 10-membered bicyclic or spirocyclic aromatic, unsaturated or saturated heterocycle having 1 to 4 N, O and/or S atoms, which may be unsubstituted or mono-, di- or trisubstituted by A, Hal, CN, $OR^3$, $[C(R^3)_2]_nN(R^3)_2$, $[C(R^3)_2]_nSO_2R^3$, $Het^2$, oxetanyl, $=NR^3$ and/or =O, and wherein a N atom may be oxidized, $Het^2$ denotes a 5- to 6-membered monocyclic aromatic or unsaturated heterocycle having 1 to 4 N, O and/or S atoms, which may be unsubstituted or mono- or disubstituted by A and/or Hal, or denotes a 7- to 10-membered bicyclic aromatic or unsaturated heterocycle having 1 to 4 N, O and/or S atoms, which may be unsubstituted or mono- or disubstituted by A and/or Hal, $Het^3$ denotes a 4- to 7-membered monocyclic saturated heterocycle having 1 to 4 N and/or O atoms, which may be unsubstituted or mono- or disubstituted by A, Hal, $OR^3$ and/or =O, $Het^4$ denotes a 4- to 7-membered monocyclic aromatic, unsaturated or saturated heterocycle having 1 to 4 and/or O atoms, which may be unsubstituted or mono-, di- or trisubstituted by A, Hal, $OR^3$, $[C(R^3)_2]Het^3$ and/or =O, or denotes a 6- to 10-membered bicyclic aromatic, unsaturated or saturated heterocycle having 1 to 4 N and/or O atoms, which may be unsubstituted or mono-, di- or trisubstituted by A, Hal, $OR^3$, $[C(R^3)_2]Het^3$ and/or =O, A denotes unbranched or branched alkyl with 1-10 C-atoms, wherein 1-3 non-adjacent CH- and/or $CH_2$-groups may be replaced by O-atoms or NH and wherein 1-7 H-atoms may be replaced by $R^5$, or denotes $(CH_2)_n$Cyc, Cyc denotes cyclic alkyl having 3-7 C atoms, $R^5$ denotes F, Cl, CN or OH, Ph denotes phenyl, which may be unsubstituted or mono-, di- or trisubstituted by A, $OR^3$ and/or Hal Hal denotes F, Cl, Br or I, m denotes 0, 1 or 2, n denotes 0, 1, 2, 3 or 4, and pharmaceutically acceptable salts, tautomers and stereoisomers thereof, including mixtures thereof in all ratios.

The invention also encompasses optically active forms (stereoisomers), enantiomers, racemates (racemic mixtures), diastereomers, tautomers and solvates of these compounds, as well as processes of making them. Any reference to a compound or salt thereof shall be understood as encompassing solvates thereof.

The term solvates of the compounds is taken to mean adductions of inert solvent molecules onto the compounds which form owing to their mutual attractive force. Solvates are, for example, hydrates, including mono- or dihydrates, or alkoxides. It is understood that the invention shall also encompass the solvates of the salts.

The invention also relates to mixtures of compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and pharmaceutically acceptable salts, tautomers and stereoisomers thereof and to a process for the preparation of compounds of the formula I and pharmaceutically acceptable salts, tautomers and stereoisomers thereof, characterised in that a) for the preparation of compounds of the formula I, in which X denotes $N(R^3)$, a compound of the formula II

II

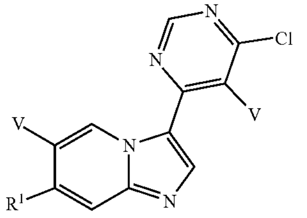

in which $R^1$ and V have the meanings indicated above and below, is reacted with a compound of formula III $H_2N—(CHR_2)—Y—Z$ III in which $R^2$, Y and Z have the meanings indicated above and below, or b) for the preparation of compounds of the formula I, a compound of the formula IV

IV

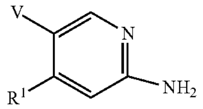

in which $R^1$ and V have the meanings indicated above and below, is reacted with a compound of formula V

V

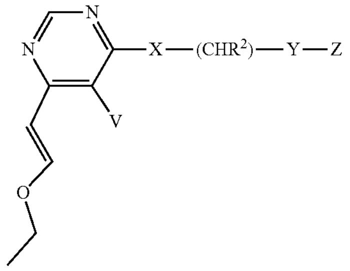

in which $R^2$, V, X, Y and Z have the meanings indicated above and below, or c) for the preparation of compounds of the formula I, by converting a compound of formula I, in which $R^1$ denotes F, into another compound of formula, wherein $R^1$ denotes $O[C(R^3)_2]_nN(R^3)_2$, $O[C(R^3)^2]_nN(R^3)Het^1$ or $O[C(R^3)_2]_nHet^1$, in which $R^3$ and $Het^1$ have the meanings indicated above and below, or d) for the preparation of compounds of the formula I, in which Z denotes $Het^4$, a compound of the formula VI

VI

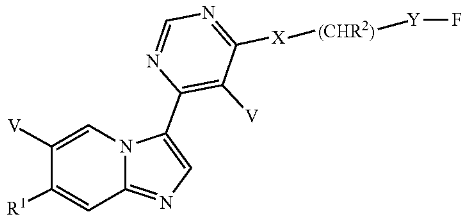

in which $R^1$, $R^2$, V, X and Y have the meanings indicated above and below, is reacted with a compound of formula VII

H—Z VII in which Z denotes $Het^4$, and/or a base or acid of the formula I, i.e. a compound of formula I (which may react as a base or an acid) is converted into one of its salts.

For all radicals which occur more than once, such as, for example, $R^3$, their meanings are independent of one another.

Above and below, the radicals $R^1$, $R^2$, V, X, Y and Z, have the meanings indicated for the formula I, unless explicitly stated otherwise. The same applies to variables n and m, and the radicals that may be designated by the afore-mentioned ones.

Exemplary embodiments of the radicals and variables disclosed herein in connection with compounds of the invention are equally applicable in the above processes for preparing them.

"A" denotes alkyl, which is unbranched (linear) or branched, and has 1, 2, 3, 4, 5, 6, 7, 8, 9 or 10 C atoms. As set out above, 1-3 non-adjacent CH- and/or $CH_2$-groups may be replaced by O-atoms or NH and 1-7 H-atoms may be replaced by $R^5$, or "A" denotes $(CH_2)_n$Cyc. "A" may, for instance, denote methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably trifluoromethyl.

In a preferred embodiment, "A" denotes alkyl having 1, 2, 3, 4, 5 or 6 C atoms, which may be unsubstituted or substituted, preferably methyl, ethyl, propyl, iso-propyl, butyl, isobutyl, sec-butyl, tert-butyl, pentyl, hexyl, trifluoromethyl, pentafluoroethyl or 1,1,1-trifluoroethyl. Cyc preferably denotes cyclopropyl, cyclobutyl, cyclopentyl or cyclohexyl. In other preferred embodiments, "A" denotes $CH_2OCH_3$, $CH_2CH_2OH$, $OCH_2CH_2OH$, $OCH_2CH_2OCH_3$, $CH_2CH_2OCH_3$, $OCH(CH_2OCH_3)_2$ or $OCH_2C(CH_3)_2OH$.

In exemplary embodiments:

$R^1$ preferably denotes H, F, $OCH_2CH_2OCH_3$, $OCH_3$, $CF_3$, $O[C(R^3)_2]_nN(R^3)_2$, $O[C(R^3)_2]_n$Het$^1$, $O[C(R^3)_2]_nN(R^3)$Het$^1$, $OCH(CH_2OCH_3)_2$, $O[C(R^3)_2]_n$Cyc, $OCH_2C(CH_3)_2OH$, $CH_3$, $O[C(R^3)_2]_n$Ph, $NO_2$, Cl, OH, $OCH_2C(CH_3)_2NH_2$, $NHCH_2C(CH_3)_2OH$, $[C(R^3)_2]_n$Het$^1$, $OCH_2CH_2OH$, $OCH_2CH_2CH_2OH$, $O[C(R^3)_2]_nS(O)_mR^3$ or $OCH_2CH_2OCH_2CH_2OH$.

$R^3$ preferably denotes H or A, most preferably H or $CH_3$.

V preferably denotes H or F, most preferably H.

X preferably denotes O or NH, most preferably NH.

Y preferably denotes 1,4-phenylene, 1,3-phenylene, pyridine-3,6-diyl, 4-methyl-pyridine-3,6-diyl, 4-fluoro-pyridine-3,6-diyl, 3-fluoro-1,4-phenylene, thiophen-2,5-diyl or pyridine-2,5-diyl.

Bicyclic compounds also include spiro compounds.

Irrespective of further substitutions, Het$^1$ denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl, azabicyclo[3.2.1]-octyl or dibenzofuranyl. The heterocyclic radicals may also be partially or fully hydrogenated. Irrespective of further substitutions, Het$^1$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, furthermore 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het$^1$ preferably denotes morpholinyl, tetrahydro-pyran-4-yl, tetrahydro-furan-3-yl, pyrrolidinyl, piperazinyl, piperidinyl, 6-oxa-3-azabicyclo[3.1.1]heptane-3-yl, pyridinyl, pyridazinyl, 2-oxa-6-azaspiro[3.3]heptane-6-yl, imidazolyl, azetidinyl, 3-aza-bicyclo[3.1.0]hexane-3-yl, 1lambda6-thiomorpholinyl, 1l4-thiomorpholinyl, 1,3-dihydro-pyrrolo[3,4-c]pyridinyl, 3,8-diaza-bicyclo[3.2.1]octane-8-yl, 2l4-thia-5-aza-bicyclo[2.2.1]heptane-5-yl, [1,4]oxazepanyl, hexahydro-pyrazino[2,1-c][1,4]oxazin-8-yl, 5,6-dihydro-8H-[1,2,4]triazolo[4,3-a]pyrazin-7-yl, 5,6-dihydro-8H-[1,2,4]triazolo[1,5-a]pyrazin-7-yl, 6-oxa-1-aza-spiro[3.3]heptane-1-yl, hexahydro-furo[3,2-b]pyridine-4-yl, hexahydro-pyrano[3,4-b][1,4]oxazin-1-yl, pyrazolyl, 1,4-diaza-bicyclo[3.2.1]octane-4-yl, 1,2,4-oxadiazolyl, 6,7-dihydro-4H-pyrazolo[1,5-a]pyrazin-5-yl, 6,7-dihydro-4H-[1,2,3]triazolo[1,5-a]pyrazin-5-yl, 3,4-dihydro-1H-pyrrolo[1,2-a]pyrazin-2-yl, 1,4-diazepanyl, triazolyl, or oxetanyl, each of which may be unsubstituted or mono-, di- or trisubstituted by A, Hal, CN, $OR^3$, $[C(R^3)_2]_nN(R^3)_2$, $[C(R^3)_2]_nSO_2R^3$, Het$^2$, oxetanyl, $=NR^3$ and/or $=O$, and wherein a N atom may be oxidized.

Irrespective of further substitutions, Het$^2$ may denote, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl, azabicyclo[3.2.1]-octyl or dibenzofuranyl.

$Het^2$ preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, pyridazinyl, pyrazinyl, 1,3-benzodiazolyl, 1,3-benzodioxolyl, indolyl, isoindolyl or indazolyl, each of which may be unsubstituted or mono- or disubstituted by A and/or Hal.

$Het^3$ preferably denotes morpholinyl, pyrrolidinyl, piperidinyl, oxetanyl or azetidinyl, each of which may be unsubstituted or mono- or disubstituted by A, Hal, $OR^3$ and/or =O.

Irrespective of further substitutions, $Het^4$ may denote, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1, 3-benzothiadiazol-4- or -5-yl, 2,1, 3-benzoxadiazol-5-yl, azabicyclo[3.2.1]-octyl or dibenzofuranyl. The heterocyclic radicals may also be partially or fully hydrogenated. Irrespective of further substitutions, $Het^4$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, furthermore 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

$Het^4$ preferably denotes pyrrolidinyl, 3-aza-bicyclo[3.1.0]hexane-3-yl, pyrazolyl, pyridinyl, imidazolyl, 4,5-dihydro-1H-imidazolyl, triazolyl, 4H,5H,6H-pyrrolo[1,2-b]pyrazol-3-yl, oxadiazolyl, 1,3-benzodiazolyl, pyrimidinyl, tetrazolyl, 8-oxa-3-aza-bicyclo[3.2.1]octane-3-yl, pyridazinyl, oxazolyl, isoxazolyl, each of which may be unsubstituted or mono-, di- or trisubstituted by A, Hal, $OR^3$, $[C(R^3)_2]_nHet^3$, $—N(R^3)_2$ and/or =O.

As already mentioned above, throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of formula I in which at least one of the said radicals has one of the preferred meanings indicated above. Some preferred groups of compounds may be expressed by the following sub-formulae Ia to Iw, which conform to the formula I and in which the radicals not designated in greater detail have the meaning indicated for formula I, but in which in Ia $R^1$ denotes H, F, $OCH_2CH_2OCH_3$, $OCH_3$, $CF_3$, $O[C(R^3)_2]_nN(R^3)_2$, $O[C(R^3)_2]_nHet^1$, $O[C(R^3)_2]_nN(R^3)Het^1$, $OCH(CH_2OCH_3)_2$, $O[C(R^3)_2]_nCyc$, $OCH_2C(CH_3)_2OH$, $CH_3$, $O[C(R^3)_2]_nPh$, $NO_2$, Cl, OH, $OCH_2C(CH_3)_2NH_2$, $NHCH_2C(CH_3)_2OH$, $[C(R^3)_2]_nHet^1$, $OCH_2CH_2OH$, $OCH_2CH_2CH_2OH$, $O[C(R^3)_2]_nS(O)_mR^3$ or $OCH_2CH_2OCH_2CH_2OH$, in Ib $R^3$ denotes H or A;

in Ic $R^3$ denotes H or $CH_3$;

in Id X denotes O or NH;

in Ie Y denotes 1,4-phenylene, 1,3-phenylene, pyridine-3,6-diyl, 4-methyl-pyridine-3,6-diyl, 4-fluoro-pyridine-3,6-diyl, 3-fluoro-1,4-phenylene, thiophen-2,5-diyl or pyridine-2,5-diyl;

in If $Het^1$ denotes morpholinyl, tetrahydro-pyran-4-yl, tetrahydro-furan-3-yl, pyrrolidinyl, piperazinyl, piperidinyl, 6-oxa-3-aza-bicyclo[3.1.1]heptane-3-yl, pyridinyl, pyridazinyl, 2-oxa-6-aza-spiro[3.3]heptane-6-yl, imidazolyl, azetidinyl, 3-aza-bicyclo[3.1.0]hexane-3-yl, 1lambda6-thiomorpholinyl, 1|4-thiomorpholinyl, 1,3-dihydro-pyrrolo[3,4-c]pyridinyl, 3,8-diaza-bicyclo[3.2.1]octane-8-yl, 2|4-thia-5-aza-bicyclo[2.2.1]heptane-5-yl, [1,4]oxazepanyl, hexahydro-pyrazino[2,1-c][1,4]oxazin-8-yl, 5,6-dihydro-8H-[1,2,4]triazolo[4,3-a]pyrazin-7-yl, 5,6-dihydro-8H-[1,2,4]triazolo[1,5-a]pyrazin-7-yl, 6-oxa-1-aza-spiro[3.3]heptane-1-yl, hexahydro-furo[3,2-b]pyridine-4-yl, hexahydro-pyrano[3,4-b][1,4]oxazin-1-yl, pyrazolyl, 1,4-diaza-bicyclo[3.2.1]octane-4-yl, 1,2,4-oxadiazolyl, 6,7-dihydro-4H-pyrazolo[1,5-a]pyrazin-5-yl, 6,7-dihydro-4H-[1,2,3]triazolo[1,5-a]pyrazin-5-yl, 3,4-dihydro-1H-pyrrolo[1,2-a]pyrazin-2-yl, 1,4-diazepanyl, triazolyl or oxetanyl, each of which may be unsubstituted or mono-, di- or trisubstituted by A, Hal, CN, $OR^3$, $[C(R^3)_2]_nN(R^3)_2$, $[C(R^3)_2]_nSO_2R^3$, $Het^2$, oxetanyl, $=NR^3$ and/or =O, and wherein a N atom may be oxidized;

in Ig $Het^2$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, pyridazinyl, pyrazinyl, 1,3-benzodiazolyl, 1,3-benzodioxolyl, indolyl, isoindolyl or indazolyl, each of which may be unsubstituted or mono- or disubstituted by A and/or Hal;

in Ih $Het^3$ denotes morpholinyl, pyrrolidinyl, piperidinyl, oxetanyl or azetidinyl, each of which may be unsubstituted or mono- or disubstituted by A, Hal, $OR^3$ and/or =O;

in Ii $Het^4$ denotes pyrrolidinyl, 3-aza-bicyclo[3.1.0]hexane-3-yl, pyrazolyl, pyridinyl, imidazolyl, 4,5-dihydro-1H-imidazolyl, triazolyl, 4H,5H,6H-pyrrolo[1,2-b]pyrazol-3-yl, oxadiazolyl, 1,3-benzodiazolyl, pyrimidinyl, tetrazolyl, 8-oxa-3-aza-bicyclo[3.2.1]octane-3-yl, pyridazinyl, oxazolyl, isoxazolyl, each of which may be unsubstituted or mono-, di- or trisubstituted by A, Hal, $OR^3$, $[C(R^3)_2]_n Het^3$ and/or =O;

in Ij $R^1$ denotes H, Hal, $CF_3$, $NO_2$, A, $[C(R^3)_2]_n N(R^3)_2$, $[C(R^3)_2]_n Het^1$, $OR^3$, $O[C(R^3)_2]_n N(R^3)_2$, $O[C(R^3)_2]_n S(O)_m R^3$, $O[C(R^3)_2]_n COOR^3$, $O[C(R^3)_2]_n COON(R^3)_2$, $O[C(R^3)_2]_n Het^1$, $O[C(R^3)_2]_n Ph$ or $O[C(R^3)_2]_n Cyc$, $R^2$ denotes H or $CH_3$, $R^3$ denotes H or A, V denotes H or Hal, X denotes O or $N(R^3)$, Y denotes phenylene, pyridin-diyl, thiophen-diyl, 1,3-thiazol-diyl or pyrazol-diyl, each of which is unsubstituted or mono-, di- or trisubstituted by Hal and/or A, Z denotes $CON(R^3)_2$, phenyl, $Het^4$ or —OA, $Het^1$ denotes morpholinyl, tetrahydro-pyran-4-yl, tetrahydro-furan-3-yl, pyrrolidinyl, piperazinyl, piperidinyl, 6-oxa-3-aza-bicyclo[3.1.1]heptane-3-yl, pyridinyl, pyridazinyl, 2-oxa-6-aza-spiro[3.3]heptane-6-yl, imidazolyl, azetidinyl, 3-aza-bicyclo[3.1.0]hexane-3-yl, 1lambda6-thiomorpholinyl, 1|4-thiomorpholinyl, 1,3-dihydro-pyrrolo[3,4-c]pyridinyl, 3,8-diaza-bicyclo[3.2.1]octane-8-yl, 2|4-thia-5-aza-bicyclo[2.2.1]heptane-5-yl, [1,4]oxazepanyl, hexahydro-pyrazino[2,1-c][1,4]oxazin-8-yl, 5,6-dihydro-8H-[1,2,4]triazolo[4,3-a]pyrazin-7-yl, 5,6-dihydro-8H-[1,2,4]triazolo[1,5-a]pyrazin-7-yl, 6-oxa-1-aza-spiro[3.3]heptane-1-yl, hexahydro-furo[3,2-b]pyridine-4-yl, hexahydro-pyrano[3,4-b][1,4]oxazin-1-yl, pyrazolyl, 1,4-diaza-bicyclo[3.2.1]octane-4-yl, 1,2,4-oxadiazolyl, 6,7-dihydro-4H-pyrazolo[1,5-a]pyrazin-5-yl, 6,7-dihydro-4H-[1,2,3]triazolo[1,5-a]pyrazin-5-yl, 3,4-dihydro-1H-pyrrolo[1,2-a]pyrazin-2-yl, 1,4-diazepanyl, triazolyl or oxetanyl, each of which may be unsubstituted or mono-, di- or trisubstituted by A, Hal, CN, $OR^3$, $[C(R^3)_2]_n N(R^3)_2$, $[C(R^3)_2]_n SO_2R^3$, $Het^2$, oxetanyl, $=NR^3$ and/or =O, and wherein a N atom may be oxidized, $Het^2$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, pyridazinyl, pyrazinyl, 1,3-benzodiazolyl, 1,3-benzodioxolyl, indolyl, isoindolyl or indazolyl, each of which may be unsubstituted or mono- or disubstituted by A and/or Hal, $Het^3$ denotes morpholinyl, pyrrolidinyl, piperidinyl, oxetanyl or azetidinyl, each of which may be unsubstituted or mono- or disubstituted by A, Hal, $OR^3$ and/or =O, $Het^4$ denotes pyrrolidinyl, 3-aza-bicyclo[3.1.0]hexane-3-yl, pyrazolyl, pyridinyl, imidazolyl, 4,5-dihydro-1H-imidazolyl, triazolyl, 4H,5H,6H-pyrrolo[1,2-b]pyrazol-3-yl, oxadiazolyl, 1,3-benzodiazolyl, pyrimidinyl, tetrazolyl, 8-oxa-3-aza-bicyclo[3.2.1]octane-3-yl, pyridazinyl, oxazolyl, isoxazolyl, each of which may be unsubstituted or mono-, di- or trisubstituted by A, Hal, $OR^3$, $[C(R^3)_2]_n Het^3$ and/or =O, A denotes unbranched or branched alkyl with 1-10 C-atoms, wherein 1-3 non-adjacent CH- and/or $CH_2$-groups may be replaced by O-atoms or NH and wherein 1-7 H-atoms may be replaced by $R^5$, or denotes $(CH_2)_n Cyc$, Cyc denotes cyclic alkyl having 3-7 C atoms, $R^5$ denotes F, Cl, CN or OH, Ph denotes phenyl, which may be unsubstituted or mono-, di- or trisubstituted by A, $OR^3$ and/or Hal Hal denotes F, Cl, Br or I, m denotes 0, 1 or 2, n denotes 0, 1, 2, 3 or 4;

in Ik $R^1$ denotes H, F, $OCH_2CH_2OCH_3$, $OCH_3$, $CF_3$, $O[C(R^3)_2]_n N(R^3)_2$, $O[C(R^3)_2]_n Het^1$, $O[C(R^3)_2]_n N(R^3)Het^1$, $OCH(CH_2OCH_3)_2$, $O[C(R^3)_2]_n Cyc$, $OCH_2C(CH_3)_2OH$, $CH_3$, $O[C(R^3)_2]_n Ph$, $NO_2$, Cl, OH, $OCH_2C(CH_3)_2NH_2$, $NHCH_2C(CH_3)_2OH$, $[C(R^3)_2]_n Het^1$, $OCH_2CH_2OH$, $OCH_2CH_2CH_2OH$, $O[C(R^3)_2]_n S(O)_m R^3$ or $OCH_2CH_2OCH_2CH_2OH$, and $R^2$, $R^3$, V, X, Y, Z, $Het^1$, $Het^2$, $Het^3$, $Het^4$, A, Cyc, $R^5$, Ph, Hal, m and n having the meanings as in subformula Ij, in Im: $R^1$ denotes $O[C(R^3)_2]_n Het^1$, $O[C(R^3)_2]_n N(R^3)Het^1$, or $[C(R^3)_2]_n Het^1$, in In: $R^2$ denotes H, in Io: $R^3$ denotes H or A, in Ip: V denotes H, in Iq: X denotes NH, in Ir: Y denotes phenylene, which is unsubstituted or mono-, di- or trisubstituted by Hal and/or A, in Is: Z denotes $Het^4$ or —OA, in It: $Het^1$ denotes tetrahydro-furan-3-yl, pyrrolidinyl, piperazinyl, piperidinyl, azetidinyl, imidazolyl, 6,7-dihydro-4H-[1,2,3]triazolo[1,5-a]pyrazin-5-yl, 1,4-diazepanyl, triazolyl or oxetanyl, each of which may be unsubstituted or mono-, di- or trisubstituted by A, Hal, oxetanyl, and/or =O, and wherein a N atom may be oxidized, in Iu: $Het^4$ denotes pyrazolyl, triazolyl, or oxazolyl, each of which may be unsubstituted or mono-, di- or trisubstituted by A, and/or in Iv: $R^5$ denotes F, Cl, or OH, in Iw: Hal denotes F or Cl, for each subformula also including pharmaceutically acceptable salts, tautomers and stereoisomers thereof, including mixtures thereof in all ratios.

Thus, in certain preferred embodiments, $R^1$ denotes $O[C(R^3)_2]_n Het^1$, $O[C(R^3)_2]_n N(R^3)Het^1$, or $[C(R^3)_2]_n Het^1$, and/or $R^2$ denotes H, and/or $R^3$ denotes H or A, and/or V denotes H, and/or X denotes NH, and/or Y denotes phenylene, which is unsubstituted or mono-, di- or trisubstituted by Hal and/or A, and/or Z denotes $Het^4$ or —OA, and/or $Het^1$ denotes tetrahydro-furan-3-yl, pyrrolidinyl, piperazinyl, piperidinyl, azetidinyl, imidazolyl, 6,7-dihydro-4H-[1,2,3]triazolo[1,5-a]pyrazin-5-yl, 1,4-diazepanyl, triazolyl or oxetanyl, each of which may be unsubstituted or mono-, di- or trisubstituted by A, Hal, oxetanyl, and/or =O, and wherein a N atom may be oxidized, and/or $Het^4$ denotes pyrazolyl, triazolyl, or oxazolyl, each of which may be unsubstituted or mono-, di- or trisubstituted by A, and/or A denotes unbranched or branched alkyl with 1-10 C-atoms, wherein 1-3 non-adjacent CH- and/or $CH_2$-groups may be replaced by O-atoms or NH and wherein 1-7 H-atoms may be replaced by $R^5$, or denotes $(CH_2)_n$Cyc, and/or Cyc denotes cyclic alkyl having 3-7 C atoms, and/or $R^5$ denotes F, Cl, or OH, and/or Hal denotes F or Cl, and/or n denotes 0, 1, 2, 3 or 4, with any further radicals and variables being defined as in formula I or any of the subformulas above.

In certain preferred embodiments of compounds of formula I according to the present invention, $R^1$ denotes $O[C(R^3)_2]_n Het^1$, $O[C(R^3)_2]_n N(R^3)Het^1$, $[C(R^3)_2]_n Het^1$, $R^2$ denotes H, $R^3$ denotes H or A, V denotes H, X denotes NH, Y denotes phenylene, which is unsubstituted or mono-, di- or trisubstituted by Hal and/or A, Z denotes $Het^4$ or —OA, $Het^1$ denotes tetrahydro-furan-3-yl, pyrrolidinyl, piperazinyl, piperidinyl, azetidinyl, imidazolyl, 6,7-dihydro-4H-[1,2,3]triazolo[1,5-a]pyrazin-5-yl, 1,4-diazepanyl, triazolyl or oxetanyl, each of which may be unsubstituted or mono-, di- or trisubstituted by A, Hal, oxetanyl, and/or =O, and wherein a N atom may be oxidized, $Het^4$ denotes pyrazolyl, triazolyl, or oxazolyl, each of which may be unsubstituted or mono-, di- or trisubstituted by A, A denotes unbranched or branched alkyl with 1-10 C-atoms, wherein 1-3 non-adjacent CH- and/or $CH_2$-groups may be replaced by O-atoms or NH and wherein 1-7 H-atoms may be replaced by $R^5$, or denotes $(CH_2)_n$Cyc, Cyc denotes cyclic alkyl having 3-7 C atoms, $R^5$ denotes F, Cl, or OH, Hal denotes F or Cl, n denotes 0, 1, 2, 3 or 4, this referring equally to pharmaceutically acceptable salts, tautomers and/or stereoisomers thereof.

Exemplary embodiments of compounds according to the present invention are set out in Table 1 below and shall also include pharmaceutically acceptable salts, tautomers, stereoisomers and racemic mixtures thereof, as well as solvates.

TABLE 1

| No. | Name |
|---|---|
| “H1” | 6-{7-fluoroimidazo[1,2-a]pyridin-3-yl}-N-{[4-(1-methyl-1H-pyrazol-4-yl)phenyl]methyl}pyrimidin-4-amine |
| “H2” | 6-{7-fluoroimidazo[1,2-a]pyridin-3-yl}-N-{[4-(2-methyl-2H-1,2,3-triazol-4-yl)phenyl]methyl}pyrimidin-4-amine |
| “H4” | 6-{7-fluoroimidazo[1,2-a]pyridin-3-yl}-N-{[4-(2-methyl-1,3-oxazol-4-yl)phenyl]methyl}pyrimidin-4-amine |
| “H6” | 6-{7-fluoroimidazo[1,2-a]pyridin-3-yl}-N-{[4-(1,3-oxazol-4-yl)phenyl]methyl}pyrimidin-4-amine |
| “A1” | 6-{7-methoxyimidazo[1,2-a]pyridin-3-yl}-N-{[4-(1-methyl-1H-pyrazol-4-yl)phenyl]methyl}pyrimidin-4-amine |
| “A2” | N-({[1,1'-biphenyl]-4-yl}methyl)-6-[7-(2-methoxyethoxy)imidazo[1,2-a]pyridin-3-yl]pyrimidin-4-amine |
| “A3” | N-({[1,1'-biphenyl]-4-yl}methyl)-6-{7-methoxyimidazo[1,2-a]pyridin-3-yl}pyrimidin-4-amine |
| “A4” | 6-[7-(2-methoxyethoxy)imidazo[1,2-a]pyridin-3-yl]-N-{[4-(1-methyl-1H-pyrazol-4-yl)phenyl]methyl}pyrimidin-4-amine |
| “A5” | 6-[7-(2-methoxyethoxy)imidazo[1,2-a]23yridine-3-yl]-N-{[4-(23yridine-3-yl)phenyl]methyl}pyrimidin-4-amine |
| “A6” | 6-{7-methoxyimidazo[1,2-a]23yridine-3-yl}-N-{[4-(23yridine-3-yl)phenyl]methyl}pyrimidin-4-amine |
| “A7” | 6-[7-(2-methoxyethoxy)imidazo[1,2-a]pyridin-3-yl]-N-{[4-(1-methyl-1H-pyrazol-3-yl)phenyl]methyl}pyrimidin-4-amine |
| “A8” | (6-Imidazo[1,2-a]23yridine-3-yl-pyrimidin-4-yl)-(4-imidazol-1-yl-benzyl)-amine |
| “A9” | (6-Imidazo[1,2-a]23yridine-3-yl-pyrimidin-4-yl)-(4-pyrazol-1-yl-benzyl)-amine |
| “A10” | N-{[4-(1-methyl-1H-pyrazol-4-yl)phenyl]methyl}-6-[7-(trifluoromethyl)imidazo[1,2-a]pyridin-3-yl]pyrimidin-4-amine |
| “A11” | 6-[7-(2-methoxyethoxy)imidazo[1,2-a]pyridin-3-yl]-N-{[6-(1-methyl-1H-pyrazol-4-yl)pyridin-3-yl]methyl}pyrimidin-4-amine |
| “A12” | 1-(4-{[(6-{7-methoxyimidazo[1,2-a]24yridine-3-yl}pyrimidin-4-yl)amino]methyl}phenyl)piperidin-2-one |
| “A13” | 4-{[(6-{7-methoxyimidazo[1,2-a]pyridin-3-yl}pyrimidin-4-yl)amino]methyl}-N,N-dimethylbenzamide |
| “A14” | (6-Imidazo[1,2-a]24yridine-3-yl-pyrimidin-4-yl)-[4-(1-methyl-1H-pyrazol-3-yl)-benzyl]-amine |
| “A15” | [4-(4,5-Dihydro-1H-imidazol-2-yl)-benzyl]-(6-imidazo[1,2-a]pyridin-3-yl-pyrimidin-4-yl)-amine |
| “A16” | 6-[7-(2-methoxyethoxy)imidazo[1,2-a]pyridin-3-yl]-N-{[4-(1H-1,2,3-triazol-1-yl)phenyl]methyl}pyrimidin-4-amine |
| “A17” | 6-[7-(2-methoxyethoxy)imidazo[1,2-a]pyridin-3-yl]-N-[(4-{4H,5H,6H-pyrrolo[1,2-b]pyrazol-3-yl}phenyl)methyl]pyrimidin-4-amine |
| “A18” | 6-{7-methoxyimidazo[1,2-a]pyridin-3-yl}-N-{[4-(1H-1,2,3-triazol-1-yl)phenyl]methyl}pyrimidin-4-amine |
| “A19” | {4-[1-(2-Methoxy-ethyl)-1H-pyrazol-4-yl]-benzyl}-[6-(7-methoxy-imidazo[1,2-a]pyridin-3-yl)-pyrimidin-4-yl]-amine |
| “A20” | [6-(7-Methoxy-imidazo[1,2-a]24yridine-3-yl)-pyrimidin-4-yl]-[4-(1-methyl-1H-imidazol-4-yl)-benzyl]-amine |
| “A21” | [4-(1-Cyclopropylmethyl-1H-pyrazol-4-yl)-benzyl]-[6-(7-methoxy-imidazo[1,2-a]pyridin-3-yl)-pyrimidin-4-yl]-amine |
| “A22” | [6-(7-Methoxy-imidazo[1,2-a]pyridin-3-yl)-pyrimidin-4-yl]-{4-[1-(2-morpholin-4-yl-ethyl)-1H-pyrazol-4-yl]-benzyl}-amine |

TABLE 1-continued

| No. | Name |
|---|---|
| “A23” | [4-(1-Ethyl-1H-pyrazol-4-yl)-benzyl]-[6-(7-methoxy-imidazo[1,2-a]24yridine-3-yl)-pyrimidin-4-yl]-amine |
| “A24” | [6-(7-Methoxy-imidazo[1,2-a]pyridin-3-yl)-pyrimidin-4-yl]-{4-[1-(2-pyrrolidin-1-yl-ethyl)-1H-pyrazol-4-yl]-benzyl}-amine |
| “A25” | [4-(1,3-Dimethyl-1H-pyrazol-4-yl)-benzyl]-[6-(7-methoxy-imidazo[1,2-a]25yridine-3-yl)-pyrimidin-4-yl]-amine |
| “A26” | 6-{7-methoxyimidazo[1,2-a]pyridin-3-yl}-N-{[4-(5-methyl-1,2,4-oxadiazol-3-yl)phenyl]methyl}pyrimidin-4-amine |
| “A27” | N-{[4-(1H-1,3-benzodiazol-1-yl)phenyl]methyl}-6-{7-methoxyimidazo[1,2-a]pyridin-3-yl}pyrimidin-4-amine |
| “A28” | [6-(7-Methoxy-imidazo[1,2-a]25yridine-3-yl)-pyrimidin-4-yl]-[3-(1-methyl-1H-pyrazol-4-yl)-benzyl]-amine |
| “A29” | N-{[3-fluoro-4-(1-methyl-1H-pyrazol-4-yl)phenyl]methyl}-6-{7-methoxyimidazo[1,2-a]pyridin-3-yl}pyrimidin-4-amine |
| “A30” | 2-[4-(4-{[6-(7-Methoxy-imidazo[1,2-a]25yridine-3-yl)-pyrimidin-4-ylamino]-methyl}-phenyl)-pyrazol-1-yl]-ethanol |
| “A31” | [6-(7-Methoxy-imidazo[1,2-a]25yridine-3-yl)-pyrimidin-4-yl]-[4-(1-methyl-1H-[1,2,3]triazol-4-yl)-benzyl]-amine |
| “A32” | [6-(7-Methoxy-imidazo[1,2-a]25yridine-3-yl)-pyrimidin-4-yl]-[4-(2-methyl-2H-[1,2,3]triazol-4-yl)-benzyl]-amine |
| “A33” | 6-{7-methoxyimidazo[1,2-a]pyridin-3-yl}-N-({4-[1-(oxetan-3-yl)-1H-pyrazol-4-yl]phenyl}methyl)pyrimidin-4-amine |
| “A34” | 6-{7-methoxyimidazo[1,2-a]pyridin-3-yl}-N-{[4-(4-methoxypyrimidin-2-yl)phenyl]methyl}pyrimidin-4-amine |
| “A35” | [4-(3-Amino-1-methyl-1H-pyrazol-4-yl)-benzyl]-[6-(7-methoxy-imidazo[1,2-a]25yridine-3-yl)-pyrimidin-4-yl]-amine |
| “A36” | 6-{7-methoxyimidazo[1,2-a]pyridin-3-yl}-N-{[5-(1-methyl-1H-pyrazol-4-yl)thiophen-2-yl]methyl}pyrimidin-4-amine |
| “A37” | 6-{7-methoxyimidazo[1,2-a]pyridin-3-yl}-N-{[4-(2-methyl-2H-1,2,3,4-tetrazol-5-yl)phenyl]methyl}pyrimidin-4-amine |
| “A38” | [6-(7-Methoxy-imidazo[1,2-a]25yridine-3-yl)-pyrimidin-4-yl]-[4-(8-oxa-3-aza-bicyclo[3.2.1]oct-3-yl)-benzyl]-amine |
| “A39” | 6-{7-methoxyimidazo[1,2-a]pyridin-3-yl}-N-{[4-(1-methyl-1H-imidazol-5-yl)phenyl]methyl}pyrimidin-4-amine |
| “A40” | 6-{7-methoxyimidazo[1,2-a]pyridin-3-yl}-N-{[4-(6-methylpyridazin-3-yl)phenyl]methyl}pyrimidin-4-amine |
| “A41” | 6-{7-methoxyimidazo[1,2-a]pyridin-3-yl}-N-{[4-(2-methylpyrimidin-5-yl)phenyl]methyl}pyrimidin-4-amine |
| “A42” | 6-{7-methoxyimidazo[1,2-a]pyridin-3-yl}-N-{[4-(2-methyl-1,3-oxazol-4-yl)phenyl]methyl}pyrimidin-4-amine |
| “A43” | 5-(4-{[(6-{7-methoxyimidazo[1,2-a]26yridine-3-yl}pyrimidin-4-yl)amino]methyl}phenyl)-2-methylpyrimidin-4-amine |
| “A44” | [6-(7-Methoxy-imidazo[1,2-a]26yridine-3-yl)-pyrimidin-4-yl]-[5-(2-methyl-2H-[1,2,3]triazol-4-yl)-pyridin-2-ylmethyl]-amine |
| “A45” | [6-(7-Methoxy-imidazo[1,2-a]26yridine-3-yl)-pyrimidin-4-yl]-[6-(2-methyl-2H-[1,2,3]triazol-4-yl)-pyridin-3-ylmethyl]-amine |
| “A46” | N-({4-[2-(2-methoxyethyl)-2H-1,2,3-triazol-4-yl]phenyl}methyl)-6-{7-methoxyimidazo[1,2-a]pyridin-3-yl}pyrimidin-4-amine |
| “A47” | 6-{7-methoxyimidazo[1,2-a]pyridin-3-yl}-N-{[4-(3-methyl-1,2,4-oxadiazol-5-yl)phenyl]methyl}pyrimidin-4-amine |
| “A48” | [6-(7-Methoxy-imidazo[1,2-a]26yridine-3-yl)-pyrimidin-4-yl]-[4-(2-methyl-oxazol-5-yl)-benzyl]-amine |
| “A49” | [4-(1-Cyclopropyl-1H-pyrazol-4-yl)-benzyl]-[6-(7-methoxy-imidazo[1,2-a]26yridine-3-yl)-pyrimidin-4-yl]-amine |
| “A50” | N-{[4-(3-methoxy-1-methyl-1H-pyrazol-4-yl)phenyl]methyl}-6-{7-methoxyimidazo[1,2-a]pyridin-3-yl}pyrimidin-4-amine |
| “A51” | [6-(7-Methoxy-imidazo[1,2-a]26yridine-3-yl)-pyrimidin-4-yl]-(4-oxazol-4-yl-benzyl)-amine |
| “A52” | [6-(7-Methoxy-imidazo[1,2-a]26yridine-3-yl)-pyrimidin-4-yl]-[4-(3-methyl-isoxazol-5-yl)-benzyl]-amine |
| “A53” | [6-(7-Methoxy-imidazo[1,2-a]27yridine-3-yl)-pyrimidin-4-yl]-[4-(5-methyl-oxazol-2-yl)-benzyl]-amine |
| “A54” | {6-[7-(2-Methoxy-1-methoxymethyl-ethoxy)-imidazo[1,2-a]pyridin-3-yl]-pyrimidin-4-yl}-[4-(1-methyl-1H-pyrazol-4-yl)-benzyl]-amine |
| “A55” | [4-(1-Methyl-1H-pyrazol-4-yl)-benzyl]-{6-[7-(tetrahydro-pyran-4-yloxy)-imidazo[1,2-a]pyridin-3-yl]-pyrimidin-4-yl}-amine |
| “A56” | [4-(1-Methyl-1H-pyrazol-4-yl)-benzyl]-{6-[7-(2-morpholin-4-yl-ethoxy)-imidazo[1,2-a]pyridin-3-yl]-pyrimidin-4-yl}-amine |
| “A57” | [4-(1-Methyl-1H-pyrazol-4-yl)-benzyl]-{6-[7-(tetrahydro-furan-3-yloxy)-imidazo[1,2-a]pyridin-3-yl]-pyrimidin-4-yl}-amine |
| “A58” | 6-[7-(cyclopropylmethoxy)imidazo[1,2-a]pyridin-3-yl]-N-{[4-(1-methyl-1H-pyrazol-4-yl)phenyl]methyl}pyrimidin-4-amine |
| “A59” | 6-{7-[2-(dimethylamino)ethoxy]imidazo[1,2-a]pyridin-3-yl}-N-{[4-(1-methyl-1H-pyrazol-4-yl)phenyl]methyl}pyrimidin-4-amine |
| “A60” | [4-(1-Methyl-1H-pyrazol-4-yl)-benzyl]-{6-[7-(2-pyrrolidin-1-yl-ethoxy)-imidazo[1,2-a]pyridin-3-yl]-pyrimidin-4-yl}-amine |
| “A61” | (6-{7-[2-(4-Methyl-piperazin-1-yl)-ethoxy]-imidazo[1,2-a]pyridin-3-yl}-pyrimidin-4-yl)-[4-(1-methyl-1H-pyrazol-4-yl)-benzyl]-amine |

TABLE 1-continued

| No. | Name |
|---|---|
| “A62” | {6-[7-(1-Methyl-piperidin-4-ylmethoxy)-imidazo[1,2-a]pyridin-3-yl]-pyrimidin-4-yl}-[4-(1-methyl-1H-pyrazol-4-yl)-benzyl]-amine |
| “A63” | {6-[7-(1-Methyl-piperidin-4-yloxy)-imidazo[1,2-a]pyridin-3-yl]-pyrimidin-4-yl}-[4-(1-methyl-1H-pyrazol-4-yl)-benzyl]-amine |
| “A64” | 2-Methyl-1-(3-{6-[4-(1-methyl-1H-pyrazol-4-yl)-benzylamino]-pyrimidin-4-yl}-imidazo[1,2-a]27yridine-7-yloxy)-propan-2-ol (3: Please note: Alphabetic order of prefixes ignored while selecting parent chain) |
| “A65” | [4-(1-Methyl-1H-pyrazol-4-yl)-benzyl]-(6-{7-[2-(4-oxetan-3-yl-piperazin-1-yl)-ethoxy]-imidazo[1,2-a]pyridin-3-yl}-pyrimidin-4-yl)-amine |
| “A66” | [6-(7-Methyl-imidazo[1,2-a]27yridine-3-yl)-pyrimidin-4-yl]-[4-(1-methyl-1H-pyrazol-4-yl)-benzyl]-amine |
| “A67” | (6-{7-[2-(4-Methyl-piperazin-1-yl)-ethoxy]-imidazo[1,2-a]pyridin-3-yl}-pyrimidin-4-yl)-(4-[1,2,3]triazol-1-yl-benzyl)-amine |
| “A68” | {6-[7-(2-Morpholin-4-yl-ethoxy)-imidazo[1,2-a]pyridin-3-yl]-pyrimidin-4-yl}-(4-[1,2,3]triazol-1-yl-benzyl)-amine |
| “A69” | [6-(6-Fluoro-7-methoxy-imidazo[1,2-a]28yridine-3-yl)-pyrimidin-4-yl]-[4-(1-methyl-1H-pyrazol-4-yl)-benzyl]-amine |
| “A70” | {6-[7-(2-Pyrrolidin-1-yl-ethoxy)-imidazo[1,2-a]pyridin-3-yl]-pyrimidin-4-yl}-(4-[1,2,3]triazol-1-yl-benzyl)-amine |
| “A71” | {6-[7-(2-Methoxy-ethoxy)-imidazo[1,2-a]pyridin-3-yl]-pyrimidin-4-yl}-[4-(2-methyl-2H-[1,2,3]triazol-4-yl)-benzyl]-amine |
| “A72” | 6-[7-(benzyloxy)imidazo[1,2-a]pyridin-3-yl]-N-{[4-(1-methyl-1H-pyrazol-4-yl)phenyl]methyl}pyrimidin-4-amine |
| “A73” | [4-(2-Methyl-2H-[1,2,3]triazol-4-yl)-benzyl]-{6-[7-(2-pyrrolidin-1-yl-ethoxy)-imidazo[1,2-a]pyridin-3-yl]-pyrimidin-4-yl}-amine |
| “A74” | [4-(1-Methyl-1H-pyrazol-4-yl)-benzyl]-{6-[7-(3-morpholin-4-yl-propoxy)-imidazo[1,2-a]pyridin-3-yl]-pyrimidin-4-yl}-amine |
| “A75” | [4-(1-Methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine |
| “A76” | [4-(2-Methyl-2H-[1,2,3]triazol-4-yl)-benzyl]-{6-[7-(1-oxetan-3-yl-piperidin-4-ylmethoxy)-imidazo[1,2-a]pyridin-3-yl]-pyrimidin-4-yl}-amine |
| “A77” | 6-{7-[2-(3,3-difluoropyrrolidin-1-yl)ethoxy]imidazo[1,2-a]pyridin-3-yl}-N-{[4-(1-methyl-1H-pyrazol-4-yl)phenyl]methyl}pyrimidin-4-amine |
| “A78” | [4-(1-Methyl-1H-pyrazol-4-yl)-benzyl]-{6-[7-(1-oxetan-3-yl-piperidin-4-ylmethoxy)-imidazo[1,2-a]pyridin-3-yl]-pyrimidin-4-yl}-amine |
| “A79” | {6-[7-(1-Methyl-piperidin-4-ylmethoxy)-imidazo[1,2-a]pyridin-3-yl]-pyrimidin-4-yl}-[4-(2-methyl-2H-[1,2,3]triazol-4-yl)-benzyl]-amine |
| “A80” | {6-[7-(1-Methyl-piperidin-4-ylmethoxy)-imidazo[1,2-a]pyridin-3-yl]-pyrimidin-4-yl}-(4-[1,2,3]triazol-1-yl-benzyl)-amine |
| “A81” | N-{[4-(1-methyl-1H-pyrazol-4-yl)phenyl]methyl}-6-{7-nitroimidazo[1,2-a]pyridin-3-yl}pyrimidin-4-amine |
| “A82” | 6-{7-chloroimidazo[1,2-a]pyridin-3-yl}-N-{[4-(1-methyl-1H-pyrazol-4-yl)phenyl]methyl}pyrimidin-4-amine |
| “A83” | {6-[7-(1-Oxetan-3-yl-piperidin-4-ylmethoxy)-imidazo[1,2-a]pyridin-3-yl]-pyrimidin-4-yl}-(4-[1,2,3]triazol-1-yl-benzyl)-amine |
| “A84” | [4-(2-Methyl-2H-[1,2,3]triazol-4-yl)-benzyl]-{6-[7-(3-pyrrolidin-1-yl-propoxy)-imidazo[1,2-a]pyridin-3-yl]-pyrimidin-4-yl}-amine |
| “A85” | 2-Methyl-1-(3-{6-[4-(2-methyl-2H-[1,2,3]triazol-4-yl)-benzylamino]-pyrimidin-4-yl}-imidazo[1,2-a]29yridine-7-yloxy)-propan-2-ol (3: Please note: Alphabetic order of prefixes ignored while selecting parent chain) |
| “A86” | 7-[2-(4-Methyl-piperazin-1-yl)-ethoxy]-3-{6-[4-(1-methyl-1H-pyrazol-4-yl)-benzyloxy]-pyrimidin-4-yl}-imidazo[1,2-a]pyridine |
| “A87” | 3-{6-[4-(1-Methyl-1H-pyrazol-4-yl)-benzyloxy]-pyrimidin-4-yl}-7-(2-pyrrolidin-1-yl-ethoxy)-imidazo[1,2-a]pyridine |
| “A88” | 4-[3-({3-[6-({[4-(1-methyl-1H-pyrazol-4-yl)phenyl]methyl}amino)pyrimidin-4-yl]imidazo[1,2-a]pyridin-7-yl}oxy)propyl]morpholin-3-one |
| “A89” | 6-{7-[2-(3-fluoropyrrolidin-1-yl)ethoxy]imidazo[1,2-a]pyridin-3-yl}-N-{[4-(1-methyl-1H-pyrazol-4-yl)phenyl]methyl}pyrimidin-4-amine |
| “A90” | 7-[2-(3,3-Difluoro-pyrrolidin-1-yl)-ethoxy]-3-{6-[4-(1-methyl-1H-pyrazol-4-yl)-benzyloxy]-pyrimidin-4-yl}-imidazo[1,2-a]pyridine |
| “A91” | {6-[7-(2,2-Dimethyl-3-pyrrolidin-1-yl-propoxy)-imidazo[1,2-a]pyridin-3-yl]-pyrimidin-4-yl}-[4-(1-methyl-1H-pyrazol-4-yl)-benzyl]-amine |
| “A92” | 4-[2-({3-[6-({[4-(1-methyl-1H-pyrazol-4-yl)phenyl]methyl}amino)pyrimidin-4-yl]imidazo[1,2-a]pyridin-7-yl}oxy)ethyl]morpholin-3-one |
| “A93” | 1-methyl-4-[2-({3-[6-({[4-(1-methyl-1H-pyrazol-4-yl)phenyl]methyl}amino)pyrimidin-4-yl]imidazo[1,2-a]pyridin-7-yl}oxy)ethyl]piperazin-2-one |
| “A94” | N-{[4-(1-methyl-1H-pyrazol-4-yl)phenyl]methyl}-6-{7-[3-(4-methylpiperazin-1-yl)propoxy]imidazo[1,2-a]pyridin-3-yl}pyrimidin-4-amine |
| “A95” | 1-[2-({3-[6-({[4-(1-methyl-1H-pyrazol-4-yl)phenyl]methyl}amino)pyrimidin-4-yl]imidazo[1,2-a]pyridin-7-yl}oxy)ethyl]-4-(oxetan-3-yl)piperazin-2-one |
| “A96” | N-{[4-(2-methyl-2H-1,2,3-triazol-4-yl)phenyl]methyl}-6-{7-[3-(4-methylpiperazin-1-yl)propoxy]imidazo[1,2-a]pyridin-3-yl}pyrimidin-4-amine |
| “A97” | 5-fluoro-6-{7-methoxyimidazo[1,2-a]pyridin-3-yl}-N-{[4-(1-methyl-1H-pyrazol-4-yl)phenyl]methyl}pyrimidin-4-amine |
| “A98” | (6-{7-[2-(1-Methyl-1H-imidazol-2-yl)-ethoxy]-imidazo[1,2-a]pyridin-3-yl}-pyrimidin-4-yl)-[4-(2-methyl-2H-[1,2,3]triazol-4-yl)-benzyl]-amine |

TABLE 1-continued

| No. | Name |
|---|---|
| "A99" | 6-{7-[2-(azetidin-1-yl)ethoxy]imidazo[1,2-a]pyridin-3-yl}-N-{[4-(1-methyl-1H-pyrazol-4-yl)phenyl]methyl}pyrimidin-4-amine |
| "A100" | 6-{7-[2-(azetidin-1-yl)ethoxy]imidazo[1,2-a]pyridin-3-yl}-N-{[4-(2-methyl-2H-1,2,3-triazol-4-yl)phenyl]methyl}pyrimidin-4-amine |
| "A101" | 6-{7-[3-(3,3-difluoropyrrolidin-1-yl)propoxy]imidazo[1,2-a]pyridin-3-yl}-N-{[4-(1-methyl-1H-pyrazol-4-yl)phenyl]methyl}pyrimidin-4-amine |
| A102 | {6-[7-(3-Azetidin-1-yl-propoxy)-imidazo[1,2-a]pyridin-3-yl]-pyrimidin-4-yl}-[4-(1-methyl-1H-pyrazol-4-yl)-benzyl]-amine |
| "A103" | [4-(1-Methyl-1H-pyrazol-4-yl)-benzyl]-(6-{7-[2-(6-oxa-3-aza-bicyclo[3.1.1]hept-3-yl)-ethoxy]-imidazo[1,2-a]pyridin-3-yl}-pyrimidin-4-yl)-amine |
| "A104" | {6-[7-(2-Amino-2-methyl-propoxy)-imidazo[1,2-a]pyridin-3-yl]-pyrimidin-4-yl}-[4-(1-methyl-1H-pyrazol-4-yl)-benzyl]-amine |
| "A105" | (6-{7-[2-(3,3-Difluoro-pyrrolidin-1-yl)-ethoxy]-imidazo[1,2-a]pyridin-3-yl}-pyrimidin-4-yl)-[4-(2-methyl-2H-[1,2,3]triazol-4-yl)-benzyl]-amine |
| "A106" | [4-(2-Methyl-2H-[1,2,3]triazol-4-yl)-benzyl]-{6-[7-(pyridin-2-ylmethoxy)-imidazo[1,2-a]pyridin-3-yl]-pyrimidin-4-yl}-amine |
| "A107" | {6-[7-(2-Methyl-2-morpholin-4-yl-propoxy)-imidazo[1,2-a]pyridin-3-yl]-pyrimidin-4-yl}-[4-(1-methyl-1H-pyrazol-4-yl)-benzyl]-amine |
| "A108" | [4-(2-Methyl-2H-[1,2,3]triazol-4-yl)-benzyl]-(6-{7-[2-(2-oxa-6-aza-spiro[3.3]hept-6-yl)-ethoxy]-imidazo[1,2-a]pyridin-3-yl}-pyrimidin-4-yl)-amine |
| "A109" | {6-[7-(2-Methyl-2-morpholin-4-yl-propoxy)-imidazo[1,2-a]pyridin-3-yl]-pyrimidin-4-yl}-[4-(2-methyl-2H-[1,2,3]triazol-4-yl)-benzyl]-amine |
| "A110" | {6-[7-(1-Methyl-1H-imidazol-2-ylmethoxy)-imidazo[1,2-a]pyridin-3-yl]-pyrimidin-4-yl}-[4-(1-methyl-1H-[1,2,3]triazol-4-yl)-benzyl]-amine |
| "A111" | (6-{7-[2-(1-Methyl-1H-imidazol-2-yl)-ethoxy]-imidazo[1,2-a]pyridin-3-yl}-pyrimidin-4-yl)-[4-(1-methyl-1H-pyrazol-4-yl)-benzyl]-amine |
| "A112" | [4-(2-Methyl-2H-[1,2,3]triazol-4-yl)-benzyl]-{6-[7-(pyridin-3-ylmethoxy)-imidazo[1,2-a]pyridin-3-yl]-pyrimidin-4-yl}-amine |
| "A113" | {6-[7-(1-Methyl-1H-imidazol-2-ylmethoxy)-imidazo[1,2-a]pyridin-3-yl]-pyrimidin-4-yl}-[4-(1-methyl-1H-pyrazol-4-yl)-benzyl]-amine |
| "A114" | [4-(1-Methyl-1H-pyrazol-4-yl)-benzyl]-(6-{7-[2-(2-oxa-6-aza-spiro[3.3]hept-6-yl)-ethoxy]-imidazo[1,2-a]pyridin-3-yl}-pyrimidin-4-yl)-amine |
| "A115" | [4-(1-Methyl-1H-pyrazol-4-yl)-benzyl]-(6-{7-[2-(1-methyl-pyrrolidin-3-yl)-ethoxy]-imidazo[1,2-a]pyridin-3-yl}-pyrimidin-4-yl)-amine |
| "A116" | (6-{7-[2-(1-Methyl-pyrrolidin-3-yl)-ethoxy]-imidazo[1,2-a]pyridin-3-yl}-pyrimidin-4-yl)-[4-(2-methyl-2H-[1,2,3]triazol-4-yl)-benzyl]-amine |
| "A117" | {6-[7-( ®-4-Methyl-morpholin-2-ylmethoxy)-imidazo[1,2-a]pyridin-3-yl]-pyrimidin-4-yl}-[4-(1-methyl-1H-pyrazol-4-yl)-benzyl]-amine |
| "A118" | {6-[7-((S)-4-Methyl-morpholin-2-ylmethoxy)-imidazo[1,2-a]31yridine-3-yl]-pyrimidin-4-yl}-[4-(1-methyl-1H-pyrazol-4-yl)-benzyl]-amine |
| "A119" | [4-(2-Methyl-2H-[1,2,3]triazol-4-yl)-benzyl]-(6-{7-[2-(1-oxetan-3-yl-pyrrolidin-3-yl)-ethoxy]-imidazo[1,2-a]pyridin-3-yl}-pyrimidin-4-yl)-amine |
| "A120" | {6-[7-(3-Azetidin-1-yl-propoxy)-imidazo[1,2-a]pyridin-3-yl]-pyrimidin-4-yl}-[4-(2-methyl-2H-[1,2,3]triazol-4-yl)-benzyl]-amine |
| "A121" | {6-[7-( ®-4-Methyl-morpholin-2-ylmethoxy)-imidazo[1,2-a]pyridin-3-yl]-pyrimidin-4-yl}-[4-(2-methyl-2H-[1,2,3]triazol-4-yl)-benzyl]-amine |
| "A122" | {6-[7-((S)-4-Methyl-morpholin-2-ylmethoxy)-imidazo[1,2-a]32yridine-3-yl]-pyrimidin-4-yl}-[4-(2-methyl-2H-[1,2,3]triazol-4-yl)-benzyl]-amine |
| "A123" | [4-(1-Methyl-1H-pyrazol-4-yl)-benzyl]-(6-{7-[2-(1-oxetan-3-yl-pyrrolidin-3-yl)-ethoxy]-imidazo[1,2-a]pyridin-3-yl}-pyrimidin-4-yl)-amine |
| "A124" | N-{[4-(1-methyl-1H-pyrazol-4-yl)phenyl]methyl}-6-(7-{[(3R)-4-methylmorpholin-3-yl]methoxy}imidazo[1,2-a]pyridin-3-yl)pyrimidin-4-amine |
| "A125" | N-{[4-(1-methyl-1H-pyrazol-4-yl)phenyl]methyl}-6-(7-{[(3S)-4-methylmorpholin-3-yl]methoxy}imidazo[1,2-a]pyridin-3-yl)pyrimidin-4-amine |
| "A126" | [4-(2-Methyl-2H-[1,2,3]triazol-4-yl)-benzyl]-{6-[7-(2-pyridin-3-yl-ethoxy)-imidazo[1,2-a]pyridin-3-yl]-pyrimidin-4-yl}-amine |
| "A127" | (6-{7-[2-(3-Aza-bicyclo[3.1.0]hex-3-yl)-ethoxy]-imidazo[1,2-a]pyridin-3-yl}-pyrimidin-4-yl)-[4-(1-methyl-1H-pyrazol-4-yl)-benzyl]-amine |
| "A128" | (6-{7-[2-(3-Aza-bicyclo[3.1.0]hex-3-yl)-ethoxy]-imidazo[1,2-a]pyridin-3-yl}-pyrimidin-4-yl)-[4-(2-methyl-2H-[1,2,3]triazol-4-yl)-benzyl]-amine |
| "A129" | (6-{7-[2-(1-Methyl-piperidin-4-yl)-ethoxy]-imidazo[1,2-a]pyridin-3-yl}-pyrimidin-4-yl)-[4-(1-methyl-1H-pyrazol-4-yl)-benzyl]-amine |
| "A130" | (6-{7-[2-(1-Methyl-piperidin-4-yl)-ethoxy]-imidazo[1,2-a]pyridin-3-yl}-pyrimidin-4-yl)-[4-(2-methyl-2H-[1,2,3]triazol-4-yl)-benzyl]-amine |
| "A131" | 3-(3-{6-[4-(1-Methyl-1H-pyrazol-4-yl)-benzylamino]-pyrimidin-4-yl}-imidazo[1,2-a]pyridin-7-yloxy)-propan-1-ol |
| "A132" | {6-[7-(3-Dimethylamino-propoxy)-imidazo[1,2-a]pyridin-3-yl]-pyrimidin-4-yl}-[4-(1-methyl-1H-pyrazol-4-yl)-benzyl]-amine |
| "A133" | [4-(2-Methyl-2H-[1,2,3]triazol-4-yl)-benzyl]-{6-[7-(3-morpholin-4-yl-propoxy)-imidazo[1,2-a]pyridin-3-yl]-pyrimidin-4-yl}-amine |
| "A134" | 3-(3-{6-[4-(2-Methyl-2H-[1,2,3]triazol-4-yl)-benzylamino]-pyrimidin-4-yl}-imidazo[1,2-a]pyridin-7-yloxy)-propan-1-ol |
| "A135" | {6-[7-(3-Dimethylamino-propoxy)-imidazo[1,2-a]33yridine-3-yl]-pyrimidin-4-yl}-[4-(2-methyl-2H-[1,2,3]triazol-4-yl)-benzyl]-amine |
| "A136" | 6-{7-[2-(3,3-difluoropiperidin-1-yl)ethoxy]imidazo[1,2-a]pyridin-3-yl}-N-{[4-(1-methyl-1H-pyrazol-4-yl)phenyl]methyl}pyrimidin-4-amine |
| "A137" | 6-{7-[3-(diethylamino)propoxy]imidazo[1,2-a]pyridin-3-yl}-N-{[4-(1-methyl-1H-pyrazol-4-yl)phenyl]methyl}pyrimidin-4-amine |

TABLE 1-continued

| No. | Name |
|---|---|
| "A138" | 4-[2-({3-[6-({[4-(1-methyl-1H-pyrazol-4-yl)phenyl]methyl}amino)pyrimidin-4-yl]imidazo[1,2-a]pyridin-7-yl}oxy)ethyl]-1lambda6-thiomorpholine-1,1-dione |
| "A139" | 6-{7-[2-(3,3-difluoroazetidin-1-yl)ethoxy]imidazo[1,2-a]pyridin-3-yl}-N-{[4-(1-methyl-1H-pyrazol-4-yl)phenyl]methyl}pyrimidin-4-amine |
| "A140" | 6-{7-[2-(3-fluoroazetidin-1-yl)ethoxy]imidazo[1,2-a]pyridin-3-yl}-N-{[4-(1-methyl-1H-pyrazol-4-yl)phenyl]methyl}pyrimidin-4-amine |
| "A141" | 4-methyl-1-[2-({3-[6-({[4-(1-methyl-1H-pyrazol-4-yl)phenyl]methyl}amino)pyrimidin-4-yl]imidazo[1,2-a]pyridin-7-yl}oxy)ethyl]piperazin-2-one |
| "A142" | 6-{7-[3-(3,3-difluoroazetidin-1-yl)propoxy]imidazo[1,2-a]pyridin-3-yl}-N-{[4-(1-methyl-1H-pyrazol-4-yl)phenyl]methyl}pyrimidin-4-amine |
| "A143" | {6-[7-(3-Methanesulfonyl-propoxy)-imidazo[1,2-a]pyridin-3-yl]-pyrimidin-4-yl}-[4-(1-methyl-1H-pyrazol-4-yl)-benzyl]-amine |
| "A144" | N-{[4-(1-methyl-1H-pyrazol-4-yl)phenyl]methyl}-6-{7-[(1-methylazetidin-3-yl)methoxy]imidazo[1,2-a]pyridin-3-yl}pyrimidin-4-amine |
| "A145" | 1-[3-({3-[6-({[4-(1-methyl-1H-pyrazol-4-yl)phenyl]methyl}amino)pyrimidin-4-yl]imidazo[1,2-a]pyridin-7-yl}oxy)propyl]pyrrolidin-2-one |
| "A146" | 6-{imidazo[1,2-a]pyridin-3-yl}-N-({6-[(3R)-3-methoxypyrrolidin-1-yl]pyridin-3-yl}methyl)pyrimidin-4-amine |
| "A147" | (6-Imidazo[1,2-a]33yridine-3-yl-pyrimidin-4-yl)-(6-pyrrolidin-1-yl-pyridin-3-ylmethyl)-amine |
| "A148" | N-({6-[(3S)-3-fluoropyrrolidin-1-yl]pyridin-3-yl}methyl)-6-{imidazo[1,2-a]pyridin-3-yl}pyrimidin-4-amine |
| "A149" | [6-(3-Aza-bicyclo[3.1.0]hex-3-yl)-pyridin-3-ylmethyl]-(6-imidazo[1,2-a]pyridin-3-yl-pyrimidin-4-yl)-amine |
| "A150" | [6-(3,3-Difluoro-pyrrolidin-1-yl)-pyridin-3-ylmethyl]-(6-imidazo[1,2-a]pyridin-3-yl-pyrimidin-4-yl)-amine |
| "A151" | 6-{imidazo[1,2-a]34yridine-3-yl}-N-({6-[(3S)-3-methoxypyrrolidin-1-yl]34yridine-3-yl}methyl)pyrimidin-4-amine |
| "A152" | (4-Fluoro-6-pyrrolidin-1-yl-pyridin-3-ylmethyl)-(6-imidazo[1,2-a]pyridin-3-yl-pyrimidin-4-yl)-amine |
| "A153" | N-({6-[(3R)-3-fluoropyrrolidin-1-yl]pyridin-3-yl}methyl)-6-{imidazo[1,2-a]pyridin-3-yl}pyrimidin-4-amine |
| "A154" | (6-Imidazo[1,2-a]34yridine-3-yl-pyrimidin-4-yl)-(4-methyl-6-pyrrolidin-1-yl-pyridin-3-ylmethyl)-amine |
| "A155" | [6-((S)-3-Fluoro-pyrrolidin-1-yl)-4-methyl-pyridin-3-ylmethyl]-(6-imidazo[1,2-a]34yridine-3-yl-pyrimidin-4-yl)-amine |
| "A156" | [6-( ®-3-Fluoro-pyrrolidin-1-yl)-4-methyl-pyridin-3-ylmethyl]-(6-imidazo[1,2-a]pyridin-3-yl-pyrimidin-4-yl)-amine |
| "A157" | (6-Imidazo[1,2-a]34yridine-3-yl-pyrimidin-4-yl)-[4-(1H-imidazol-2-yl)-benzyl]-amine |
| "A158" | 7-Methoxy-3-{6-[4-(1-methyl-1H-pyrazol-4-yl)-benzyloxy]-pyrimidin-4-yl}-imidazo[1,2-a]pyridine |
| "A159" | N-[(4-{1-[(azetidin-3-yl)methyl]-1H-pyrazol-4-yl}phenyl)methyl]-6-{7-methoxyimidazo[1,2-a]pyridin-3-yl}pyrimidin-4-amine |
| "A160" | 3-[6-({[4-(1-methyl-1H-pyrazol-4-yl)phenyl]methyl}amino)pyrimidin-4-yl]imidazo[1,2-a]pyridin-7-ol |
| "A161" | [4-(4-{[6-(7-Methoxy-imidazo[1,2-a]34yridine-3-yl)-pyrimidin-4-ylamino]-methyl}-phenyl)-2-methyl-2H-pyrazol-3-yl]-methanol |
| "A162" | 6-{7-aminoimidazo[1,2-a]pyridin-3-yl}-N-{[4-(1-methyl-1H-pyrazol-4-yl)phenyl]methyl}pyrimidin-4-amine |
| "A163" | 2-Methyl-2-(3-{6-[4-(1-methyl-1H-pyrazol-4-yl)-benzylamino]-pyrimidin-4-yl}-imidazo[1,2-a]35yridine-7-ylamino)-propan-1-ol |
| "A164" | N-{[4-(1-methyl-1H-pyrazol-4-yl)phenyl]methyl}-6-[7-(piperidin-4-yloxy)imidazo[1,2-a]pyridin-3-yl]pyrimidin-4-amine |
| "A165" | [4-(2-Methyl-2H-[1,2,3]triazol-4-yl)-benzyl]-{6-[7-(piperidin-4-ylmethoxy)-imidazo[1,2-a]pyridin-3-yl]-pyrimidin-4-yl}-amine |
| "A166" | [4-(1-Methyl-1H-pyrazol-4-yl)-benzyl]-{6-[7-(piperidin-4-ylmethoxy)-imidazo[1,2-a]pyridin-3-yl]-pyrimidin-4-yl}-amine |
| "A167" | 6-{7-[(azetidin-3-yl)methoxy]imidazo[1,2-a]pyridin-3-yl}-N-{[4-(1-methyl-1H-pyrazol-4-yl)phenyl]methyl}pyrimidin-4-amine |
| "A168" | [4-(1-Methyl-1H-pyrazol-4-yl)-benzyl]-{6-[7-(2-pyrrolidin-1-yl-ethyl)-imidazo[1,2-a]pyridin-3-yl]-pyrimidin-4-yl}-amine |
| "A169" | (6-{7-[2-(3,3-Difluoro-pyrrolidin-1-yl)-ethyl]-imidazo[1,2-a]pyridin-3-yl}-pyrimidin-4-yl)-[4-(1-methyl-1H-pyrazol-4-yl)-benzyl]-amine |
| "A170" | [4-(1-Methyl-1H-pyrazol-4-yl)-benzyl]-(6-{7-[2-(4-oxetan-3-yl-piperazin-1-yl)-ethyl]-imidazo[1,2-a]pyridin-3-yl}-pyrimidin-4-yl)-amine |
| "A171" | 7-Methoxy-3-(6-{1-[4-(1-methyl-1H-pyrazol-4-yl)-phenyl]-ethoxy}-pyrimidin-4-yl)-imidazo[1,2-a]pyridine |
| "A172" | 2-({3-[6-({[4-(1-methyl-1H-pyrazol-4-yl)phenyl]methyl}amino)pyrimidin-4-yl]imidazo[1,2-a]pyridin-7-yl}oxy)ethan-1-ol |
| "A173" | 2-({3-[6-({[4-(2-methyl-2H-1,2,3-triazol-4-yl)phenyl]methyl}amino)pyrimidin-4-yl]imidazo[1,2-a]pyridin-7-yl}oxy)ethan-1-ol |
| "A174" | [5-(4-{[6-(7-Methoxy-imidazo[1,2-a]pyridin-3-yl)-pyrimidin-4-ylamino]-methyl}-phenyl)-1-methyl-1H-imidazol-2-yl]-methanol |
| "A175" | [4-(1-Methyl-1H-pyrazol-4-yl)-benzyl]-{6-[7-(2-pyrrolidin-3-yl-ethoxy)-imidazo[1,2-a]pyridin-3-yl]-pyrimidin-4-yl}-amine |

TABLE 1-continued

| No. | Name |
|---|---|
| "A176" | [4-(2-Methyl-2H-[1,2,3]triazol-4-yl)-benzyl]-{6-[7-(2-pyrrolidin-3-yl-ethoxy)-imidazo[1,2-a]pyridin-3-yl]-pyrimidin-4-yl}-amine |
| "A177" | [4-(1-Methyl-1H-pyrazol-4-yl)-benzyl]-[6-(7-pyrrolidin-1-yl-imidazo[1,2-a]pyridin-3-yl)-pyrimidin-4-yl]-amine |
| "A178" | 2-[1-(3-{6-[4-(1-Methyl-1H-pyrazol-4-yl)-benzylamino]-pyrimidin-4-yl}-imidazo[1,2-a]pyridin-7-yl)-pyrrolidin-3-yl]-ethanol |
| "A179" | 2-[1-(3-{6-[4-(2-Methyl-2H-[1,2,3]triazol-4-yl)-benzylamino]-pyrimidin-4-yl}-imidazo[1,2-a]pyridin-7-yl)-pyrrolidin-3-yl]-ethanol |
| "A180" | [4-(1-Methyl-1H-pyrazol-4-yl)-benzyl]-[6-(7-morpholin-4-yl-imidazo[1,2-a]36yridine-3-yl)-pyrimidin-4-yl]-amine |
| "A181" | {6-[7-(4-Methyl-piperazin-1-yl)-imidazo[1,2-a]pyridin-3-yI]-pyrimidin-4-yl}-[4-(1-methyl-1H-pyrazol-4-yl)-benzyl]-amine |
| "A182" | N-{[4-(1-methyl-1H-pyrazol-4-yl)phenyl]methyl}-6-(7-{[1-(oxetan-3-yl)piperidin-4-yl]oxy}imidazo[1,2-a]pyridin-3-yl)pyrimidin-4-amine |
| "A183" | N-{[4-(1-methyl-1H-pyrazol-4-yl)phenyl]methyl}-6-(7-{[1-(oxetan-3-yl)azetidin-3-yl]methoxy}imidazo[1,2-a]pyridin-3-yl)pyrimidin-4-amine |
| "A184" | [4-(1-Methyl-1H-pyrazol-4-yl)-benzyl]-(6-{7-[3-(4-oxetan-3-yl-piperazin-1-yl)-propoxy]-imidazo[1,2-a]pyridin-3-yl}-pyrimidin-4-yl)-amine |
| "A185" | [4-(2-Methyl-2H-[1,2,3]triazol-4-yl)-benzyl]-(6-{7-[3-(4-oxetan-3-yl-piperazin-1-yl)-propoxy]-imidazo[1,2-a]pyridin-3-yl}-pyrimidin-4-yl)-amine |
| "A186" | {6-[7-(1-Cyclopropyl-piperidin-4-ylmethoxy)-imidazo[1,2-a]pyridin-3-yl]-pyrimidin-4-yl}-[4-(2-methyl-2H-[1,2,3]triazol-4-yl)-benzyl]-amine |
| "A187" | {6-[7-(1-Cyclopropyl-piperidin-4-ylmethoxy)-imidazo[1,2-a]pyridin-3-yl]-pyrimidin-4-yl}-[4-(1-methyl-1H-pyrazol-4-yl)-benzyl]-amine |
| "A188" | [4-(3-{6-[4-(1-Methyl-1H-pyrazol-4-yl)-benzylamino]-pyrimidin-4-yl}-imidazo[1,2-a]pyridin-7-yloxymethyl)-piperidin-1-yl]-acetonitrile |
| "A189" | [4-(3-{6-[4-(2-Methyl-2H-[1,2,3]triazol-4-yl)-benzylamino]-pyrimidin-4-yl}-imidazo[1,2-a]pyridin-7-yloxymethyl)-piperidin-1-yl]-acetonitrile |
| "A190" | (6-{7-[1-(2-Methoxy-ethyl)-piperidin-4-ylmethoxy]-imidazo[1,2-a]pyridin-3-yl}-pyrimidin-4-yl)-[4-(1-methyl-1H-pyrazol-4-yl)-benzyl]-amine |
| "A191" | (6-{7-[1-(2-Methoxy-ethyl)-piperidin-4-ylmethoxy]-imidazo[1,2-a]pyridin-3-yl}-pyrimidin-4-yl)-[4-(2-methyl-2H-[1,2,3]triazol-4-yl)-benzyl]-amine |
| "A192" | (6-{7-[1-(2,2-Difluoro-ethyl)-piperidin-4-ylmethoxy]-imidazo[1,2-a]pyridin-3-yl}-pyrimidin-4-yl)-[4-(1-methyl-1H-pyrazol-4-yl)-benzyl]-amine |
| "A193" | (6-{7-[1-(2,2-Difluoro-ethyl)-piperidin-4-ylmethoxy]-imidazo[1,2-a]pyridin-3-yl}-pyrimidin-4-yl)-[4-(2-methyl-2H-[1,2,3]triazol-4-yl)-benzyl]-amine |
| "A194" | [4-(1-Methyl-1H-pyrazol-4-yl)-benzyl]-(6-{7-[2-(1-oxo-1l4-thiomorpholin-4-yl)-ethoxy]-imidazo[1,2-a]pyridin-3-yl}-pyrimidin-4-yl)-amine |
| "A195" | (6-{7-[2-(1,3-Dihydro-pyrrolo[3,4-c]pyridin-2-yl)-ethoxy]-imidazo[1,2-a]pyridin-3-yl}-pyrimidin-4-yl)-[4-(1-methyl-1H-pyrazol-4-yl)-benzyl]-amine |
| "A196" | (6-{7-[2-(4-Fluoro-4-methyl-piperidin-1-yl)-ethoxy]-imidazo[1,2-a]pyridin-3-yl}-pyrimidin-4-yl)-[4-(1-methyl-1H-pyrazol-4-yl)-benzyl]-amine |
| "A197" | (6-{7-[2-(4-Cyclopropyl-piperazin-1-yl)-ethoxy]-imidazo[1,2-a]pyridin-3-yl}-pyrimidin-4-yl)-[4-(1-methyl-1H-pyrazol-4-yl)-benzyl]-amine |
| "A198" | (6-{7-[2-(3-Methyl-3,8-diaza-bicyclo[3.2.1]oct-8-yl)-ethoxy]-imidazo[1,2-a]pyridin-3-yl}-pyrimidin-4-yl)-[4-(1-methyl-1H-pyrazol-4-yl)-benzyl]-amine |
| "A199" | [4-(1-Methyl-1H-pyrazol-4-yl)-benzyl]-(6-{7-[2-(2-oxo-2l4-thia-5-aza-bicyclo[2.2.1]hept-5-yl)-ethoxy]-imidazo[1,2-a]pyridin-3-yl}-pyrimidin-4-yl)-amine |
| "A200" | (6-{7-[2-(6,6-Difluoro-[1,4]oxazepan-4-yl)-ethoxy]-imidazo[1,2-a]pyridin-3-yl}-pyrimidin-4-yl)-[4-(1-methyl-1H-pyrazol-4-yl)-benzyl]-amine |
| "A201" | (6-{7-[2-(Hexahydro-pyrazino[2,1-c][1,4]oxazin-8-yl)-ethoxy]-imidazo[1,2-a]pyridin-3-yl}-pyrimidin-4-yl)-[4-(1-methyl-1H-pyrazol-4-yl)-benzyl]-amine |
| "A202" | (6-{7-[2-(4,4-Difluoro-piperidin-1-yl)-ethoxy]-imidazo[1,2-a]pyridin-3-yl}-pyrimidin-4-yl)-[4-(1-methyl-1H-pyrazol-4-yl)-benzyl]-amine |
| "A203" | (6-{7-[2-(5,6-Dihydro-8H-[1,2,4]triazolo[4,3-a]pyrazin-7-yl)-ethoxy]-imidazo[1,2-a]pyridin-3-yl}-pyrimidin-4-yl)-[4-(1-methyl-1H-pyrazol-4-yl)-benzyl]-amine |
| "A204" | (6-{7-[2-(2-Methyl-5,6-dihydro-8H-[1,2,4]triazolo[1,5-a]pyrazin-7-yl)-ethoxy]-imidazo[1,2-a]pyridin-3-yl}-pyrimidin-4-yl)-[4-(1-methyl-1H-pyrazol-4-yl)-benzyl]-amine |
| "A205" | {Methyl-[2-(3-{6-[4-(1-methyl-1H-pyrazol-4-yl)-benzylamino]-pyrimidin-4-yl}-imidazo[1,2-a]pyridin-7-yloxy)-ethyl]-amino}-acetonitrile |
| "A206" | 3-Methyl-1-[2-(3-{6-[4-(1-methyl-1H-pyrazol-4-yl)-benzylamino]-pyrimidin-4-yl}-imidazo[1,2-a]pyridin-7-yloxy)-ethyl]-azetidine-3-carbonitrile |
| "A207" | [4-(1-Methyl-1H-pyrazol-4-yl)-benzyl]-(6-{7-[2-(6-oxa-1-aza-spiro[3.3]hept-1-yl)-ethoxy]-imidazo[1,2-a]pyridin-3-yl}-pyrimidin-4-yl)-amine |
| "A208" | [4-(1-Methyl-1H-pyrazol-4-yl)-benzyl]-[6-(7-{2-[methyl-(2,2,2-trifluoro-ethyl)-amino]-ethoxy}-imidazo[1,2-a]pyridin-3-yl)-pyrimidin-4-yl]-amine |
| "A209" | (6-{7-[2-((3S,4R)-3,4-Difluoro-pyrrolidin-1-yl)-ethoxy]-imidazo[1,2-a]pyridin-3-yl}-pyrimidin-4-yl)-[4-(1-methyl-1H-pyrazol-4-yl)-benzyl]-amine |
| "A210" | (6-{7-[(3aS,7aS)-2-(Hexahydro-furo[3,2-b]pyridin-4-yl)-ethoxy]-imidazo[1,2-a]pyridin-3-yl}-pyrimidin-4-yl)-[4-(1-methyl-1H-pyrazol-4-yl)-benzyl]-amine |
| "A211" | (6-{7-[(4aS,8aS)-2-(Hexahydro-pyrano[3,4-b][1,4]oxazin-1-yl)-ethoxy]-imidazo[1,2-a]pyridin-3-yl}-pyrimidin-4-yl)-[4-(1-methyl-1H-pyrazol-4-yl)-benzyl]-amine |

TABLE 1-continued

| No. | Name |
|---|---|
| "A212" | (6-{7-[2-(1,4-Diaza-bicyclo[3.2.1]oct-4-yl)-ethoxy]-imidazo[1,2-a]pyridin-3-yl}-pyrimidin-4-yl)-[4-(1-methyl-1H-pyrazol-4-yl)-benzyl]-amine |
| "A213" | [6-(7-{2-[3-(3-Methyl-[1,2,4]ox3diazol-5-yl)-azetidin-1-yl]-ethoxy}-imidazo[1,2-a]pyridin-3-yl)-pyrimidin-4-yl]-[4-(1-methyl-1H-pyrazol-4-yl)-benzyl]-amine |
| "A214" | (6-{7-[2-(2,2-Difluoro-morpholin-4-yl)-ethoxy]-imidazo[1,2-a]pyridin-3-yl}-pyrimidin-4-yl)-[4-(1-methyl-1H-pyrazol-4-yl)-benzyl]-amine |
| "A215" | (6-{7-[2-(3-Methanesulfonyl-azetidin-1-yl)-ethoxy]-imidazo[1,2-a]pyridin-3-yl}-pyrimidin-4-yl)-[4-(1-methyl-1H-pyrazol-4-yl)-benzyl]-amine |
| "A216" | (6-{7-[2-(6,7-Dihydro-4H-pyrazolo[1,5-a]pyrazin-5-yl)-ethoxy]-imidazo[1,2-a]pyridin-3-yl}-pyrimidin-4-yl)-[4-(1-methyl-1H-pyrazol-4-yl)-benzyl]-amine |
| "A217" | (6-{7-[2-(6,7-Dihydro-4H-[1,2,3]triazolo[1,5-a]pyrazin-5-yl)-ethoxy]-imidazo[1,2-a]pyridin-3-yl}-pyrimidin-4-yl)-[4-(1-methyl-1H-pyrazol-4-yl)-benzyl]-amine |
| "A218" | (6-{7-[2-(3,4-Dihydro-1H-pyrrolo[1,2-a]pyrazin-2-yl)-ethoxy]-imidazo[1,2-a]pyridin-3-yl}-pyrimidin-4-yl)-[4-(1-methyl-1H-pyrazol-4-yl)-benzyl]-amine |
| "A219" | 4-Methyl-1-[2-(3-{6-[4-(1-methyl-1H-pyrazol-4-yl)-benzylamino]-pyrimidin-4-yl}-imidazo[1,2-a]pyridin-7-yloxy)-ethyl]-[1,4]diazepan-5-one |
| "A220" | (6-{7-[2-(4-Methoxy-4-methyl-piperidin-1-yl)-ethoxy]-imidazo[1,2-a]pyridin-3-yl}-pyrimidin-4-yl)-[4-(1-methyl-1H-pyrazol-4-yl)-benzyl]-amine |
| "A221" | (6-{7-[2-(3-Methyl-5,6-dihydro-8H-[1,2,4]triazolo[4,3-a]pyrazin-7-yl)-ethoxy]-imidazo[1,2-a]pyridin-3-yl}-pyrimidin-4-yl)-[4-(1-methyl-1H-pyrazol-4-yl)-benzyl]-amine |
| "A222" | 4-Methyl-1-[2-(3-{6-[4-(1-methyl-1H-pyrazol-4-yl)-benzylamino]-pyrimidin-4-yl}-imidazo[1,2-a]pyridin-7-yloxy)-ethyl]-piperidine-4-carbonitrile |
| "A223" | {6-[7-(3-Amino-3-methyl-butoxy)-imidazo[1,2-a]pyridin-3-yl]-pyrimidin-4-yl}-[4-(1-methyl-1H-pyrazol-4-yl)-benzyl]-amine |
| "A224" | {6-[7-(2-Methanesulfonyl-ethoxy)-imidazo[1,2-a]pyridin-3-yl]-pyrimidin-4-yl}-[4-(1-methyl-1H-pyrazol-4-yl)-benzyl]-amine |
| "A225" | {6-[7-(4-Azetidin-1-yl-butoxy)-imidazo[1,2-a]pyridin-3-yl]-pyrimidin-4-yl}-[4-(1-methyl-1H-pyrazol-4-yl)-benzyl]-amine |
| "A226" | 6-[7-(1-methyl-1H-pyrazol-4-yl)imidazo[1,2-a]pyridin-3-yl]-N-{[4-(1-methyl-1H-pyrazol-4-yl)phenyl]methyl}pyrimidin-4-amine |
| "A227" | {6-[7-(2-Methyl-3-pyrrolidin-1-yl-propoxy)-imidazo[1,2-a]pyridin-3-yl]-pyrimidin-4-yl}-[4-(2-methyl-2H-[1,2,3]triazol-4-yl)-benzyl]-amine |
| "A228" | 1-[3-({3-[6-({[4-(1-methyl-1H-pyrazol-4-yl)phenyl]methyl}amino)pyrimidin-4-yl]imidazo[1,2-a]pyridin-7-yl}oxy)propyl]pyrrolidin-1-ium-1-olate |
| "A229" | 1-[3-Amino-4-(4-{[6-(7-methoxy-imidazo[1,2-a]39yridine-3-yl)-pyrimidin-4-ylamino]-methyl}-phenyl)-pyrazol-1-yl]-2-methyl-propan-2-ol (3: Please note: Alphabetic order of prefixes ignored while selecting parent chain) |
| "A230" | [4-(1-Methyl-1H-pyrazol-4-yl)-benzyl]-{6-[7-(4-oxetan-3-yl-piperazin-1-yl)-imidazo[1,2-a]pyridin-3-yl]-pyrimidin-4-yl}-amine |
| "A231" | {6-[7-(3-Methanesulfonyl-propoxy)-imidazo[1,2-a]pyridin-3-yl]-pyrimidin-4-yl}-[4-(2-methyl-2H-[1,2,3]triazol-4-yl)-benzyl]-amine |
| "A232" | [4-(2-Methyl-2H-[1,2,3]triazol-4-yl)-benzyl]-[6-(7-pyrrolidin-1-yl-imidazo[1,2-a]pyridin-3-yl)-pyrimidin-4-yl]-amine |
| "A233" | (6-{7-[2-(3-Amino-oxetan-3-yl)-ethoxy]-imidazo[1,2-a]pyridin-3-yl}-pyrimidin-4-yl)-[4-(1-methyl-1H-pyrazol-4-yl)-benzyl]-amine |
| "A234" | 2-[2-(3-{6-[4-(1-Methyl-1H-pyrazol-4-yl)-benzylamino]-pyrimidin-4-yl}-imidazo[1,2-a]pyridin-7-yloxy)-ethoxy]-ethanol |
| "A235" | [4-(1-Methyl-1H-pyrazol-4-yl)-benzyl]-{6-[7-(2-methyl-3-pyrrolidin-1-yl-propoxy)-imidazo[1,2-a]pyridin-3-yl]-pyrimidin-4-yl}-amine |
| "A236" | 2-(3-{6-[4-(2-Methyl-oxazol-4-yl)-benzylamino]-pyrimidin-4-yl}-imidazo[1,2-a]pyridin-7-yloxy)-ethanol |
| "A237" | N-{[4-(1-methyl-1H-pyrazol-4-yl)phenyl]methyl}-6-{7-[3-(piperidin-1-yl)propoxy]imidazo[1,2-a]pyridin-3-yl}pyrimidin-4-amine |
| "A238" | [4-(1-Methyl-1H-pyrazol-4-yl)-benzyl]-(6-{7-[3-(2-oxa-6-aza-spiro[3.3]hept-6-yl)-propoxy]-imidazo[1,2-a]pyridin-3-yl}-pyrimidin-4-yl)-amine |
| "A239" | [4-(2-Methyl-2H-[1,2,3]triazol-4-yl)-benzyl]-(6-{7-[3-(2-oxa-6-aza-spiro[3.3]hept-6-yl)-propoxy]-imidazo[1,2-a]pyridin-3-yl}-pyrimidin-4-yl)-amine |
| "A240" | (6-{7-[3-(3-Fluoro-azetidin-1-yl)-propoxy]-imidazo[1,2-a]pyridin-3-yl}-pyrimidin-4-yl)-[4-(1-methyl-1H-pyrazol-4-yl)-benzyl]-amine |
| "A241" | [4-(1-Methyl-1H-pyrazol-4-yl)-benzyl]-(6-{7-[3-(1-oxo-1l4-thiomorpholin-4-yl)-propoxy]-imidazo[1,2-a]pyridin-3-yl}-pyrimidin-4-yl)-amine |
| "A242" | [4-(2-Methyl-oxazol-4-yl)-benzyl]-{6-[7-(3-pyrrolidin-1-yl-propoxy)-imidazo[1,2-a]pyridin-3-yl]-pyrimidin-4-yl}-amine |
| "A243" | (6-{7-[3-(4-Cyclopropyl-piperazin-1-yl)-propoxy]-imidazo[1,2-a]pyridin-3-yl}-pyrimidin-4-yl)-[4-(1-methyl-1H-pyrazol-4-yl)-benzyl]-amine |
| "A244" | [4-(2-Methyl-2H-[1,2,3]triazol-4-yl)-benzyl]-{6-[7-(4-oxetan-3-yl-piperazin-1-yl)-imidazo[1,2-a]pyridin-3-yl]-pyrimidin-4-yl}-amine |
| "A245" | 1-(3-{6-[4-(1-Methyl-1H-pyrazol-4-yl)-benzylamino]-pyrimidin-4-yl}-imidazo[1,2-a]pyridin-7-yl)-pyrrolidin-3-ol |
| "A246" | [4-(1-Methyl-1H-pyrazol-4-yl)-benzyl]-{6-[7-(2-oxa-6-aza-spiro[3.3]hept-6-yl)-imidazo[1,2-a]pyridin-3-yl]-pyrimidin-4-yl}-amine |
| "A247" | [4-(1-Methyl-1H-pyrazol-4-yl)-benzyl]-{6-[7-(2-oxa-6-aza-spiro[3.4]oct-6-yl)-imidazo[1,2-a]pyridin-3-yl]-pyrimidin-4-yl}-amine |
| "A248" | 7-Methyl-2-[2-(3-{6-[4-(1-methyl-1H-pyrazol-4-yl)-benzylamino]-pyrimidin-4-yl}-imidazo[1,2-a]pyridin-7-yloxy)-ethyl]-5-oxa-2,7-diaza-spiro[3.4]octan-6-one |
| "A249" | {6-[7-(3-Azetidin-1-yl-propoxy)-imidazo[1,2-a]pyridin-3-yl]-pyrimidin-4-yl}-{1-[4-(1-methyl-1H-pyrazol-4-yl)-phenyl]-ethyl}-amine |

TABLE 1-continued

| No. | Name |
|---|---|
| "A250" | {1-[4-(1-Methyl-1H-pyrazol-4-yl)-phenyl]-ethyl}-{6-[7-(3-pyrrolidin-1-yl-propoxy)-imidazo[1,2-a]pyridin-3-yl]-pyrimidin-4-yl}-amine |
| "A251" | 2-{3-[6-(4-Oxazol-4-yl-benzylamino)-pyrimidin-4-yl]-imidazo[1,2-a]pyridin-7-yloxy}-ethanol |
| "A252" | (4-Oxazol-4-yl-benzyl)-{6-[7-(3-pyrrolidin-1-yl-propoxy)-imidazo[1,2-a]pyridin-3-yl]-pyrimidin-4-yl}-amine |
| "A253" | (6-{7-[3-(4-Cyclopropyl-piperazin-1-yl)-propoxy]-imidazo[1,2-a]pyridin-3-yl}-pyrimidin-4-yl)-[4-(2-methyl-2H-[1,2,3]triazol-4-yl)-benzyl]-amine |
| "A254" | N-{[4-(1-methyl-1H-pyrazol-4-yl)phenyl]methyl}-6-(7-{[1-(2,2,2-trifluoroethyl)azetidin-3-yl]methoxy}imidazo[1,2-a]pyridin-3-yl)pyrimidin-4-amine |
| "A255" | N-{[4-(1-methyl-1H-pyrazol-4-yl)phenyl]methyl}-6-{7-[2-(1H-pyrazol-1-yl)ethoxy]imidazo[1,2-a]pyridin-3-yl}pyrimidin-4-amine |
| "A256" | 6-{7-[(3-fluoro-1-methylazetidin-3-yl)methoxy]imidazo[1,2-a]pyridin-3-yl}-N-{[4-(1-methyl-1H-pyrazol-4-yl)phenyl]methyl}pyrimidin-4-amine |
| "A257" | N-{[4-(1-methyl-1H-pyrazol-4-yl)phenyl]methyl}-6-{7-[3-(1H-pyrazol-1-yl)propoxy]imidazo[1,2-a]pyridin-3-yl}pyrimidin-4-amine |
| "A258" | [4-(1-Methyl-1H-pyrazol-4-yl)-benzyl]-(6-{7-[3-(oxetan-3-ylamino)-propoxy]-imidazo[1,2-a]pyridin-3-yl}-pyrimidin-4-yl)-amine |
| "A259" | N-{[4-(2-methyl-2H-1,2,3-triazol-4-yl)phenyl]methyl}-6-(7-{3-[(oxetan-3-yl)amino]propoxy}imidazo[1,2-a]pyridin-3-yl)pyrimidin-4-amine |
| "A260" | [4-(1-Methyl-1H-pyrazol-4-yl)-benzyl]-[6-(7-{3-[ ®-(tetrahydro-furan-3-yl)amino]-propoxy}-imidazo[1,2-a]pyridin-3-yl)-pyrimidin-4-yl]-amine |
| "A261" | 4-methyl-1-[2-({3-[6-({[4-(2-methyl-1,3-oxazol-4-yl)phenyl]methyl}amino)pyrimidin-4-yl]imidazo[1,2-a]pyridin-7-yl}oxy)ethyl]-1,4-diazepan-5-one |
| "A262" | (6-{7-[3-(4-Fluoro-4-methyl-piperidin-1-yl)-propoxy]-imidazo[1,2-a]pyridin-3-yl}-pyrimidin-4-yl)-[4-(1-methyl-1H-pyrazol-4-yl)-benzyl]-amine |
| "A263" | 6-{7-[3-(4-fluoro-4-methylpiperidin-1-yl)propoxy]imidazo[1,2-a]pyridin-3-yl}-N-{[4-(1,3-oxazol-4-yl)phenyl]methyl}pyrimidin-4-amine |
| "A264" | N-{[4-(2-methyl-1,3-oxazol-4-yl)phenyl]methyl}-6-[7-(2-{4H,5H,6H,7H-[1,2,3]triazolo[1,5-a]pyrazin-5-yl}ethoxy)imidazo[1,2-a]pyridin-3-yl]pyrimidin-4-amine |
| "A265" | 6-[7-(2-{4H,5H,6H,7H-[1,2,3]triazolo[1,5-a]pyrazin-5-yl}ethoxy)imidazo[1,2-a]pyridin-3-yl]-N-{[4-(trifluoromethoxy)phenyl]methyl}pyrimidin-4-amine |
| "A266" | [4-(1-Methyl-1H-pyrazol-4-yl)-benzyl]-[6-(7-[1,2,4]triazol-1-yl-imidazo[1,2-a]pyridin-3-yl)-pyrimidin-4-yl]-amine |
| "A267" | {6-[7-(4-Methyl-imidazol-1-yl)-imidazo[1,2-a]pyridin-3-yl]-pyrimidin-4-yl}-[4-(1-methyl-1H-pyrazol-4-yl)-benzyl]-amine |
| "A268" | {6-[7-(3-Methylamino-azetidin-1-yl)-imidazo[1,2-a]pyridin-3-yl]-pyrimidin-4-yl}-[4-(1-methyl-1H-pyrazol-4-yl)-benzyl]-amine |

Examples A75, A185, A217 and A258 to 268 are particularly preferred. Also preferred are those compounds found to have good solubility as described further below and those listed in Table 3.

Preparation and properties of those exemplary embodiments will be discussed further below.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made of variants known per se which are not mentioned here in greater detail.

Compounds of the formula I in which X denotes $N(R^3)$ can preferably be obtained by reacting a compound of the formula II with a compound of the formula III. The starting compounds of the formula II and III are generally known. If they are novel, however, they can be prepared by methods known per se. The reaction is generally carried out in the presence of an alkali or alkaline earth metal hydroxide, carbonate or bicarbonate or another salt of a weak acid of the alkali or alkaline earth metals, preferably of potassium, sodium, calcium or caesium, or in the presence of an organic base, such as diisopropylamine (DIPEA). Preferably the reaction is carried out in the presence of compounds such as $K_2CO_3$ and/or KI.

Depending on the conditions used, the reaction time is between a few minutes and 14 days, the reaction temperature is between about −30° and 140°, normally between 60° and 130°, in particular between about 80° and about 110°. Examples of suitable inert solvents are hydrocarbons, such as hexane, petroleumether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide, 1-methylpyrrolidin-2-one or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to DMSO.

Compounds of the formula can preferably be obtained by reacting a compound of the formula IV with a compound of the formula V. The starting compounds of the formula IV and V are generally known. If they are novel, however, they can be prepared by methods known per se. Preferably the reaction is carried out in the presence of compounds such as N-bromosuccinimde (NBS). Depending on the conditions used, the reaction time is between a few minutes and 14 days, the reaction temperature is between about −30° and 120°, normally between −10° and 80°, in particular between about −5° and about 70°. Examples of suitable inert solvents are hydrocarbons, such as hexane, petroleumether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to 1,4-dioxane and/or water.

Compounds of the formula I can preferably be obtained by converting a compound of formula I, wherein $R^1$ denotes F, into another compound of formula, wherein $R^1$ denotes $O[C(R^3)_2]_nN(R^3)_2$ or $O[C(R^3)_2]_nHet^1$.

A compound of formula I, wherein $R^1$ denotes F is reacted with an alcohol $HO[C(R^3)_2]_nN(R^3)_2$, wherein $R^3$ and n have the meanings as given above, or with an alcohol $HO[C(R^3)_2]_nHet^1$, wherein $R^3$, $Het^1$ and n have the meanings as given above.

Preferably the reaction is carried out in the presence of compounds such as potassium tert-butanolate ($KO^tBu$). Depending on the conditions used, the reaction time is between a few minutes and 14 days, the reaction temperature is between about −10° and 140°, normally between 0° and 120°, in particular between about 20° and about 110°. Examples of suitable inert solvents are hydrocarbons, such as hexane, petroleumether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to 1,4-dioxane.

Compounds of the formula I in which Z denotes $Het^4$ can preferably be obtained by reacting a compound of the formula VI with a compound of the formula VII. The starting compounds of the formula VI and VII are generally known. If they are novel, however, they can be prepared by methods known per se. The reaction is generally carried out in the presence of an alkali or alkaline earth metal hydroxide, carbonate or bicarbonate or another salt of a weak acid of the alkali or alkaline earth metals, preferably of potassium, sodium, calcium or caesium. Preferably the reaction is carried out in the presence of compounds such as $K_2CO_3$. Depending on the conditions used, the reaction time is between a few minutes and 14 days, the reaction temperature is between about −30° and 140°, normally between 60° and 130°, in particular between about 80° and about 110°. Examples of suitable inert solvents are hydrocarbons, such as hexane, petroleumether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to acetonitrile.

Pharmaceutical Salts and Other Forms

The compounds according to the invention can be used in their final non-salt form, i.e. free form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassiumethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, per-sulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium, the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the abovementioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t½), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33 (10) 2927-2937, 1994, and Jarman et al. Carcinogenesis 16 (4), 683-688, 1995.

The invention furthermore relates to medicaments comprising at least one compound of the formula I and/or pharmaceutically acceptable salts, tautomers and stereoisomers thereof, including mixtures thereof in all ratios, and optionally excipients and/or adjuvants. Of course, this shall be understood as including solvates of the compounds and salts.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent. Pharmaceutical formulations adapted for topical application in the mouth encompass lozenges, pastilles and mouthwashes. Pharmaceutical formulations adapted for rectal administration can be administered in the form of suppositories or enemas. Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil. Pharmaceutical formulations adapted for administration by inhalation encompass finely particulate dusts or mists, which can be generated by various types of pressurised dispensers with aerosols, nebulisers or insufflators. Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, tautomers and stereoisomers thereof, including mixtures thereof in all ratios, and at least one further pharmaceutically active ingredient (being synonymous with a medicament active ingredient).

The invention also relates to a set (kit) consisting of separate packs of (a) an effective amount of a compound of the formula I and/or pharmaceutically acceptable salt, tautomer and stereoisomer thereof, including mixtures thereof in all ratios, and (b) an effective amount of a further pharmaceutically active ingredient.

The kit comprises suitable containers, such as boxes, individual bottles, bags or ampoules. The kit may, for example, comprise separate ampoules, each containing an effective amount of a compound of the formula I and/or pharmaceutically acceptable salts, tautomers and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula I can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

The expression "effective amount" denotes the amount of a medicament or of a pharmaceutical active ingredient which causes in a tissue, system, animal or human a biological or medical response which is sought or desired, for example, by a researcher or physician. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

In one embodiment an effective amount of a compound of formula I is an amount that inhibits c-KIT kinase in a cell, such as, for example, in vitro or in vivo. In some embodiments, the effective amount of the compound of formula I inhibits c-Kit in a cell by 10%, 20%, 30%, 40%, 50%, 60%, 70%, 80%, 90% or 99%, compared to the activity of c-KIT kinase in an untreated cell. The effective amount of the compound of formula I, for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of cancer, such as gastrointestinal stromal tumor.

The present invention encompasses the use of the compounds of the formula I and/or pharmaceutically acceptable salts, tautomers and stereoisomers thereof for the preparation of a medicament for the treatment or prevention of cancer, preferably for the treatment of gastrointestinal stromal tumor.

Preferably, the present invention relates to a method for treating a disease, wherein the disease is a cancer, preferably a gastrointestinal stromal tumor.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used herein, the term "anticancer agent" relates to any agent which is administered to a patient with cancer for the purpose of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone;

apaziquone, fotemustine, glufosfamide, palifosfamide, pipobroman, trofosfamide, uramustine, TH-302[4], VAL-083[4];

Platinum Compounds such as carboplatin, cisplatin, eptaplatin, miriplatine hydrate, oxaliplatin, lobaplatin, nedaplatin, picoplatin, satraplatin;

lobaplatin, nedaplatin, picoplatin, satraplatin;

DNA Altering Agents such as amrubicin, bisantrene, decitabine, mitoxantrone, procarbazine, trabectedin, clofarabine;

amsacrine, brostallicin, pixantrone, laromustine[1,3];

Topoisomerase Inhibitors such as etoposide, irinotecan, razoxane, sobuzoxane, teniposide, topotecan; amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine;

fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;

doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin;

aclarubicin, peplomycin, pirarubicin;

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], fedratinib[1], XL-647[4];

Photosensitizers such as methoxsalen[3];

porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];

catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines such as aldesleukin, interferon alfa[2], interferon alfa2a[3], interferon alfa2b[2,3];

celmoleukin, tasonermin, teceleukin, oprelvekin[1,3], recombinant interferon beta-1a[4];

Drug Conjugates such as denileukin diftitox, ibritumomab tiuxetan, iobenguane I123, prednimustine, trastuzumab emtansine, estramustine, gemtuzumab, ozogamicin, aflibercept;

cintredekin besudotox, edotreotide, inotuzumab ozogamicin, naptumomab estafenatox, oportuzumab monatox, technetium (99mTc) arcitumomab[1,3], vintafolide[1,3];

Vaccines such as sipuleucel[3]; vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat;

celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

[1]Prop. INN (Proposed International Nonproprietary Name)

[2]Rec. INN (Recommended International Nonproprietary Names)

[3]USAN (United States Adopted Name)

[4]no INN.

Moreover, the invention relates to intermediates selected from:

6-chloro-N-{[4-(1-methyl-1H-pyrazol-4-yl)-phenyl]-methyl}-pyrimidin-4-amine

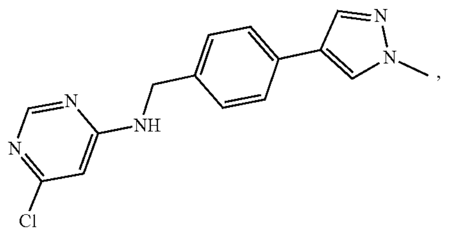 [SMILES: Cn1cc(-c2ccc(CNc3cc(Cl)ncn3)cc2)cn1]

6-[I-2-ethoxyethenyl]-N-{[4-(1-methyl-1H-pyrazol-4-yl)phenyl]methyl}pyrimidin-4-amine

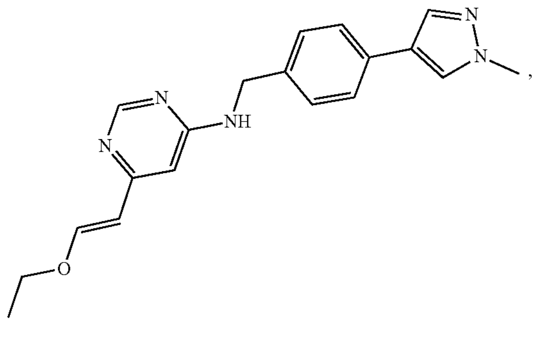 [SMILES: CCO/C=C/c1cc(NCc2ccc(-c3cnn(C)c3)cc2)ncn1]

4-chloro-6-[(E)-2-ethoxyethenyl]pyrimidine

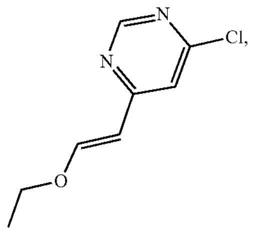

4-chloro-6-{7-fluoroimidazo[1,264yridinedin-3-yl}pyrimidine

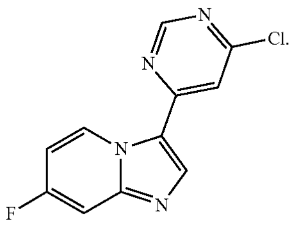 [SMILES: Fc1ccn2c(-c3cc(Cl)ncn3)cnc2c1]

The following abbreviations are used throughout herein: aq (aqueous), h (hour), g (gram), l (liter), mg (milligram), MHz (Megahertz), min. (minute), mm (millimeter), mmol (millimole), mM (millimolar), m.p. (melting point), eq (equivalent), ml (milliliter), ||l (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIPEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethyl-carbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), $NaHCO_3$ (sodium bicarbonate), $NaBH_4$ (sodium borohydride), NMM (N-methyl morpholine), NMR (Nuclear Magnetic Resonance), PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UPLC (Ultra Performance Liquid Chromatography), UV (Ultraviolet).

Above and below, all temperatures are indicated in ° C. $^1H$ NMR was recorded on Bruker DPX-300, DRX-400, AVII-400 or on a 500 MHz spectrometer, using residual signal of deuterated solvent as internal reference. Chemical shifts (δ) are reported in ppm relative to the residual solvent signal (δ=2.49 ppm for $^1H$ NMR in DMSO-$d_6$). $^1H$ NMR data are reported as follows: chemical shift (multiplicity, coupling constants, and number of hydrogens). Multiplicity is abbreviated as follows: s (singlet), d (doublet), t (triplet), q (quartet), m (multiplet), br (broad), bs (broad singlet), p (pentet).

HPLC/MS conditions A:

HPLC/MS: Agilent 1200/6100 eluent A: water+0.05% formic acid eluent B: acetonitrile+0.04% formic acid column: Chromolith HR RP-18e; 50-4.6 mm flow rate: 3.3 ml/min gradient: 0%→100% B: 0.0→2.0 min|100% B: 2.0→2.5 min UV detection: 220 nm MS detection: 65-800 amu positive HPLC/MS conditions B:

HPLC/MS: Agilent 1200/6100 eluent A: water+0.05% formic acid eluent B: acetonitrile+0.04% formic acid+1% $H_2O$ column: Kinetex XB-C18; 2.6 μm; 50-4.6 mm flow rate: 3.3 ml/min column temperature: 40° C.

gradient: 1%→99% B: 0.0→0.8 min 199% B: 0.8→1.1 min

UV detection: 220 nm

MS detection: 65-800 amu positive

UPLC/MS conditions:

UPLC/MS: Waters Acquity/SQD eluent A: water+0.05% formic acid eluent B: acetonitrile+0.04% formic acid+1% $H_2O$ column: Kinetex XB-C18; 1.7 μm; 50-2.1 mm flow rate: 0.9 ml/min gradient: 1%→99% B: 0.0→1.0 min 199% B: 1.0→1.3 min column temperature: 40° C.

UV detection: 220 nm

MS detection: 61-800 amu positive+46-1000 amu negative

Assays and Measurements c-Kit(V654A) assay:

c-Kit(V654A) (N-terminal GST-tagged, recombinant human c-Kit, amino acids 544-end containing the V654A mutation) is incubated with 8 mM MOPS pH 7.0, 0.2 mM EDTA, 250 μM GGMEDIYEFMGGKKK, 10 mM MgAcetate and [gamma-33P-ATP] (specific activity approx. 500 cpm/pmol, concentration 200 μM). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

Assay Principle for Cellular Testing of cKIT Mutant Inhibitors

The GIST430 cell line expressing constitutive active cKIT receptor tyrosine kinase (Δ560-576 deletion) and the Imatinib resistant GIST430/654 cell line expressing mutated constitutively active cKIT receptor tyrosine kinase (Δ560-576 deletion and V654A point mutation) were employed for assessing cellular potency of compounds. Cellular activity of mutant cKIT was determined by the degree of cKIT autophosphorylation at tyrosine 307 using a Luminex-based bead assay. GIST430 cells were plated with 22,000 cells per well of a 96-well plate in 100 μl medium (85% IMDM/15% FCS) and GIST430/654 cells were plated with 25,000 cells per well of a 96-well plate in 100 μl medium (85% IMDM/15% FCS supplemented with 100 nM Imatinib). At the following day compounds were added in a serial dilution for 45 min. Then, cells were lysed with 90 μl lysis buffer (20 mM Hepes pH 7.5, 200 mM NaCl, 1.5 mM MgCl2×6H2O, 0.4 mM EDTA, 1% Triton-X-100, 1% Phosphatase-Inhibitor II, 20 mM β-Glycerolphosphat, 0.1% Protease-Inhibitor Cocktail III, 0.01% Benzonase) and lysates were cleared by centrifugation through a 96-well filter plate (0.65 μm). Samples were incubated with Luminex-beads which were coupled with an anti-total cKIT antibody overnight at 4° C. under gentle agitation. For detection of phospho-Y307-cKIT a phosphospecific antibody and a species-specific PE-labeled secondary antibody were added. The amount of phospho-Y307-cKIT was determined in a Luminex 200 instrument measuring 100 events per well within 60 seconds.

Counts from samples treated with compounds were calculated as percent of control from solvent treated (0.3% DMSO) samples. Dose-response curves were fitted and $IC_{50}$ values were determined using Genedata Screener software.

Determination of Efflux-Ratio (ER) in Caco-2 Cells

The efflux ratio of the test compounds was determined in Caco-2 human epithelial colorectal adenocarcinoma cell line (TC7 clone) using calculation of apparent permeability ($P_{app}$). Cell monolayers were differentiated in vitro for 14 days before the experiment. Subsequently, the test compound (in HBSS pH 7.4 at 1 μM final concentration) was applied on the donor side while HBSS buffer (pH 7.4) was added to the receiver wells. The final DMSO concentration at incubation did not exceed 1%. The plate was then incubated in a 5% $CO_2$ incubator (37° C., 100% humidity). At the end of the 2 hours incubation period, 50 μL sample was removed from both donor and receiver wells and diluted 1:1 with equal volumes of acetonitrile for LC-MS/MS analysis. The LC-MS/MS analysis used a one-point calibration method from a 1 μM standard solution diluted 1:1 with equal volume of acetonitrile (consistent to the test samples).

The data was used to calculate the apparent permeabilities of the compounds in both apical to basolateral ($P_{app,AB}$) and basolateral to apical ($P_{app,BA}$) directions at 1 μM concentration in duplicate. The $P_{app}$ values were calculated from the concentrations in the donor and receiver compartments using the following formula:

$$P_{app} = \frac{\Delta C_{rec}}{\Delta t} \cdot \frac{V_{rec}}{A \cdot C_0} \cdot 10^6$$

Efflux ratio was calculated according to the following formula:

$$ER = \frac{P_{app,BA}}{P_{app,AB}}$$

$P_{app}$=apparent permeability through cell monolayer ($10^{-6}$ cm/s)

$\Delta c_{rec}/\Delta t$=Concentration change in receiver well over time (nM/s)

$V_{don}$, $V_{rec}$=Volume of donor/receiver wells=0.25 mL (apical) or 0.75 mL (basolateral)

$c_{don}$, $c_{acc}$=Concentration in donor/receiver well at the end of the experiment (nM)

$c_{t0,don}$=Concentration in donor well at the beginning of the experiment (nM)

A=Surface area of well membrane=0.33 $cm^2$

Determination of Solubility

In a 96 well filtration plate, 2 μL of a 10 mM solution of the test compound in DMSO is added to 98 μL of 20 mM Sorensen phosphate buffer with pH 7.4. The mixture is incubated at room temperature for 120 min while agitating at 250 rpm followed by centrifugation at 2500 rpm for 3 min. After dilution by a factor of 2, the concentration of the test compound is determined using HPLC/UPLC with detection at a suitable wavelength and by comparison to a corresponding compound standard.

EXAMPLES

As depicted and described in the examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The following data, determined by the assays described above and set out in Tables 2 and 3 below, illustrate the potency of embodiments of the present invention in terms of cKit (V654A) respectively GIST 430/654 inhibition. As apparent from the Tables, the compounds have excellent IC50 values, many in the low nanomolar range. In addition, the compounds are selective, in particular as compared to closely related kinase FLT3 ("fms like tyrosine kinase 3"). Embodiments that were tested against a broader panel of kinases, including JAK, have been found to show very good selectivity over those kinases, too.

In addition to the excellent inhibitory potencies, certain preferred embodiments of the present invention have been found to have a balance of promising pharmacokinetic properties, including bioavailability, as experimentally determined by solubility and efflux, and acceptable to excellent values concerning the undesired blockage of the hERG potassium channel. Results of experimental efflux measurements are given in Table 4 below.

Exemplary embodiments A8, A12, A15, A60, A73, A75, A83, A84, A99, A100, A102, A120, A149, A153, A154, A156, A168, A170, A212, A242 and A252 were determined as having a favourable solubility of at least 25 μM.

Pharmacological Data

TABLE 2

Inhibition ($IC_{50}$) of c-KIT (V654A) and GIST 430/654 of compounds of the formula I

| Compound No. | c-KIT (V654A) IC50 [M] | GIST 430/654 IC50 [M] |
|---|---|---|
| "H1" | 1.2E−08 | 2.4E−07 |
| "A1" | 8.6E−09 | 5.5E−08 |
| "A2" | 4.6E−09 | 1.6E−07 |
| "A3" | 5.5E−09 | 2.6E−06 |
| "A4" | 7.3E−09 | 4.8E−08 |
| "A5" | 8.2E−09 | 1.7E−07 |
| "A6" | 6.4E−09 | 3.5E−07 |
| "A7" | 4.7E−09 | 3.0E−07 |
| "A8" | 2.3E−08 | 5.0E−07 |
| "A9" | 2.2E−09 | 1.9E−07 |
| "A10" | 1.3E−08 | 1.0E−06 |
| "A11" | 1.5E−08 | 1.7E−07 |
| "A12" | 8.7E−08 | 1.1E−06 |
| "A13" | 1.0E−07 | 2.3E−06 |
| "A14" | 5.5E−09 | 2.0E−07 |
| "A15" | 3.2E−07 | |
| "A16" | 6.3E−09 | 1.3E−07 |
| "A17" | 9.7E−09 | 1.1E−07 |
| "A18" | 1.3E−08 | 2.0E−07 |
| "A19" | 9.4E−09 | 7.1E−08 |
| "A20" | 5.5E−08 | 6.5E−07 |
| "A21" | 4.8E−09 | 5.8E−08 |
| "A22" | 1.1E−07 | |
| "A23" | 6.2E−09 | 6.6E−08 |
| "A24" | 1.6E−07 | |
| "A25" | 2.6E−08 | 2.1E−07 |
| "A26" | 8.6E−09 | 1.3E−07 |
| "A27" | 6.3E−08 | |
| "A28" | 3.5E−08 | 1.4E−06 |
| "A29" | 1.5E−08 | 1.2E−07 |
| "A30" | 2.7E−08 | 1.8E−07 |
| "A31" | 4.9E−08 | 8.1E−07 |
| "A32" | 4.4E−09 | 7.8E−08 |
| "A33" | 1.6E−08 | 1.2E−07 |
| "A34" | 5.2E−08 | 7.4E−07 |
| "A35" | 7.1E−08 | 8.9E−07 |
| "A36" | 4.2E−09 | 1.4E−07 |
| "A37" | 1.5E−08 | 2.2E−07 |
| "A38" | 5.5E−08 | 7.1E−07 |
| "A39" | 2.7E−08 | 6.4E−07 |
| "A40" | 3.6E−08 | 1.1E−06 |
| "A41" | 4.6E−08 | 1.6E−06 |
| "A42" | 1.3E−09 | 5.9E−08 |
| "A43" | 2.6E−07 | |
| "A44" | 2.7E−08 | 5.1E−07 |
| "A45" | 1.3E−07 | |
| "A46" | 6.4E−09 | 9.5E−08 |
| "A47" | 1.0E−08 | 1.9E−07 |
| "A48" | 2.5E−08 | 4.7E−07 |
| "A49" | 7.3E−09 | 8.9E−08 |
| "A50" | 2.5E−08 | 4.9E−07 |
| "A51" | 1.6E−09 | 5.3E−08 |
| "A52" | 5.7E−09 | 1.5E−07 |
| "A53" | 6.3E−09 | 3.4E−07 |
| "A54" | 1.2E−07 | |
| "A55" | 2.2E−08 | 6.5E−07 |
| "A56" | 7.3E−09 | 5.0E−08 |
| "A57" | 1.1E−08 | 2.7E−07 |

TABLE 2-continued

Inhibition ($IC_{50}$) of c-KIT (V654A) and GIST 430/654 of compounds of the formula I

| Compound No. | c-KIT (V654A) IC50 [M] | GIST 430/654 IC50 [M] |
|---|---|---|
| "A58" | 1.9E−08 | 1.5E−07 |
| "A59" | 1.1E−08 | 8.2E−08 |
| "A60" | 8.0E−09 | 7.0E−08 |
| "A61" | 6.5E−09 | 3.4E−08 |
| "A62" | 4.1E−09 | 3.2E−08 |
| "A63" | 1.2E−08 | 8.4E−08 |
| "A64" | 6.7E−09 | 8.4E−08 |
| "A65" | 1.1E−08 | 4.6E−08 |
| "A66" | 7.8E−09 | 1.9E−07 |
| "A67" | 4.8E−09 | 6.5E−08 |
| "A68" | 5.7E−09 | 6.3E−08 |
| "A69" | 1.3E−08 | 2.4E−07 |
| "A70" | 2.1E−08 | 2.3E−07 |
| "A71" | 4.6E−09 | 4.5E−08 |
| "A72" | 7.2E−08 | 5.4E−07 |
| "A73" | 4.0E−09 | 9.8E−08 |
| "A74" | 4.8E−09 | 4.9E−08 |
| "A75" | 8.5E−09 | 5.9E−08 |
| "A76" | 7.8E−09 | 5.2E−08 |
| "A77" | 1.4E−08 | 4.0E−08 |
| "A78" | 9.1E−09 | 7.9E−08 |
| "A79" | 1.5E−09 | 2.8E−08 |
| "A80" | 3.4E−09 | 3.8E−08 |
| "A81" | 2.7E−08 | 9.7E−07 |
| "A82" | 9.2E−09 | 2.7E−07 |
| "A83" | 2.5E−08 | 3.1E−07 |
| "A84" | 2.8E−09 | 4.5E−08 |
| "A85" | 6.5E−09 | 6.5E−08 |
| "A86" | 5.0E−09 | 1.1E−07 |
| "A87" | 1.1E−08 | 5.0E−07 |
| "A88" | 1.2E−08 | 8.9E−08 |
| "A89" | 8.6E−09 | 8.2E−08 |
| "A90" | 1.0E−08 | 2.6E−07 |
| "A91" | 8.6E−09 | 7.6E−08 |
| "A92" | 8.2E−09 | 8.7E−08 |
| "A93" | 1.3E−08 | 1.1E−07 |
| "A94" | 6.8E−09 | 6.4E−08 |
| "A95" | 9.8E−09 | 2.1E−07 |
| "A96" | 2.9E−09 | 3.1E−08 |
| "A97" | 6.6E−09 | 2.3E−07 |
| "A98" | 8.3E−09 | 9.8E−08 |
| "A99" | 8.2E−09 | 6.2E−08 |
| "A100" | 9.2E−09 | 3.8E−08 |
| "A101" | 2.2E−08 | 1.5E−07 |
| A102 | 9.8E−09 | 4.6E−08 |
| "A103" | 9.5E−09 | 1.2E−07 |
| "A104" | 7.0E−09 | 1.7E−07 |
| "A105" | 9.5E−09 | 1.2E−07 |
| "A106" | 9.5E−09 | 3.7E−07 |
| "A107" | 1.3E−08 | 1.2E−07 |
| "A108" | 3.3E−09 | 4.0E−08 |
| "A109" | 7.5E−09 | 7.9E−08 |
| "A110" | 1.1E−07 | |
| "A111" | 7.9E−09 | 6.3E−08 |
| "A112" | 4.0E−08 | 2.6E−07 |
| "A113" | 1.4E−08 | 6.2E−07 |
| "A114" | 9.4E−09 | 8.6E−08 |
| "A115" | 3.7E−09 | 4.9E−08 |
| "A116" | 1.6E−09 | 4.8E−08 |
| "A117" | 6.0E−09 | 3.0E−08 |
| "A118" | 4.7E−09 | 4.0E−08 |
| "A119" | 3.4E−09 | 6.2E−08 |
| "A120" | 2.9E−09 | 5.2E−08 |
| "A121" | 3.6E−09 | 3.4E−08 |
| "A122" | 2.6E−08 | 2.6E−07 |
| "A123" | 5.8E−09 | 5.6E−08 |
| "A124" | 7.4E−09 | 5.3E−08 |
| "A125" | 2.3E−08 | 2.1E−07 |
| "A126" | 1.6E−08 | 1.4E−07 |
| "A127" | 6.7E−09 | 1.0E−07 |
| "A128" | 9.9E−09 | 1.3E−07 |
| "A129" | 6.1E−09 | 6.2E−08 |
| "A130" | 3.5E−09 | 4.0E−08 |

TABLE 2-continued

Inhibition ($IC_{50}$) of c-KIT (V654A) and GIST 430/654 of compounds of the formula I

| Compound No. | c-KIT (V654A) IC50 [M] | GIST 430/654 IC50 [M] |
|---|---|---|
| "A131" | 7.5E-09 | 6.9E-08 |
| "A132" | 5.0E-09 | 4.3E-08 |
| "A133" | 2.6E-09 | 3.0E-08 |
| "A134" | 4.6E-09 | 5.2E-08 |
| "A135" | 2.0E-09 | 2.1E-07 |
| "A136" | 1.0E-08 | 1.5E-07 |
| "A137" | 5.6E-09 | 4.5E-08 |
| "A138" | 6.9E-09 | 6.4E-08 |
| "A139" | 9.6E-09 | 1.6E-07 |
| "A140" | 1.1E-08 | 2.6E-08 |
| "A141" | 1.5E-08 | 8.5E-08 |
| "A142" | 7.3E-09 | 6.5E-08 |
| "A143" | 2.1E-08 | 3.8E-07 |
| "A144" | 5.1E-09 | 6.1E-08 |
| "A145" | 4.1E-08 | 2.5E-07 |
| "A146" | 7.0E-09 | 3.4E-07 |
| "A147" | 5.4E-09 | 4.3E-07 |
| "A148" | 4.9E-09 | 2.2E-07 |
| "A149" | 6.2E-09 | 2.7E-07 |
| "A150" | 8.9E-09 | 1.4E-07 |
| "A151" | 1.5E-08 | 3.0E-07 |
| "A152" | 3.8E-09 | 3.7E-07 |
| "A153" | 6.4E-09 | 1.2E-07 |
| "A154" | 1.8E-07 | |
| "A155" | 9.2E-08 | 3.0E-05 |
| "A156" | 1.8E-07 | |
| "A157" | 3.3E-08 | 1.5E-06 |
| "A158" | 1.3E-08 | 1.4E-07 |
| "A159" | 8.8E-08 | |
| "A160" | 3.8E-08 | 1.0E-06 |
| "A161" | 2.2E-08 | 1.8E-07 |
| "A162" | 7.4E-09 | 1.8E-07 |
| "A163" | 8.5E-08 | 1.9E-06 |
| "A164" | 9.0E-09 | 2.6E-07 |
| "A165" | 2.0E-09 | 5.7E-08 |
| "A166" | 4.0E-09 | 1.2E-07 |
| "A167" | 7.5E-09 | 5.0E-07 |
| "A168" | 2.7E-08 | 6.3E-07 |
| "A169" | 3.2E-08 | 3.0E-07 |
| "A170" | 3.3E-08 | 3.3E-07 |
| "A171" | 5.8E-08 | |
| "A172" | 6.3E-09 | 7.5E-08 |
| "A173" | 3.7E-09 | 5.7E-08 |
| "A174" | 2.6E-07 | |
| "A175" | 9.8E-09 | 4.8E-07 |
| "A176" | 3.2E-09 | 8.4E-08 |
| "A177" | 1.7E-08 | 3.4E-08 |
| "A178" | 1.9E-08 | 4.7E-08 |
| "A179" | 3.1E-09 | 2.4E-08 |
| "A180" | 7.8E-09 | 7.7E-08 |
| "A181" | 1.5E-08 | 1.1E-07 |
| "A182" | 1.1E-08 | 9.2E-08 |
| "A183" | 7.7E-09 | 2.7E-08 |
| "A184" | 2.0E-08 | 7.6E-08 |
| "A185" | 6.7E-09 | 5.9E-08 |
| "A186" | 7.0E-09 | 8.0E-08 |
| "A187" | 7.5E-09 | 3.8E-07 |
| "A188" | 9.5E-09 | 1.9E-07 |
| "A189" | 9.8E-09 | 1.6E-07 |
| "A190" | 3.8E-09 | 1.7E-07 |
| "A191" | 2.2E-09 | 3.9E-08 |
| "A192" | 2.8E-08 | 6.7E-08 |
| "A193" | 1.9E-08 | 2.6E-08 |
| "A194" | 6.1E-09 | 9.2E-08 |
| "A195" | 9.7E-09 | 7.2E-08 |
| "A196" | 1.4E-08 | 1.4E-07 |
| "A197" | 1.2E-08 | 1.5E-07 |
| "A198" | 1.0E-08 | 1.2E-07 |
| "A199" | 9.7E-09 | 1.0E-07 |
| "A200" | 2.7E-08 | 1.9E-07 |
| "A201" | 1.3E-08 | 9.9E-08 |
| "A202" | 1.7E-08 | 2.0E-07 |
| "A203" | 9.8E-09 | 4.2E-07 |

TABLE 2-continued

Inhibition ($IC_{50}$) of c-KIT (V654A) and GIST 430/654 of compounds of the formula I

| Compound No. | c-KIT (V654A) IC50 [M] | GIST 430/654 IC50 [M] |
|---|---|---|
| "A204" | 1.2E-08 | 1.7E-07 |
| "A205" | 1.0E-08 | 1.1E-07 |
| "A206" | 7.1E-09 | 1.0E-07 |
| "A207" | 8.7E-09 | |
| "A208" | 3.8E-08 | 2.3E-07 |
| "A209" | 9.5E-09 | 7.8E-08 |
| "A210" | 6.5E-09 | 1.0E-07 |
| "A211" | 1.0E-08 | 8.5E-08 |
| "A212" | 7.3E-09 | 2.1E-07 |
| "A213" | 1.6E-08 | 1.8E-07 |
| "A214" | 2.1E-08 | 1.8E-07 |
| "A215" | 1.0E-08 | 1.2E-07 |
| "A216" | 8.2E-09 | 1.3E-07 |
| "A217" | 7.8E-09 | 7.6E-08 |
| "A218" | 1.1E-08 | 2.0E-07 |
| "A219" | 1.1E-08 | 1.0E-07 |
| "A220" | 1.1E-08 | 1.4E-07 |
| "A221" | 1.4E-08 | 4.0E-07 |
| "A222" | 1.7E-08 | 9.3E-08 |
| "A223" | 1.1E-08 | 1.9E-07 |
| "A224" | 6.5E-09 | 9.9E-08 |
| "A225" | 1.5E-08 | 5.7E-08 |
| "A226" | 4.2E-09 | 5.1E-08 |
| "A227" | 3.3E-09 | 4.8E-08 |
| "A228" | 1.1E-08 | 4.4E-08 |
| "A229" | 8.7E-08 | 6.6E-07 |
| "A230" | 2.4E-08 | 6.3E-08 |
| "A231" | 1.5E-08 | 2.5E-07 |
| "A232" | 2.3E-08 | 1.7E-07 |
| "A233" | 8.7E-09 | 1.3E-07 |
| "A234" | 8.5E-09 | 7.0E-08 |
| "A235" | 4.3E-09 | 8.7E-08 |
| "A236" | 1.5E-09 | 7.4E-08 |
| "A237" | 4.3E-09 | 3.5E-08 |
| "A238" | 6.4E-09 | 6.2E-08 |
| "A239" | 3.2E-09 | 9.4E-08 |
| "A240" | 7.3E-09 | |
| "A241" | 6.5E-09 | |
| "A242" | 1.1E-09 | 1.0E-05 |
| "A243" | 6.7E-09 | 4.0E-08 |
| "A244" | 2.1E-08 | |
| "A245" | 1.3E-08 | 8.4E-08 |
| "A246" | 8.0E-09 | 3.8E-08 |
| "A247" | 7.8E-09 | 6.2E-08 |
| "A248" | 2.1E-08 | 1.6E-07 |
| "A249" | 8.7E-08 | 4.4E-07 |
| "A250" | 1.1E-07 | 4.1E-07 |
| "A251" | 2.0E-09 | 4.4E-08 |
| "A252" | 2.2E-09 | 4.7E-08 |
| "A253" | 6.5E-09 | |
| "A254" | 2.4E-08 | |
| "A255" | 1.5E-08 | 1.0E-07 |
| "A256" | 1.2E-08 | |
| "A257" | 1.6E-08 | 1.3E-07 |
| "A258" | 5.1E-09 | 5.6E-08 |
| "A259" | 3.8E-09 | 3.3E-08 |
| "A260" | 6.0E-09 | 4.3E-08 |
| "A261" | 2.1E-09 | 5.4E-08 |
| "A262" | 5.0E-09 | 7.3E-08 |
| "A263" | 2.3E-09 | 6.6E-08 |
| "A264" | 1.6E-09 | 3.6E-08 |
| "A265" | 6.8E-09 | 7.8E-08 |
| "A266" | 7.9E-09 | 1.3E-07 |
| "A267" | 4.4E-09 | 6.3E-08 |
| "A268" | 1.1E-08 | 1.4E-07 |

TABLE 3

Inhibition ($IC_{50}$) of GIST 430 of compounds of the formula I

| Compound No. | GIST 430 $IC_{50}$ [M] |
|---|---|
| "A1" | 3.2E−09 |
| "A2" | 7.7E−09 |
| "A4" | 4.8E−09 |
| "A5" | 5.3E−09 |
| "A6" | 2.0E−08 |
| "A7" | 6.1E−09 |
| "A9" | 2.4E−09 |
| "A11" | 7.0E−09 |
| "A16" | 4.2E−09 |
| "A18" | 7.2E−09 |
| "A42" | 1.8E−09 |
| "A56" | 3.9E−09 |
| "A60" | 4.9E−09 |
| "A62" | 3.7E−09 |
| "A75" | 2.9E−09 |
| "A76" | 2.1E−09 |
| "A78" | 3.6E−09 |
| "A79" | 4.1E−09 |
| "A84" | 2.4E−09 |
| "A85" | 3.3E−09 |
| "A97" | 8.8E−09 |
| A102 | 3.0E−09 |
| "A108" | 1.5E−09 |
| "A120" | 2.3E−09 |
| "A146" | 4.8E−08 |
| "A147" | 7.3E−09 |
| "A148" | 7.3E−09 |
| "A150" | 1.2E−08 |
| "A151" | 9.9E−09 |
| "A153" | 6.4E−09 |
| "A155" | 5.1E−08 |
| "A172" | 2.7E−09 |
| "A173" | 2.2E−08 |
| "A177" | 1.5E−08 |
| "A178" | 3.8E−09 |
| "A185" | 1.3E−09 |
| "A217" | 4.4E−09 |
| "A258" | 2.7E−09 |
| "A259" | 1.8E−09 |
| "A260" | 1.9E−09 |
| "A261" | 1.4E−09 |
| "A262" | 4.4E−09 |
| "A263" | 4.3E−09 |
| "A264" | 1.1E−09 |
| "A265" | 3.3E−09 |
| "A266" | 5.1E−09 |
| "A267" | 1.7E−09 |
| "A268" | 1.0E−08 |

Explanation: 1,4E-06 means $1.4\times10^{-6}$. "E" thus stands for "times ten raised to the power of".

TABLE 4

| No. | Efflux Ratio |
|---|---|
| "A1" | A |
| "A2" | A |
| "A4" | A |
| "A8" | A |
| "A16" | A |
| "A17" | A |
| "A18" | A |
| "A19" | A |
| "A21" | A |
| "A26" | A |
| "A32" | A |
| "A36" | A |
| "A42" | A |
| "A46" | A |
| "A51" | A |
| "A56" | A |
| "A60" | A |
| "A61" | A |
| "A62" | A |
| "A63" | A |
| "A64" | A |
| "A65" | A |
| "A67" | C |
| "A71" | A |
| "A73" | A |
| "A74" | A |
| "A75" | A |
| "A76" | A |
| "A77" | A |
| "A78" | A |
| "A79" | A |
| "A80" | C |
| "A84" | A |
| "A85" | A |
| "A91" | A |
| "A99" | B |
| "A100" | A |
| A102 | B |
| "A104" | B |
| "A108" | A |
| "A114" | B |
| "A120" | A |
| "A131" | A |
| "A133" | A |
| "A140" | A |
| "A141" | C |
| "A144" | C |
| "A146" | A |
| "A147" | A |
| "A148" | A |
| "A150" | A |
| "A151" | A |
| "A153" | A |
| "A158" | A |
| "A165" | C |
| "A166" | C |
| "A167" | C |
| "A168" | A |
| "A172" | A |
| "A173" | A |
| "A175" | C |
| "A176" | C |
| "A177" | A |
| "A178" | A |
| "A179" | C |
| "A183" | A |
| "A184" | A |
| "A185" | A |
| "A186" | A |
| "A189" | A |
| "A192" | A |
| "A194" | C |
| "A195" | A |
| "A196" | A |
| "A197" | A |
| "A198" | B |
| "A199" | C |
| "A200" | A |
| "A201" | A |
| "A202" | A |
| "A203" | C |
| "A204" | B |
| "A205" | A |
| "A206" | A |
| "A208" | A |
| "A211" | A |
| "A212" | C |
| "A213" | A |
| "A214" | A |
| "A215" | C |
| "A216" | A |
| "A217" | B |
| "A218" | A |
| "A219" | B |
| "A220" | A |
| "A221" | C |

TABLE 4-continued

| No. | Efflux Ratio |
|---|---|
| "A222" | A |
| "A223" | C |
| "A224" | B |
| "A225" | B |
| "A226" | A |
| "A230" | A |
| "A231" | B |
| "A233" | C |
| "A234" | A |
| "A236" | A |
| "A242" | A |
| "A243" | A |
| "A245" | C |
| "A246" | A |
| "A247" | A |
| "A248" | C |
| "A249" | C |
| "A250" | C |
| "A251" | A |
| "A252" | A |
| "A255" | A |
| "A257" | A |
| "A258" | A |
| "A259" | A |
| "A260" | B |
| "A261" | A |
| "A262" | A |
| "A263" | A |
| "A264" | B |
| "A265" | A |
| "A266" | A |
| "A267" | A |
| "A268" | A |

A: ≤15;
B: >15-50;
C > 50

SYNTHESIS OF INTERMEDIATES

Arylmethylamines

Synthesis of 1-[4-(1-methyl-1H-pyrazol-4-yl)phenyl]-methanamine (D1)

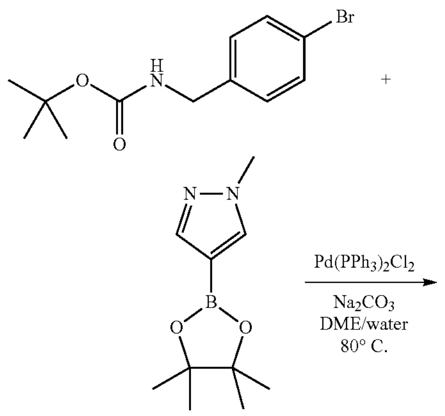

-continued

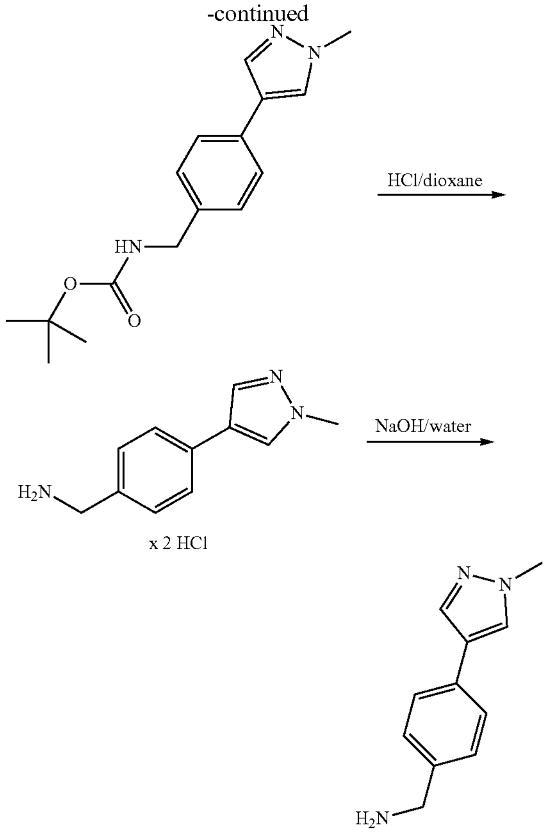

To a solution of N-Boc-4-bromobenzylamine (29.4 g, 103 mmol) in 1,2-dimethoxyethane (275 ml) are added 1-methyl-1H-pyrazole-4-boronic acid pinacol ester (25.5 g, 122.6 mmol), water (105 ml) and sodium carbonate (16.3 g, 154 mmol) and the resultant suspension is flushed with argon. Under argon, bis(triphenylphosphine)palladium(II) chloride (2.9 g, 4.13 mmol) is added. The mixture is heated to 80° C. and stirred at this temperature for 2 days. The reaction mixture is allowed to reach room temperature and treated with water and ethyl acetate. The organic phase is separated and the aqueous phase is extracted two times with ethyl acetate. The combined organic phases are dried over sodium sulfate and evaporated. The residue is chromatographed on a silica gel column with cyclohexane/ethyl acetate as eluent to afford tert-butyl N-{[4-(1-methyl-1H-pyrazol-4-yl)phenyl]methyl}carbamate as pale yellow crystalline solid; UPLC/MS 0.709 min, $[M+H]^+$ 288.

$^1H$ NMR (400 MHz, DMSO-$d_6$) δ 8.07 (s, 1H), 7.81 (s, 1H), 7.49 (d, J=8.0 Hz, 2H), 7.33 (t, J=6.3 Hz, 1H), 7.20 (d, J=8.1 Hz, 2H), 4.09 (d, J=6.2 Hz, 2H), 3.85 (s, 3H), 1.39 (s, 9H).

To a solution of tert-butyl N-{[4-(1-methyl-1H-pyrazol-4-yl)phenyl]methyl}carbamate (24.7 g, 85.6 mmol) in 1,4-dioxane (170 ml) is added a 4 N solution of hydrogen chloride in dioxane and the mixture is stirred for 18 hours at room temperature. The resultant precipitate is filtered off, washed with tert-butyl-methylether and dried under vacuum to afford 1-[4-(1-methyl-1H-pyrazol-4-yl)phenyl]-methanamine dihydrochloride as pale yellow powder; UPLC/MS 0.286 min, $[M-NH_2]^+$ 171.

To a solution of 1-[4-(1-methyl-1H-pyrazol-4-yl)phenyl]-methanamine dihydrochloride (22.4 g, 86.0 mmol) in water (500 ml) is added 2 N aqueous sodium hydroxide (129 ml) dropwise under stirring. The resultant precipitate is filtered off, washed with water and dried for 3 days at 50° C. under vacuum to afford 1-[4-(1-methyl-1H-pyrazol-4-yl)phenyl]methanamine as pale brown powder; UPLC/MS 0.286 min, $[M-NH_2]^+$ 171.

$^1H$ NMR (400 MHz, DMSO-$d_6$) δ 8.08 (d, J=0.8 Hz, 1H), 7.82 (d, J=0.8 Hz, 1H), 7.48 (d, J=8.2 Hz, 2H), 7.29 (d, J=8.2 Hz, 2H), 3.85 (s, 3H), 3.68 (s, 2H), 1.76 (s, 2H).

Synthesis of 1-[4-(2-methyl-2H-1,2,3-triazol-4-yl)phenyl]methanamine (D2)

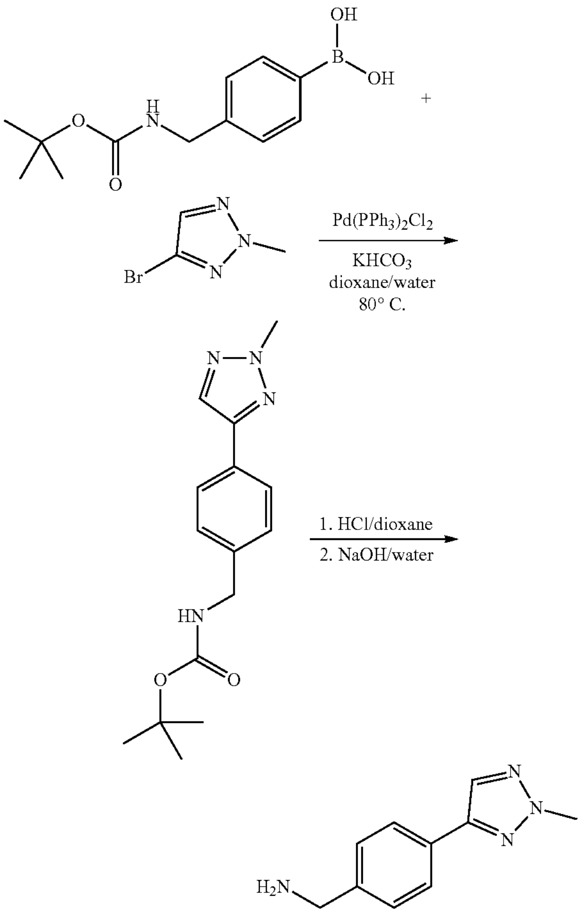

To a solution of 4-bromo-2-methyl-2H-1,2,3-triazole (3.23 g, 19.9 mmol) in 1,4-dioxane (40 ml) are added 4-N-(Boc)aminomethylphenylboronic acid (5.24 g, 20.9 mmol), water (4.0 ml) and potassium hydrogen carbonate (4.0 g, 40.0 mmol) and the resultant suspension is flushed with argon. Under argon, bis(triphenylphosphine)palladium (II) chloride (710 mg, 1.01 mmol) is added. The mixture is heated to 80° C. and stirred at this temperature for 18 hours. The reaction mixture is allowed to reach room temperature and treated with water and dichloromethane. The organic phase is separated and the aqueous phase is extracted two times with dichloromethane. The combined organic phases are dried over sodium sulfate and evaporated. The residue is chromatographed on a silica gel column with cyclohexane/ethyl acetate as eluent to afford tert-butyl N-{[4-(2-methyl-2H-1,2,3-triazol-4-yl)phenyl]methyl}carbamate as white crystalline solid; UPLC/MS 0.739 min, $[M-BocNH_2]^+$ 172.

$^1H$ NMR (400 MHz, DMSO-$d_6$) δ 8.17 (s, 1H), 7.77 (d, J=8.1 Hz, 2H), 7.38 (t, J=6.2 Hz, 1H), 7.31 (d, J=8.0 Hz, 2H), 4.18 (s, 3H), 4.15 (d, J=6.2 Hz, 2H), 1.40 (s, 9H).

tert-Butyl N-{[4-(2-methyl-2H-1,2,3-triazol-4-yl)phenyl]methyl}carbamate (3.2 g, 11.1 mmol) is dissolved in a 4 N solution of hydrogen chloride in dioxane (75 ml) and the mixture is stirred for 18 hours at room temperature. The resultant precipitate is filtered off and washed with dichloromethane. The residue is treated with 1 N aqueous sodium hydroxide until a basic pH value of 14 is reached. The solids are filtered off and washed with water. The residue is taken up in acetonitrile and filtered. The filtrate is evaporated and dried under vacuum to afford 1-[4-(2-methyl-2H-1,2,3-triazol-4-yl)phenyl]methanamine as white crystalline solid; UPLC/MS 0.302 min, $[M-NH_2]^+$ 172.

$^1H$ NMR (500 MHz, DMSO-$d_6$) δ 8.16 (s, 1H), 7.75 (d, J=8.2 Hz, 2H), 7.51-7.02 (m, 2H), 4.18 (s, 3H), 3.72 (s, 2H), $NH_2$ peak not visible.

4-(5,6-Dihydro-4H-pyrrolo[1,2-b]pyrazol-3-yl)-benzylamine (D3)

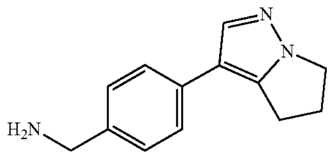 [SMILES: NCc1ccc(-c2cnn3c2CCC3)cc1]

This compound is prepared similarly to D1; off-white solid; HPLC/MS (A) 0.93 min, $[M+H]^+$ 214.

1-{4-[1-(2-methoxyethyl)-1H-pyrazol-4-yl]phenyl}methanamine (D4)

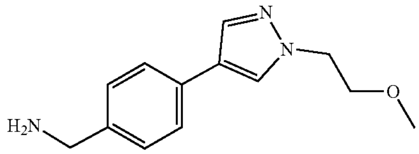 [SMILES: COCCn1cc(-c2ccc(CN)cc2)cn1]

This compound is prepared similarly to D2; yellow solid; HPLC/MS $[M+H]^+$ 215.

1-[4-(1-methyl-1H-imidazol-4-yl)phenyl]methanamine (D5)

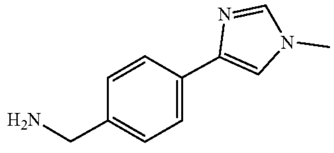

This compound is prepared similarly to D2; yellow solid; HPLC/MS $[M+H]^+$ 188.

1-{4-[1-(cyclopropylmethyl)-1H-pyrazol-4-yl]phenyl}methanamine (D6)

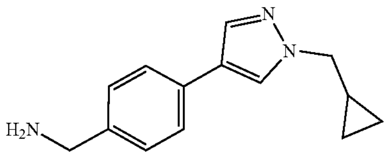 [SMILES: NCc1ccc(-c2cnn(CC3CC3)c2)cc1]

This compound is prepared similarly to D2; yellow solid; HPLC/MS $[M+H]^+$ 228.

1-(4-{1-[2-(morpholin-4-yl)ethyl]-1H-pyrazol-4-yl}phenyl)methanamine (D7)

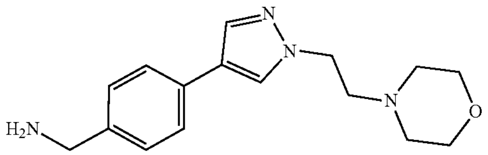 [SMILES: NCc1ccc(-c2cnn(CCN3CCOCC3)c2)cc1]

This compound is prepared similarly to D2; yellow solid; HPLC/MS $[M+H]^+$ 287.

1-(4-{1-[2-(pyrrolidin-1-yl)ethyl]-1H-pyrazol-4-yl}phenyl)methanamine (D8)

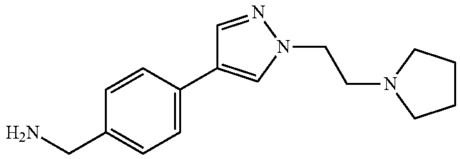 [SMILES: NCc1ccc(-c2cnn(CCN3CCCC3)c2)cc1]

This compound is prepared similarly to D2; yellow solid; HPLC/MS $[M+H]^+$ 271.

1-[3-(1-methyl-1H-pyrazol-4-yl)phenyl]methanamine (D9)

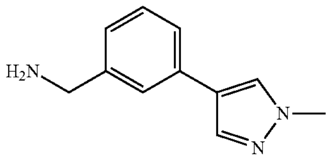

This compound is prepared similarly to D2; yellow solid; HPLC/MS $[M+H]^+$ 188.

1-[3-fluoro-4-(1-methyl-1H-pyrazol-4-yl)phenyl]methanamine (D10)

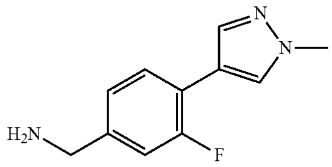

This compound is prepared similarly to D1; off-white solid; UPLC/MS 0.315 min, $[M-NH_2]^+$ 189.

2-{4-[4-(aminomethyl)phenyl]-1H-pyrazol-1-yl}ethan-1-ol (D11)

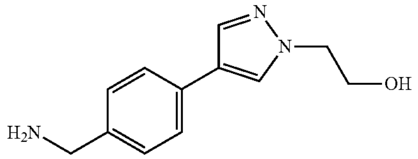 [SMILES: NCc1ccc(-c2cnn(CCO)c2)cc1]

This compound is prepared similarly to D2; yellow solid; HPLC/MS $[M-NH_2]^+$ 201.

1-[4-(1-methyl-1H-1,2,3-triazol-4-yl)phenyl]methanamine (D12)

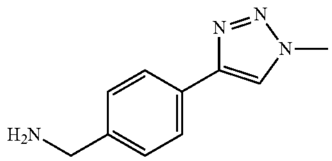

This compound is prepared similarly to D2; yellow solid; HPLC/MS $[M+H]^+$ 189.

Synthesis of 1-{4-[1-(oxetan-3-yl)-1H-pyrazol-4-yl]phenyl}methanamine (D13)

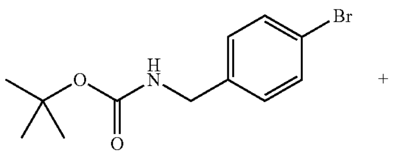

-continued

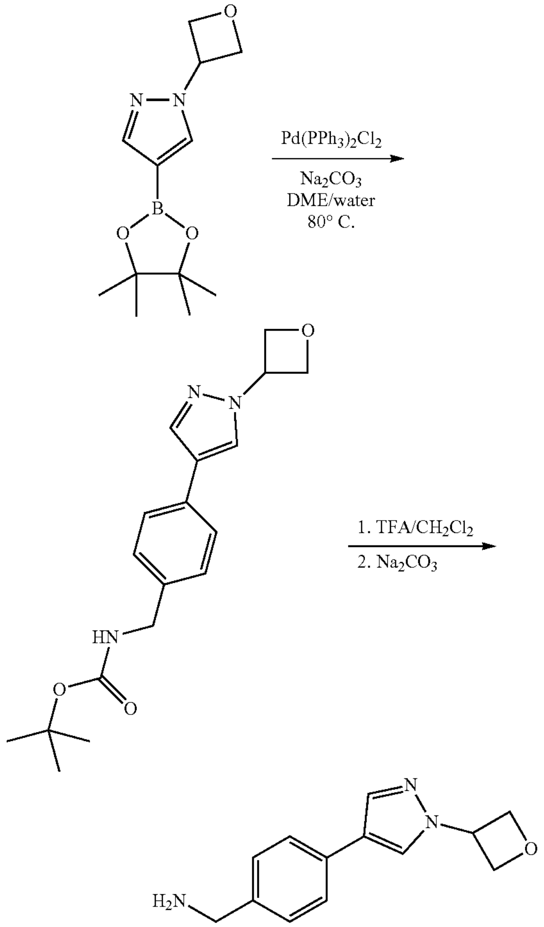

To a solution of tert-butyl N-({4-[1-(oxetan-3-yl)-1H-pyrazol-4-yl]phenyl}methyl)carbamate (168 mg, 0.51 mmol), which is prepared similarly to the first reaction step for intermediate D1, in dichloromethane (5 ml) is added trifluoroacetic acid (393 μl, 5.1 mmol) and the mixture is stirred for 3 hours at room temperature. The reaction mixture is treated with saturated aqueous sodium carbonate solution. The organic phase is separated and evaporated to afford 1-{4-[1-(oxetan-3-yl)-1H-pyrazol-4-yl]phenyl}methanamine as pale yellow solid; UPLC/MS 0.307 min, $[M-NH_2]^+$ 213.

1-[4-(4-methoxypyrimidin-2-yl)phenyl]methanamine (D14)

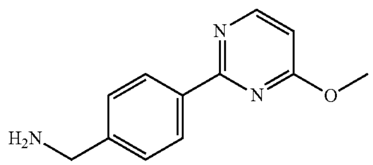 [SMILES: COc1ccnc(-c2ccc(CN)cc2)n1]

This compound is prepared similarly to D2; off-white crystalline solid; HPLC/MS (A) 0.89 min, $[M+H]^+$ 216.

$^1$H NMR (500 MHz, DMSO-$d_6$) δ 8.63 (d, J=5.2 Hz, 1H), 8.14 (d, J=8.3 Hz, 2H), 7.68 (d, J=5.2 Hz, 1H), 7.50 (d, J=8.1 Hz, 2H), 3.99 (s, 3H), 3.79 (s, 2H), 1.90 (bs, 2H).

4-[4-(aminomethyl)phenyl]-1-methyl-1H-pyrazol-3-amine (D15)

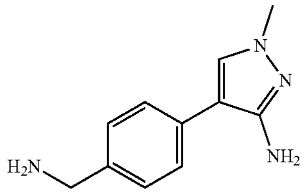

This compound is prepared similarly to D2; yellow solid; HPLC/MS $[M+H]^+$ 203.

6-{7-methoxyimidazo[1,2-a]pyridin-3-yl}-N-{[5-(1-methyl-1H-pyrazol-4-yl)thiophen-2-yl]methyl}pyrimidin-4-amine (D16)

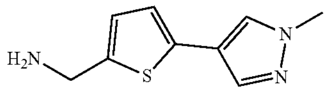

This compound is prepared similarly to D1; off-white solid; HPLC/MS(A) 0.84 min, $[M-NH_2]^+$ 177.

$^1$H NMR (400 MHz, DMSO-$d_6$) δ 7.92 (d, J=0.7 Hz, 1H), 7.62 (d, J=0.8 Hz, 1H), 6.94 (d, J=3.5 Hz, 1H), 6.80 (dt, J=3.5, 1.0 Hz, 1H), 3.84 (d, J=1.1 Hz, 2H), 3.83 (s, 3H), 1.89 (bs, 2H).

1-[4-(2-methyl-2H-1,2,3,4-tetrazol-5-yl)phenyl]methanamine (D17)

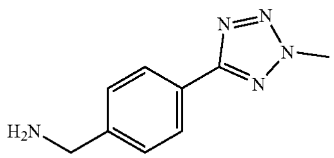

This compound is prepared similarly to D2; yellow solid; UPLC/MS 0.294 min, $[M-NH_2—N_2]^+$ 145.

Synthesis of 1-(4-{8-oxa-3-azabicyclo[3.2.1]octan-3-yl}phenyl)methanamine (D18)

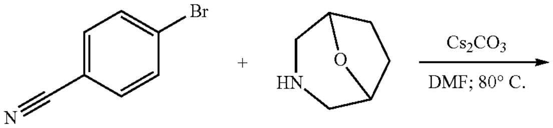

-continued

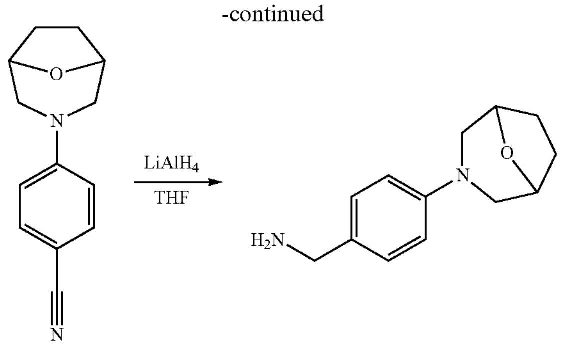

To a stirred solution of 4-fluorobenzonitrile (474 mg, 3.92 mmol) and 8-oxa-3-azabicyclo[3.2.1]octane (443 mg, 3.92 mmol) in DMF (8 mL) is added cesium carbonate (2.55 g, 7.84 mmol). The resulting mixture is stirred for 16 h at 80° C. The resulting mixture is filtered, the filter cake is washed with methanol and the filtrate is concentrated under reduced pressure. The residue is purified by silica gel column chromatography, eluted with PE/EtOAc (1:1) to afford 4-[8-oxa-3-azabicyclo[3.2.1]octan-3-yl]benzonitrile as white solid; HPLC/MS $[M+H]^+$ 215.

To a stirred solution of 4-[8-oxa-3-azabicyclo[3.2.1]octan-3-yl]benzonitrile (165 mg, 0.77 mmol) in THF(8 mL) is added lithium aluminium hydride (116 mg, 3.06 mmol) at 0° C. under nitrogen atmosphere. The resulting mixture is stirred for 3 hours at 25° C. under nitrogen atmosphere. The reaction is quenched by the addition of water (10 mL) at 0° C. The aqueous layer is extracted with ethyl acetate (3×10 mL). The organic phase is evaporated under reduced pressure to afford 1-(4-[8-oxa-3-azabicyclo[3.2.1]octan-3-yl]phenyl)methanamine as white solid; HPLC/MS $[M-NH_2]^+$ 202.

1-[4-(1-methyl-1H-imidazol-5-yl)phenyl]methanamine (D19)

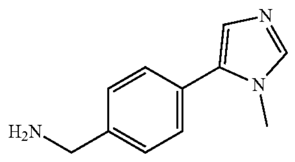

This compound is prepared similarly to D1; orange-red resin; UPLC/MS 0.113 min, $[M+H]^+$ 188.

$^1$H NMR (400 MHz, DMSO-$d_6$) δ 7.67 (d, J=1.3 Hz, 1H), 7.41 (s, 4H), 7.00 (d, J=1.2 Hz, 1H), 3.75 (s, 2H), 3.66 (s, 3H), $NH_2$ peak not visible.

1-[4-(6-methylpyridazin-3-yl)phenyl]methanamine (D20)

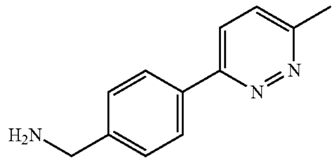

This compound is prepared similarly to D2; off-white solid; UPLC/MS 0.288 min, $[M+H]^+$ 200.

1-[4-(6-methylpyridazin-3-yl)phenyl]methanamine (D21)

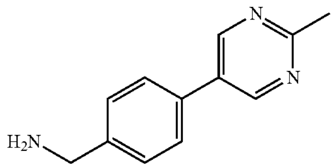

This compound is prepared similarly to D2; off-white powder; UPLC/MS 0.299 min, $[M-NH_2]^+$ 183.

Synthesis of 1-[4-(2-methyl-1,3-oxazol-4-yl)phenyl]methanamine (D22)

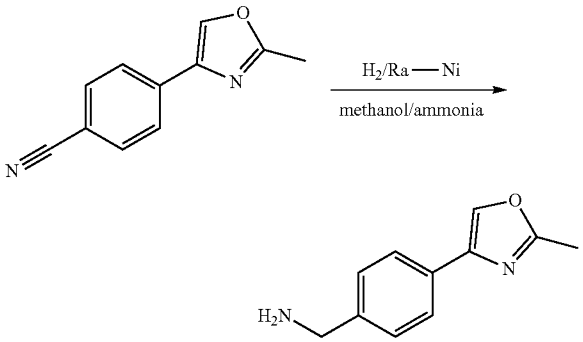

To solution of 4-(2-methyl-1,3-oxazol-4-yl)benzonitrile (369 mg, 2.00 mmol) in methanol (15 ml) is added a 20% solution of ammonia in methanol (15 ml) and wet Raney-Nickel (300 mg). The mixture is hydrogenated at a pressure of 5 bar and 60° C. The catalyst is filtered off and the filtrate is evaporated. The residue is triturated with tert-butyl methyl ether to afford 1-[4-(2-methyl-1,3-oxazol-4-yl)phenyl]methanamine as off-white powder; UPLC/MS 0.319 min, $[M-NH_2]^+$ 202.

5-[4-(aminomethyl)phenyl]-2-methylpyrimidin-4-amine (D23)

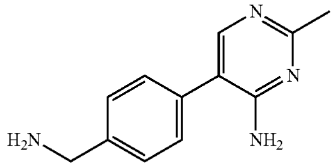 [SMILES: Cc1ncc(-c2ccc(CN)cc2)c(N)n1]

This compound is prepared similarly to D2; off-white solid; UPLC/MS 0.118 min, $[M+H]^+$ 215.

Synthesis of 1-[5-(2-methyl-2H-1,2,3-triazol-4-yl)pyridin-2-yl]methanamine (D24)

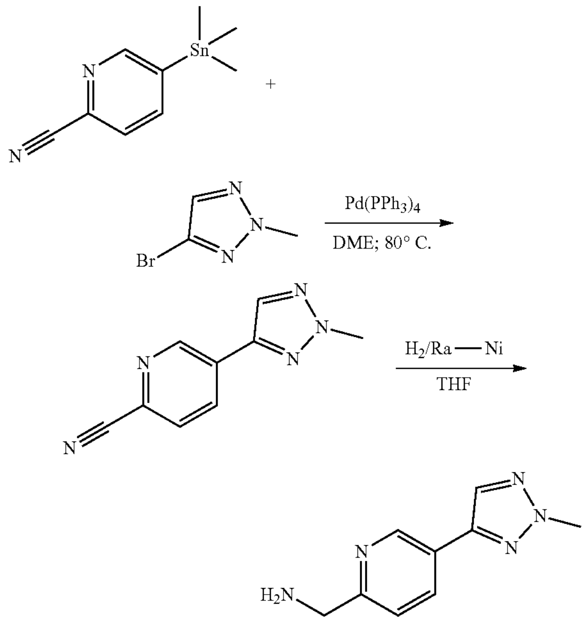

Yellow solid; HPLC/MS $[M+H]^+$ 186.

1-[6-(2-methyl-2H-1,2,3-triazol-4-yl)pyridin-3-yl]methanamine (D25)

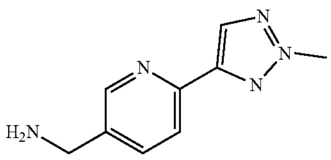

This compound is prepared similarly to D24; white solid; HPLC/MS $[M+H]^+$ 190.

1-{4-[2-(2-methoxyethyl)-2H-1,2,3-triazol-4-yl]phenyl}methanamine (D26)

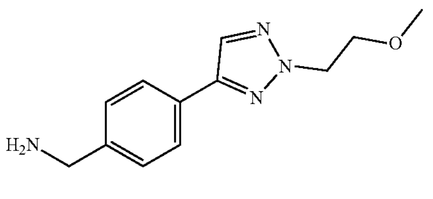 [SMILES: COCCn1ncc(-c2ccc(CN)cc2)n1]

This compound is prepared similarly to D2; white solid; UPLC/MS 0.311 min, $[M+H]^+$ 233.

Synthesis of 1-[4-(1-cyclopropyl-1H-pyrazol-4-yl)phenyl]methanamine (D27)

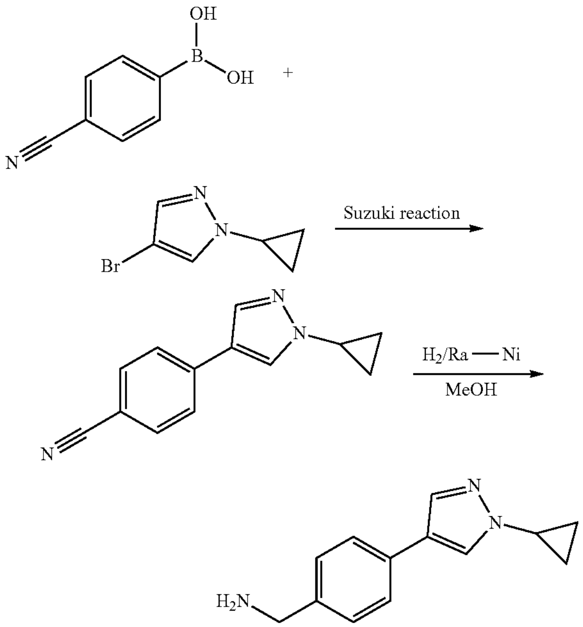

Light yellow oil; HPLC/MS $[M+H]^+$ 214.

1-[4-(3-methoxy-1-methyl-1H-pyrazol-4-yl)phenyl]methanamine (D28)

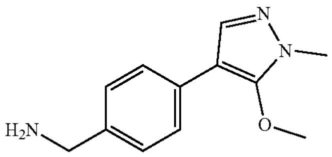 [SMILES: COc1c(-c2ccc(CN)cc2)cnn1C]

This compound is prepared similarly to D2; pale yellow oil; HPLC/MS(B) 0.601 min, $[M+H]^+$ 218.

$^1$H NMR (400 MHz, DMSO-d$_6$) δ 7.92 (s, 1H), 7.51 (d, J=8.2 Hz, 2H), 7.31-7.18 (m, 2H), 3.88 (s, 3H), 3.71 (s, 3H), 3.67 (s, 2H), 2.00 (bs, 2H).

Synthesis of 1-[4-(1,3-oxazol-4-yl)phenyl]methanamine (D29)

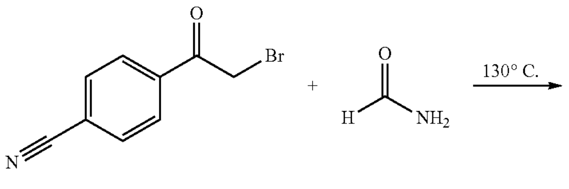

-continued
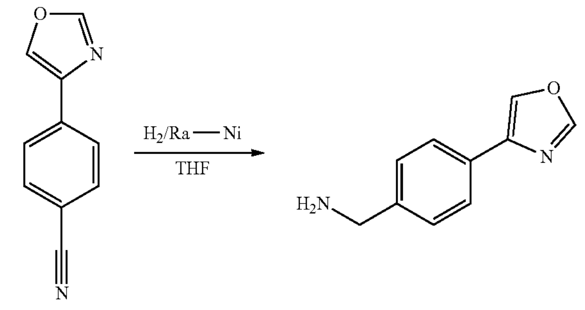
Yellow solid; HPLC/MS $[M+H]^+$ 171.
Synthesis of 1-[4-(3-methyl-1,2-oxazol-5-yl)phenyl]methanamine (D30)
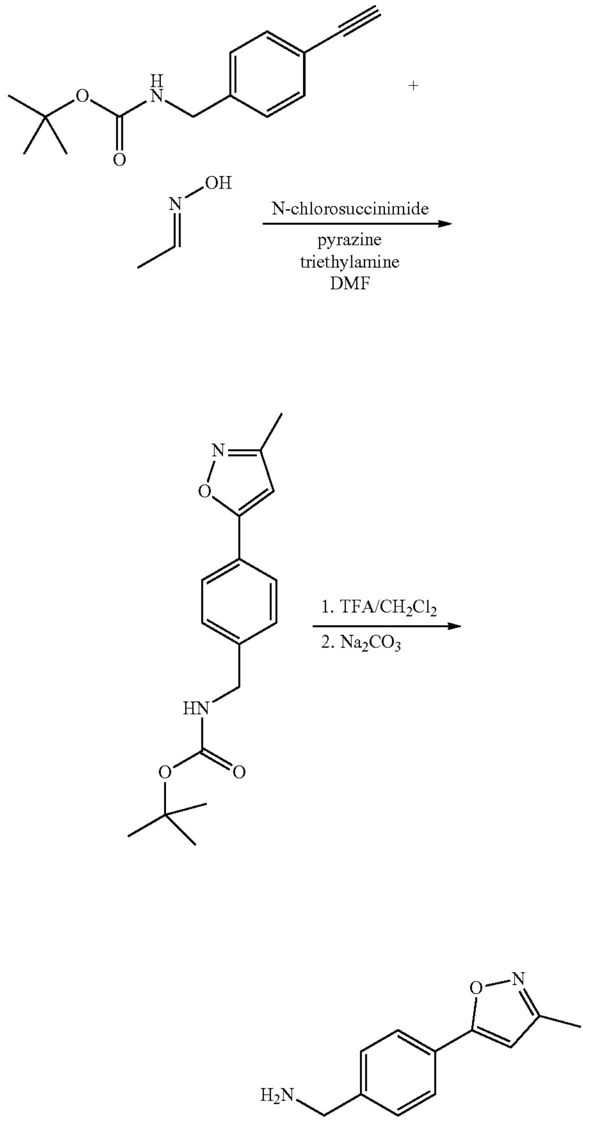
Yellow solid; HPLC/MS $[M+H]^+$ 189.
Synthesis of 1-[4-(5-methyl-1,3-oxazol-2-yl)phenyl]methanamine (D31)
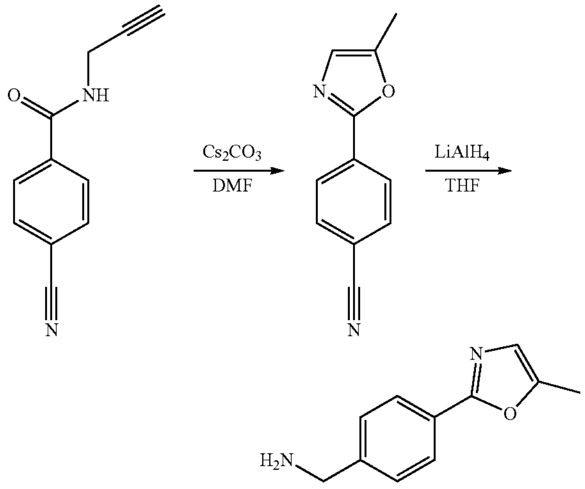
yellow solid; HPLC/MS $[M+H]^+$ 189.
Synthesis of 1-[4-(1-methyl-1H-pyrazol-4-yl)phenyl]ethan-1-amine (D32)
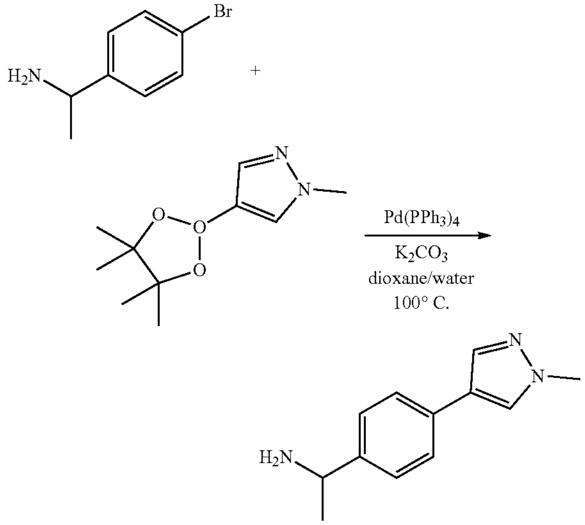
brown solid; HPLC/MS $[M+H]^+$ 185.
Alkoxy-Pyridylamines
Synthesis of 4-(2-methoxy-ethoxy)-pyridin-2-ylamine (E1)
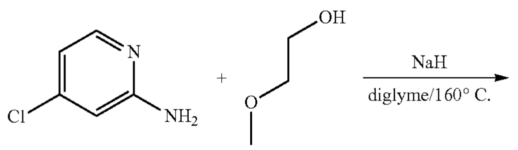

-continued

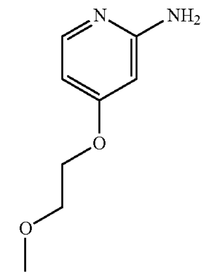

Under nitrogen, a reaction flask is charged with diethylene glycol dimethyl ether (20 ml) and with sodium hydride (60% suspension in paraffin oil, 915 mg, 23.0 mmol). A solution of ethylene glycol monomethyl ether (1.16 g, 15.3 mmol) in diethylene glycol dimethyl ether (10 ml) is added slowly at room temperature. The mixture is heated to 40° C. and stirred at this temperature for 1 hour. 2-Amino-4-chloropyridine (980 mg, 7.62 mmol) is added. The mixture is heated to 160° C. and stirred at this temperature for 20 hours. The reaction mixture is allowed to reach room temperature and reduced in volume under vacuum. The residue is treated with water and dichloromethane. The organic phase is separated and the aqueous phase is extracted several times with dichloromethane. The combined organic phases are dried over sodium sulfate and evaporated. The residue is chromatographed on a silica gel column with ethyl acetate/methanol as eluent to afford 4-(2-methoxy-ethoxy)-pyridin-2-ylamine as brown solid; HPLC/MS (A) 0.79 min, $[M+H]^+$ 261.

4-[(1,3-dimethoxypropan-2-yl)oxy]pyridin-2-amine (E2)

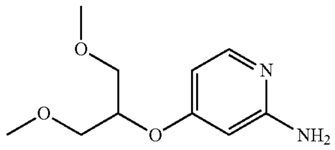

The compound is prepared similarly to E1; brown oil; HPLC/MS $[M+H]^+$ 213

4-(oxan-4-yloxy)pyridin-2-amine (E3)

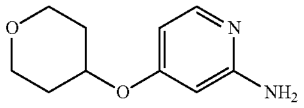 [SMILES: Nc1cc(OC2CCOCC2)ccn1]

The compound is prepared similarly to E1; brown oil; HPLC/MS $[M+H]^+$ 195

4-[2-(morpholin-4-yl)ethoxy]pyridin-2-amine (E4)

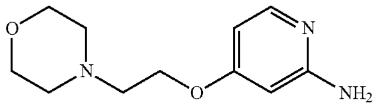 [SMILES: Nc1cc(OCCN2CCOCC2)ccn1]

The compound is prepared similarly to E1; off-white crystals; HPLC/MS (A) 0.273 min, $[M+H]^+$ 224.

$^1$H NMR (500 MHz, DMSO-d6) δ 7.70 (d, J=5.8 Hz, 1H), 6.12 (dd, J=5.8, 2.3 Hz, 1H), 5.95 (d, J=2.3 Hz, 1H), 5.75 (s, 2H), 4.03 (t, J=5.8 Hz, 2H), 3.60-3.53 (m, 4H), 2.66 (t, J=5.8 Hz, 2H), 2.48-2.40 (m, 4H).

4-(oxolan-3-yloxy)pyridin-2-amine (E5)

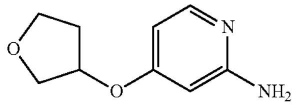 [SMILES: Nc1cc(OC2CCOC2)ccn1]

The compound is prepared similarly to E1; brown oil; HPLC/MS $[M+H]^+$ 181

4-(cyclopropylmethoxy)pyridin-2-amine (E6)

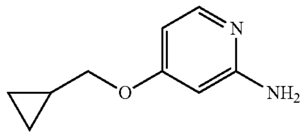 [SMILES: Nc1cc(OCC2CC2)ccn1]

The compound is prepared similarly to E1; white solid; HPLC/MS $[M+H]^+$ 165

4-[2-(dimethylamino)ethoxy]pyridin-2-amine (E7)

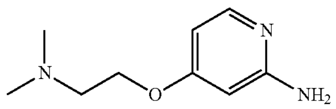

The compound is prepared similarly to E1; yellow solid; HPLC/MS $[M+H]^+$ 182

4-[2-(pyrrolidin-1-yl)ethoxy]pyridin-2-amine (E8)

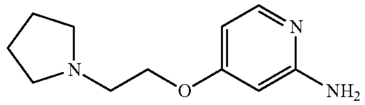 [SMILES: Nc1cc(OCCN2CCCC2)ccn1]

The compound is prepared similarly to E1; pale orange solid; UPLC/MS 0.113 min, $[M+H]^+$ 208.

$^1$H NMR (400 MHz, DMSO-d6) δ 7.70 (d, J=5.8 Hz, 1H), 6.11 (dd, J=5.8, 2.3 Hz, 1H), 5.94 (d, J=2.3 Hz, 1H), 5.76 (s, 2H), 4.00 (t, J=5.9 Hz, 2H), 2.74 (t, J=5.9 Hz, 2H), 2.48 (m, 4H), 1.73-1.61 (m, 4H).

4-[2-(4-methylpiperazin-1-yl)ethoxy]pyridin-2-amine (E9)

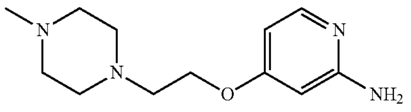 [SMILES: CN1CCN(CCOc2ccnc(N)c2)CC1]

The compound is prepared similarly to E1; pale brown solid; HPLC/MS $[M+H]^+$ 237.

4-[(1-methylpiperidin-4-yl)methoxy]pyridin-2-amine (E10)

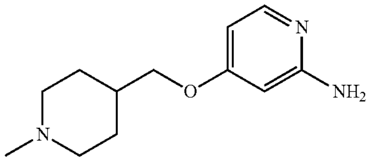 [SMILES: CN1CCC(COc2ccnc(N)c2)CC1]

The compound is prepared similarly to E1; white solid; HPLC/MS $[M+H]^+$ 222.

4-[(1-methylpiperidin-4-yl)oxy]pyridin-2-amine (E11)

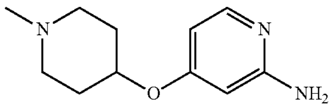

The compound is prepared similarly to E1; white solid; HPLC/MS $[M+H]^+$ 208.

Synthesis of 1-[(2-aminopyridin-4-yl)oxy]-2-methylpropan-2-ol (E12)

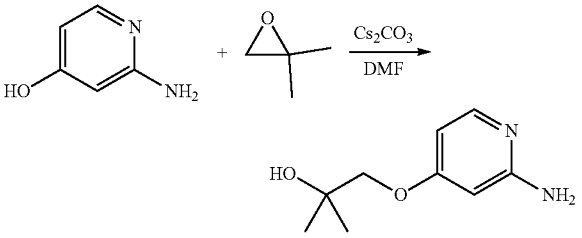

To a solution of 2-aminopyridin-4-ol (200 mg, 1.73 mmol) in DMF (5 ml) is added 2,2-dimethyloxirane (393 mg, 5.18 mmol) and cesium carbonate (1.13 g, 3.46 mmol) and the resultant slurry is stirred for 18 hours at 40° C. The solids are filtered off and washed with dichloromethane. The filtrate is evaporated and chromatographed on a silica gel column with dichloromethane/methanol as eluent to afford 1-[(2-aminopyridin-4-yl)oxy]-2-methylpropan-2-ol as white solid; HPLC/MS $[M+H]^+$ 183.

Synthesis of 2-[4-(oxetan-3-yl)piperazin-1-yl]ethan-1-ol (E13)

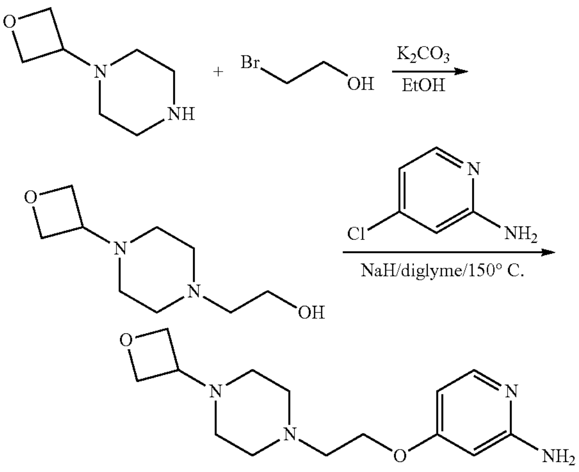

To a solution of 1-(oxetan-3-yl)piperazine (284 mg, 1.73 mmol) in ethanol (5 ml) is added potassium carbonate (554 mg, 3.98 mmol) and 2-bromoethan-1-ol (524 mg, 3.98 mmol) and the resultant slurry is stirred for 18 hours at 40° C. The solids are filtered off and washed with dichloromethane. The filtrate is evaporated to afford 2-[4-(oxetan-3-yl)piperazin-1-yl]ethan-1-ol as white solid; HPLC/MS $[M+H]^+$ 187. The subsequent synthesis step is performed similarly to the synthesis of E1 to afford 4-{2-[4-(oxetan-3-yl)piperazin-1-yl]ethoxy}pyridin-2-amine as yellow oil; HPLC/MS $[M+H]^+$ 279.

4-[3-(morpholin-4-yl)propoxy]pyridin-2-amine (E14)

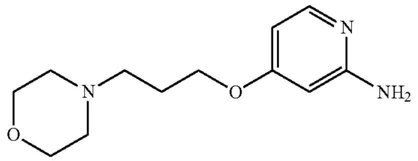 [SMILES: Nc1cc(OCCCN2CCOCC2)ccn1]

The compound is prepared similarly to E1; yellow solid; HPLC/MS $[M+H]^+$ 238.

Synthesis of 4-[3-(pyrrolidin-1-yl)propoxy]pyridin-2-amine (E15)

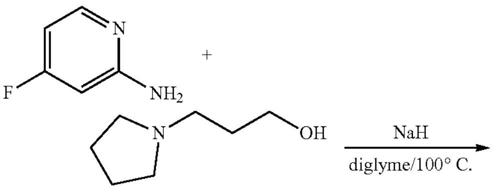

-continued

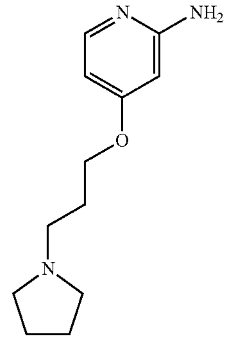

Under nitrogen, a reaction flask is charged with diethylene glycol dimethyl ether (75 ml) and with sodium hydride (60% suspension in paraffin oil, 6.15 g, 154 mmol). 3-(Pyrrolidin-1-yl)propan-1-ol (10.2 g, 79.1 mmol) is added slowly and the mixture is stirred for one hour at room temperature. A solution of 2-amino-4-fluoropyridine (8.87 g, 79.1 mmol) in diethylene glycol dimethyl ether (60 ml) is added dropwise. The mixture is heated to 100° C. and stirred at this temperature for 18 hours. The reaction mixture is allowed to cool to room temperature and reduced in volume under vacuum. The residue is taken up in acetonitrile. The solids are filtered off and the filtrate is evaporated. The residue is taken up in ethyl acetate and dried over sodium sulfate. Sodium sulfate is filtered off and the filtrate is cooled to 0° C. The crystalline solid that is subsequently formed, is filtered off, washed with cold ethyl acetate and dried under vacuum to afford 4-[3-(pyrrolidin-1-yl)propoxy]pyridin-2-amine as beige solid; UPLC/MS 0.116 min, $[M+H]^+$ 222.

1H NMR (400 MHz, DMSO-$d_6$) δ 7.70 (d, J=5.8 Hz, 1H), 6.10 (dd, J=5.9, 2.3 Hz, 1H), 5.95 (d, J=2.2 Hz, 1H), 5.72 (s, 2H), 3.96 (t, J=6.5 Hz, 2H), 2.54-2.46 (m, 3H), 2.48-2.36 (m, 4H), 1.85 (p, J=6.8 Hz, 2H), 1.75-1.61 (m, 4H).

tert-Butyl 4-{[(2-aminopyridin-4-yl)oxy]methyl}piperidine-1-carboxylate (E16)

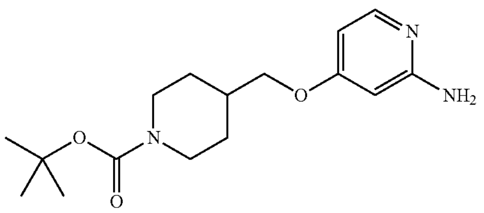 [SMILES: CC(C)(C)OC(=O)N1CCC(COc2ccnc(N)c2)CC1]

The compound is prepared similarly to E15; pale yellow solid; HPLC/MS(A) 1.24 min, $[M+H]^+$ 308.

$^1$H NMR (400 MHz, DMSO-$d_6$) δ 7.69 (d, J=5.8 Hz, 1H), 6.10 (dd, J=5.8, 2.2 Hz, 1H), 5.93 (d, J=2.2 Hz, 1H), 5.76 (s, 2H), 4.10-3.92 (m, 4H), 3.78 (d, J=6.4 Hz, 2H), 2.72 (bs, 4H), 2.00-1.81 (m, 1H), 1.71 (dd, J=13.4, 3.4 Hz, 4H), 1.12 (qd, J=12.5, 4.3 Hz, 4H).

Synthesis of 4-{[1-(oxetan-3-yl)piperidin-4-yl]methoxy}pyridin-2-amine (E17)

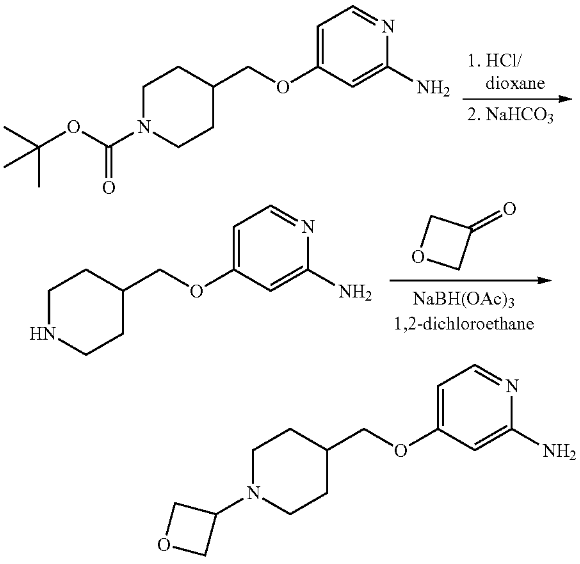

tert-Butyl 4-{[(2-aminopyridin-4-yl)oxy]methyl}piperidine-1-carboxylate (E16) (1.80 g, 4.98 mmol) is dissolved in a 4 N solution of hydrogen chloride in dioxane (15 ml) and stirred for 2 hours at room temperature. Water and saturated sodium hydrogen carbonate solution is added to reach a neutral pH value. The mixture is extracted with ethyl acetate. The organic phase is evaporated to afford 4-[(piperidin-4-yl)methoxy]pyridin-2-amine as yellow solid; HPLC/MS $[M+H]^+$ 208.

A solution of 4-[(piperidin-4-yl)methoxy]pyridin-2-amine (1.00 g, 4.68 mmol) and oxetan-3-one (355 mg, 4.68 mmol) in 1,2-dichloroethane (5 ml) is stirred for 2 hours at room temperature. 3.96 g (18.7 mmol) sodium triacetoxyborohydride is added and the resultant mixture is stirred for 16 hours at room temperature. The reaction mixture is treated with water and dichloromethane. The organic phase is separated and evaporated. The residue is chromatographed on a silica gel column with dichloromethane/methanol as eluent to afford 4-{[1-(oxetan-3-yl)piperidin-4-yl]methoxy}pyridin-2-amine as yellow solid; HPLC/MS $[M+H]^+$ 264.

4-[2-(3,3-difluoropyrrolidin-1-yl)ethoxy]pyridin-2-amine (E18)

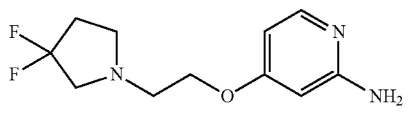 [SMILES: Nc1cc(OCCN2CCC(F)(F)C2)ccn1]

The compound is prepared similarly to E1; orange resin; UPLC/MS 0.164 min, $[M+H]^+$ 244.

$^1$H NMR (500 MHz, DMSO-$d_6$) δ 7.71 (d, J=5.9 Hz, 1H), 6.12 (dd, J=5.9, 2.3 Hz, 1H), 5.95 (d, J=2.3 Hz, 1H), 5.74 (s, 2H), 4.02 (t, J=5.6 Hz, 2H), 2.96 (t, J=13.5 Hz, 2H), 2.87-2.72 (m, 4H), 2.22 (tt, J=15.3, 7.0 Hz, 2H).

4-[(1-methylpiperidin-4-yl)methoxy]pyridin-2-amine (E19)

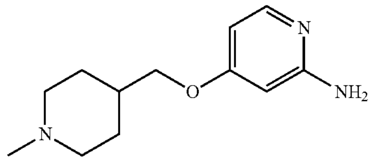 [SMILES: CN1CCC(COc2ccnc(N)c2)CC1]

The compound is prepared similarly to E15; yellow solid; HPLC/MS $[M+H]^+$ 222.

4-{3-[(2-aminopyridin-4-yl)oxy]propyl}morpholin-3-one (E20)

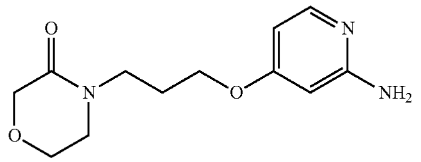 [SMILES: Nc1cc(OCCCN2CCOCC2=O)ccn1]

The compound is prepared similarly to E15; colorless resin; UPLC/MS 0.288 min, $[M+H]^+$ 252.

$^1$H NMR (400 MHz, DMSO-$d_6$) δ 7.70 (d, J=5.9 Hz, 1H), 6.10 (dd, J=5.9, 2.3 Hz, 1H), 5.92 (d, J=2.3 Hz, 1H), 5.78 (s, 2H), 4.01 (s, 2H), 3.93 (t, J=6.3 Hz, 2H), 3.82 (dd, J=5.9, 4.3 Hz, 2H), 3.44 (t, J=7.0 Hz, 2H), 3.38-3.34 (m, 2H), 1.93 (p, J=6.6 Hz, 2H).

4-[2-(3-fluoropyrrolidin-1-yl)ethoxy]pyridin-2-amine (E21)

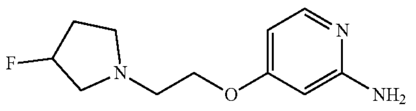 [SMILES: Nc1cc(OCCN2CCC(F)C2)ccn1]

The compound is prepared similarly to E15; colorless resin; UPLC/MS 0.112 min, $[M+H]^+$ 226.

$^1$H NMR (400 MHz, DMSO-$d_6$) δ 7.70 (d, J=5.9 Hz, 1H), 6.12 (dd, J=5.9, 2.2 Hz, 1H), 5.94 (d, J=2.2 Hz, 1H), 5.77 (s, 2H), 5.18 (dt, J=56.1, 6.3 Hz, 1H), 4.02 (t, J=5.8 Hz, 2H), 2.97-2.80 (m, 2H), 2.78 (t, J=5.8 Hz, 2H), 2.65 (ddd, J=31.7, 11.6, 5.1 Hz, 1H), 2.37 (q, J=8.0 Hz, 1H), 2.11 (ddq, J=27.8, 14.0, 7.0 Hz, 1H), 1.85 (ddt, J=29.4, 14.3, 7.2 Hz, 1H).

4-[2-(3-fluoropyrrolidin-1-yl)ethoxy]pyridin-2-amine (E22)

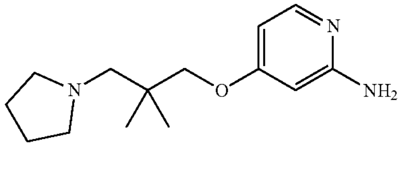 [SMILES: CC(C)(COc1ccnc(N)c1)CN1CCCC1]

The compound is prepared similarly to E15; yellow solid; HPLC/MS $[M+H]^+$ 250.

tert-Butyl 4-[(2-aminopyridin-4-yl)oxy]piperidine-1-carboxylate (E23)

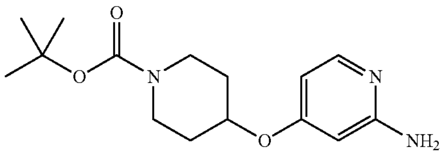 [SMILES: CC(C)(C)OC(=O)N1CCC(Oc2ccnc(N)c2)CC1]

The compound is prepared similarly to E15; off-white solid; HPLC/MS(A) 1.17 min, $[M+H]^+$ 294.

$^1$H NMR (500 MHz, DMSO-$d_6$) δ 7.71 (d, J=5.9 Hz, 1H), 6.14 (dd, J=5.9, 2.3 Hz, 1H), 5.98 (d, J=2.2 Hz, 1H), 5.71 (s, 2H), 4.51 (tt, J=7.9, 3.7 Hz, 1H), 3.64 (ddd, J=13.4, 6.6, 4.3 Hz, 2H), 3.23-3.01 (m, 2H), 1.95-1.83 (m, 1H), 1.50 (ddt, J=17.1, 8.6, 3.9 Hz, 2H), 1.40 (s, 9H).

4-{2-[(2-aminopyridin-4-yl)oxy]ethyl}morpholin-3-one (E24)

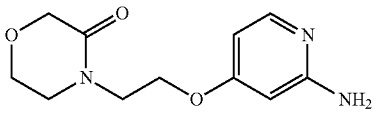 [SMILES: Nc1cc(OCCN2CCOCC2=O)ccn1]

The compound is prepared similarly to E15; off-white solid; HPLC/MS(A) 0.76 min, $[M+H]^+$ 238.

$^1$H NMR (500 MHz, DMSO-$d_6$) δ 7.72 (d, J=5.9 Hz, 1H), 6.13 (dd, J=5.8, 2.3 Hz, 1H), 5.96 (d, J=2.3 Hz, 1H), 5.75 (s, 2H), 4.09 (t, J=5.6 Hz, 2H), 4.03 (s, 2H), 3.87-3.74 (m, 2H), 3.66 (t, J=5.6 Hz, 2H), 3.50-3.41 (m, 2H).

4-[2-(oxan-2-yloxy)ethoxy]pyridin-2-amine (E25)

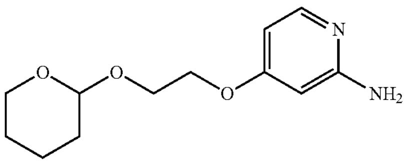 [SMILES: Nc1cc(OCCOC2CCCCO2)ccn1]

The compound is prepared similarly to E1; brown oil; HPLC/MS(A) 1.82 min, $[M+H]^+$ 239.

$^1$H NMR (500 MHz, DMSO-$d_6$) δ 7.71 (d, J=5.9 Hz, 1H), 6.12 (dd, J=5.9, 2.3 Hz, 1H), 5.95 (d, J=2.3 Hz, 1H), 5.72 (s, 2H), 4.63 (dd, J=4.4, 3.1 Hz, 1H), 4.07 (td, J=4.1, 1.9 Hz, 1H), 3.93-3.83 (m, 1H), 3.80-3.73 (m, 1H), 3.73-3.66 (m, 1H), 3.48-3.38 (m, 1H), 1.81-1.66 (m, 1H), 1.62 (tdd, J=9.9, 4.8, 2.7 Hz, 1H), 1.53-1.38 (m, 5H).

4-{2-[(2-aminopyridin-4-yl)oxy]ethyl}-1-methylpiperazin-2-one (E26)

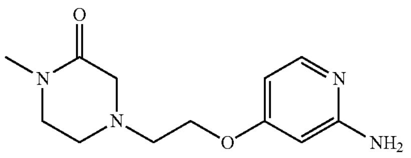 [SMILES: CN1CCN(CCOc2ccnc(N)c2)CC1=O]

The compound is prepared similarly to E15; brown resin; UPLC/MS 0.196 min, $[M+H]^+$ 251.

4-[3-(4-methylpiperazin-1-yl)propoxy]pyridin-2-amine (E27)

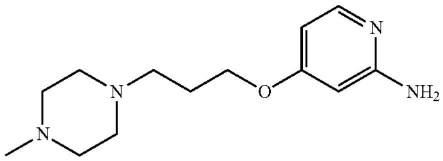 [SMILES: CN1CCN(CCCOc2ccnc(N)c2)CC1]

The compound is prepared similarly to E15; white solid; UPLC/MS 0.115 min, $[M+H]^+$ 251.

Synthesis of 1-{2-[(2-aminopyridin-4-yl)oxy]ethyl}-4-(oxetan-3-yl)piperazin-2-one (E28)

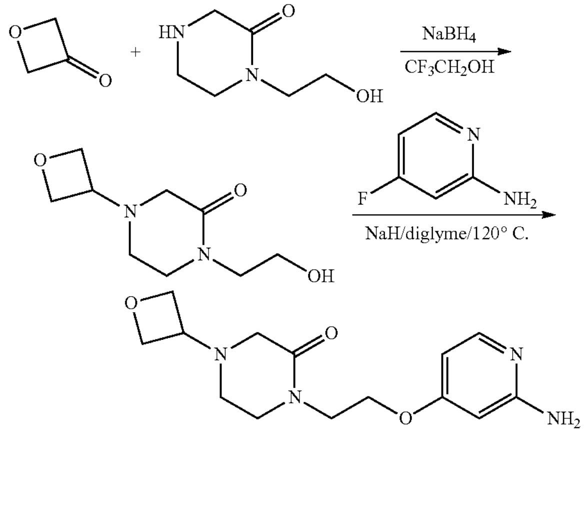

Pale orange wax; HPLC/MS(A) 0.772 min, $[M+H]^+$ 293.

$^1$H NMR (500 MHz, DMSO-d6) δ 7.72 (d, J=5.8 Hz, 1H), 6.13 (dd, J=5.8, 2.2 Hz, 1H), 5.95 (d, J=2.3 Hz, 1H), 5.73 (s, 2H), 4.53 (t, J=6.6 Hz, 2H), 4.44 (t, J=6.1 Hz, 2H), 4.07 (t, J=5.6 Hz, 2H), 3.63 (t, J=5.6 Hz, 2H), 3.56-3.47 (m, 1H), 3.44-3.40 (m, 2H), 2.95 (s, 2H), 2.65-2.53 (m, 2H).

tert-Butyl 3-{[(2-aminopyridin-4-yl)oxy]methyl}azetidine-1-carboxylate (E29)

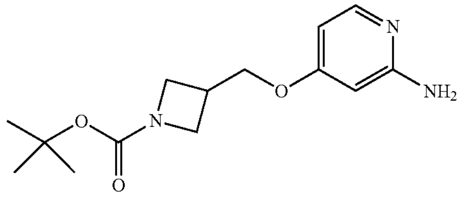 [SMILES: CC(C)(C)OC(=O)N1CC(COc2ccnc(N)c2)C1]

The compound is prepared similarly to E15; off-white powder; UPLC/MS 0.407 min, $[M+H]^+$ 280.

4-[2-(1-methyl-1H-imidazol-2-yl)ethoxy]pyridin-2-amine (E30)

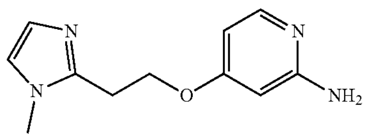 [SMILES: Cn1ccnc1CCOc1ccnc(N)c1]

The compound is prepared similarly to E15; yellow oil; HPLC/MS $[M+H]^+$ 219.

4-[2-(azetidin-1-yl)ethoxy]pyridin-2-amine (E31)

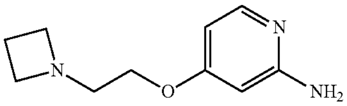 [SMILES: Nc1cc(OCCN2CCC2)ccn1]

The compound is prepared similarly to E15; yellow powder; UPLC/S 0.109 min, $[M+2H]^{++}/2$ 97.5.

$^1$H NMR (400 MHz, DMSO-$d_6$) δ 7.70 (d, J=5.8 Hz, 1H), 6.08 (dd, J=5.9, 2.3 Hz, 1H), 5.92 (d, J=2.2 Hz, 1H), 5.72 (s, 2H), 3.85 (t, J=5.7 Hz, 2H), 3.16 (t, J=6.9 Hz, 4H), 2.66 (t, J=5.7 Hz, 2H), 1.96 (p, J=6.9 Hz, 2H).

4-[3-(3,3-difluoropyrrolidin-1-yl)propoxy]pyridin-2-amine (E32)

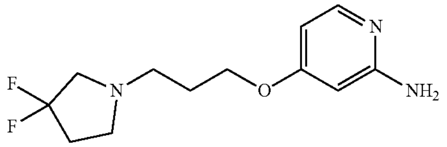 [SMILES: Nc1cc(OCCCN2CCC(F)(F)C2)ccn1]

The compound is prepared similarly to E15; beige solid; HPLC/MS(B) 0.165 min, $[M+H]^+$ 258.

$^1$H NMR (400 MHz, DMSO-$d_6$) δ 7.69 (d, J=5.8 Hz, 1H), 6.09 (dd, J=5.9, 2.2 Hz, 1H), 5.94 (d, J=2.2 Hz, 1H), 5.72 (s, 2H), 3.95 (t, J=6.4 Hz, 2H), 2.87 (t, J=13.5 Hz, 2H), 2.69 (t, J=7.0 Hz, 2H), 2.53 (t, J=7.1 Hz, 2H), 2.22 (tt, J=15.4, 7.0 Hz, 2H), 1.84 (p, J=6.7 Hz, 2H).

Chloro-imidazopyridinyl-pyrimidines

Synthesis of 3-(6-chloro-pyrimidin-4-yl)-7-methoxy-imidazo[1,2-a]pyridine (F1)

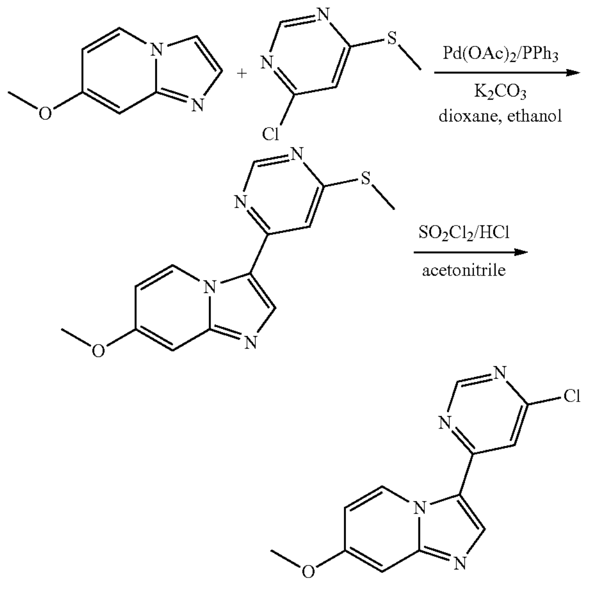

To a solution of 7-methoxyimidazo[1,2-a]pyridine (3.70 g, 25 mmol) and 4-chloro-6-methylthiopyrimidine (6.02 g, 37.5 mmol) in a mixture of 1,4-dioxane (34 ml) and ethanol (17 ml) are added potassium carbonate (6.91 g, 50.0 mmol) and triphenylphosphine (2.1 g, 8.0 mmol). The suspension is flushed with argon and palladium(II)acetate (898 mg, 4.00 mmol) is added. The mixture is stirred in a closed flask at 100° C. for 18 hours. The reaction mixture is allowed to reach room temperature and 150 ml water is added. The resultant precipitate is filtered off, washed with water and dried. The residue is chromatographed on a silica gel column with methanol/dichloromethane as eluent to afford 7-methoxy-3-(6-methylsulfanyl-pyrimidin-4-yl)-imidazo[1,2-a]pyridine as pale brown solid; HPLC/MS (A) 1.17 min, $[M+H]^+$ 273.

To a suspension of 7-methoxy-3-(6-methylsulfanyl-pyrimidin-4-yl)-imidazo[1,2-a]pyridine (3.23 g, 11.9 mmol) in acetonitrile (31 ml) is added 37% hydrochloric acid, immediately followed by addition of sulfuryl chloride (4.33 ml, 53.4 mmol). The reaction mixture is stirred for 20 minutes at room temperature and then is poured into ice water (150 ml). The mixture is stirred for 45 minutes at room temperature. Saturated sodium hydrogen carbonate solution is added until a pH value of 10-11 is reached. The resultant precipitate is filtered off and washed with water. The residue is crystallized from methanol to afford 3-(6-chloro-pyrimidin-4-yl)-7-methoxy-imidazo[1,2-a]pyridine as off-white solid; HPLC/MS (A) 1.13 min, $[M+H]^+$ 261.

$^1H$ NMR (500 MHz, DMSO-$d_6$) δ 9.74 (dd, J=7.7, 0.7 Hz, 1H), 8.97 (d, J=1.1 Hz, 1H), 8.67 (s, 1H), 8.20 (d, J=1.1 Hz, 1H), 7.21 (dd, J=2.7, 0.6 Hz, 1H), 6.95 (dd, J=7.7, 2.7 Hz, 1H), 3.91 (s, 3H).

Synthesis of 3-(6-chloro-pyrimidin-4-yl)-7-methoxy-imidazo[1,2-a]pyridine (F2)

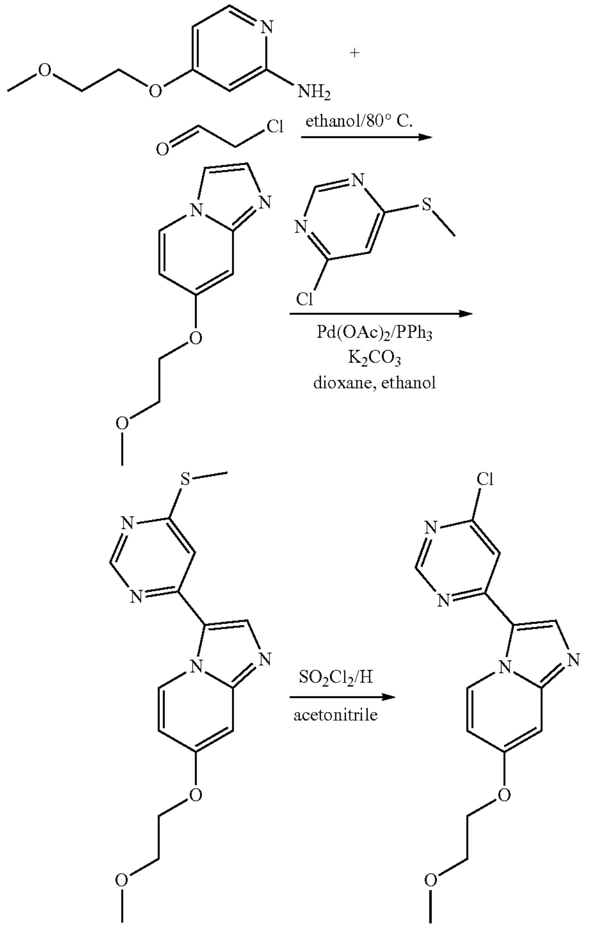

To a solution of 4-(2-methoxy-ethoxy)-pyridin-2-ylamine (879 mg, 5.23 mmol) in ethanol (20 ml) is added chloroacetaldehyde (ca. 50% solution in water, 903 mg, 5.75 mmol). The mixture is heated to 80° C. and stirred at this temperature for 18 hours. The reaction mixture is reduced in volume under vacuum and the residue is treated with water and sodium hydrogen carbonate solution. The organic phase is separated and the aqueous phase is extracted twice with dichloromethane. The organic phase is dried over sodium sulfate and evaporated. The residue is chromatographed on a silica gel column with dichloromethane/methanol as eluent to afford 7-(2-methoxy-ethoxy)-imidazo[1,2-a]pyridine as brown solid;

UPLC-MS System:

Waters Acquity H Class—SQD method: polar MS pos; polar MS neg.

column: column: BEH C-18 2.1-50 1.7 μm; column temp.: 40° C.

eluent A: water+0.1% HCOOH eluent B: acetonitrile+0.08% HCOOH flow: 0.9 ml/min gradient: 0 min 4% B, in 1 min up to 100% B till 1.3 min 100% B till 1.4 min to 4% B till 2 min 4% B Rt=0.556 min, $[M+H]^+$ 193.

The remaining steps are performed in analogy to the synthesis of 3-(6-chloro-pyrimidin-4-yl)-7-methoxy-imidazo[1,2-a]pyridine (F1); pale brown solid; HPLC/MS (A) 1.14 min, $[M+H]^+$ 305.

$1^H$ NMR (500 MHz, DMSO-$d_6$) δ 9.75 (d, J=7.7 Hz, 1H), 8.98 (s, 1H), 8.67 (s, 1H), 8.21 (s, 1H), 7.22 (d, J=2.6 Hz, 1H), 6.97 (dd, J=7.6, 2.7 Hz, 1H), 4.36-4.16 (m, 2H), 3.83-3.55 (m, 2H), 3.33 (s, 3H).

Synthesis of 4-chloro-6-{imidazo[1,2-a]pyridin-3-yl}pyrimidine (F3)

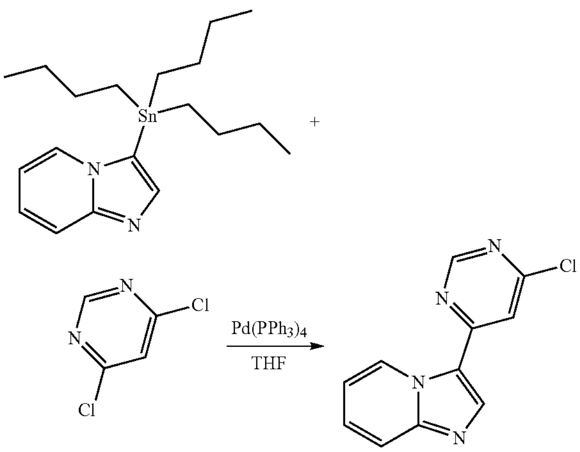

Under nitrogen, to a solution of 3-(tributylstannyl)imidazo[1,2-a]pyridine (11.0 g, 20.3 mmol) and 4,6-dichloropyrimidine (4.80 g, 30.6 mmol) in DMF (25 ml) is added tetrakis(triphenylphosphane)palladium (1.64 g, 1.42 mmol). The reaction mixture is stirred for 16 hours at 110° C. The reaction mixture is allowed to reach room temperature and concentrated under vacuum. The residue is chromatographed on a silica gel column with dichloromethane/methanol as eluent to afford 4-chloro-6-{imidazo[1,2-a]pyridin-3-yl}pyrimidine as off-white solid; HPLC/MS $[M+H]^+$ 231.

3-(6-Methylsulfanyl-pyrimidin-4-yl)-7-trifluoromethyl-imidazo[1,2-a]pyridine (F4)

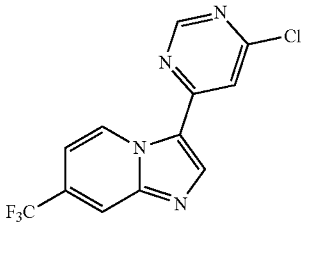 [SMILES: FC(F)(F)c1ccn2c(-c3cc(Cl)ncn3)cnc2c1]

This compound is prepared similarly to F1; off-white solid; HPLC/MS (A) 1.66 min, $[M+H]^+$ 299.

Ethoxy-ethenyl-pyrimidines

6-[(E)-2-ethoxyethenyl]-N-{[4-(1-methyl-1H-pyrazol-4-yl)phenyl]methyl}pyrimidin-4-amine (G1)

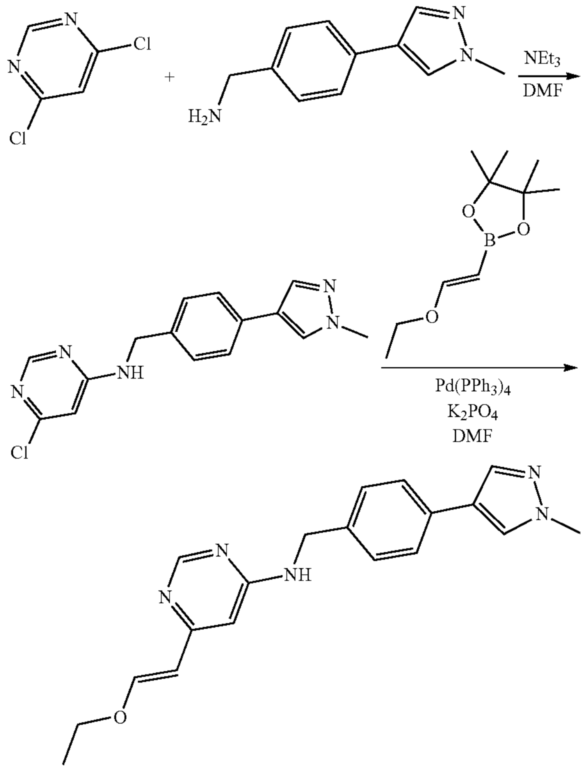

To a suspension of of 1-[4-(1-methyl-1H-pyrazol-4-yl)phenyl]methanamine (10.8 g, 54.6 mmol) (D1) and 4,6-dichloropyrimidine (8.95 g, 60.1 mmol) in DMF (80 ml) is added trimethylamine (9.09 ml, 65.6 mmol) and the reaction mixture is stirred for 2 hours at 30° C. The solids are filtered off and washed with DMF. The filtrate is evaporated under vacuum and the residue is treated with water and stirred for 15 minutes at room temperature. The precipitate is filtered off, washed with water and dried under vacuum. The residue is slurried in tert-butyl methyl ether and stirred for 10 minutes. The solids are filtered off, washed with tert-butyl methyl ether and dried under vacuum to afford 6-chloro-N-{[4-(1-methyl-1H-pyrazol-4-yl)-phenyl]-methyl}-pyrimidin-4-amine as beige solid; HPLC/MS (B) 0.682 min, $[M+H]^+$ 300. $^1$H NMR (500 MHz, DMSO-$d_6$) δ 8.28 (s, 1H), 8.15 (s, 1H), 8.08 (d, J=0.8 Hz, 1H), 7.81 (d, J=0.8 Hz, 1H), 7.51 (d, J=8.2 Hz, 2H), 7.29 (d, J=8.0 Hz, 2H), 6.58 (s, 1H), 4.52 (s, 2H), 3.85 (s, 3H).

A suspension of 6-chloro-N-{[4-(1-methyl-1H-pyrazol-4-yl)phenyl]-methyl}-pyrimidin-4-amine (5.15 g, 17.2 mmol), (E)-1-ethoxyethene-2-boronic acid pinacol ester (5.11 g, 25.8 mmol) and tripotassium triphosphate (7.30 g, 34.4 mmol) in DMF is flushed with argon. Tetrakis(triphenylphosphine)-palladium (994 mg, 0.86 mmol) is added. The reaction mixture is heated to 100° C. and stirred at this temperature for 16 hours. The reaction mixture is allowed to reach room temperature and treated with water. The precipitate is filtered off and dried. The filtrate is extracted several times with dichloromethane. The combined organic phases are dried over sodium sulfate and evaporated. The residue is combined with the earlier obtained precipitate and chromatographed on a silica gel column with dichloromethane/methanol as eluent. The product containing fractions are combined and evaporated. The residue is triturated with tert-butyl methyl ether to afford 6-[(E)-2-ethoxyethenyl]-N-{[4-(1-methyl-1H-pyrazol-4-yl)phenyl]methyl}pyrimidin-4-amine as beige crystalline solid; HPLC/MS (B) 0.696 min, $[M+H]^+$ 336.

$^1H$ NMR (400 MHz, DMSO-$d_6$) δ 8.21 (d, J=1.0 Hz, 1H), 8.07 (d, J=0.8 Hz, 1H), 7.80 (d, J=0.8 Hz, 1H), 7.72-7.57 (m, 2H), 7.49 (d, J=8.2 Hz, 2H), 7.27 (d, J=8.2 Hz, 2H), 6.19 (d, J=1.2 Hz, 1H), 5.65 (d, J=12.4 Hz, 1H), 4.46 (d, J=5.9 Hz, 2H), 3.93 (q, J=7.0 Hz, 2H), 3.85 (s, 3H), 1.25 (t, J=7.0 Hz, 3H).

6-[(E)-2-ethoxyethenyl]-N-{[4-(1H-1,2,3-triazol-1-yl)phenyl]methyl}pyrimidin-4-amine (G2)

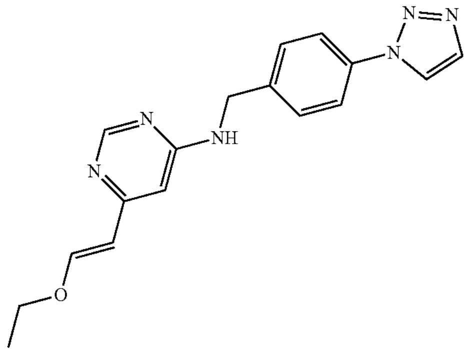 [SMILES: CCO/C=C/c1cc(NCc2ccc(-n3ccnn3)cc2)ncn1]

The compound is prepared similarly to G1; yellow solid; HPLC/MS $[M+H]^+$ 323.

6-[(E)-2-ethoxyethenyl]-N-{[4-(2-methyl-2H-1,2,3-triazol-4-yl)phenyl]methyl}pyrimidin-4-amine (G3)

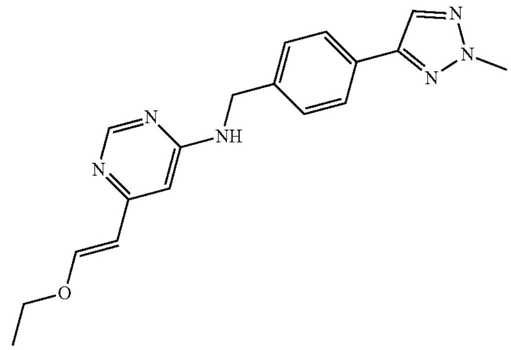 [SMILES: CCO/C=C/c1cc(NCc2ccc(-c3cnn(C)n3)cc2)ncn1]

The compound is prepared similarly to G1; off-white crystalline solid; HPLC/MS (B) 0.708 min, $[M+H]^+$ 337.

$^1H$ NMR (400 MHz, DMSO-$d_6$) δ 8.21 (s, 1H), 8.16 (s, 1H), 7.77 (d, J=8.3 Hz, 2H), 7.69 (t, J=6.2 Hz, 1H), 7.64 (d, J=12.4 Hz, 1H), 7.37 (d, J=8.2 Hz, 2H), 6.20 (s, 1H), 5.66 (d, J=12.4 Hz, 1H), 4.51 (d, J=6.0 Hz, 2H), 4.18 (s, 3H), 3.93 (q, J=7.0 Hz, 2H), 1.25 (t, J=7.0 Hz, 3H).

4-[(E)-2-ethoxyethenyl]-6-{[4-(1-methyl-1H-pyrazol-4-yl)phenyl]methoxy}pyrimidine (G4)

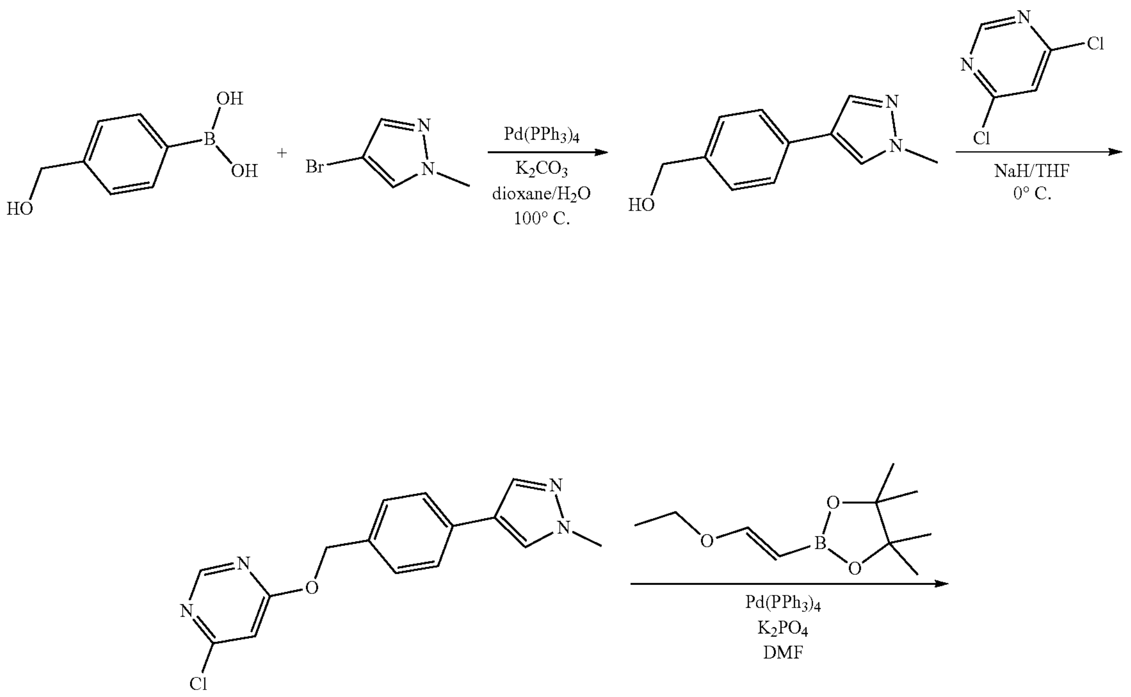

-continued

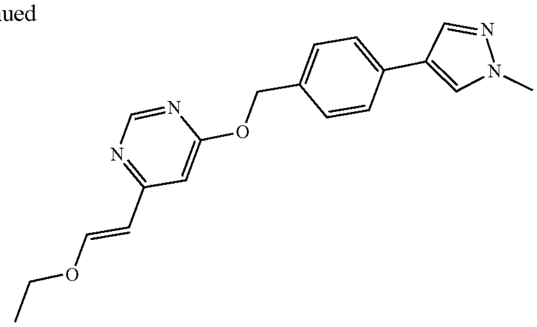

brown solid; HPLC/MS $[M+H]^+$ 337.

6-[(E)-2-Ethoxyethenyl]-5-fluoro-N-{[4-(1-methyl-1H-pyrazol-4-yl)phenyl]methyl}pyrimidin-4-amine (G5)

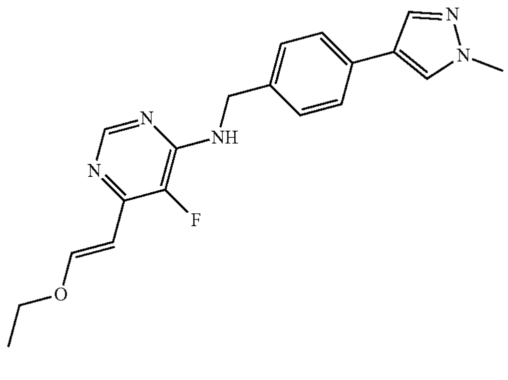 [SMILES: CCO/C=C/c1ncnc(NCc2ccc(-c3cnn(C)c3)cc2)c1F]

The compound is prepared similarly to G1; off-white powder; UPLC/MS 0.635 min, $[M+H]^+$ 354.

6-[(E)-2-ethoxyethenyl]-N-{1-[4-(1-methyl-1H-pyrazol-4-yl)phenyl]ethyl}pyrimidin-4-amine (G6)

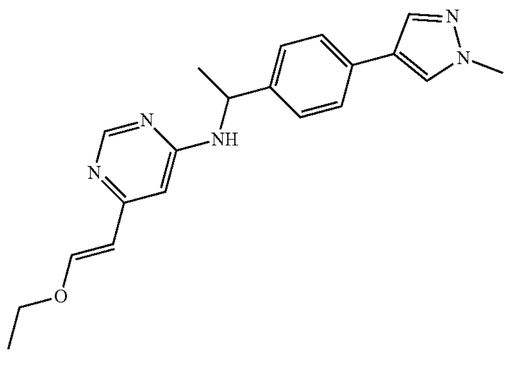 [SMILES: CCO/C=C/c1cc(NC(C)c2ccc(-c3cnn(C)c3)cc2)ncn1]

The compound is prepared from D32 similarly to G1; brown oil; HPLC/MS $[M+H]^+$ 350.

Fluoroimidazopyridines

6-{7-fluoroimidazo[1,2-a]pyridin-3-yl}-N-{[4-(1-methyl-1H-pyrazol-4-yl)phenyl]methyl}pyrimidin-4-amine (H1)

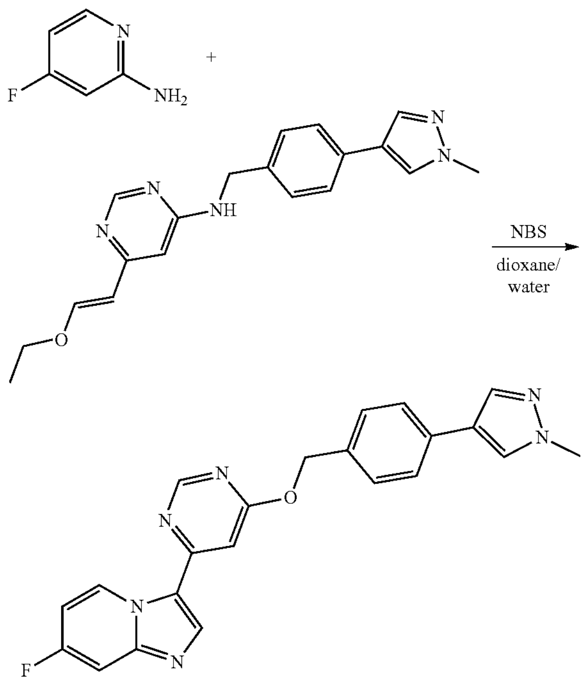

A suspension of 6-[(E)-2-ethoxyethenyl]-N-{[4-(1-methyl-1H-pyrazol-4-yl)phenyl]methyl}pyrimidin-4-amine (G1) (335 mg, 1.00 mmol) in a mixture of 1,4-dioxane (4.5 ml) and water (1.5 ml) is cooled to 0° C. and N-bromosuccinimide (196 mg, 1.10 mmol) is added in portions over a period of 15 minutes. After the last addition, the reaction mixture is stirred for 20 minutes at 0° C. 2-Amino-4-fluoropyridine (118 mg, 1.00 mmol) is added. The reaction solution is heated to 60° C. and stirred at this temperature for 2 hours. The reaction mixture is allowed to reach temperature and poured into aqueous 1 N NaOH solution (25 ml). The resultant mixture is stirred for several hours. The resultant solid material is filtered off, washed with water, dried and chromatographed on a silica gel column with dichloromethane/methanol as eluent to afford 6-{7-fluoroimidazo[1,2-a]pyridin-3-yl}-N-{[4-(1-methyl-1H-pyrazol-4-yl)phenyl]methyl}pyrimidin-4-amine as pale yellow crystalline solid; HPLC/MS(B) 0.794 min, $[M+H]^+$ 400.

$^{1}$H NMR (500 MHz, DMSO-$d_6$) δ 9.94-9.85 (m, 1H), 8.55 (s, 1H), 8.28 (s, 1H), 8.07 (s, 1H), 7.91 (t, J=6.1 Hz, 1H), 7.80 (d, J=0.9 Hz, 1H), 7.57 (dd, J=9.8, 2.7 Hz, 1H), 7.51 (d, J=8.2 Hz, 2H), 7.34 (d, J=7.8 Hz, 2H), 7.15 (td, J=7.6, 2.8 Hz, 1H), 6.96 (d, J=1.2 Hz, 1H), 4.55 (d, J=5.8 Hz, 2H), 3.84 (s, 3H).

6-{7-fluoroimidazo[1,2-a]pyridin-3-yl}-N-{[4-(2-methyl-2H-1,2,3-triazol-4-yl)phenyl]methyl}pyrimidin-4-amine (H2)

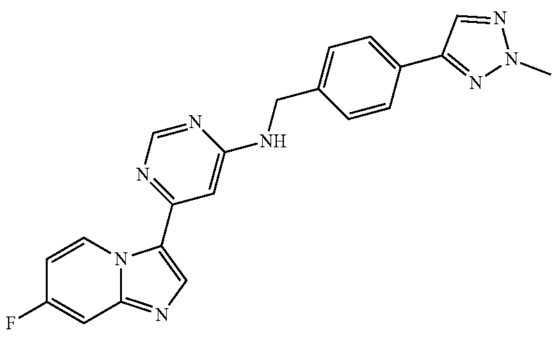 [SMILES: Cn1ncc(-c2ccc(CNc3cc(-c4cnc5cc(F)ccn45)ncn3)cc2)n1]

The compound is prepared similarly to H1; off-white powder; UPLC/MS 0.574 min, $[M+H]^+$ 401.

$^{1}$H NMR (700 MHz, DMSO-$d_6$) δ 9.90 (t, J=6.9 Hz, 1H), 8.55 (s, 1H), 8.29 (s, 1H), 8.16 (s, 1H), 7.95 (t, J=6.2 Hz, 1H), 7.79 (d, J=8.2 Hz, 2H), 7.56 (dd, J=9.8, 2.7 Hz, 1H), 7.44 (d, J=7.8 Hz, 2H), 7.15 (td, J=7.6, 2.7 Hz, 1H), 6.97 (d, J=1.2 Hz, 1H), 4.61 (d, J=6.0 Hz, 2H), 4.17 (s, 3H).

6-{7-fluoroimidazo[1,2-a]pyridin-3-yl}-N-{[4-(1-methyl-1H-1,2,3-triazol-4-yl)phenyl]methyl}pyrimidin-4-amine (H3)

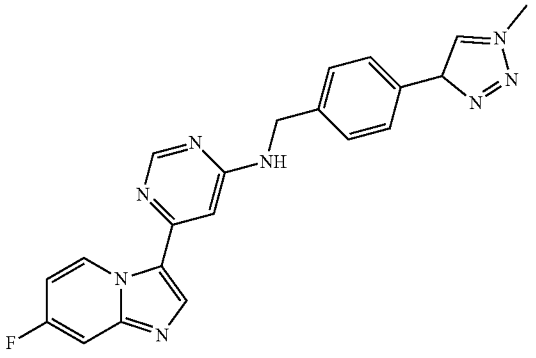

The compound is prepared analogously to H1; brown solid; HPLC/MS $[M+H]^+$ 401.

6-{7-fluoroimidazo[1,2-a]pyridin-3-yl}-N-{[4-(2-methyl-1,3-oxazol-4-yl)phenyl]methyl}pyrimidin-4-amine (H4)

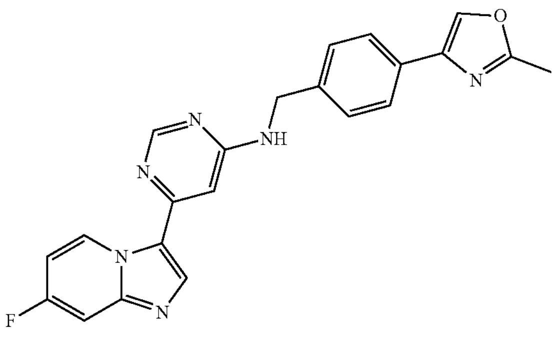 [SMILES: Cc1nc(-c2ccc(CNc3cc(-c4cnc5cc(F)ccn45)ncn3)cc2)co1]

The compound is prepared from the intermediate D22 analogously to the alternative synthesis of H1; yellow solid; HPLC/MS $[M+H]^+$ 401.

6-{7-fluoroimidazo[1,2-a]pyridin-3-yl}-N-{1-[4-(1-methyl-1H-pyrazol-4-yl)phenyl]ethyl}pyrimidin-4-amine (H5)

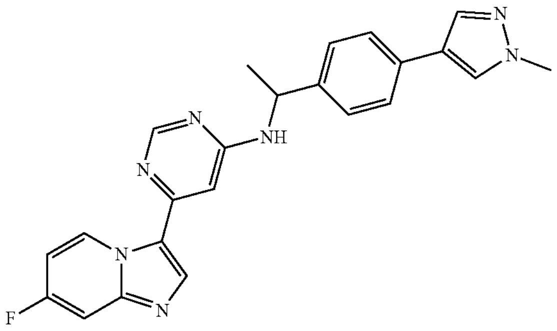 [SMILES: CC(Nc1cc(-c2cnc3cc(F)ccn23)ncn1)c1ccc(-c2cnn(C)c2)cc1]

The compound is prepared from G6 analogously to H1; brown oil; HPLC/MS $[M+H]^+$ 414.

6-{7-fluoroimidazo[1,2-a]pyridin-3-yl}-N-{[4-(1,3-oxazol-4-yl)phenyl]methyl}pyrimidin-4-amine (H6)

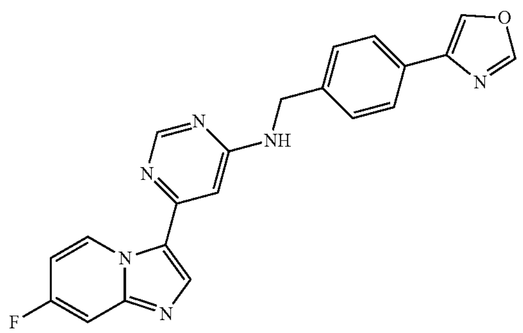 [SMILES: Fc1ccn2c(-c3cc(NCc4ccc(-c5cocn5)cc4)ncn3)cnc2c1]

The compound is prepared from the intermediate D29 analogously to the alternative synthesis of H1; brown solid; HPLC/MS $[M+H]^+$ 387.

6-{7-fluoroimidazo[1,2-a]pyridin-3-yl}-N-{[4-(trifluoromethoxy)phenyl]methyl}pyrimidin-4-amine (H7)

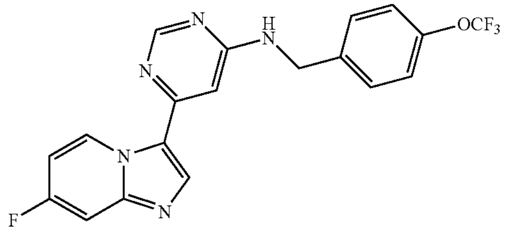 [SMILES: Fc1ccn2c(-c3cc(NCc4ccc(OC(F)(F)F)cc4)ncn3)cnc2c1]

The compound is prepared from [4-(trifluoromethoxy)phenyl]methanamine analogously to the alternative synthesis of H1; brown solid; HPLC/MS $[M+H]^+$ 404.

Alternative Synthesis of Fluoroimidazopyridines

6-{7-fluoroimidazo[1,2-a]pyridin-3-yl}-N-{[4-(1-methyl-1H-pyrazol-4-yl)phenyl]methyl}pyrimidin-4-amine ("H1")

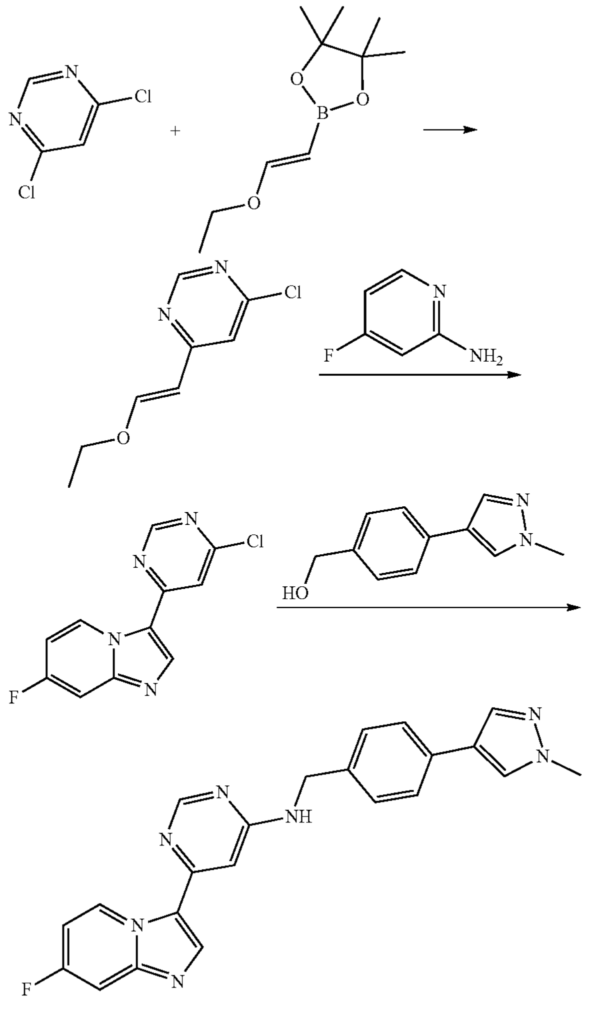

To a solution of 4,6-dichloropyrimidine (9.87 g, 66.3 mmol) and 2-[(E)-2-ethoxyethenyl]-4,4,5,5-tetramethyl-1,3,2-dioxaborolane (12.5 g, 63.1 mmol) in dioxane (90 ml) are added water (10 ml) and tripotassium phosphate (26.8 g, 126 mmol). Argon is bubbled through the mixture and tetrakis (triphenylphosphine)palladium (3.65 g, 3.16 mmol) is added. The mixture is heated to 80° C. and stirred at this temperature under an argon atmosphere for three hours. The reaction mixture is allowed to reach room temperature and concentrated under vacuum. The residue is partitioned between water and dichloromethane. The combined organic phases are dried over sodium sulfate and evaporated. The residue is chromatographed on a silica gel column with cyclohexane/ethyl acetate as eluent to afford 4-chloro-6-[(E)-2-ethoxyethenyl]pyrimidine as off-white crystalline solid; UPLC/MS 0.645 min, $[M+H]^+$ 185.

$^1$H NMR (400 MHz, DMSO-$d_6$) δ 8.73 (d, J=1.0 Hz, 1H), 7.97 (d, J=12.5 Hz, 1H), 7.48 (d, J=1.0 Hz, 1H), 5.89 (d, J=12.5 Hz, 1H), 4.05 (q, J=7.0 Hz, 3H), 1.29 (t, J=7.0 Hz, 4H).

To a solution of 4-chloro-6-[(E)-2-ethoxyethenyl]pyrimidine (9.70 g, 52.5 mmol) in dioxane (375 ml) are added water (125 ml) and N-bromosuccinimide (8.88 g, 49.9 mmol). The mixture is stirred for 1 hour at room temperature. Then, 4-fluoropyridin-2-amine (7.07 g, 63.1 mmol) is added. The reaction mixture is heated to 60° C. and stirred at this temperature for 2 hours. The reaction mixture is allowed to reach room temperature and saturated sodium carbonate solution is added to reach a pH value of 9. The mixture is concentrated under vacuum. The solids are filtered off, washed with water and dried under vacuum. The residue is triturated with a small amount of acetonitrile and a small amount of tert-butyl methyl ether to afford 4-chloro-6-{7-fluoroimidazo[1,2-a]pyridin-3-yl}pyrimidine as brown powder; UPLC/MS 0.577 min, $[M+H]^+$ 249.

$^1$H NMR (400 MHz, DMSO-$d_6$) δ 9.96 (ddd, J=7.8, 6.0, 0.8 Hz, 1H), 9.05 (d, J=1.1 Hz, 1H), 8.81 (s, 1H), 8.32 (d, J=1.2 Hz, 1H), 7.73 (ddd, J=9.7, 2.8, 0.7 Hz, 1H), 7.32 (td, J=7.6, 2.8 Hz, 1H).

To a solution of 4-chloro-6-{7-fluoroimidazo[1,2-a]pyridin-3-yl}pyrimidine (497 mg, 2.00 mmol) and 1-[4-(1-methyl-1H-pyrazol-4-yl)phenyl]methanamine (D1, 497 mg, 2.00 mmol) in N,N-dimethylacetamide (4 ml) is added potassium carbonate (553 mg, 4.00 mmol) and the resultant mixture is heated for 16 hours at 80° C. The reaction mixture is allowed to reach room temperature and water is added. The resultant precipitate is filtered off, washed with water and dried under vacuum. The residue is chromatographed on a silica gel column with dichlormethane/methanol as eluent to afford 6-{7-fluoroimidazo[1,2-a]pyridin-3-yl}-N-{[4-(1-methyl-1H-pyrazol-4-yl)phenyl]methyl}pyrimidin-4-amine as pale yellow crystalline solid; HPLC/MS(B) 0.794 min, $[M+H]^+$ 400.

Example 1

Synthesis of [6-(7-methoxy-imidazo[1,2-a]pyridin-3-yl)-pyrimidin-4-yl]-[4-(1-methyl-1H-pyrazol-4-yl)-benzyl]-amine ("A1")

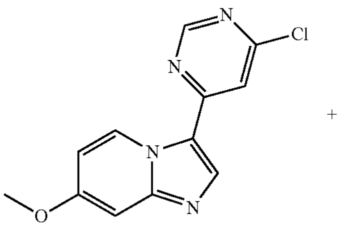

-continued

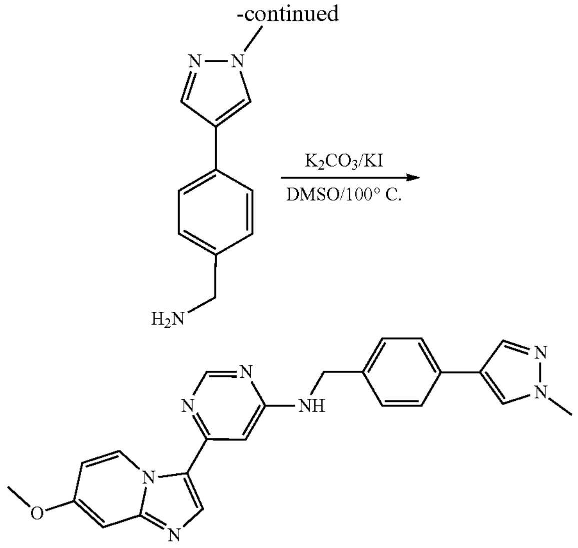

To a solution of 4-chloro-6-{7-methoxyimidazo[1,2-a]pyridin-3-yl}pyrimidine (F1) (75.6 mg, 0.29 mmol) and 1-[4-(1-methyl-1H-pyrazol-4-yl)phenyl]methanamine (D1) (56 mg, 0.30 mmol) in dimethylsulfoxide (1.3 ml) are added potassium carbonate (81 mg, 0.59 mmol) and potassium iodide (5.0 mg, 30 μmol). The mixture is heated to 100° C. and stirred at this temperature for 18 hours; The reaction mixture is allowed to reach room temperature and treated with excess water. The resultant precipitate is filtered off and washed with water. The residue is chromatographed on a silica gel column with methanol/dichloromethane as eluent to afford [6-(7-methoxy-imidazo[1,2-a]pyridin-3-yl)-pyrimidin-4-yl]-[4-(1-methyl-1H-pyrazol-4-yl)-benzyl]-amine as pale yellow powder; HPLC/MS(A) 1.23 min, $[M+H]^+$ 412.

$^1$H NMR (400 MHz, DMSO-$d_6$) δ 9.69 (d, J=7.7 Hz, 1H), 8.51 (s, 1H), 8.14 (s, 1H), 8.07 (s, 1H), 7.84 (t, J=6.4 Hz, 1H), 7.81 (d, J=0.8 Hz, 1H), 7.51 (d, J=8.2 Hz, 2H), 7.34 (d, J=8.0 Hz, 2H), 7.08 (d, J=2.6 Hz, 1H), 6.89 (d, J=1.3 Hz, 1H), 6.80 (dd, J=7.7, 2.7 Hz, 1H), 4.54 (d, J=6.1 Hz, 2H), 3.87 (s, 3H), 3.84 (s, 3H).

The following compounds are prepared analogously:

N-({[1,1'-biphenyl]-4-yl}methyl)-6-[7-(2-methoxy-ethoxy)imidazo[1,2-a]pyridin-3-yl]pyrimidin-4-amine ("A2")

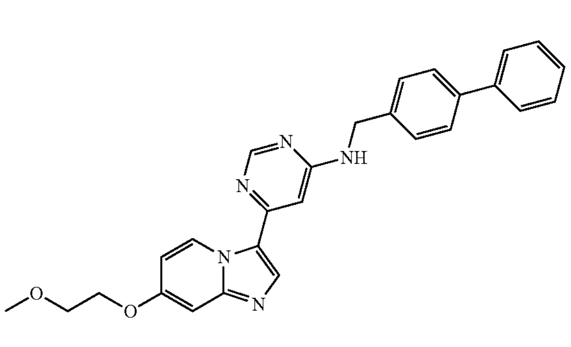 [SMILES: COCCOc1ccn2c(-c3cc(NCc4ccc(-c5ccccc5)cc4)ncn3)cnc2c1]

from F2; pale brown powder; HPLC/MS (A) 1.99 min, $[M+H]^+$ 452.

$^1$H NMR (500 MHz, DMSO-$d_6$) δ 9.71 (d, J=7.7 Hz, 1H), 8.53 (s, 1H), 8.17 (s, 1H), 7.94 (t, J=6.2 Hz, 1H), 7.69-7.56 (m, 4H), 7.45 (t, J=7.7 Hz, 4H), 7.40-7.31 (m, 1H), 7.10 (d, J=2.6 Hz, 1H), 6.92 (d, J=1.3 Hz, 1H), 6.83 (dd, J=7.7, 2.6 Hz, 1H), 4.62 (s, 2H), 4.28-4.19 (m, 2H), 3.78-3.68 (m, 2H), 3.33 (s, 3H).

N-({[1,1'-biphenyl]-4-yl}methyl)-6-{7-methoxyimidazo[1,2-a]pyridin-3-yl}pyrimidin-4-amine ("A3")

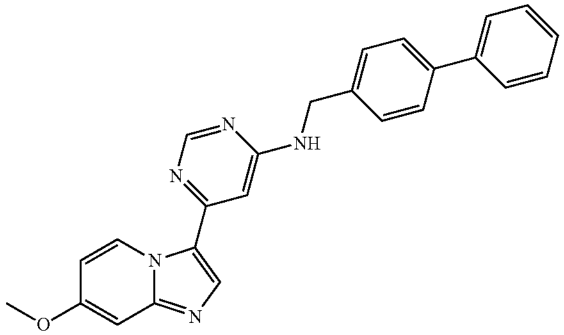 [SMILES: COc1ccn2c(-c3cc(NCc4ccc(-c5ccccc5)cc4)ncn3)cnc2c1]

from F1; off-white crystals; HPLC/MS (A) 1.55 min, $[M+H]^+$ 408.

$^1$H NMR (400 MHz, DMSO-$d_6$) δ 9.69 (d, J=7.7 Hz, 1H), 8.52 (s, 1H), 8.16 (s, 1H), 7.91 (t, J=6.2 Hz, 1H), 7.69-7.61 (m, 5H), 7.52-7.40 (m, 7H), 7.40-7.28 (m, 2H), 7.08 (d, J=2.6 Hz, 1H), 6.91 (d, J=1.2 Hz, 1H), 6.80 (dd, J=7.7, 2.7 Hz, 1H), 4.61 (d, J=6.0 Hz, 2H), 3.87 (s, 3H).

6-[7-(2-methoxyethoxy)imidazo[1,2-a]pyridin-3-yl]-N-{[4-(1-methyl-1H-pyrazol-4-yl)phenyl]methyl}pyrimidin-4-amine ("A4")

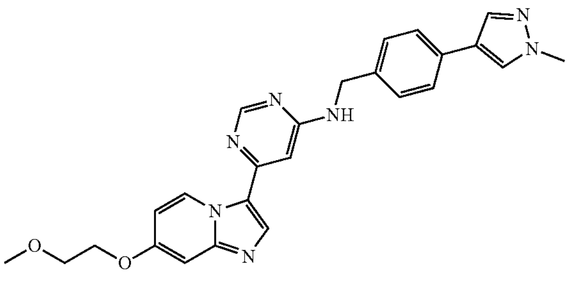

from D1 and F2; pale yellow solid; HPLC/MS (A) 1.30 min, $[M+H]^+$ 456.

$^1$H NMR (400 MHz, DMSO-$d_6$) δ 9.70 (d, J=7.7 Hz, 1H), 8.51 (s, 1H), 8.14 (s, 1H), 8.07 (d, J=0.8 Hz, 1H), 7.84 (t, J=6.3 Hz, 1H), 7.81 (d, J=0.8 Hz, 1H), 7.51 (d, J=8.2 Hz, 2H), 7.34 (d, J=7.9 Hz, 2H), 7.09 (d, J=2.6 Hz, 1H), 6.89 (d, J=1.2 Hz, 1H), 6.82 (dd, J=7.7, 2.6 Hz, 1H), 4.54 (d, J=6.0 Hz, 2H), 4.29-4.17 (m, 2H), 3.84 (s, 3H), 3.73-3.67 (m, 2H), 3.32 (s, 3H).

6-[7-(2-methoxyethoxy)imidazo[1,2-a]pyridin-3-yl]-N-{[4-(pyridin-3-yl)phenyl]methyl}pyrimidin-4-amine ("A5")

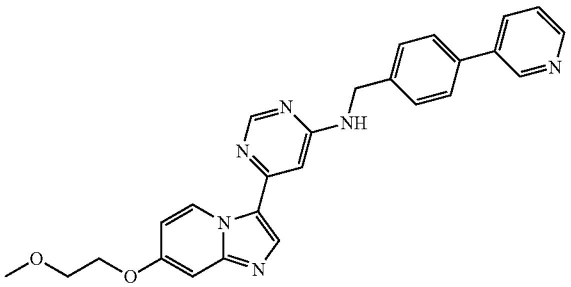 [SMILES: COCCOc1ccn2c(-c3cc(NCc4ccc(-c5cccnc5)cc4)ncn3)cnc2c1]

from F2; pale yellow solid; HPLC/MS (A) 1.15 min, ([M+2H]$^{2+}$)/2 227.

$^1$H NMR (500 MHz, DMSO-d$_6$) δ 9.70 (d, J=7.7 Hz, 1H), 8.87 (dd, J=2.5, 0.9 Hz, 1H), 8.55 (dd, J=4.8, 1.6 Hz, 1H), 8.52 (s, 1H), 8.16 (s, 1H), 8.07-8.01 (m, 1H), 7.93 (t, J=6.2 Hz, 1H), 7.70 (d, J=8.2 Hz, 2H), 7.54-7.44 (m, 3H), 7.09 (d, J=2.6 Hz, 1H), 6.92 (d, J=1.3 Hz, 1H), 6.82 (dd, J=7.7, 2.6 Hz, 1H), 4.62 (d, J=6.0 Hz, 2H), 4.26-4.12 (m, 2H), 3.80-3.67 (m, 2H), 3.33 (s, 3H).

6-{7-methoxyimidazo[1,2-a]pyridin-3-yl}-N-{[4-(pyridin-3-yl)phenyl]methyl}pyrimidin-4-amine ("A6")

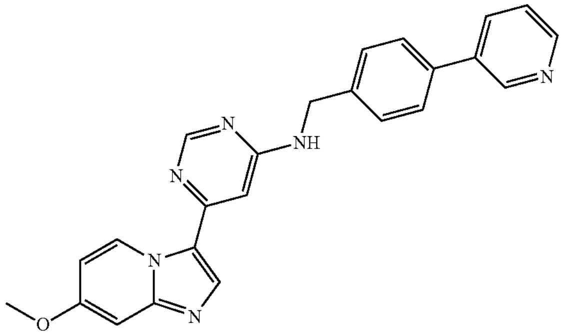 [SMILES: COc1ccn2c(-c3cc(NCc4ccc(-c5cccnc5)cc4)ncn3)cnc2c1]

from F1; off-white solid; HPLC/MS (A) 1.06 min, [M+H]$^+$ 409.

$^1$H NMR (500 MHz, DMSO-d$_6$) δ 9.69 (d, J=7.7 Hz, 1H), 8.87 (dd, J=2.5, 0.9 Hz, 1H), 8.55 (dd, J=4.8, 1.6 Hz, 1H), 8.52 (s, 1H), 8.16 (s, 1H), 8.05 (ddd, J=7.9, 2.5, 1.7 Hz, 1H), 7.93 (t, J=6.2 Hz, 1H), 7.70 (d, J=8.2 Hz, 2H), 7.56-7.43 (m, 3H), 7.08 (d, J=2.6 Hz, 1H), 6.92 (d, J=1.2 Hz, 1H), 6.80 (dd, J=7.7, 2.6 Hz, 1H), 4.62 (d, J=5.9 Hz, 2H), 3.87 (s, 3H).

6-[7-(2-methoxyethoxy)imidazo[1,2-a]pyridin-3-yl]-N-{[4-(1-methyl-1H-pyrazol-3-yl)phenyl]methyl}pyrimidin-4-amine ("A7")

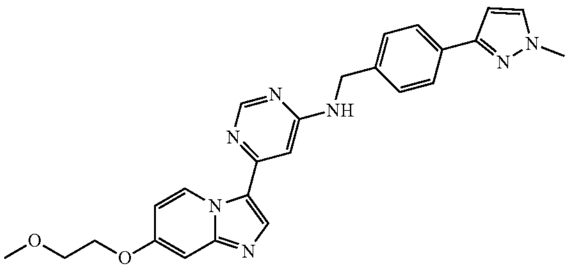

(from F2); pale yellow solid; HPLC/MS (A) 1.06 min, [M+H]$^+$ 456.

$^1$H NMR (500 MHz, DMSO-d$_6$) δ 9.76-9.63 (m, 1H), 8.51 (s, 1H), 8.14 (s, 1H), 7.87 (t, J=6.1 Hz, 1H), 7.74 (d, J=8.3 Hz, 2H), 7.69 (d, J=2.3 Hz, 1H), 7.37 (d, J=7.8 Hz, 2H), 7.14-7.08 (m, 1H), 6.90 (d, J=1.3 Hz, 1H), 6.82 (dd, J=7.7, 2.6 Hz, 1H), 6.64 (d, J=2.2 Hz, 1H), 4.57 (d, J=5.9 Hz, 2H), 4.32-4.16 (m, 2H), 3.86 (s, 3H), 3.77-3.64 (m, 2H), 3.33 (s, 3H).

(6-imidazo[1,2-a]pyridin-3-yl-pyrimidin-4-yl)-(4-imidazol-1-yl-benzyl)-amine ("A8")

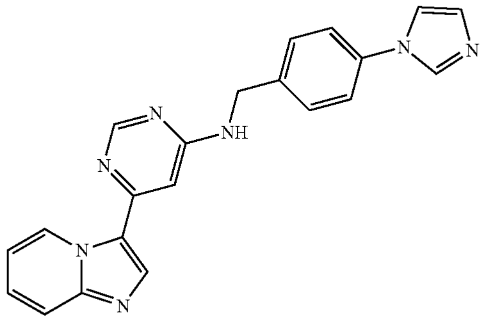 [SMILES: c1ccn2c(-c3cc(NCc4ccc(-n5ccnc5)cc4)ncn3)cnc2c1]

from F3; off-white solid; HPLC/MS [M+H]$^+$ 368.

(6-imidazo[1,2-a]pyridin-3-yl-pyrimidin-4-yl)-(4-pyrazol-1-yl-benzyl)-amine ("A9")

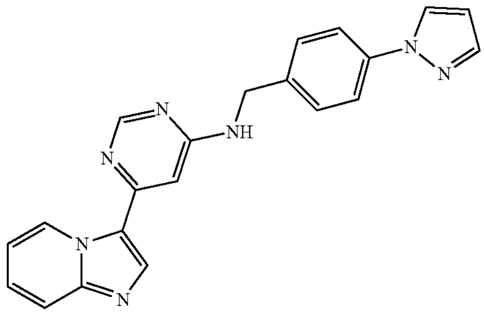 [SMILES: c1ccn2c(-c3cc(NCc4ccc(-n5cccn5)cc4)ncn3)cnc2c1]

from F3; off-white solid; m.p. 217-219° C.; HPLC/MS [M+H]$^+$ 368.

$^1$H NMR (400 MHz, DMSO-$d_6$,): δ 9.86 (d, J=7.0 Hz, 1H), 8.57 (s, 1H), 8.46 (d, J=2.5 Hz, 1H), 8.32 (s, 1H), 8.01 (m, 1H), 7.85-7.77 (m, 2H), 7.75-7.68 (m, 2H), 7.49 (d, J=8.1 Hz, 2H), 7.42 (m, 1H), 7.10 (m, 1H), 7.00 (d, J=1.3 Hz, 1H), 6.53 (m, 1H), 4.62 (s, 2H).

N-{[4-(1-methyl-1H-pyrazol-4-yl)phenyl]methyl}-6-[7-(trifluoromethyl)imidazo[1,2-a]pyridin-3-yl]pyrimidin-4-amine ("A10")

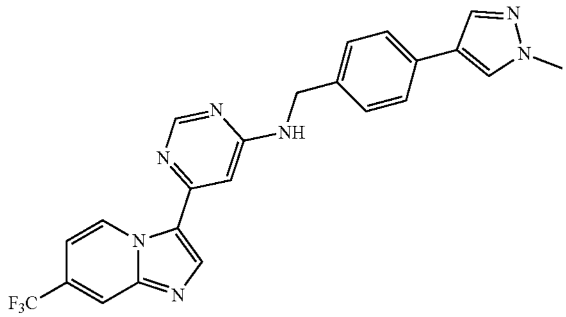 [SMILES: Cn1cc(-c2ccc(CNc3cc(-c4cnc5cc(C(F)(F)F)ccn45)ncn3)cc2)cn1]

from F4 and D1; white solid; HPLC/MS (A) 1.64 min, $[M+H]^+$ 450.

$^1$H NMR (400 MHz, DMSO-$d_6$) δ 10.01 (d, J=7.4 Hz, 1H), 8.60 (s, 1H), 8.49 (s, 1H), 8.19 (s, 1H), 8.08 (s, 1H), 8.02 (t, J=6.1 Hz, 1H), 7.81 (s, 1H), 7.52 (d, J=8.2 Hz, 2H), 7.41-7.32 (m, 3H), 7.05 (d, J=1.3 Hz, 1H), 4.60-4.52 (m, 2H), 3.85 (s, 3H).

6-[7-(2-methoxyethoxy)imidazo[1,2-a]pyridin-3-yl]-N-{[6-(1-methyl-1H-pyrazol-4-yl)pyridin-3-yl]methyl}pyrimidin-4-amine ("A11")

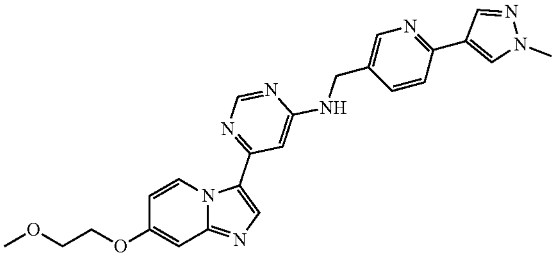

from F2; off-white powder; HPLC/MS (A) 1.02 min, $[M+H]^+$ 457.

$^1$H NMR (400 MHz, DMSO-$d_6$) δ 9.71 (d, J=7.8 Hz, 1H), 8.56-8.49 (m, 2H), 8.22 (s, 1H), 8.19 (s, 1H), 7.94 (d, J=0.7 Hz, 1H), 7.88 (t, J=6.1 Hz, 1H), 7.73 (dd, J=8.2, 2.2 Hz, 1H), 7.59 (dd, J=8.1, 0.9 Hz, 1H), 7.10 (d, J=2.6 Hz, 1H), 6.91 (d, J=1.3 Hz, 1H), 6.83 (dd, J=7.7, 2.6 Hz, 1H), 4.55 (d, J=6.0 Hz, 2H), 4.28-4.16 (m, 2H), 3.87 (s, 3H), 3.78-3.64 (m, 2H).

1-(4-{[(6-{7-methoxyimidazo[1,2-a]pyridin-3-yl}pyrimidin-4-yl)amino]methyl}phenyl)piperidin-2-one ("A12")

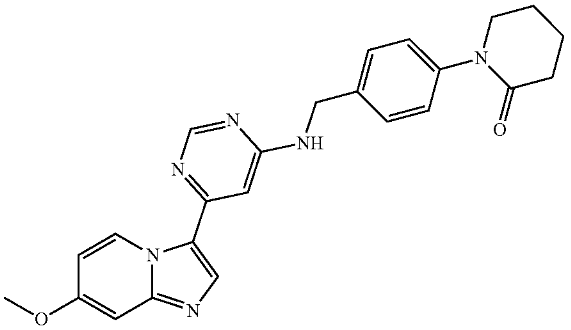 [SMILES: COc1ccn2c(-c3cc(NCc4ccc(N5CCCCC5=O)cc4)ncn3)cnc2c1]

from F1; pale brown powder; HPLC/MS (A) 1.18 min, $[M+H]^+$ 429.

$^1$H NMR (400 MHz, DMSO-$d_6$) δ 9.69 (d, J=7.7 Hz, 1H), 8.51 (s, 1H), 8.14 (s, 1H), 7.87 (t, J=6.1 Hz, 1H), 7.35 (d, J=8.1 Hz, 2H), 7.27-7.16 (m, 2H), 7.08 (d, J=2.6 Hz, 1H), 6.90 (d, J=1.3 Hz, 1H), 6.80 (dd, J=7.7, 2.6 Hz, 1H), 4.61-4.46 (m, 2H), 3.87 (s, 3H), 3.63-3.49 (m, 2H), 2.36 (t, J=6.3 Hz, 2H), 1.89-1.77 (m, 4H).

4-{[(6-{7-methoxyimidazo[1,2-a]pyridin-3-yl}pyrimidin-4-yl)amino]methyl}-N,N-dimethylbenzamide ("A13")

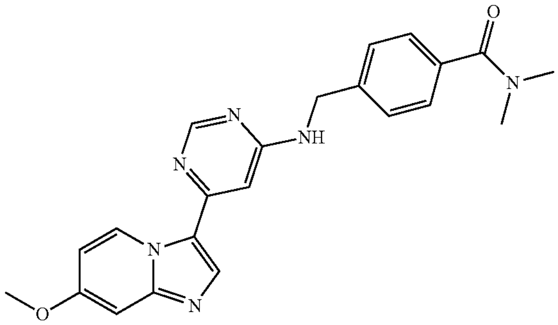

from F1; off-white solid; HPLC/MS (A) 1.19 min, $[M+H]^+$ 403.

$^1$H NMR (400 MHz, DMSO-$d_6$) δ 9.79 (d, J=7.6 Hz, 1H), 8.59 (s, 1H), 8.20 (t, J=6.2 Hz, 1H), 7.45-7.31 (m, 4H), 7.26 (d, J=2.6 Hz, 1H), 7.15 (dd, J=7.7, 2.6 Hz, 1H), 7.00 (s, 1H), 4.63 (s, 2H), 3.98 (s, 3H), 2.96 (s, 3H), 2.90 (s, 3H).

(6-imidazo[1,2-a]pyridin-3-yl-pyrimidin-4-yl)-[4-(1-methyl-1H-pyrazol-3-yl)-benzyl]-amine ("A14")

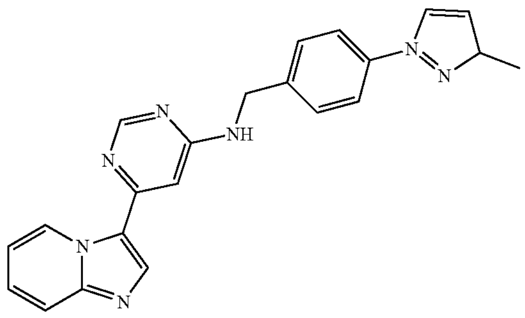

from F3; white solid; m.p. 165-166° C.; HPLC/MS $[M+H]^+$ 382.

$^1$H NMR (300 MHz, DMSO-$d_6$) δ 9.83 (d, J=7.0 Hz, 1H), 8.54 (s, 1H), 8.28 (s, 1H), 7.99-7.92 (m, 1H), 7.86-7.66 (m, 5H), 7.37 (dd, J=7.5, 5.0 Hz, 2H), 7.07 (t, J=6.8 Hz, 1H), 6.96 (d, J=1.3 Hz, 1H), 6.63 (d, J=2.3 Hz, 1H), 4.57 (s, 2H), 3.84 (s, 3H).

[4-(4,5-dihydro-1H-imidazol-2-yl)-benzyl]-(6-imidazo[1,2-a]pyridin-3-yl-pyrimidin-4-yl)-amine ("A15")

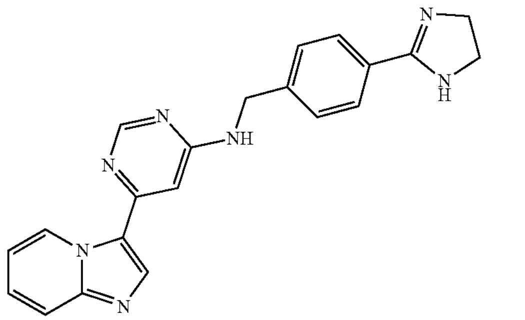 [SMILES: c1ccn2c(-c3cc(NCc4ccc(C5=NCCN5)cc4)ncn3)cnc2c1]

from F3; white solid; HPLC/MS $[M+H]^+$ 370.

6-[7-(2-methoxyethoxy)imidazo[1,2-a]pyridin-3-yl]-N-{[4-(1H-1,2,3-triazol-1-yl)phenyl]methyl}pyrimidin-4-amine ("A16")

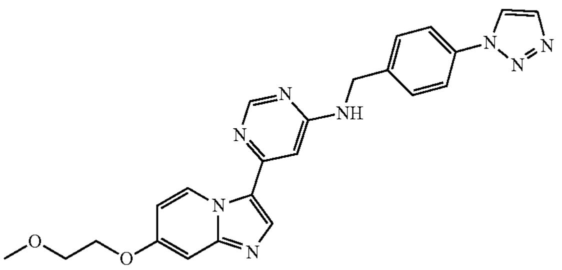 [SMILES: COCCOc1ccn2c(-c3cc(NCc4ccc(-n5ccnn5)cc4)ncn3)cnc2c1]

from F2; pale yellow solid; HPLC/MS (A) 1.17 min, $[M+H]^+$ 443.

$^1$H NMR (400 MHz, DMSO-$d_6$) δ 9.71 (d, J=7.7 Hz, 1H), 8.79 (d, J=1.3 Hz, 1H), 8.52 (s, 1H), 8.18 (s, 1H), 8.00 (t, J=6.2 Hz, 1H), 7.96 (d, J=1.1 Hz, 1H), 7.92-7.70 (m, 2H), 7.66-7.51 (m, 2H), 7.10 (d, J=2.6 Hz, 1H), 6.93 (d, J=1.3 Hz, 1H), 6.83 (dd, J=7.8, 2.6 Hz, 1H), 4.64 (d, J=5.9 Hz, 2H), 4.32-4.14 (m, 2H), 3.87-3.51 (m, 2H), 3.32 (s, 3H).

6-[7-(2-methoxyethoxy)imidazo[1,2-a]pyridin-3-yl]-N-[(4-{4H,5H,6H-pyrrolo[1,2-b]pyrazol-3-yl}phenyl)methyl]pyrimidin-4-amine ("A17")

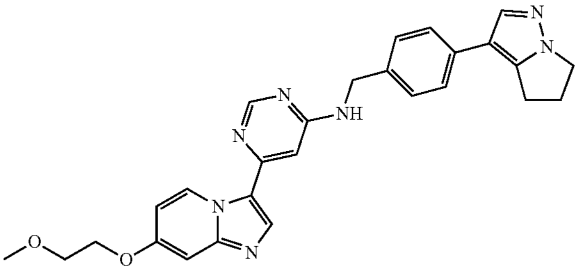 [SMILES: COCCOc1ccn2c(-c3cc(NCc4ccc(-c5cnn6c5CCC6)cc4)ncn3)cnc2c1]

from F2 and D3; pale yellow solid; HPLC/MS (A) 1.29 min, $[M+H]^+$ 482.

$^1$H NMR (400 MHz, DMSO-$d_6$) δ 9.70 (d, J=7.7 Hz, 1H), 8.51 (s, 1H), 8.16 (s, 1H), 7.89 (t, J=6.2 Hz, 1H), 7.84 (s, 1H), 7.52-7.43 (m, 2H), 7.35 (d, J=7.8 Hz, 2H), 7.10 (d, J=2.6 Hz, 1H), 6.89 (d, J=1.3 Hz, 1H), 6.83 (dd, J=7.7, 2.6 Hz, 1H), 4.54 (s, 2H), 4.24-4.18 (m, 2H), 4.07 (t, J=7.3 Hz, 2H), 3.76-3.61 (m, 2H), 3.32 (s, 3H), 3.04 (t, J=7.3 Hz, 2H).

6-{7-methoxyimidazo[1,2-a]pyridin-3-yl}-N-{[4-(1H-1,2,3-triazol-1-yl)phenyl]methyl}pyrimidin-4-amine ("A18")

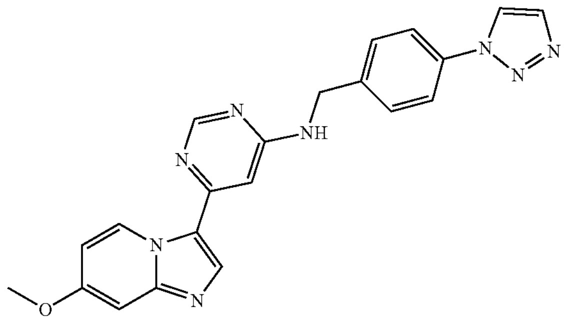 [SMILES: COc1ccn2c(-c3cc(NCc4ccc(-n5ccnn5)cc4)ncn3)cnc2c1]

from F1; pale brown solid; HPLC/MS (A) 1.18 min, $[M+H]^+$ 399.

$^1$H NMR (400 MHz, DMSO-$d_6$) δ 9.70 (d, J=7.7 Hz, 1H), 8.79 (d, J=1.2 Hz, 1H), 8.52 (s, 1H), 8.18 (s, 1H), 8.00 (t, J=6.3 Hz, 1H), 7.96 (d, J=1.2 Hz, 1H), 7.87 (d, J=8.5 Hz, 2H), 7.58 (d, J=8.1 Hz, 2H), 7.09 (d, J=2.6 Hz, 1H), 6.93 (d, J=1.3 Hz, 1H), 6.81 (dd, J=7.7, 2.7 Hz, 1H), 4.65 (s, 2H), 3.87 (s, 3H).

{4-[1-(2-methoxy-ethyl)-1H-pyrazol-4-yl]-benzyl}-[6-(7-methoxy-imidazo[1,2-a]pyridin-3-yl)-pyrimidin-4-yl]-amine ("A19")

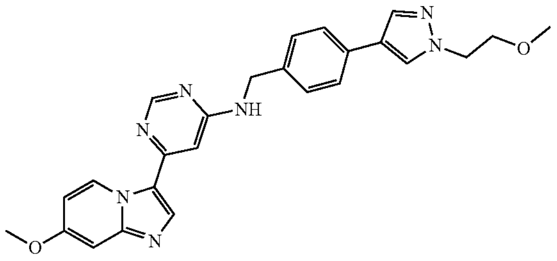

from F1 and D4; off-white solid; m.p. 212-213° C.; HPLC/MS $[M+H]^+$ 456.

$^1$H NMR (400 MHz, DMSO-$d_6$) δ 9.70 (d, J=7.8 Hz, 1H), 8.51 (s, 1H), 8.12 (s, 1H), 7.86 (s, 1H), 7.92-7.82 (m, 2H), 7.53 (d, J=8.2 Hz, 2H), 7.34 (d, J=8.0 Hz, 2H), 7.08 (d, J=2.6 Hz, 1H), 6.89 (d, J=1.2 Hz, 1H), 6.80 (d, J=2.7 Hz, 1H), 4.54 (s, 2H), 4.25 (t, J=5.3 Hz, 2H), 3.87 (s, 3H), 3.70 (t, J=5.3 Hz, 2H), 3.24 (s, 3H).

[6-(7-methoxy-imidazo[1,2-a]pyridin-3-yl)-pyrimidin-4-yl]-[4-(1-methyl-1H-imidazol-4-yl)-benzyl]-amine ("A20")

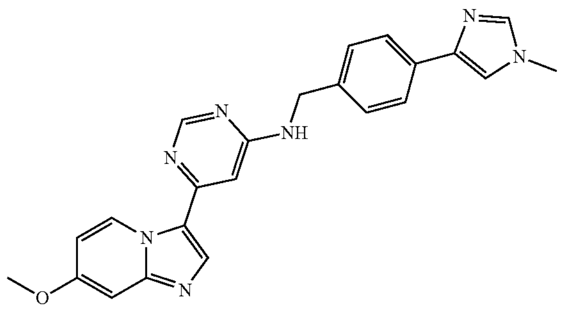

from F1 and D5; pale yellow solid; m.p. 234-235° C.; HPLC/MS $[M+H]^+$ 412.

$^1$H NMR (400 MHz, DMSO-$d_6$) δ 9.69 (d, J=7.7 Hz, 1H), 8.51 (s, 1H), 8.15 (s, 1H), 7.87 (t, J=5.6 Hz, 1H), 7.69 (d, J=8.4 Hz, 2H), 7.60 (s, 1H), 7.55 (s, 1H), 7.33 (d, J=8.4 Hz, 2H), 7.08 (d, J=2.4 Hz, 1H), 6.89 (s, 1H), 6.80 (dd, J=7.6, 2.4 Hz, 1H), 4.55 (s, 2H), 3.87 (s, 3H), 3.67 (s, 3H).

[4-(1-cyclopropylmethyl-1H-pyrazol-4-yl)-benzyl]-[6-(7-methoxy-imidazo[1,2-a]pyridin-3-yl)-pyrimidin-4-yl]-amine ("A21")

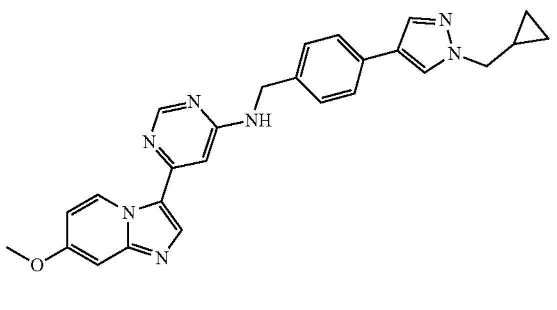 [SMILES: COc1ccn2c(-c3cc(NCc4ccc(-c5cnn(CC6CC6)c5)cc4)ncn3)cnc2c1]

from F1 and D6; white solid; m.p. 248-249° C.; HPLC/MS $[M+H]^+$ 452.

$^1$H NMR (400 MHz, DMSO-$d_6$) δ 9.70 (d, J=7.6 Hz, 1H), 8.51 (s, 1H), 8.16 (s, 2H), 7.88 (t, J=6.1 Hz, 1H), 7.83 (s, 1H), 7.53 (d, J=8.4 Hz, 2H), 7.35 (d, J=7.6 Hz, 2H), 7.08 (d, J=2.4 Hz, 1H), 6.90 (d, J=0.8 Hz, 1H), 6.80 (dd, J=6.4, 2.8 Hz, 1H), 4.54 (s, 2H), 3.96 (d, J=7.2 Hz, 2H), 3.87 (s, 3H), 1.29-1.21 (m, 1H), 0.55-0.51 (m, 2H), 0.37-0.34 (m, 2H).

[6-(7-methoxy-imidazo[1,2-a]pyridin-3-yl)-pyrimidin-4-yl]-{4-[1-(2-morpholin-4-yl-ethyl)-1H-pyrazol-4-yl]-benzyl}-amine ("A22")

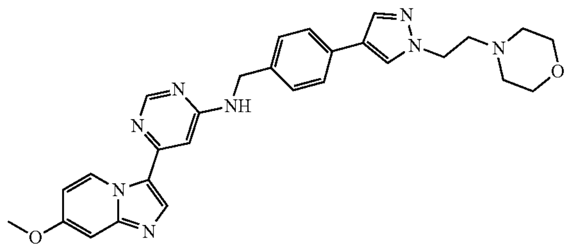 [SMILES: COc1ccn2c(-c3cc(NCc4ccc(-c5cnn(CCN6CCOCC6)c5)cc4)ncn3)cnc2c1]

from F1 and D7; white solid; m.p. 217-218° C.; HPLC/MS $[M+H]^+$ 511.

$^1$H NMR (400 MHz, DMSO-$d_6$) δ 9.69 (d, J=7.7 Hz, 1H), 8.51 (s, 1H), 8.14 (d, J=0.8 Hz, 1H), 7.87 (t, J=6.1 Hz, 1H), 7.83 (d, J=0.8 Hz, 1H), 7.52 (d, J=8.2 Hz, 2H), 7.35 (d, J=7.8 Hz, 2H), 7.08 (d, J=2.6 Hz, 1H), 6.89 (d, J=1.2 Hz, 1H), 6.80 (dd, J=7.7, 2.7 Hz, 1H), 4.54 (s, 2H), 4.22 (t, J=6.6 Hz, 2H), 3.87 (s, 3H), 3.57-3.50 (m, 4H), 2.72 (t, J=6.6 Hz, 2H), 2.40 (t, J=4.6 Hz, 4H).

[4-(1-ethyl-1H-pyrazol-4-yl)-benzyl]-[6-(7-methoxy-imidazo[1,2-a]pyridin-3-yl)-pyrimidin-4-yl]-amine ("A23")

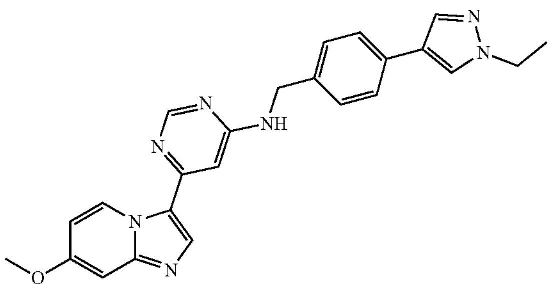 [SMILES: CCn1cc(-c2ccc(CNc3cc(-c4cnc5cc(OC)ccn45)ncn3)cc2)cn1]

from F1; pale yellow solid; m.p. 251-252° C.; HPLC/MS $[M+H]^+$ 426.

$^1$H NMR (400 MHz, DMSO-$d_6$) δ 9.70 (d, J=7.7 Hz, 1H), 8.52 (s, 1H), 8.15 (d, J=0.8 Hz, 2H), 7.89 (t, J=6.1 Hz, 1H), 7.83 (d, J=0.8 Hz, 1H), 7.58-7.47 (m, 2H), 7.35 (d, J=7.8 Hz, 2H), 7.09 (d, J=2.6 Hz, 1H), 6.90 (d, J=1.2 Hz, 1H), 6.85-6.77 (m, 1H), 4.64-4.52 (m, 2H), 4.18-4.08 (m, 2H), 3.88 (s, 3H), 1.39 (t, J=7.3 Hz, 3H).

[6-(7-methoxy-imidazo[1,2-a]pyridin-3-yl)-pyrimidin-4-yl]-{4-[1-(2-pyrrolidin-1-yl-ethyl)-1H-pyrazol-4-yl]-benzyl}-amine ("A24")

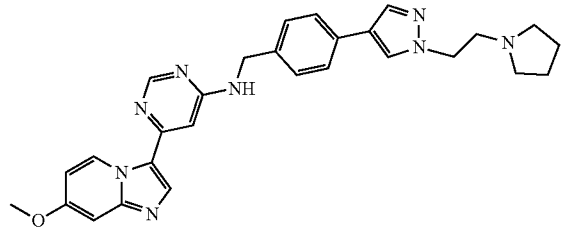 [SMILES: COc1ccn2c(-c3cc(NCc4ccc(-c5cnn(CCN6CCCC6)c5)cc4)ncn3)cnc2c1]

from F1 and D8; white solid; m.p. 203-205° C.; HPLC/MS $[M+H]^+$ 495.

$^1$H NMR (400 MHz, DMSO-$d_6$) δ 9.69 (d, J=7.7 Hz, 1H), 8.51 (s, 1H), 8.14 (d, J=0.9 Hz, 2H), 7.88 (t, J=6.2 Hz, 1H), 7.83 (d, J=0.8 Hz, 1H), 7.55-7.49 (m, 2H), 7.35-7.33 (m, 2H), 7.08 (d, J=2.6 Hz, 1H), 6.89 (d, J=1.2 Hz, 1H), 6.80 (dd, J=7.7, 2.7 Hz, 1H), 4.54 (s, 2H), 4.20 (t, J=6.6 Hz, 2H), 3.87 (s, 3H), 2.83 (t, J=6.6 Hz, 2H), 2.50-2.45 (m, 4H), 1.66-1.62 (m, 4H).

[4-(1,3-dimethyl-1H-pyrazol-4-yl)-benzyl]-[6-(7-methoxy-imidazo[1,2-a]pyridin-3-yl)-pyrimidin-4-yl]-amine ("A25")

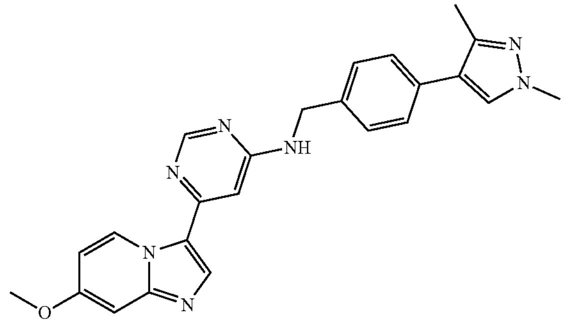

from F1; white solid; m.p. 264-265° C.; HPLC/MS $[M+H]^+$ 426.

$^1$H NMR (400 MHz, DMSO-$d_6$) δ 9.70 (d, J=7.7 Hz, 1H), 8.52 (s, 1H), 8.15 (s, 1H), 7.90 (t, J=6.1 Hz, 1H), 7.84 (s, 1H), 7.37 (s, 4H), 7.09 (d, J=2.7 Hz, 1H), 6.90 (d, J=1.2 Hz, 1H), 6.80 (dd, J=7.7, 2.6 Hz, 1H), 4.56 (s, 2H), 3.87 (s, 3H), 3.76 (s, 3H), 2.26 (s, 3H).

6-{7-methoxyimidazo[1,2-a]pyridin-3-yl}-N-{[4-(5-methyl-1,2,4-oxadiazol-3-yl)phenyl]methyl}pyrimidin-4-amine ("A26")

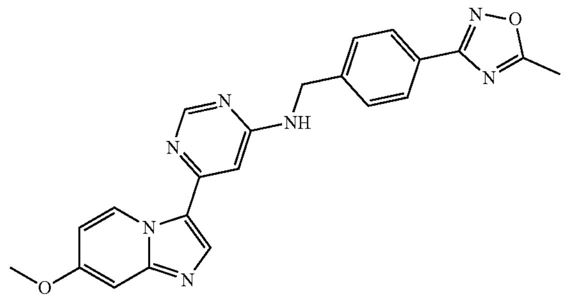

from F1; off-white solid; HPLC/MS (A) 1.28 min, $[M+H]^+$ 414.

$^1$H NMR (500 MHz, DMSO-$d_6$) δ 9.69 (d, J=7.7 Hz, 1H), 8.52 (d, J=1.1 Hz, 1H), 8.16 (s, 1H), 8.04-7.90 (m, 3H), 7.53 (d, J=7.9 Hz, 2H), 7.08 (d, J=2.7 Hz, 1H), 6.92 (d, J=1.2 Hz, 1H), 6.80 (dd, J=7.7, 2.6 Hz, 1H), 4.65 (d, J=6.1 Hz, 2H), 3.87 (s, 3H), 2.65 (s, 3H).

N-{[4-(1H-1,3-benzodiazol-1-yl)phenyl]methyl}-6-{7-methoxyimidazo[1,2-a]pyridin-3-yl}pyrimidin-4-amine ("A27")

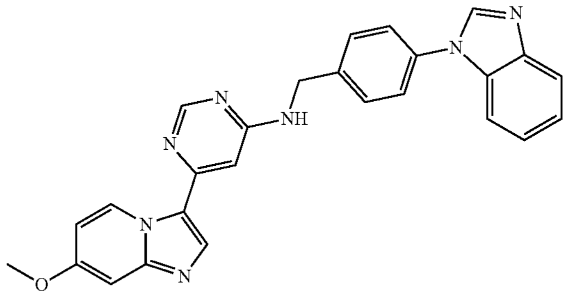 [SMILES: COc1ccn2c(-c3cc(NCc4ccc(-n5cnc6ccccc65)cc4)ncn3)cnc2c1]

from F1; off-white solid; HPLC/MS (A) 1.21 min, $[M+H]^+$ 448.

$^1$H NMR (500 MHz, DMSO-$d_6$) δ 9.70 (d, J=7.7 Hz, 1H), 8.54 (s, 1H), 8.52 (s, 1H), 8.18 (s, 1H), 7.99 (t, J=6.2 Hz, 1H), 7.79-7.72 (m, 1H), 7.69-7.53 (m, 5H), 7.37-7.25 (m, 2H), 7.08 (d, J=2.6 Hz, 1H), 6.95 (d, J=1.2 Hz, 1H), 6.81 (dd, J=7.7, 2.7 Hz, 1H), 4.68 (d, J=5.7 Hz, 2H), 3.88 (s, 3H).

[6-(7-methoxy-imidazo[1,2-a]pyridin-3-yl)-pyrimidin-4-yl]-[3-(1-methyl-1H-pyrazol-4-yl)-benzyl]-amine ("A28")

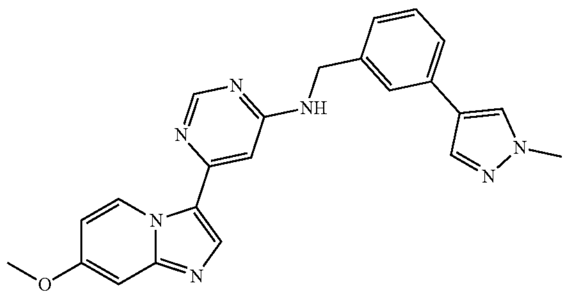

from F1 and D9; pale yellow solid; m.p. 258-259° C.; HPLC/MS $[M+H]^+$ 412.

$^1$H NMR (400 MHz, DMSO-$d_6$) δ 9.70 (d, J=7.7 Hz, 1H), 8.53 (s, 1H), 8.18-8.13 (m, 1H), 8.11 (s, 1H), 7.90 (t, J=6.1 Hz, 1H), 7.83 (s, 1H), 7.58 (s, 1H), 7.44 (d, J=7.6, 1.5 Hz, 1H), 7.32 (t, J=7.6 Hz, 1H), 7.20-7.17 (m, 1H), 7.09 (d, J=2.6 Hz, 1H), 6.92 (d, J=1.2 Hz, 1H), 6.81 (dd, J=7.7, 2.6 Hz, 1H), 4.60-4.52 (m, 2H), 3.89-3.83 (m, 6H).

N-{[3-fluoro-4-(1-methyl-1H-pyrazol-4-yl)phenyl]methyl}-6-{7-methoxyimidazo[1,2-a]pyridin-3-yl}pyrimidin-4-amine ("A29")

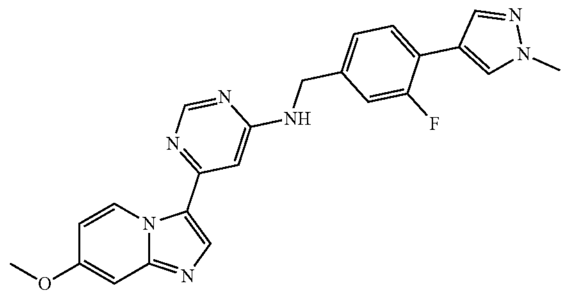

from F1 and D10; off-white powder; UPLC/MS 0.799 min, $[M+H]^+$ 430.

$^1$H NMR (500 MHz, DMSO-$d_6$) δ 9.70 (d, J=7.7 Hz, 1H), 8.52 (d, J=1.1 Hz, 1H), 8.17 (s, 1H), 8.08 (d, J=2.2 Hz, 1H), 7.89 (t, J=6.2 Hz, 1H), 7.84 (dd, J=1.5, 0.8 Hz, 1H), 7.65 (t, J=8.2 Hz, 1H), 7.25-7.17 (m, 2H), 7.08 (d, J=2.6 Hz, 1H), 6.91 (d, J=1.2 Hz, 1H), 6.80 (dd, J=7.7, 2.7 Hz, 1H), 4.57 (d, J=5.9 Hz, 2H), 3.88 (s, 3H), 3.30 (s, 3H).

2-[4-(4-{[6-(7-methoxy-imidazo[1,2-a]pyridin-3-yl)-pyrimidin-4-ylamino]-methyl}-phenyl)-pyrazol-1-yl]-ethanol ("A30")

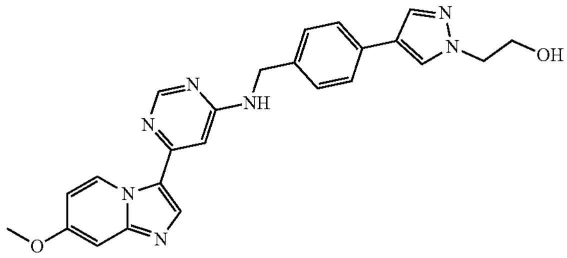 [SMILES: COc1ccn2c(-c3cc(NCc4ccc(-c5cnn(CCO)c5)cc4)ncn3)cnc2c1]

from F1 and D11; off-white solid; m.p. 257-258° C.; HPLC/MS $[M+H]^+$ 442.

$^1$H NMR (400 MHz, DMSO-$d_6$) δ 9.70 (d, J=7.7 Hz, 1H), 8.51 (s, 1H), 8.17-8.12 (m, 1H), 8.10 (s, 1H), 7.91-7.82 (m, 2H), 7.53 (d, J=8.4 Hz, 2H), 7.34 (d, J=7.8 Hz, 2H), 7.08 (d, J=2.6 Hz, 1H), 6.90 (d, J=1.3 Hz, 1H), 6.80 (dd, J=7.7, 2.6 Hz, 1H), 4.91 (t, J=5.3 Hz, 1H), 4.54 (s, 2H), 4.14 (t, J=5.7 Hz, 2H), 3.87 (s, 3H), 3.81-3.71 (m, 2H).

[6-(7-methoxy-imidazo[1,2-a]pyridin-3-yl)-pyrimidin-4-yl]-[4-(1-methyl-1H-[1,2,3]triazol-4-yl)-benzyl]-amine ("A31")

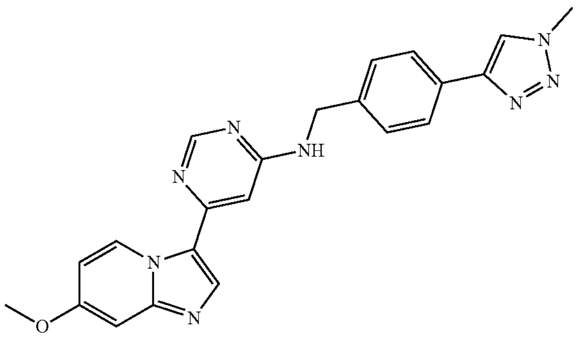

from F1 and D12; white solid; m.p. 254-255° C.; HPLC/MS $[M+H]^+$ 413.

$^1$H NMR (400 MHz, DMSO-$d_6$) δ 9.70 (d, J=7.7 Hz, 1H), 8.52 (s, 1H), 8.47 (s, 1H), 8.16 (s, 1H), 7.92 (t, J=6.2 Hz, 1H), 7.83-7.76 (m, 2H), 7.43 (d, J=7.8 Hz, 2H), 7.08 (d, J=2.6 Hz, 1H), 6.93-6.91-6.90 (m, 1H), 6.80 (dd, J=7.7, 2.6 Hz, 1H), 4.59 (s, 2H), 4.08 (s, 3H), 3.87 (s, 3H).

[6-(7-methoxy-imidazo[1,2-a]pyridin-3-yl)-pyrimidin-4-yl]-[4-(2-methyl-2H-[1,2,3]triazol-4-yl)-benzyl]-amine ("A32")

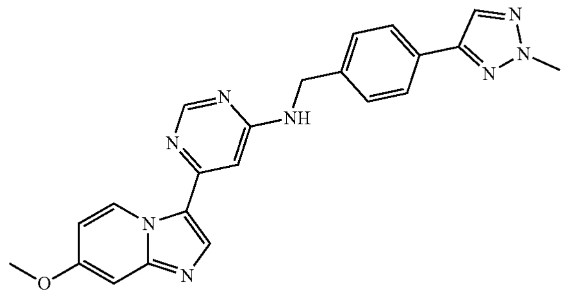

(from F1 and D2); white solid; m.p. 253-254° C.; HPLC/MS $[M+H]^+$ 413.

$^1$H NMR (400 MHz, DMSO-$d_6$) δ 9.70 (d, J=7.7 Hz, 1H), 8.52 (s, 1H), 8.18-8.17 (m, 2H), 7.93 (t, J=6.2 Hz, 1H), 7.83-7.76 (m, 2H), 7.44 (d, J=7.8 Hz, 2H), 7.08 (d, J=2.6 Hz, 1H), 6.93-6.88 (m, 1H), 6.80 (dd, J=7.7, 2.7 Hz, 1H), 4.60 (s, 2H), 4.18 (s, 3H), 3.87 (s, 3H).

6-{7-methoxyimidazo[1,2-a]pyridin-3-yl}-N-({4-[1-(oxetan-3-yl)-1H-pyrazol-4-yl]phenyl}methyl)pyrimidin-4-amine ("A33")

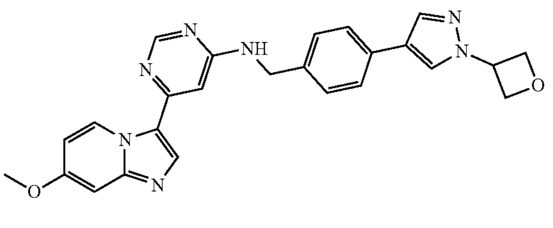 [SMILES: COc1ccn2c(-c3cc(NCc4ccc(-c5cnn(C6COC6)c5)cc4)ncn3)cnc2c1]

from F1 and D13; pale yellow powder; UPLC/MS 0.478 min, $[M+H]^+$ 454.

$^1H$ NMR (500 MHz, DMSO-$d_6$) δ 9.69 (d, J=7.7 Hz, 1H), 8.51 (s, 1H), 8.31 (d, J=0.8 Hz, 1H), 8.15 (s, 1H), 7.98 (d, J=0.8 Hz, 1H), 7.85 (t, J=6.1 Hz, 1H), 7.56 (d, J=8.3 Hz, 2H), 7.36 (d, J=7.8 Hz, 2H), 7.08 (d, J=2.7 Hz, 1H), 6.89 (d, J=1.3 Hz, 1H), 6.80 (dd, J=7.7, 2.6 Hz, 1H), 5.62-5.50 (m, 1H), 4.97-4.81 (m, 4H), 4.55 (d, J=6.1 Hz, 2H), 3.87 (s, 3H).

6-{7-methoxyimidazo[1,2-a]pyridin-3-yl}-N-{[4-(4-methoxypyrimidin-2-yl)phenyl]methyl}pyrimidin-4-amine ("A34")

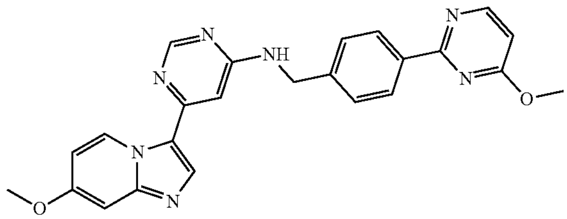

from F1 and D14; pale yellow solid; UPLC/MS 0.500 min, $[M+H]^+$ 441.

$^1H$ NMR (400 MHz, DMSO-$d_6$) δ 9.69 (d, J=7.7 Hz, 1H), 8.64 (d, J=5.2 Hz, 1H), 8.52 (d, J=1.1 Hz, 1H), 8.16 (d, J=8.4 Hz, 2H), 7.95 (t, J=6.2 Hz, 1H), 7.67 (d, J=5.3 Hz, 1H), 7.52 (d, J=8.0 Hz, 2H), 7.08 (d, J=2.6 Hz, 1H), 6.92 (d, J=1.3 Hz, 1H), 6.80 (dd, J=7.7, 2.6 Hz, 1H), 4.65 (d, J=6.0 Hz, 2H), 3.98 (s, 4H), 3.87 (s, 3H).

[4-(3-amino-1-methyl-1H-pyrazol-4-yl)-benzyl]-[6-(7-methoxy-imidazo[1,2-a]pyridin-3-yl)-pyrimidin-4-yl]-amine ("A35")

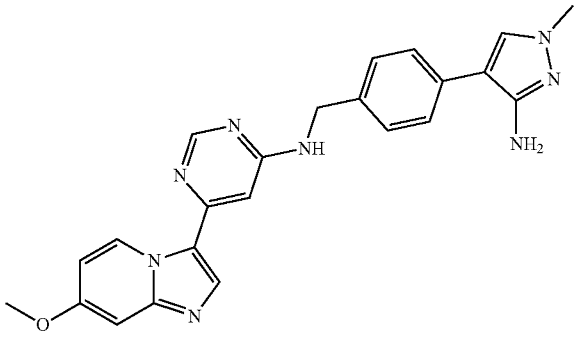

from F1 and D15; white solid; m.p. 271-272° C.; HPLC/MS $[M+H]^+$ 427.

$^1H$ NMR (400 MHz, DMSO-$d_6$) δ 9.69 (d, J=7.7 Hz, 1H), 8.50 (s, 1H), 8.17-8.13 (m, 1H), 7.88 (t, J=6.2 Hz, 1H), 7.65 (s, 1H), 7.42 (d, J=8.0 Hz, 2H), 7.34-7.28 (m, 2H), 7.07 (d, J=2.6 Hz, 1H), 6.91-6.86 (m, 1H), 6.80 (dd, J=7.7, 2.6 Hz, 1H), 4.59 (s, 2H), 4.52 (s, 2H), 3.87 (s, 3H), 3.60 (s, 3H).

6-{7-methoxyimidazo[1,2-a]pyridin-3-yl}-N-{[5-(1-methyl-1H-pyrazol-4-yl)thiophen-2-yl]methyl}pyrimidin-4-amine ("A36")

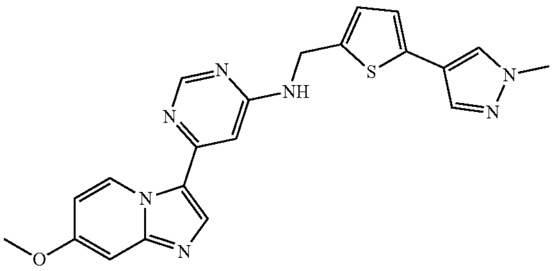

from F1 and D16; pale yellow solid; HPLC/MS (A) 1.24 min, $[M+H]^+$ 418.

$^1H$ NMR (500 MHz, DMSO-$d_6$) δ 9.70 (d, J=7.7 Hz, 1H), 8.56 (s, 1H), 8.16 (s, 1H), 7.93 (d, J=0.7 Hz, 1H), 7.88 (t, J=6.1 Hz, 1H), 7.62 (d, J=0.8 Hz, 1H), 7.08 (d, J=2.6 Hz, 1H), 7.01-6.94 (m, 4H), 6.91 (s, 1H), 6.81 (dd, J=7.7, 2.6 Hz, 1H), 4.69 (d, J=6.0 Hz, 2H), 3.88 (s, 3H), 3.81 (s, 3H).

6-{7-methoxyimidazo[1,2-a]pyridin-3-yl}-N-{[4-(2-methyl-2H-1,2,3,4-tetrazol-5-yl)phenyl]methyl}pyrimidin-4-amine ("A37")

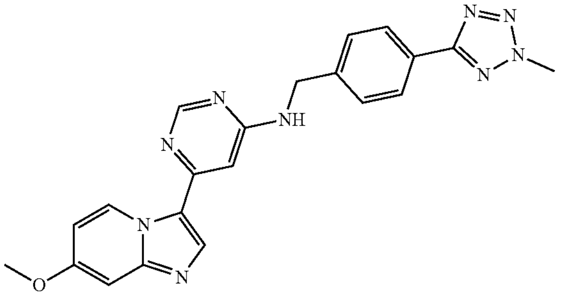

from F1 and D17; yellow powder; UPLC/MS 0.476 min, $[M+H]^+$ 414.

$^1H$ NMR (500 MHz, DMSO-$d_6$) δ 9.69 (d, J=7.7 Hz, 1H), 8.52 (d, J=1.2 Hz, 1H), 8.16 (s, 1H), 8.02 (d, J=8.2 Hz, 2H), 7.93 (t, J=6.2 Hz, 1H), 7.54 (d, J=7.9 Hz, 2H), 7.08 (d, J=2.6 Hz, 1H), 6.92 (d, J=1.2 Hz, 1H), 6.80 (dd, J=7.7, 2.6 Hz, 1H), 4.65 (d, J=6.1 Hz, 2H), 4.41 (s, 3H), 3.88 (s, 3H).

[6-(7-methoxy-imidazo[1,2-a]pyridin-3-yl)-pyrimidin-4-yl]-[4-(8-oxa-3-aza-bicyclo[3.2.1]oct-3-yl)-benzyl]-amine ("A38")

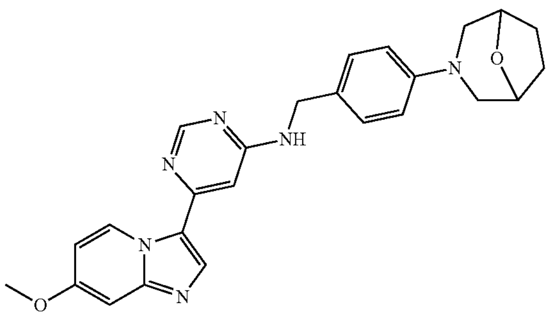 [SMILES: COc1ccn2c(-c3cc(NCc4ccc(N5CC6CCC(C5)O6)cc4)ncn3)cnc2c1]

from F1 and D18; yellow solid; m.p. 201-202° C.; HPLC/MS $[M+H]^+$ 443.

$^1$H NMR (300 MHz, DMSO-$d_6$) δ 9.68 (d, J=7.8 Hz, 1H), 8.49 (s, 1H), 8.23-8.02 (m, 1H), 7.77 (t, J=6.2 Hz, 1H), 7.29-7.16 (m, 2H), 7.08 (s, 1H), 6.92-6.66 (m, 4H), 4.51-4.27 (m, 4H), 3.87 (s, 3H), 3.43-3.35 (m, 1H), 3.32-3.26 (m, 1H), 2.79-2.69 (m, 2H), 1.93-1.71 (m, 4H).

6-{7-methoxyimidazo[1,2-a]pyridin-3-yl}-N-{[4-(1-methyl-1H-imidazol-5-yl)phenyl]methyl}pyrimidin-4-amine ("A39")

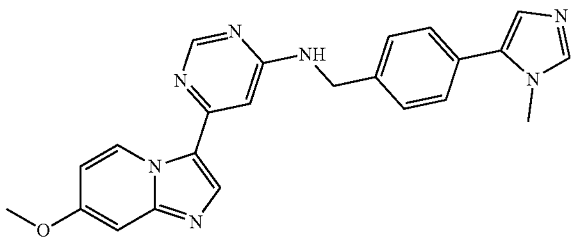 [SMILES: COc1ccn2c(-c3cc(NCc4ccc(-c5cncn5C)cc4)ncn3)cnc2c1]

from F1 and D19; yellow powder; UPLC/MS 0.342 min, $([M+2H]^{2+})/2$ 206.5.

$^1$H NMR (400 MHz, DMSO-$d_6$) δ 9.80 (s, 1H), 9.14 (s, 1H), 8.60 (s, 1H), 8.28 (s, 1H), 7.83 (d, J=1.5 Hz, 1H), 7.67-7.43 (m, 5H), 7.28 (d, J=2.6 Hz, 1H), 7.26-7.12 (m, 1H), 7.03 (s, 1H), 4.68 (s, 2H), 3.98 (s, 3H), 3.82 (s, 3H).

6-{7-methoxyimidazo[1,2-a]pyridin-3-yl}-N-{[4-(6-methylpyridazin-3-yl)phenyl]methyl}pyrimidin-4-amine ("A40")

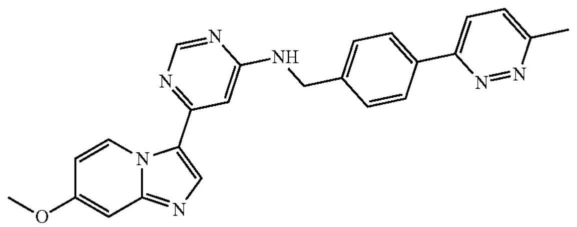

from F1 and D20; off-white resin; UPLC/MS 0.452 min, $[M+H]^+$ 424.

$^1$H NMR (400 MHz, DMSO-$d_6$) δ 8.73 (s, 1H), 8.63 (s, 1H), 8.37 (t, J=6.2 Hz, 1H), 8.14 (d, J=8.8 Hz, 1H), 8.11 (d, J=8.3 Hz, 2H), 7.69 (d, J=8.8 Hz, 1H), 7.52 (d, J=7.8 Hz, 2H), 7.32 (d, J=2.6 Hz, 1H), 7.26 (dd, J=7.7, 2.6 Hz, 1H), 7.05 (s, 1H), 4.70 (bs, 2H), 4.02 (s, 3H), 2.66 (s, 3H).

6-{7-methoxyimidazo[1,2-a]pyridin-3-yl}-N-{[4-(2-methylpyrimidin-5-yl)phenyl]methyl}pyrimidin-4-amine ("A41")

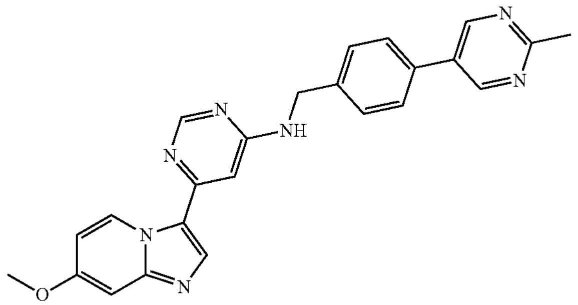

from F1 and D21; pale yellow powder; UPLC/MS 0.456 min, $[M+H]^+$ 424.

$^1$H NMR (400 MHz, DMSO-$d_6$) δ 9.73 (s, 1H), 9.00 (s, 2H), 8.52 (s, 1H), 8.23 (s, 1H), 7.98 (t, J=6.2 Hz, 1H), 7.82-7.69 (m, 2H), 7.51 (d, J=7.8 Hz, 2H), 7.09 (s, 1H), 6.92 (s, 1H), 6.81 (d, J=7.7 Hz, 1H), 4.62 (s, 2H), 3.87 (s, 3H), 2.65 (s, 3H).

6-{7-methoxyimidazo[1,2-a]pyridin-3-yl}-N-{[4-(2-methyl-1,3-oxazol-4-yl)phenyl]methyl}pyrimidin-4-amine ("A42")

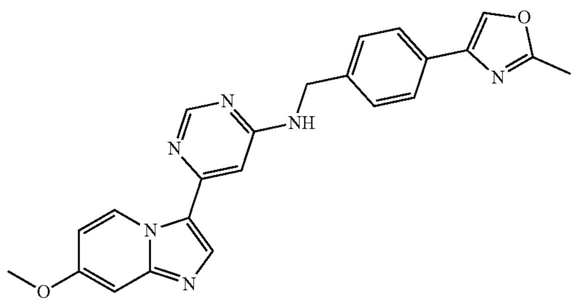

from F1 and D22; off-white powder; UPLC/MS 0.495 min, $[M+H]^+$ 495.

$^1$H NMR (500 MHz, DMSO-$d_6$) δ 8.51 (s, 1H), 8.40 (s, 1H), 8.14 (s, 1H), 7.86 (t, J=6.1 Hz, 1H), 7.70 (d, J=7.9 Hz, 2H), 7.40 (d, J=7.9 Hz, 2H), 7.07 (d, J=2.6 Hz, 1H), 6.90 (s, 1H), 6.80 (dd, J=7.7, 2.6 Hz, 1H), 4.58 (d, J=6.1 Hz, 2H), 3.87 (s, 2H), 2.45 (s, 3H).

5-(4-{[(6-{7-methoxyimidazo[1,2-a]pyridin-3-yl}pyrimidin-4-yl)amino]methyl}phenyl)-2-methylpyrimidin-4-amine ("A43")

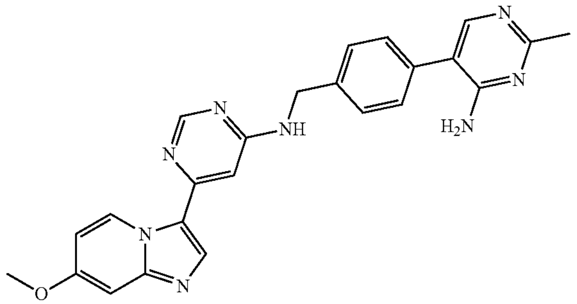

from F1 and D23; off-white solid; HPLC/MS(A) 0.95 min, $[M+H]^+$ 439.

$^1$H NMR (500 MHz, DMSO-$d_6$) δ 9.69 (d, J=7.7 Hz, 1H), 8.52 (d, J=1.1 Hz, 1H), 8.16 (s, 1H), 7.91 (t, J=6.5 Hz, 1H), 7.89 (s, 1H), 7.45 (d, J=7.9 Hz, 2H), 7.38 (s, 1H), 7.36 (d, J=4.8 Hz, 1H), 7.09-7.06 (m, 1H), 6.91 (d, J=1.2 Hz, 1H), 6.80 (dd, J=7.7, 2.6 Hz, 1H), 6.42 (s, 3H), 4.61 (d, J=5.9 Hz, 2H), 3.88 (s, 3H), 2.35 (s, 3H).

[6-(7-methoxy-imidazo[1,2-a]pyridin-3-yl)-pyrimidin-4-yl]-[5-(2-methyl-2H-[1,2,3]triazol-4-yl)-pyridin-2-ylmethyl]-amine ("A44")

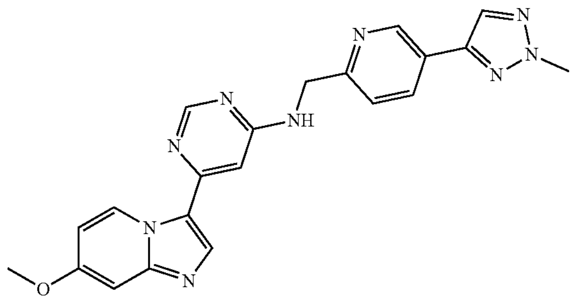

from F1 and D24; white solid; m.p. 254-256° C.; HPLC/MS $[M+H]^+$ 414.

$^1$H NMR (300 MHz, DMSO-$d_6$) δ 9.70 (d, J=7.8 Hz, 1H), 8.99 (d, J=2.1 Hz, 1H), 8.51 (s, 1H), 8.31 (s, 1H), 8.15 (d, J=7.9 Hz, 2H), 7.96 (s, 1H), 7.44 (d, J=8.1 Hz, 1H), 7.09 (d, J=2.6 Hz, 1H), 6.99 (s, 1H), 6.81 (dd, J=7.7, 2.6 Hz, 1H), 4.70 (d, J=6.0 Hz, 2H), 4.21 (s, 3H), 3.87 (s, 3H).

[6-(7-methoxy-imidazo[1,2-a]pyridin-3-yl)-pyrimidin-4-yl]-[6-(2-methyl-2H-[1,2,3]triazol-4-yl)-pyridin-3-ylmethyl]-amine ("A45")

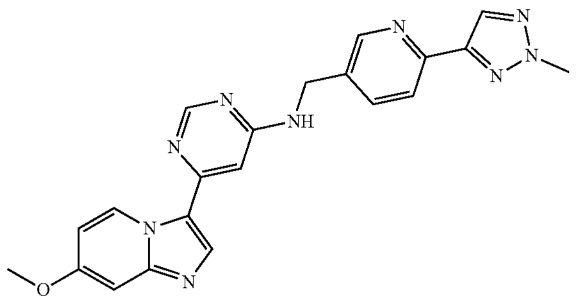

from F1 and D25; yellow solid; m.p. 260-261° C.; HPLC/MS $[M+H]^+$ 414.

$^1$H NMR (300 MHz, DMSO-$d_6$) δ 9.27 (s, 1H), 8.86 (s, 1H), 8.79 (s, 3H), 8.59 (s, 1H), 8.40 (d, J=8.4 Hz, 1H), 7.43 (d, J=2.6 Hz, 2H), 7.28 (dd, J=7.7, 2.7 Hz, 1H), 4.94 (s, 2H), 4.27 (s, 3H), 3.98 (s, 3H).

N-({4-[2-(2-methoxyethyl)-2H-1,2,3-triazol-4-yl]phenyl}methyl)-6-{7-methoxyimidazo[1,2-a]pyridin-3-yl}pyrimidin-4-amine ("A46")

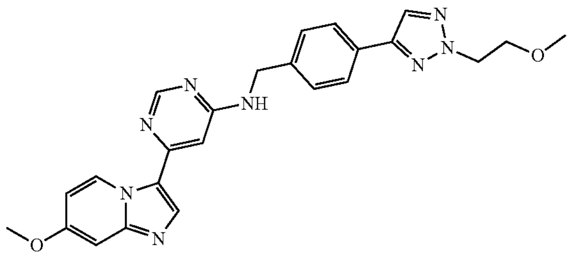

from F1 and D26; pale brown solid; UPLC/MS 0.491 min, $[M+H]^+$ 457.

$^1$H NMR (500 MHz, DMSO-$d_6$) δ 9.74-9.68 (m, 1H), 8.52 (d, J=1.2 Hz, 1H), 8.19 (s, 1H), 8.16 (s, 1H), 7.95-7.86 (m, 1H), 7.80 (d, J=8.2 Hz, 2H), 7.46 (d, J=7.9 Hz, 2H), 7.08 (d, J=2.6 Hz, 1H), 6.92 (d, J=1.3 Hz, 1H), 6.80 (dd, J=7.7, 2.7 Hz, 1H), 4.67-4.53 (m, 5H), 3.88 (s, 3H), 3.85 (t, J=5.3 Hz, 2H), 3.23 (s, 3H).

6-{7-methoxyimidazo[1,2-a]pyridin-3-yl}-N-{[4-(3-methyl-1,2,4-oxadiazol-5-yl)phenyl]methyl}pyrimidin-4-amine ("A47")

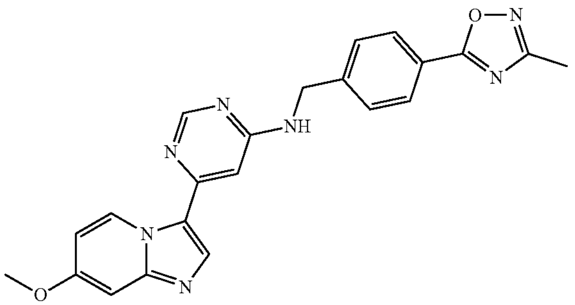

from F1; beige powder; UPLC/MS 0.488 min, $[M+H]^+$ 414.

$^1$H NMR (500 MHz, DMSO-$d_6$) δ 9.69 (d, J=7.7 Hz, 1H), 8.51 (d, J=1.1 Hz, 1H), 8.16 (s, 1H), 8.06 (d, J=8.3 Hz, 2H), 7.98 (t, J=6.2 Hz, 1H), 7.59 (d, J=8.0 Hz, 2H), 7.08 (d, J=2.6 Hz, 1H), 6.93 (s, 1H), 6.80 (dd, J=7.7, 2.7 Hz, 1H), 4.68 (d, J=6.1 Hz, 2H), 3.88 (s, 3H), 2.40 (s, 3H).

[6-(7-methoxy-imidazo[1,2-a]pyridin-3-yl)-pyrimidin-4-yl]-[4-(2-methyl-oxazol-5-yl)-benzyl]-amine ("A48")

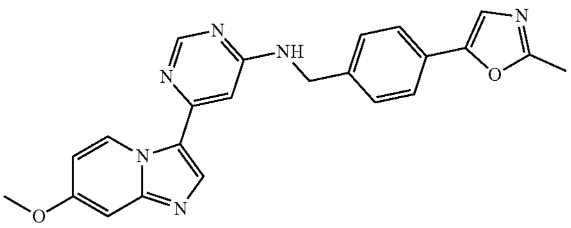

from F1; white solid; m.p. 225-226° C.; HPLC/MS $[M+H]^+$ 413.

$^1$H NMR (400 MHz, DMSO-$d_6$) δ 9.69 (d, J=7.7 Hz, 1H), 8.51 (s, 1H), 8.25-8.13 (m, 1H), 7.91 (t, J=6.3 Hz, 1H), 7.66-7.60 (m, 2H), 7.49-7.40 (m, 3H), 7.08 (d, J=2.6 Hz, 1H), 6.90 (s, 1H), 6.80 (dd, J=7.7, 2.6 Hz, 1H), 4.63-4.54 (m, 2H), 3.87 (s, 3H), 2.46 (s, 3H).

[4-(1-cyclopropyl-1H-pyrazol-4-yl)-benzyl]-[6-(7-methoxy-imidazo[1,2-a]pyridin-3-yl)-pyrimidin-4-yl]-amine ("A49")

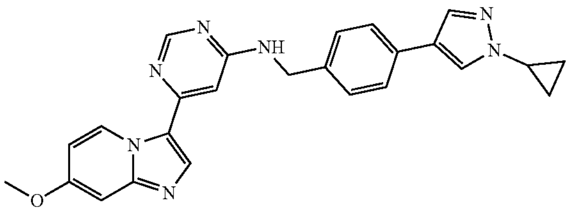 [SMILES: COc1ccn2c(-c3cc(NCc4ccc(-c5cnn(C6CC6)c5)cc4)ncn3)cnc2c1]

from F1 and D27; white solid; m.p. 261-262° C.; HPLC/MS $[M+H]^+$ 438.

$^1$H NMR (400 MHz, DMSO-$d_6$) δ 9.69 (d, J=7.8 Hz, 1H), 8.51 (s, 1H), 8.20-8.09 (m, 2H), 7.89-7.78 (m, 2H), 7.56-7.50 (m, 2H), 7.34 (d, J=7.8 Hz, 2H), 7.08 (d, J=2.7 Hz, 1H), 6.89 (d, J=1.3 Hz, 1H), 6.80 (dd, J=7.7, 2.7 Hz, 1H), 4.61-4.51 (m, 2H), 3.87 (s, 3H), 3.72 (tt, J=7.3, 3.8 Hz, 1H), 1.10-1.00 (m, 2H), 0.96 (ddd, J=7.7, 6.4, 4.4 Hz, 2H).

N-{[4-(3-methoxy-1-methyl-1H-pyrazol-4-yl)phenyl]methyl}-6-{7-methoxyimidazo[1,2-a]pyridin-3-yl}pyrimidin-4-amine ("A50")

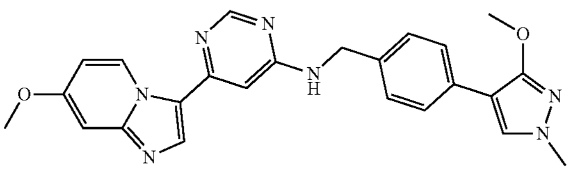

from F1 and D28; off-white solid; HPLC/MS(B) 0.753 min, $[M+H]^+$ 442.

$^1$H NMR (400 MHz, DMSO-$d_6$) δ 9.69 (d, J=7.7 Hz, 1H), 8.51 (s, 1H), 8.13 (s, 1H), 7.92 (s, 1H), 7.81 (t, J=6.1 Hz, 1H), 7.54 (d, J=8.3 Hz, 2H), 7.31 (d, J=7.9 Hz, 2H), 7.07 (d, J=2.6 Hz, 1H), 6.88 (d, J=1.2 Hz, 1H), 6.79 (dd, J=7.7, 2.6 Hz, 1H), 4.52 (d, J=6.0 Hz, 2H), 3.87 (s, 6H), 3.70 (s, 3H).

[6-(7-methoxy-imidazo[1,2-a]pyridin-3-yl)-pyrimidin-4-yl]-(4-oxazol-4-yl-benzyl)-amine ("A51")

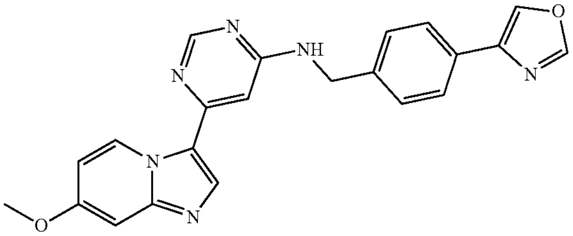 [SMILES: COc1ccn2c(-c3cc(NCc4ccc(-c5cocn5)cc4)ncn3)cnc2c1]

from F1 and D29; pale yellow solid; m.p. 268-269° C.; HPLC/MS $[M+H]^+$ 399.

$^1$H NMR (300 MHz, DMSO-$d_6$) δ 9.68 (d, J=7.7 Hz, 1H), 8.57 (d, J=1.0 Hz, 1H), 8.50 (d, J=1.1 Hz, 1H), 8.42 (d, J=1.0 Hz, 1H), 8.14 (s, 1H), 7.90 (t, J=6.1 Hz, 1H), 7.79-7.70 (m, 2H), 7.41 (d, J=7.9 Hz, 2H), 7.06 (d, J=2.6 Hz, 1H), 6.89 (d, J=1.3 Hz, 1H), 6.78 (dd, J=7.7, 2.7 Hz, 1H), 4.57 (d, J=5.9 Hz, 2H), 3.85 (s, 3H).

[6-(7-methoxy-imidazo[1,2-a]pyridin-3-yl)-pyrimidin-4-yl]-[4-(3-methyl-isoxazol-5-yl)-benzyl]-amine ("A52")

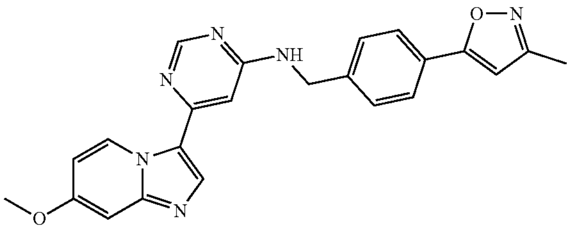

from F1 and D30; pale yellow solid; m.p. 198-199° C.; HPLC/MS $[M+H]^+$ 413.

$^1$H NMR (300 MHz, DMSO-$d_6$) δ 9.69 (d, J=7.7 Hz, 1H), 8.51 (s, 1H), 8.20-8.14 (m, 1H), 7.95 (t, J=6.2 Hz, 1H), 7.79 (d, J=8.1 Hz, 2H), 7.49 (d, J=7.9 Hz, 2H), 7.08 (d, J=2.6 Hz, 1H), 6.91 (s, 1H), 6.85-6.75 (m, 2H), 4.66-4.58 (m, 2H), 3.87 (s, 3H), 2.27 (s, 3H).

[6-(7-methoxy-imidazo[1,2-a]pyridin-3-yl)-pyrimidin-4-yl]-[4-(5-methyl-oxazol-2-yl)-benzyl]-amine ("A53")

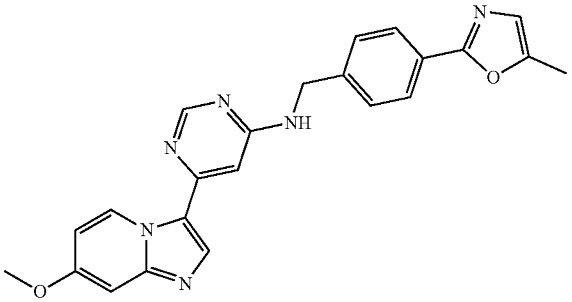

from F1 and D31; yellow solid; m.p. 281-282° C.; HPLC/MS $[M+H]^+$ 413.

$^1H$ NMR (400 MHz, DMSO-$d_6$) δ 9.70 (d, J=7.7 Hz, 1H), 8.52 (d, J=1.1 Hz, 1H), 8.19-8.14 (m, 1H), 7.95 (t, J=6.2 Hz, 1H), 7.92-7.86 (m, 2H), 7.48 (d, J=7.9 Hz, 2H), 7.08 (d, J=2.7 Hz, 1H), 6.99-6.89 (m, 2H), 6.80 (dd, J=7.7, 2.7 Hz, 1H), 4.69-4.55 (m, 2H), 3.87 (s, 3H), 2.37 (s, 3H).

Example 2

Synthesis of 6-{7-fluoroimidazo[1,2-a]pyridin-3-yl}-N-{[4-(1-methyl-1H-pyrazol-4-yl)phenyl]methyl}pyrimidin-4-amine ("H1")

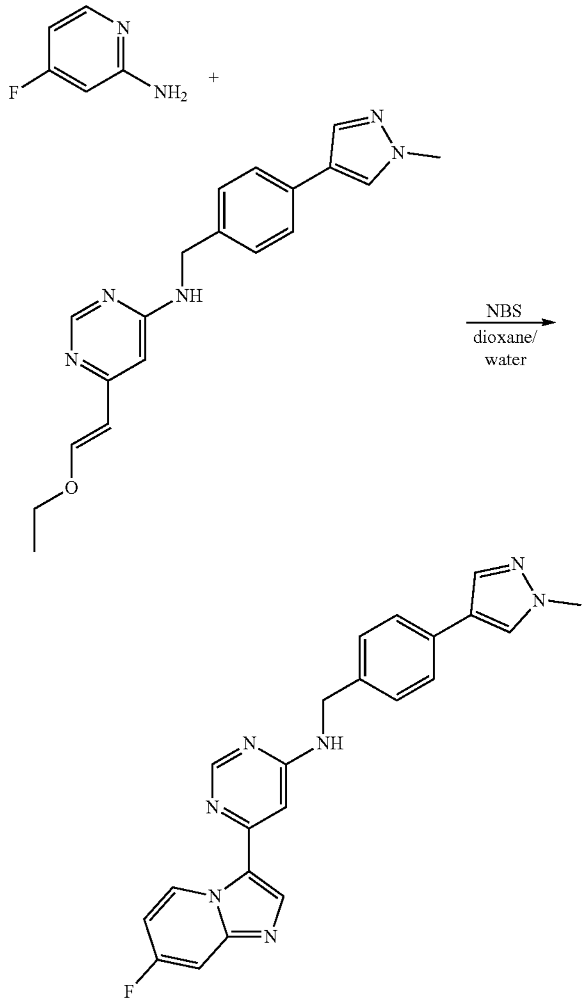

A suspension of 6-[(E)-2-ethoxyethenyl]-N-{[4-(1-methyl-1H-pyrazol-4-yl)phenyl]methyl}pyrimidin-4-amine (G1) (335 mg, 1.00 mmol) in a mixture of 1,4-dioxane (4.5 ml) and water (1.5 ml) is cooled to 0° C. and N-bromosuccinimide (196 mg, 1.10 mmol) is added in portions over a period of 15 minutes. After the last addition, the reaction mixture is stirred for 20 minutes at 0° C. 2-Amino-4-fluoropyridine (118 mg, 1.00 mmol) is added. The reaction solution is heated to 60° C. and stirred at this temperature for 2 hours. The reaction mixture is allowed to reach temperature and poured into aqueous 1 N NaOH solution (25 ml). The resultant mixture is stirred for several hours. The resultant solid material is filtered off, washed with water, dried and chromatographed on a silica gel column with dichloromethane/methanol as eluent to afford 6-{7-fluoroimidazo[1,2-a]pyridin-3-yl}-N-{[4-(1-methyl-1H-pyrazol-4-yl)phenyl]methyl}pyrimidin-4-amine as pale yellow crystalline solid; HPLC/MS(B) 0.794 min, $[M+H]^+$ 400.

$^1H$ NMR (500 MHz, DMSO-$d_6$) δ 9.94-9.85 (m, 1H), 8.55 (s, 1H), 8.28 (s, 1H), 8.07 (s, 1H), 7.91 (t, J=6.1 Hz, 1H), 7.80 (d, J=0.9 Hz, 1H), 7.57 (dd, J=9.8, 2.7 Hz, 1H), 7.51 (d, J=8.2 Hz, 2H), 7.34 (d, J=7.8 Hz, 2H), 7.15 (td, J=7.6, 2.8 Hz, 1H), 6.96 (d, J=1.2 Hz, 1H), 4.55 (d, J=5.8 Hz, 2H), 3.84 (s, 3H).

The following compounds are prepared analogously:

{6-[7-(2-methoxy-1-methoxymethyl-ethoxy)-imidazo[1,2-a]pyridin-3-yl]-pyrimidin-4-yl}-[4-(1-methyl-1H-pyrazol-4-yl)-benzyl]-amine ("A54")

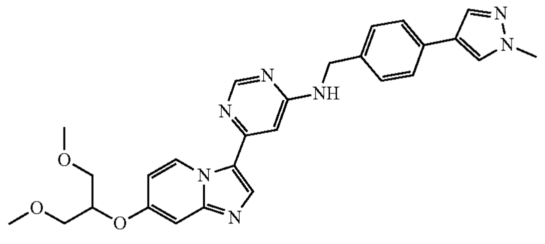

from G1 and E2; yellow solid; m.p. 52-53° C.; HPLC/MS $[M+H]^+$ 452.

$^1H$ NMR (300 MHz, DMSO-$d_6$) δ 9.80 (s, 1H), 8.71 (s, 1H), 8.60 (s, 1H), 8.31 (s, 1H), 8.08 (s, 1H), 7.82 (s, 1H), 7.55-7.44 (m, 3H), 7.38-7.23 (m, 3H), 7.02 (s, 1H), 5.02 (t, J=4.9 Hz, 1H), 4.63-4.48 (m, 2H), 3.85 (s, 3H), 3.73-3.51 (m, 4H), 3.27 (s, 6H).

[4-(1-methyl-1H-pyrazol-4-yl)-benzyl]-{6-[7-(tetrahydro-pyran-4-yloxy)-imidazo[1,2-a]pyridin-3-yl]-pyrimidin-4-yl}-amine ("A55")

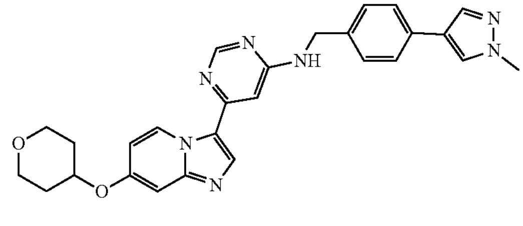 [SMILES: Cn1cc(-c2ccc(CNc3cc(-c4cnc5cc(OC6CCOCC6)ccn45)ncn3)cc2)cn1]

from G1 and E3; white solid; m.p. 215-216° C.; HPLC/MS $[M+H]^+$ 482.

$^1H$ NMR (300 MHz, DMSO-$d_6$) δ 9.69 (d, J=7.8 Hz, 1H), 8.59-8.41 (m, 1H), 8.41-8.02 (m, 2H), 7.95-7.85 (m, 1H), 7.80 (s, 1H), 7.50 (d, J=7.9 Hz, 2H), 7.30 (m, 2H), 7.20 (s, 1H), 6.97-6.71 (m, 2H), 4.79-4.77 (m, 1H), 4.62-4.48 (m, 2H), 3.94-3.80 (m, 5H), 3.52 (t, J=10.4 Hz, 2H), 2.15-1.92 (m, 2H), 1.71-1.51 (m, 2H).

[4-(1-methyl-1H-pyrazol-4-yl)-benzyl]-{6-[7-(2-morpholin-4-yl-ethoxy)-imidazo[1,2-a]pyridin-3-yl]-pyrimidin-4-yl}-amine ("A56")

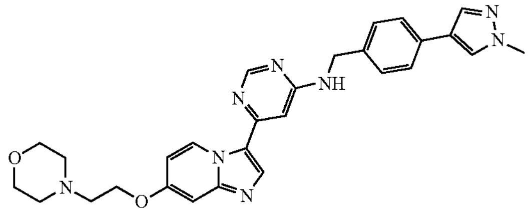 [SMILES: Cn1cc(-c2ccc(CNc3cc(-c4cnc5cc(OCCN6CCOCC6)ccn45)ncn3)cc2)cn1]

from G1 and E4; off-white solid; m.p. 220-221° C.; HPLC/MS $[M+H]^+$ 511.

$^1H$ NMR (300 MHz, DMSO-$d_6$) δ 9.68 (d, J=7.6 Hz, 1H), 8.49 (s, 1H), 8.14 (s, 1H), 8.07 (s, 1H), 7.86 (t, J=6.1 Hz, 1H), 7.80 (s, 1H), 7.50 (d, J=7.9 Hz, 2H), 7.32 (d, J=7.9 Hz, 2H), 7.09 (d, J=2.6 Hz, 1H), 6.87 (s, 1H), 6.84-6.75 (m, 1H), 4.52 (s, 2H), 4.19 (t, J=5.5 Hz, 2H), 3.83 (s, 3H), 3.57 (t, J=4.7 Hz, 4H), 2.72 (t, J=5.5 Hz, 2H), 2.51-2.42 (s, 4H).

[4-(1-methyl-1H-pyrazol-4-yl)-benzyl]-{6-[7-(tetra-hydro-furan-3-yloxy)-imidazo[1,2-a]pyridin-3-yl]-pyrimidin-4-yl}-amine ("A57")

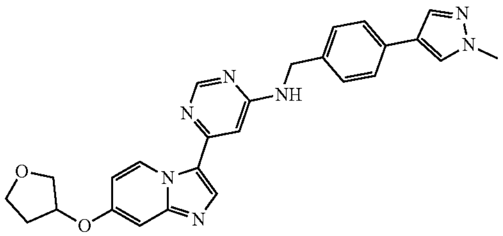 [SMILES: Cn1cc(-c2ccc(CNc3cc(-c4cnc5cc(OC6CCOC6)ccn45)ncn3)cc2)cn1]

from G1 and E5; off-white solid; m.p. 283-294° C.; HPLC/MS $[M+H]^+$ 468.

$^1H$ NMR (300 MHz, DMSO-$d_6$) δ 9.69 (d, J=7.7 Hz, 1H), 8.50 (s, 1H), 8.15 (s, 1H), 8.07 (s, 1H), 7.87 (t, J=6.0 Hz, 1H), 7.80 (s, 1H), 7.50 (d, J=8.1 Hz, 2H), 7.32 (d, J=7.8 Hz, 2H), 7.07 (d, J=2.6 Hz, 1H), 6.88 (s, 1H), 6.85-6.67 (m, 1H), 5.22-5.15 (m, 1H), 4.62-4.51 (m, 2H), 3.96-3.72 (m, 7H), 2.39-2.21 (m, 1H), 2.06-1.96 (m, 1H).

6-[7-(cyclopropylmethoxy)imidazo[1,2-a]pyridin-3-yl]-N-{[4-(1-methyl-1H-pyrazol-4-yl)phenyl]methyl}pyrimidin-4-amine ("A58")

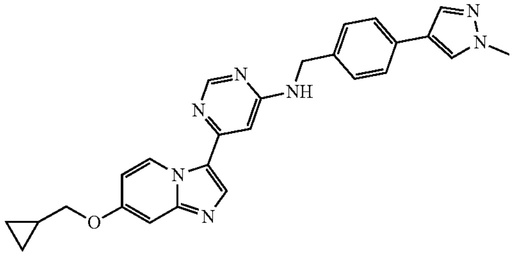 [SMILES: Cn1cc(-c2ccc(CNc3cc(-c4cnc5cc(OCC6CC6)ccn45)ncn3)cc2)cn1]

from G1 and E6; pale yellow solid; m.p. 236-237° C.; HPLC/MS $[M+H]^+$ 452.

$^1H$ NMR (300 MHz, DMSO-$d_6$) δ 9.68 (d, J=7.7 Hz, 1H), 8.49 (s, 1H), 8.12 (s, 1H), 8.07 (s, 1H), 7.86 (t, J=6.1 Hz, 1H), 7.80 (s, 1H), 7.54-7.46 (m, 2H), 7.32 (d, J=7.9 Hz, 2H), 7.00 (d, J=2.6 Hz, 1H), 6.87 (d, J=1.2 Hz, 1H), 6.81 (dd, J=7.7, 2.6 Hz, 1H), 4.52 (d, 2H), 3.92 (d, J=7.1 Hz, 2H), 3.83 (s, 3H), 1.31-1.19 (m, 1H), 0.65-0.50 (m, 2H), 0.42-0.28 (m, 2H).

6-{7-[2-(dimethylamino)ethoxy]imidazo[1,2-a]pyridin-3-yl}-N-{[4-(1-methyl-1H-pyrazol-4-yl)phenyl]methyl}pyrimidin-4-amine ("A59")

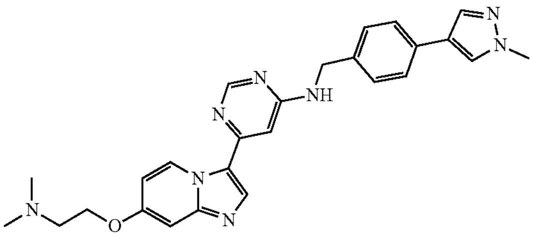

from G1 and E7; off-white solid; m.p. 235-236° C.; HPLC/MS $[M+H]^+$ 469.

$^1H$ NMR (300 MHz, DMSO-$d_6$) δ 9.68 (d, J=7.7 Hz, 1H), 8.49 (s, 1H), 8.14 (s, 1H), 8.07 (s, 1H), 7.86 (t, J=6.1 Hz, 1H), 7.80 (d, J=0.8 Hz, 1H), 7.50 (d, J=8.2 Hz, 2H), 7.32 (d, J=7.9 Hz, 2H), 7.09 (d, J=2.6 Hz, 1H), 6.87 (d, J=1.2 Hz, 1H), 6.79 (dd, J=7.7, 2.6 Hz, 1H), 4.57-4.49 (m, 2H), 4.14 (t, J=5.7 Hz, 2H), 3.83 (s, 3H), 2.65 (t, J=5.6 Hz, 2H), 2.21 (s, 6H).

[4-(1-methyl-1H-pyrazol-4-yl)-benzyl]-{6-[7-(2-pyrrolidin-1-yl-ethoxy)-imidazo[1,2-a]pyridin-3-yl]-pyrimidin-4-yl}-amine ("A60")

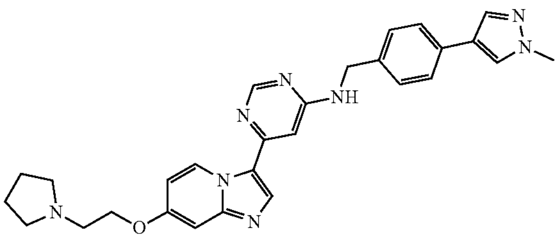 [SMILES: Cn1cc(-c2ccc(CNc3cc(-c4cnc5cc(OCCN6CCCC6)ccn45)ncn3)cc2)cn1]

from G1 and E8; off-white solid; UPLC/MS 0.376 min, $[M+H]^+$ 495.

$^1H$ NMR (400 MHz, DMSO-$d_6$) δ 9.69 (d, J=7.7 Hz, 1H), 8.51 (s, 1H), 8.14 (s, 1H), 8.07 (s, 1H), 7.84 (t, J=6.2 Hz, 1H), 7.81 (s, 1H), 7.51 (d, J=8.2 Hz, 2H), 7.34 (d, J=7.8 Hz, 2H), 7.09 (d, J=2.6 Hz, 1H), 6.89 (d, J=1.2 Hz, 1H), 6.81 (dd, J=7.7, 2.6 Hz, 1H), 4.54 (d, J=4.8 Hz, 2H), 4.19 (t, J=5.5 Hz, 2H), 3.84 (s, 3H), 2.87 (bs, 2H), 2.57 (bs, 4H), 1.71 (bs, 4H).

(6-{7-[2-(4-methyl-piperazin-1-yl)-ethoxy]-imidazo[1,2-a]pyridin-3-yl}-pyrimidin-4-yl)-[4-(1-methyl-1H-pyrazol-4-yl)-benzyl]-amine ("A61")

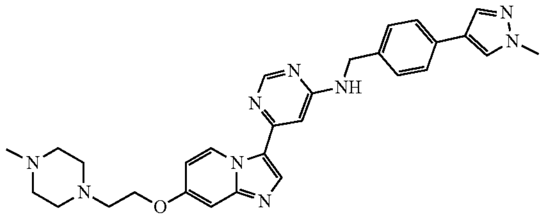

from G1 and E9; white solid; m.p. 200-201° C.; HPLC/MS $[M+H]^+$ 524.

$^1$H NMR (300 MHz, DMSO-$d_6$) δ 9.68 (d, J=7.7 Hz, 1H), 8.49 (s, 1H), 8.14 (s, 1H), 8.07 (s, 1H), 7.86 (t, J=6.1 Hz, 1H), 7.80 (d, J=0.8 Hz, 1H), 7.50 (d, J=8.2 Hz, 2H), 7.32 (d, J=7.9 Hz, 2H), 7.08 (d, J=2.6 Hz, 1H), 6.87 (d, J=1.2 Hz, 1H), 6.79 (dd, J=7.7, 2.6 Hz, 1H), 4.59-4.47 (m, 2H), 4.16 (t, J=5.6 Hz, 2H), 3.83 (s, 3H), 2.71 (t, J=5.6 Hz, 2H), 2.57 (s, 2H), 2.44 (s, 2H), 2.30 (s, 4H), 2.13 (s, 3H).

{6-[7-(1-methyl-piperidin-4-ylmethoxy)-imidazo[1,2-a]pyridin-3-yl]-pyrimidin-4-yl}-[4-(1-methyl-1H-pyrazol-4-yl)-benzyl]-amine ("A62")

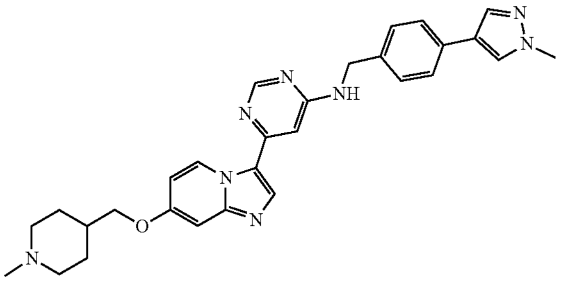

from G1 and E10; white solid; m.p. 238-239° C.; HPLC/MS $[M+H]^+$ 509.

$^1$H NMR (300 MHz, DMSO-$d_6$) δ 9.68 (d, J=7.7 Hz, 1H), 8.49 (s, 1H), 8.13 (s, 1H), 8.07 (s, 1H), 7.86 (t, J=6.0 Hz, 1H), 7.80 (d, J=0.8 Hz, 1H), 7.50 (d, J=8.2 Hz, 2H), 7.32 (d, J=7.9 Hz, 2H), 7.05 (d, J=2.5 Hz, 1H), 6.87 (d, J=1.2 Hz, 1H), 6.78 (dd, J=7.7, 2.6 Hz, 1H), 4.55-4.49 (m, 2H), 3.93 (d, J=5.9 Hz, 2H), 3.83 (s, 3H), 2.77 (d, J=11.0 Hz, 2H), 2.14 (s, 3H), 1.86 (t, J=11.5 Hz, 2H), 1.73 (d, J=11.7 Hz, 3H), 1.40-1.25 (m, 2H).

{6-[7-(1-methyl-piperidin-4-yloxy)-imidazo[1,2-a]pyridin-3-yl]-pyrimidin-4-yl}-[4-(1-methyl-1H-pyrazol-4-yl)-benzyl]-amine ("A63")

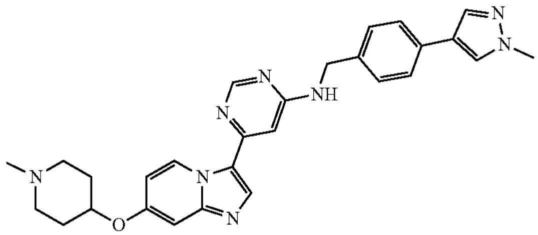

from G1 and E11; off-white solid; m.p. 224-225° C.; HPLC/MS $[M+H]^+$ 495.

$^1$H NMR (300 MHz, DMSO-$d_6$) δ 9.68 (d, J=7.7 Hz, 1H), 8.49 (s, 1H), 8.13 (s, 1H), 8.07 (s, 1H), 7.86 (t, J=6.1 Hz, 1H), 7.80 (d, J=0.8 Hz, 1H), 7.50 (d, J=8.2 Hz, 2H), 7.32 (d, J=7.8 Hz, 2H), 7.12 (d, J=2.6 Hz, 1H), 6.87 (d, J=1.2 Hz, 1H), 6.77 (dd, J=7.7, 2.6 Hz, 1H), 4.70-4.46 (m, 3H), 3.83 (s, 3H), 2.65-2.54 (m, 2H), 2.31-2.12 (m, 5H), 2.08-1.88 (m, 2H), 1.83-1.59 (m, 2H).

2-methyl-1-(3-{6-[4-(1-methyl-1H-pyrazol-4-yl)-benzylamino]-pyrimidin-4-yl}-imidazo[1,2-a]pyridin-7-yloxy)-propan-2-ol ("A64")

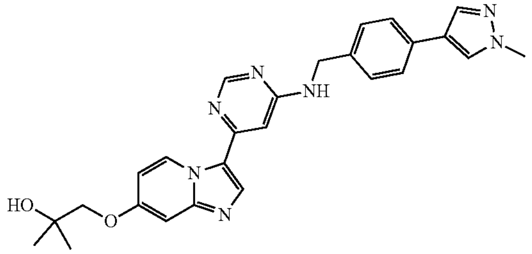 [SMILES: Cn1cc(-c2ccc(CNc3cc(-c4cnc5cc(OCC(C)(C)O)ccn45)ncn3)cc2)cn1]

from G1 and E12; off-white solid; m.p. 229-230° C.; HPLC/MS $[M+H]^+$ 480.

$^1$H NMR (300 MHz, DMSO-$d_6$) δ 9.69 (d, J=7.7 Hz, 1H), 8.50 (s, 1H), 8.19-8.03 (m, 2H), 7.91-7.77 (m, 2H), 7.50 (d, J=7.8 Hz, 2H), 7.32 (d, J=7.8 Hz, 2H), 7.07-7.01 (m, 1H), 6.88 (s, 1H), 6.85-6.76 (m, 1H), 4.71 (s, 1H), 4.60-4.42 (m, 2H), 3.83 (s, 5H), 1.21 (s, 6H).

[4-(1-methyl-1H-pyrazol-4-yl)-benzyl]-(6-{7-[2-(4-oxetan-3-yl-piperazin-1-yl)-ethoxy]-imidazo[1,2-a]pyridin-3-yl}-pyrimidin-4-yl)-amine ("A65")

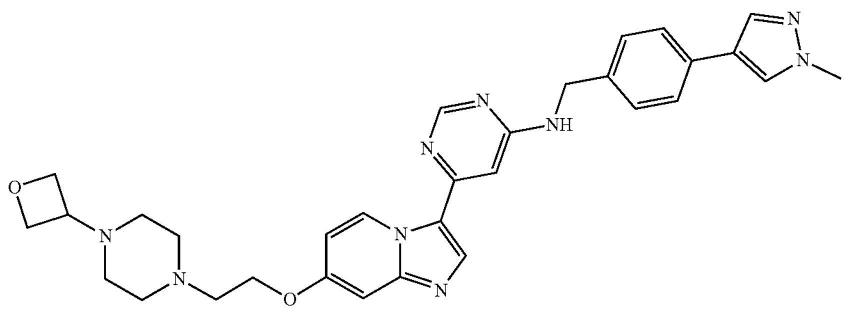 [SMILES: Cn1cc(-c2ccc(CNc3cc(-c4cnc5cc(OCCN6CCN(C7COC7)CC6)ccn45)ncn3)cc2)cn1]

from G1 and E13; yellow solid; m.p. 209-210° C.; HPLC/MS $[M+H]^+$ 566.

$^1H$ NMR (300 MHz, DMSO-$d_6$) δ 9.68 (d, J=7.6 Hz, 1H), 8.49 (s, 1H), 8.16-8.05 (m, 2H), 7.93-7.85 (m, 1H), 7.80 (d, J=0.8 Hz, 1H), 7.50 (d, J=8.1 Hz, 2H), 7.32 (d, J=7.9 Hz, 2H), 7.09 (d, J=2.6 Hz, 1H), 6.87 (s, 1H), 6.79 (dd, J=7.8, 2.6 Hz, 1H), 4.50 (t, J=6.5 Hz, 4H)

[6-(7-methyl-imidazo[1,2-a]pyridin-3-yl)-pyrimidin-4-yl]-[4-(1-methyl-1H-pyrazol-4-yl)-benzyl]-amine ("A66")

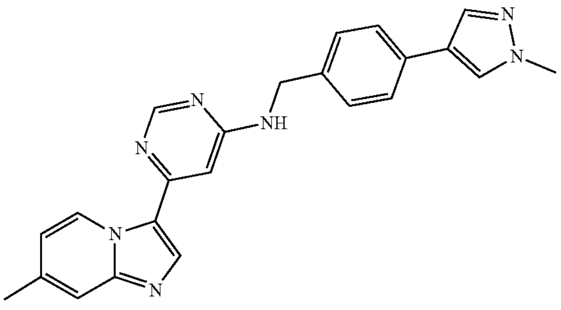

from G1; off-white solid; m.p. 229-230° C.; HPLC/MS $[M+H]^+$ 396.

$^1H$ NMR (300 MHz, DMSO-$d_6$) δ 9.71 (d, J=7.2 Hz, 1H), 8.52 (s, 1H), 8.20 (s, 1H), 8.07 (s, 1H), 7.90 (t, J=6.1 Hz, 1H), 7.80 (s, 1H), 7.55-7.44 (m, 3H), 7.33 (d, J=7.8 Hz, 2H), 6.98-6.88 (m, 2H), 4.59-4.46 (m, 2H), 3.83 (s, 3H), 2.38 (s, 3H).

(6-{7-[2-(4-methyl-piperazin-1-yl)-ethoxy]-imidazo[1,2-a]pyridin-3-yl}-pyrimidin-4-yl)-(4-[1,2,3]triazol-1-yl-benzyl)-amine ("A67")

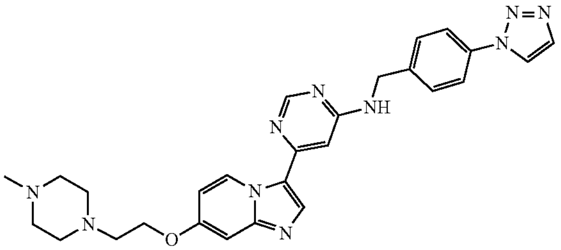 [SMILES: CN1CCN(CCOc2ccn3c(-c4cc(NCc5ccc(-n6ccnn6)cc5)ncn4)cnc3c2)CC1]

from G2 and E9) white solid; m.p. 233-234° C.; HPLC/MS $[M+H]^+$ 511.

$^1H$ NMR (400 MHz, methanol-$d_4$) δ 9.72 (d, J=7.7 Hz, 1H), 8.53 (d, J=8.0, 1.2 Hz, 2H), 8.07 (s, 1H), 7.90 (s, 1H), 7.88-7.82 (m, 2H), 7.62 (d, J=8.3 Hz, 2H), 7.00 (d, J=2.6 Hz, 1H), 6.90 (s, 1H), 6.80 (dd, J=7.7, 2.6 Hz, 1H), 4.74 (s, 2H), 4.27 (t, J=5.4 Hz, 2H), 2.90 (t, J=5.4 Hz, 2H), 2.72-2.67 (m, 4H), 2.57-2.53 (m, 4H), 2.31 (s, 3H).

{6-[7-(2-morpholin-4-yl-ethoxy)-imidazo[1,2-a]pyridin-3-yl]-pyrimidin-4-yl}-(4-[1,2,3]triazol-1-yl-benzyl)-amine ("A68")

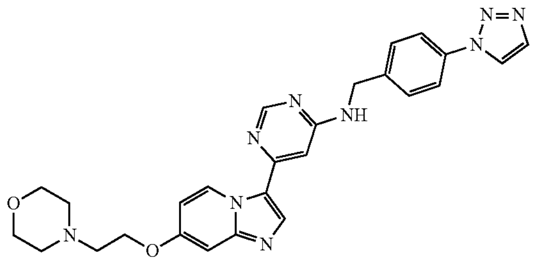 [SMILES: c1cn(-c2ccc(CNc3cc(-c4cnc5cc(OCCN6CCOCC6)ccn45)ncn3)cc2)nn1]

from G2 and E4; white solid; m.p. 234-235° C.; HPLC/MS $[M+H]^+$ 498.

$^1H$ NMR (400 MHz, DMSO-$d_6$) δ 9.69 (d, J=7.7 Hz, 1H), 8.77 (s, 1H), 8.52 (s, 1H), 8.18 (s, 1H), 8.02-7.93 (m, 2H), 7.86 (d, J=8.2 Hz, 2H), 7.57 (d, J=8.0 Hz, 2H), 7.10 (d, J=2.6

Hz, 1H), 6.92 (s, 1H), 6.81 (dd, J=7.7, 2.6 Hz, 1H), 4.67-4.61 (m, 2H), 4.20 (t, J=5.6 Hz, 2H), 3.58 (t, J=4.6 Hz, 4H), 2.73 (t, J=5.5 Hz, 2H), 2.50-2.45 (m, 4H).

[6-(6-fluoro-7-methoxy-imidazo[1,2-a]pyridin-3-yl)-pyrimidin-4-yl]-[4-(1-methyl-1H-pyrazol-4-yl)-benzyl]-amine ("A69")

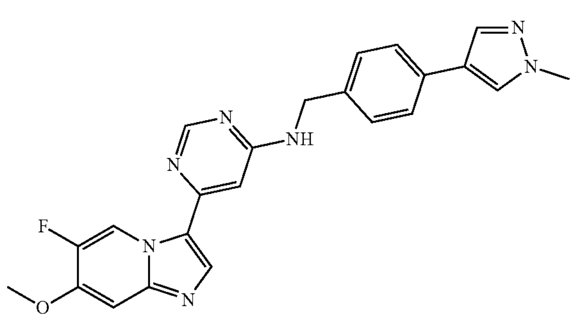

(from G1; yellow solid; m.p. 299-300° C.; HPLC/MS $[M+H]^+$ 430.

$^1H$ NMR (400 MHz, DMSO-$d_6$) δ 8.58 (d, J=2.8 Hz, 1H), 8.44 (s, 1H), 8.27 (s, 1H), 8.23-8.13 (m, 1H), 8.08 (s, 1H), 7.81 (s, 1H), 7.74-7.65 (m, 2H), 7.51 (d, J=7.8 Hz, 2H), 7.37-7.26 (m, 2H), 4.60-4.48 (m, 2H), 3.95 (s, 3H), 3.84 (s, 3H).

{6-[7-(2-pyrrolidin-1-yl-ethoxy)-imidazo[1,2-a]pyridin-3-yl]-pyrimidin-4-yl}-(4-[1,2,3]triazol-1-yl-benzyl)-amine ("A70")

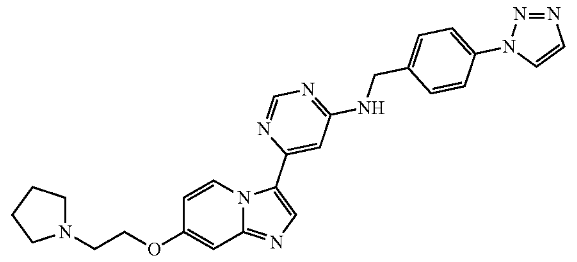 [SMILES: c1cn(-c2ccc(CNc3cc(-c4cnc5cc(OCCN6CCCC6)ccn45)ncn3)cc2)nn1]

from G2 and E8; white solid; m.p. 250-251° C.; HPLC/MS $[M+H]^+$ 482.

$^1H$ NMR (400 MHz, DMSO-$d_6$) δ 9.70 (d, J=7.7 Hz, 1H), 8.78 (s, 1H), 8.52 (s, 1H), 8.18 (s, 1H), 8.02-7.93 (m, 2H), 7.90-7.83 (m, 2H), 7.57 (d, J=8.1 Hz, 2H), 7.09 (d, J=2.6 Hz, 1H), 6.92 (s, 1H), 6.81 (dd, J=7.7, 2.6 Hz, 1H), 4.64 (d, J=5.3 Hz, 2H), 4.18 (t, J=5.7 Hz, 2H), 2.83 (t, J=5.7 Hz, 2H), 2.57-2.51 (m, 4H), 1.75-1.65 (m, 4H).

{6-[7-(2-methoxy-ethoxy)-imidazo[1,2-a]pyridin-3-yl]-pyrimidin-4-yl}-[4-(2-methyl-2H-[1,2,3]triazol-4-yl)-benzyl]-amine ("A71")

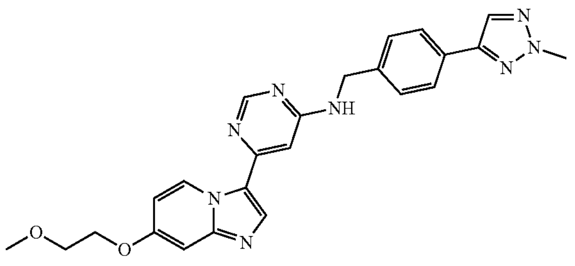

from G3 and E1; white solid; m.p. 240-241° C.; HPLC/MS $[M+H]^+$ 457.

$^1H$ NMR (400 MHz, DMSO-$d_6$) δ 9.71 (d, J=7.8 Hz, 1H), 8.52 (s, 1H), 8.24-8.12 (m, 2H), 7.94 (t, J=6.2 Hz, 1H), 7.80 (d, J=8.1 Hz, 2H), 7.49-7.40 (m, 2H), 7.10 (d, J=2.6 Hz, 1H), 6.91 (s, 1H), 6.83 (dd, J=7.8, 2.7 Hz, 1H), 4.66-4.55 (m, 2H), 4.26-4.20 (m, 2H), 4.18 (s, 3H), 3.74-3.68 (m, 2H), 3.31 (s, 3H).

6-[7-(benzyloxy)imidazo[1,2-a]pyridin-3-yl]-N-{[4-(1-methyl-1H-pyrazol-4-yl)phenyl]methyl}pyrimidin-4-amine ("A72")

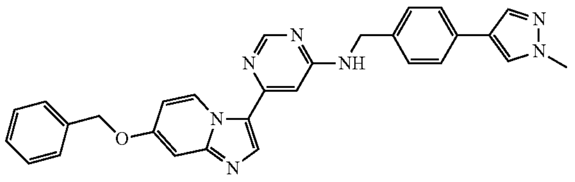 [SMILES: Cn1cc(-c2ccc(CNc3cc(-c4cnc5cc(OCc6ccccc6)ccn45)ncn3)cc2)cn1]

from G1; white solid; HPLC/MS (A) 1.43 min, $[M+H]^+$ 488.

$^1H$ NMR (500 MHz, DMSO-$d_6$) δ 9.71 (d, J=7.7 Hz, 1H), 8.51 (s, 1H), 8.15 (s, 1H), 8.07 (s, 1H), 7.84 (t, J=6.1 Hz, 1H), 7.81 (s, 1H), 7.54-7.46 (m, 4H), 7.46-7.38 (m, 2H), 7.40-7.31 (m, 3H), 7.17 (d, J=2.6 Hz, 1H), 6.89 (s, 1H), 6.87 (dd, J=7.7, 2.7 Hz, 1H), 5.23 (s, 2H), 4.54 (bs, 2H), 3.84 (s, 3H).

[4-(2-methyl-2H-[1,2,3]triazol-4-yl)-benzyl]-{6-[7-(2-pyrrolidin-1-yl-ethoxy)-imidazo[1,2-a]pyridin-3-yl]-pyrimidin-4-yl}-amine ("A73")

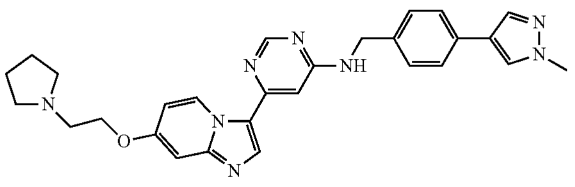 [SMILES: Cn1cc(-c2ccc(CNc3cc(-c4cnc5cc(OCCN6CCCC6)ccn45)ncn3)cc2)cn1]

from G3 and E8; white solid; m.p. 235-236° C.; HPLC/MS $[M+H]^+$ 496.

$^1H$ NMR (400 MHz, DMSO-$d_6$) δ 9.70 (d, J=7.7 Hz, 1H), 8.52 (s, 1H), 8.21-8.16 (m, 1H), 7.94 (t, 1H), 7.85-7.75 (m, 2H), 7.45 (d, J=7.8 Hz, 2H), 7.10 (d, J=2.6 Hz, 1H), 6.94-6.89 (m, 1H), 6.82 (dd, J=7.7, 2.6 Hz, 1H), 4.68-4.55 (m, 2H), 4.35-4.06 (m, 5H), 2.83 (t, J=5.7 Hz, 2H), 2.56-2.52 (m, 4H), 1.81-1.59 (m, 4H).

[4-(1-methyl-1H-pyrazol-4-yl)-benzyl]-{6-[7-(3-morpholin-4-yl-propoxy)-imidazo[1,2-a]pyridin-3-yl]-pyrimidin-4-yl}-amine ("A74")

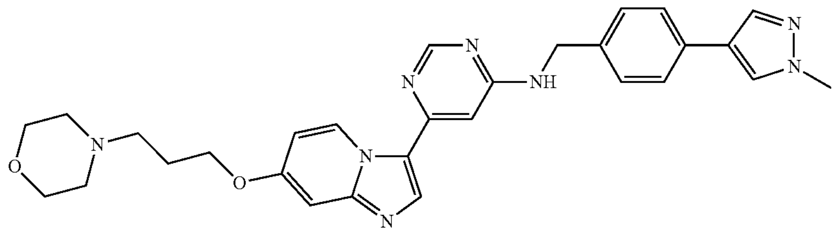 [SMILES: Cn1cc(-c2ccc(CNc3cc(-c4cnc5cc(OCCCN6CCOCC6)ccn45)ncn3)cc2)cn1]

from G1 and E14; white solid; m.p. 213-214° C.; HPLC/MS $[M+H]^+$ 496.

$^1H$ NMR (400 MHz, DMSO-$d_6$) δ 9.69 (d, J=7.7 Hz, 1H), 8.51 (s, 1H), 8.17-8.12 (m, 1H), 8.08 (s, 1H), 7.87 (t, J=6.2 Hz, 1H), 7.84 (s, 1H), 7.55-7.48 (m, 2H), 7.37-7.31 (m, 2H), 7.07 (d, J=2.6 Hz, 1H), 6.86 (s, 1H), 6.80 (dd, J=7.7, 2.6 Hz, 1H), 4.55-4.48 (m, 2H), 4.13 (t, J=6.3 Hz, 2H), 3.84 (s, 3H), 3.58 (t, J=4.6 Hz, 4H), 2.44 (t, J=7.2 Hz, 2H), 2.40-2.35 (m, 4H), 1.92 (p, J=6.6 Hz, 2H).

[4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine ("A75")

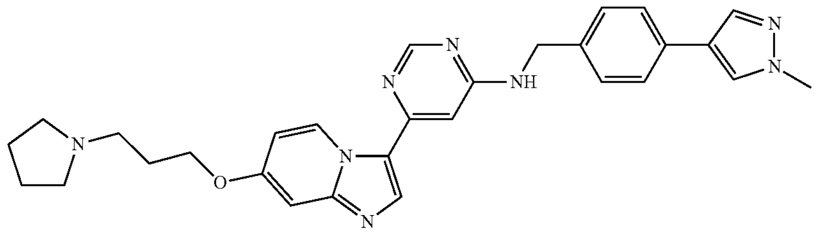 [SMILES: Cn1cc(-c2ccc(CNc3cc(-c4cnc5cc(OCCCN6CCCC6)ccn45)ncn3)cc2)cn1]

from G1 and E15: off-white solid; m.p. 213° C.; UPLC/MS 0.377 min $[M+H]^+$ 509.

$^1H$ NMR (500 MHz, DMSO-$d_6$) δ 9.69 (d, J=7.7 Hz, 1H), 8.52 (s, 1H), 8.14 (s, 1H), 8.08 (s, 1H), 7.83 (t, J=6.2 Hz, 1H), 7.81 (d, J=0.8 Hz, 1H), 7.52 (d, J=8.2 Hz, 2H), 7.35 (d, J=7.8 Hz, 2H), 7.06 (d, J=2.6 Hz, 1H), 6.89 (d, J=1.3 Hz, 1H), 6.80 (dd, J=7.7, 2.6 Hz, 1H), 4.54 (d, J=5.9 Hz, 2H), 4.14 (t, J=6.3 Hz, 2H), 3.85 (s, 3H), 2.55 (t, J=7.2 Hz, 2H), 2.49-2.41 (m, 4H), 1.93 (p, J=6.7 Hz, 2H), 1.75-1.63 (m, 4H).

[4-(2-methyl-2H-[1,2,3]triazol-4-yl)-benzyl]-{6-[7-(1-oxetan-3-yl-piperidin-4-ylmethoxy)-imidazo[1,2-a]pyridin-3-yl]-pyrimidin-4-yl}-amine ("A76")

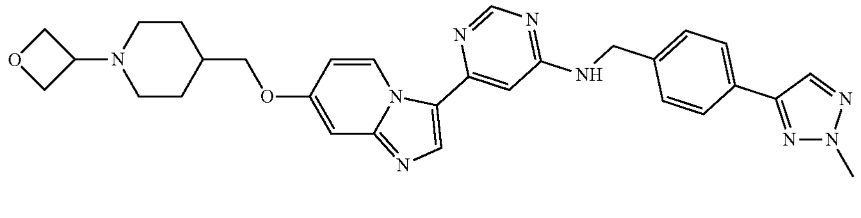 [SMILES: Cn1ncc(-c2ccc(CNc3cc(-c4cnc5cc(OCC6CCN(C7COC7)CC6)ccn45)ncn3)cc2)n1]

from G3 and E17) yellow solid; m.p. 181-182° C.; HPLC/MS $[M+H]^+$ 552.

$^1$H NMR (300 MHz, DMSO-$d_6$) δ 9.68 (d, J=7.7 Hz, 1H), 8.50 (s, 1H), 8.20-8.07 (m, 2H), 7.92 (t, J=6.1 Hz, 1H), 7.82-7.73 (m, 2H), 7.42 (d, J=7.9 Hz, 2H), 7.05 (d, J=2.6 Hz, 1H), 6.89 (s, 1H), 6.79 (dd, J=7.7, 2.6 Hz, 1H), 4.70-4.47 (m, 4H), 4.40 (t, J=6.0 Hz, 2H), 4.16 (s, 3H), 3.94 (d, J=5.8 Hz, 2H), 3.40-3.33 (m, 1H), 2.78-2.62 (m, 2H), 1.87-1.62 (m, 5H), 1.43-1.22 (m, 2H).

6-{7-[2-(3,3-difluoropyrrolidin-1-yl)ethoxy]imidazo[1,2-a]pyridin-3-yl}-N-{[4-(1-methyl-1H-pyrazol-4-yl)phenyl]methyl}pyrimidin-4-amine ("A77")

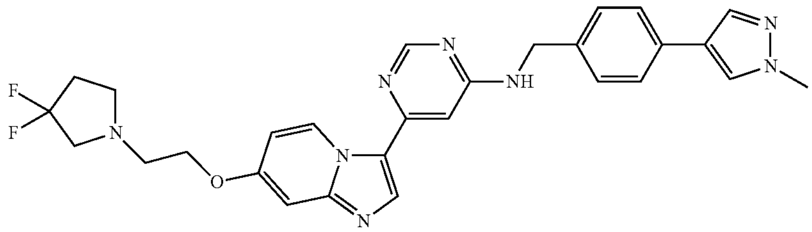 [SMILES: Cn1cc(-c2ccc(CNc3cc(-c4cnc5cc(OCCN6CCC(F)(F)C6)ccn45)ncn3)cc2)cn1]

from G1 and E18; pale orange solid; UPLC/MS 0.439 min, $[M+H]^+$ 531.

$^1$H NMR (500 MHz, DMSO-$d_6$) δ 9.69 (d, J=7.7 Hz, 1H), 8.51 (s, 1H), 8.14 (s, 1H), 8.07 (s, 1H), 7.83 (t, J=6.2 Hz, 1H), 7.80 (d, J=0.8 Hz, 1H), 7.51 (d, J=8.3 Hz, 2H), 7.34 (d, J=7.8 Hz, 2H), 7.10 (d, J=2.6 Hz, 1H), 6.89 (d, J=1.2 Hz, 1H), 6.81 (dd, J=7.7, 2.6 Hz, 1H), 4.54 (d, J=5.3 Hz, 2H), 4.20 (t, J=5.5 Hz, 2H), 3.84 (s, 3H), 3.00 (t, J=13.5 Hz, 2H), 2.88 (t, J=5.5 Hz, 2H), 2.82 (t, J=7.0 Hz, 2H), 2.24 (tt, J=15.3, 7.0 Hz, 2H).

[4-(1-methyl-1H-pyrazol-4-yl)-benzyl]-{6-[7-(1-oxetan-3-yl-piperidin-4-ylmethoxy)-imidazo[1,2-a]pyridin-3-yl]-pyrimidin-4-yl}-amine ("A78")

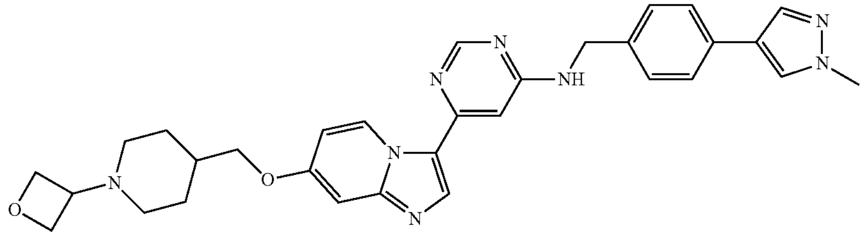 [SMILES: Cn1cc(-c2ccc(CNc3cc(-c4cnc5cc(OCC6CCN(C7COC7)CC6)ccn45)ncn3)cc2)cn1]

from G1 and E17; white solid; m.p. 241-242° C.; HPLC/MS $[M+H]^+$ 551.

$^1$H NMR (400 MHz, DMSO-$d_6$) δ 9.69 (d, J=7.7 Hz, 1H), 8.51 (s, 1H), 8.22-8.06 (m, 2H), 7.91-7.80 (m, 2H), 7.55-7.48 (m, 2H), 7.37-7.27 (m, 2H), 7.09-7.04 (m, 1H), 6.89 (s, 1H), 6.80 (dd, J=7.7, 2.6 Hz, 1H), 4.59-4.37 (m, 6H), 3.96 (d, J=5.9 Hz, 2H), 3.84 (s, 3H), 3.42-3.36 (m, 1H), 2.75-2.68 (m, 2H), 1.84-1.68 (m, 5H), 1.41-1.27 (m, 2H).

{6-[7-(1-methyl-piperidin-4-ylmethoxy)-imidazo[1,2-a]pyridin-3-yl]-pyrimidin-4-yl}-[4-(2-methyl-2H-[1,2,3]triazol-4-yl)-benzyl]-amine ("A79")

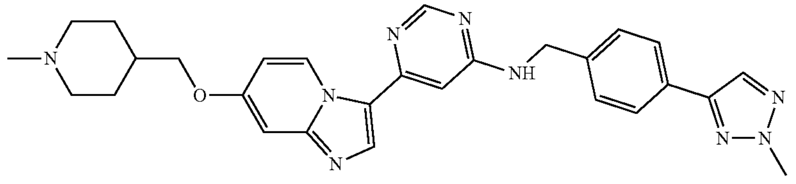

from G3 and E19; white solid; m.p. 240-241° C.; HPLC/MS $[M+H]^+$ 510.

$^1$H NMR (400 MHz, DMSO-$d_6$) 9.70 (d, J=7.8 Hz, 1H), 8.51 (s, 1H), 8.24-8.09 (m, 2H), 7.93 (t, J=6.2 Hz, 1H), 7.79 (d, J=8.2 Hz, 2H), 7.51-7.39 (m, 2H), 7.09-7.04 (m, 1H), 6.90 (s, 1H), 6.80 (dd, J=7.8, 2.6 Hz, 1H), 4.66-4.51 (m, 2H), 4.18 (s, 3H), 3.94 (d, J=5.8 Hz, 2H), 2.78 (d, J=11.0 Hz, 2H), 2.15 (s, 3H), 1.85 (t, 2H), 1.78-1.67 (m, 3H), 1.39-1.25 (m, 2H).

{6-[7-(1-methyl-piperidin-4-ylmethoxy)-imidazo[1,2-a]pyridin-3-yl]-pyrimidin-4-yl}-(4-[1,2,3]triazol-1-yl-benzyl)-amine ("A80")

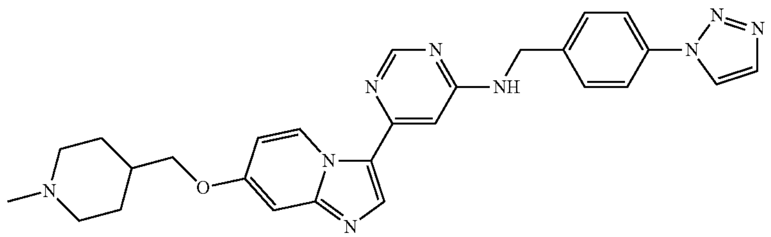 [SMILES: CN1CCC(COc2ccn3c(-c4cc(NCc5ccc(-n6ccnn6)cc5)ncn4)cnc3c2)CC1]

from G2 and E19; white solid; m.p. 221-222° C.; HPLC/MS $[M+H]^+$ 496.

$^1$H NMR (400 MHz, DMSO-$d_6$) δ 9.70 (d, J=7.7 Hz, 1H), 8.79 (s, 1H), 8.52 (s, 1H), 8.23-8.11 (m, 1H), 8.03-7.93 (m, 2H), 7.91-7.83 (m, 2H), 7.57 (d, J=8.1 Hz, 2H), 7.07 (d, J=2.6 Hz, 1H), 6.92 (d, J=1.3 Hz, 1H), 6.80 (dd, J=7.7, 2.6 Hz, 1H), 4.69-4.59 (m, 2H), 3.95 (d, J=5.9 Hz, 2H), 2.80 (d, J=11.0 Hz, 2H), 2.17 (s, 3H), 1.98-1.70 (m, 2H), 1.75 (d, J=11.5 Hz, 3H), 1.39-1.22 (m, 2H).

N-{[4-(1-methyl-1H-pyrazol-4-yl)phenyl]methyl}-6-{7-nitroimidazo[1,2-a]pyridin-3-yl}pyrimidin-4-amine ("A81")

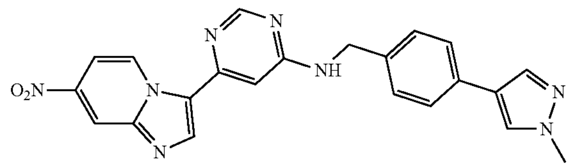 [SMILES: Cn1cc(-c2ccc(CNc3cc(-c4cnc5cc([N+](=O)[O-])ccn45)ncn3)cc2)cn1]

from G1; yellow powder; UPLC/MS 0.740 min, $[M+H]^+$ 427.

$^1$H NMR (400 MHz, DMSO-$d_6$) δ 9.99 (d, J=7.8 Hz, 1H), 8.73-8.53 (m, 3H), 8.08 (d, J=5.0 Hz, 2H), 7.85 (dd, J=7.7, 2.5 Hz, 1H), 7.81 (d, J=0.8 Hz, 1H), 7.66-7.47 (m, 2H), 7.35 (d, J=7.8 Hz, 2H), 7.10 (d, J=1.2 Hz, 1H), 4.58 (s, 2H), 3.84 (s, 3H).

6-{7-chloroimidazo[1,2-a]pyridin-3-yl}-N-{[4-(1-methyl-1H-pyrazol-4-yl)phenyl]methyl}pyrimidin-4-amine ("A82")

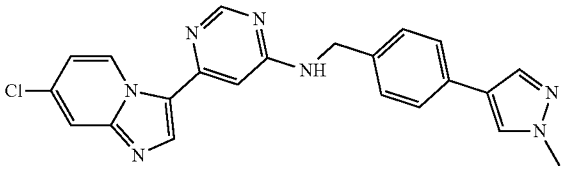 [SMILES: Cn1cc(-c2ccc(CNc3cc(-c4cnc5cc(Cl)ccn45)ncn3)cc2)cn1]

from G1; off-white solid; UPLC/MS 0.645 min, $[M+H]^+$ 416.

$^1$H NMR (400 MHz, DMSO-$d_6$) δ 9.85 (d, J=7.5 Hz, 1H), 8.56 (s, 1H), 8.32 (s, 1H), 8.07 (s, 1H), 7.95 (t, J=6.1 Hz, 1H), 7.88 (dd, J=2.2, 0.8 Hz, 1H), 7.81 (d, J=0.8 Hz, 1H), 7.51 (d, J=8.2 Hz, 2H), 7.34 (d, J=7.7 Hz, 2H), 7.18 (dd, J=7.5, 2.3 Hz, 1H), 6.98 (d, J=1.2 Hz, 1H), 4.55 (s, 2H), 3.84 (s, 3H).

{6-[7-(1-oxetan-3-yl-piperidin-4-ylmethoxy)-imidazo[1,2-a]pyridin-3-yl]-pyrimidin-4-yl}-(4-[1,2,3]triazol-1-yl-benzyl)-amine ("A83")

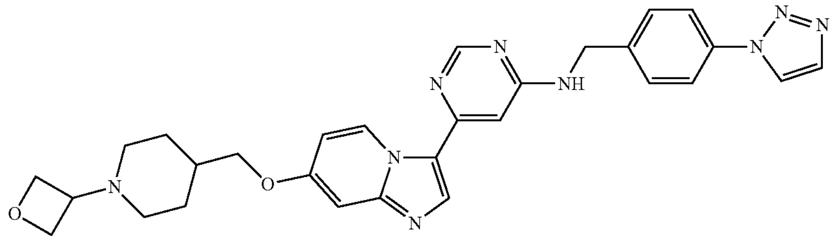 [SMILES: c1cn(-c2ccc(CNc3cc(-c4cnc5cc(OCC6CCN(C7COC7)CC6)ccn45)ncn3)cc2)nn1]

from G2 and E17; off-white solid; m.p. 272-273° C.; HPLC/MS $[M+H]^+$ 538.

$^1$H NMR (400 MHz, DMSO-$d_6$) δ 9.70 (d, J=7.7 Hz, 1H), 8.81-8.76 (m, 1H), 8.52 (s, 1H), 8.18 (s, 1H), 8.03-7.93 (m, 2H), 7.87 (d, J=8.5 Hz, 2H), 7.57 (d, J=8.2 Hz, 2H), 7.07 (d, J=2.6 Hz, 1H), 6.95-6.90 (m, 1H), 6.81 (dd, J=7.7, 2.6 Hz, 1H), 4.64 (s, 2H), 4.52 (t, J=6.4 Hz, 2H), 4.42 (t, J=6.1 Hz, 2H), 3.96 (d, J=5.8 Hz, 2H), 2.75-2.68 (m, 2H), 2.72 (d, J=8.2 Hz, 2H), 1.77 (t, J=10.1 Hz, 5H), 1.35 (t, J=12.2 Hz, 2H).

[4-(2-methyl-2H-[1,2,3]triazol-4-yl)-benzyl]-{6-[7-(3-pyrrolidin-1-yl-propoxy)-imidazo[1,2-a]pyridin-3-yl]-pyrimidin-4-yl}-amine ("A84")

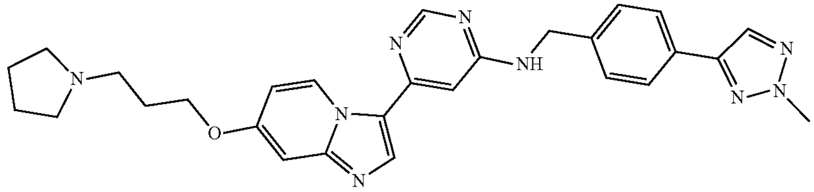 [SMILES: Cn1ncc(-c2ccc(CNc3cc(-c4cnc5cc(OCCCN6CCCC6)ccn45)ncn3)cc2)n1]

from G3 and E15; yellow solid; m.p. 251-242° C.; HPLC/MS $[M+H]^+$ 510.

$^1$H NMR (300 MHz, DMSO-$d_6$) δ 9.69 (d, J=7.8 Hz, 1H), 8.51 (s, 1H), 8.22-8.11 (m, 2H), 7.93 (t, J=6.1 Hz, 1H), 7.79 (d, J=8.2 Hz, 2H), 7.44 (d, J=7.8 Hz, 2H), 7.06 (d, J=2.6 Hz, 1H), 6.90 (s, 1H), 6.80 (dd, J=7.8, 2.6 Hz, 1H), 4.68-4.52 (m, 2H), 4.17 (s, 3H), 4.12 (t, J=6.3 Hz, 2H), 2.60-2.53 (m, 2H), 2.47-2.41 (m, 3H), 1.92 (p, J=6.7 Hz, 2H), 1.77-1.60 (m, 4H).

2-methyl-1-(3-{6-[4-(2-methyl-2H-[1,2,3]triazol-4-yl)-benzylamino]-pyrimidin-4-yl}-imidazo[1,2-a]pyridin-7-yloxy)-propan-2-ol ("A85")

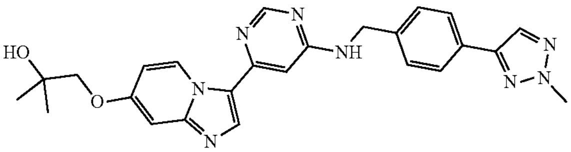 [SMILES: Cn1ncc(-c2ccc(CNc3cc(-c4cnc5cc(OCC(C)(C)O)ccn45)ncn3)cc2)n1]

from G3 and E12; white solid; m.p. 195-196° C.; HPLC/MS $[M+H]^+$ 471.

$^1$H NMR (400 MHz, DMSO-$d_6$) δ 8.53 (s, 1H), 8.22-8.10 (m, 2H), 7.94 (t, J=6.2 Hz, 1H), 7.80 (d, J=8.2 Hz, 2H), 7.45 (d, J=7.8 Hz, 2H), 7.06 (d, J=2.6 Hz, 1H), 6.91 (d, J=1.2 Hz, 1H), 6.83 (dd, J=7.7, 2.6 Hz, 1H), 4.73 (s, 1H), 4.60 (s, 2H), 4.18 (s, 3H), 3.84 (s, 2H), 1.23 (s, 6H).

7-[2-(4-methyl-piperazin-1-yl)-ethoxy]-3-{6-[4-(1-methyl-1H-pyrazol-4-yl)-benzyloxy]-pyrimidin-4-yl}-imidazo[1,2-a]pyridine ("A86")

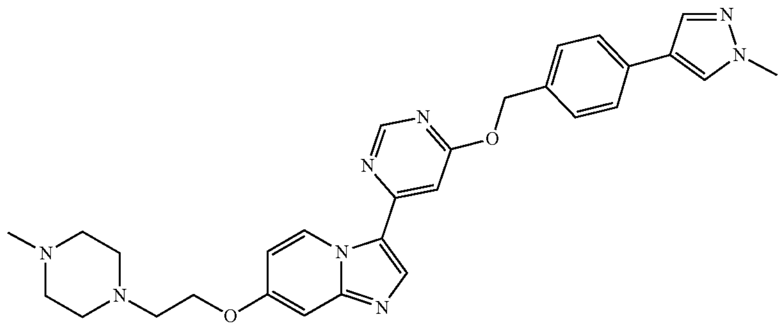

from G4 and E9; pale brown solid; m.p. 210-211° C.; HPLC/MS $[M+H]^+$ 525.

$^1$H NMR (300 MHz, DMSO-$d_6$) δ 9.75 (d, J=7.7 Hz, 1H), 8.83 (d, J=1.1 Hz, 1H), 8.48 (s, 1H), 8.13 (s, 1H), 7.85 (d, J=0.8 Hz, 1H), 7.63-7.52 (m, 2H), 7.47 (d, J=1.2 Hz, 1H), 7.45 (d, J=8.1 Hz, 2H), 7.15 (d, J=2.6 Hz, 1H), 6.87 (dd, J=7.7, 2.6 Hz, 1H), 5.42 (s, 2H), 4.18 (t, J=5.6 Hz, 2H), 3.84 (s, 4H), 2.71 (t, J=5.5 Hz, 2H), 2.55-2.23 (m, 8H), 2.14 (s, 3H).

3-{6-[4-(1-methyl-1H-pyrazol-4-yl)-benzyloxy]-pyrimidin-4-yl}-7-(2-pyrrolidin-1-yl-ethoxy)-imidazo[1,2-a]pyridine ("A87")

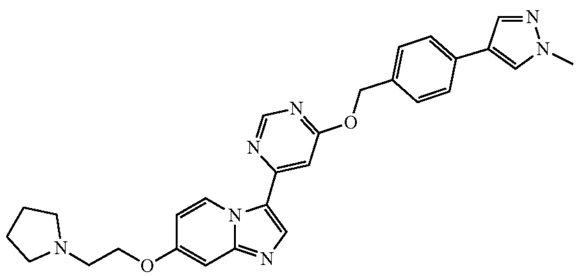 [SMILES: Cn1cc(-c2ccc(COc3cc(-c4cnc5cc(OCCN6CCCC6)ccn45)ncn3)cc2)cn1]

from G4 and E8; white solid; m.p. 177-178° C.; HPLC/MS $[M+H]^+$ 496.

$^1$H NMR (300 MHz, DMSO-$d_6$) δ 9.75 (d, J=7.7 Hz, 1H), 8.83 (d, J=1.0 Hz, 1H), 8.48 (s, 1H), 8.13 (s, 1H), 7.85 (s, 1H), 7.57 (d, J=8.2 Hz, 2H), 7.49-7.42 (m, 3H), 7.14 (d, J=2.6 Hz, 1H), 6.87 (dd, J=7.7, 2.6 Hz, 1H), 5.42 (s, 2H), 4.17 (t, J=5.6 Hz, 2H), 3.84 (s, 3H), 2.81 (t, J=5.7 Hz, 2H), 2.55-2.46 (m, 4H), 1.67 (p, J=3.0 Hz, 4H).

4-[3-({3-[6-({[4-(1-methyl-1H-pyrazol-4-yl)phenyl] methyl}amino)pyrimidin-4-yl]imidazo[1,2-a]pyridin-7-yl}oxy)propyl]morpholin-3-one ("A88")

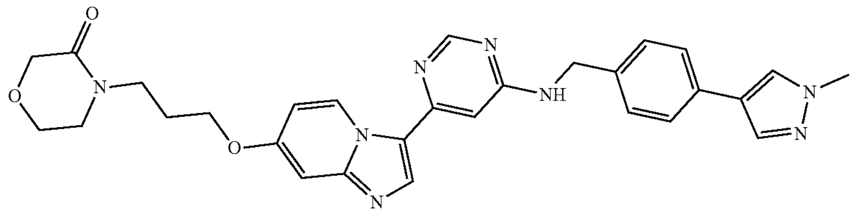 [SMILES: Cn1cc(-c2ccc(CNc3cc(-c4cnc5cc(OCCCN6CCOCC6=O)ccn45)ncn3)cc2)cn1]

from G1 and E20; off-white solid; UPLC/MS 0.478 min, $[M+H]^+$ 539.

$^1H$ NMR (500 MHz, DMSO-$d_6$) δ 9.69 (d, J=7.7 Hz, 1H), 8.51 (s, 1H), 8.14 (s, 1H), 8.07 (d, J=0.8 Hz, 1H), 7.83 (t, J=6.1 Hz, 1H), 7.80 (d, J=0.8 Hz, 1H), 7.51 (d, J=8.2 Hz, 2H), 7.34 (d, J=7.9 Hz, 2H), 7.05 (d, J=2.6 Hz, 1H), 6.89 (d, J=1.2 Hz, 1H), 6.80 (dd, J=7.7, 2.6 Hz, 1H), 4.54 (d, J=5.9 Hz, 2H), 4.11 (t, J=6.2 Hz, 2H), 4.01 (s, 2H), 3.84 (s, 3H), 3.84-3.81 (m, 3H), 3.50 (t, J=7.1 Hz, 2H), 3.38 (dd, J=5.9, 4.4 Hz, 2H), 2.02 (p, J=6.5 Hz, 2H).

6-{7-[2-(3-fluoropyrrolidin-1-yl)ethoxy]imidazo[1,2-a]pyridin-3-yl}-N-{[4-(1-methyl-1H-pyrazol-4-yl)phenyl]methyl}pyrimidin-4-amine ("A89")

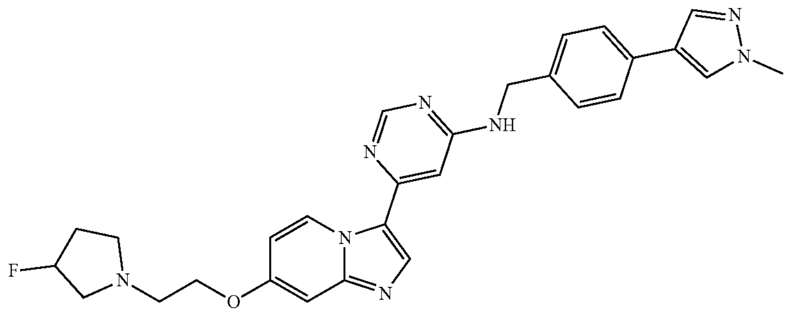 [SMILES: Cn1cc(-c2ccc(CNc3cc(-c4cnc5cc(OCCN6CCC(F)C6)ccn45)ncn3)cc2)cn1]

from G1 and E21; off-white solid; UPLC/MS 0.382 min, $[M+H]^+$ 513.

$^1H$ NMR (500 MHz, DMSO-$d_6$) δ 9.75 (d, J=7.7 Hz, 1H), 8.53 (s, 1H), 8.24 (s, 1H), 8.07 (d, J=0.9 Hz, 1H), 7.92 (t, J=6.1 Hz, 1H), 7.80 (d, J=0.8 Hz, 1H), 7.51 (d, J=8.2 Hz, 2H), 7.34 (d, J=7.8 Hz, 2H), 7.22 (d, J=2.6 Hz, 1H), 5.46 (d, J=53.8 Hz, 1H), 4.55 (d, J=5.9 Hz, 2H), 4.49 (t, J=5.0 Hz, 2H), 3.84 (s, 3H), 3.9-3.1 (m, 6H), 2.22 (bs, 2H).

7-[2-(3,3-difluoro-pyrrolidin-1-yl)-ethoxy]-3-{6-[4-(1-methyl-1H-pyrazol-4-yl)-benzyloxy]-pyrimidin-4-yl}-imidazo[1,2-a]pyridine ("A90")

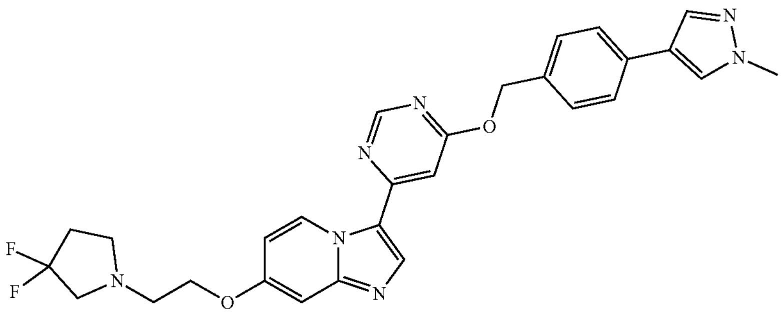 [SMILES: Cn1cc(-c2ccc(COc3cc(-c4cnc5cc(OCCN6CCC(F)(F)C6)ccn45)ncn3)cc2)cn1]

from G4 and E18; white solid; m.p. 178-179° C.; HPLC/MS $[M+H]^+$ 532.

$^1$H NMR (300 MHz, DMSO-$d_6$) δ 9.76 (d, J=7.7 Hz, 1H), 8.84 (d, J=1.1 Hz, 1H), 8.49 (s, 1H), 8.13 (s, 1H), 7.86 (s, 1H), 7.57 (d, J=8.2 Hz, 2H), 7.47 (d, J=1.1 Hz, 1H), 7.45 (d, J=8.2 Hz, 2H), 7.16 (d, J=2.7 Hz, 1H), 6.89 (dd, J=7.7, 2.6 Hz, 1H), 5.42 (s, 2H), 4.20 (t, J=5.5 Hz, 2H), 3.84 (s, 3H), 2.99 (t, J=13.5 Hz, 2H), 2.87 (t, J=5.4 Hz, 2H), 2.80 (t, J=7.0 Hz, 2H), 2.23 (tt, J=15.0, 7.0 Hz, 2H).

{6-[7-(2,2-dimethyl-3-pyrrolidin-1-yl-propoxy)-imidazo[1,2-a]pyridin-3-yl]-pyrimidin-4-yl}-[4-(1-methyl-1H-pyrazol-4-yl)-benzyl]-amine ("A91")

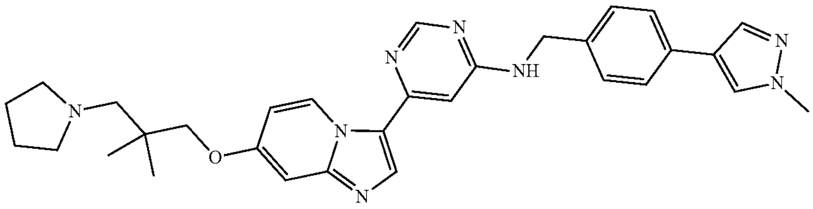 [SMILES: Cn1cc(-c2ccc(CNc3cc(-c4cnc5cc(OCC(C)(C)CN6CCCC6)ccn45)ncn3)cc2)cn1]

from G1 and E22; white solid; m.p. 251-252° C.; HPLC/MS $[M+H]^+$ 537.

$^1$H NMR (300 MHz, DMSO-$d_6$) δ 9.68 (d, J=7.7 Hz, 1H), 8.51 (s, 1H), 8.14 (s, 1H), 8.08 (d, J=0.8 Hz, 1H), 7.87 (t, J=6.1 Hz, 1H), 7.81 (d, J=0.8 Hz, 1H), 7.51 (d, J=8.2 Hz, 2H), 7.34 (d, J=7.9 Hz, 2H), 7.05 (d, J=2.6 Hz, 1H), 6.89 (d, J=1.2 Hz, 1H), 6.81 (dd, J=7.7, 2.6 Hz, 1H), 4.54 (s, 2H), 3.84 (s, 3H), 3.82 (s, 2H), 2.57-2.51 (m, 4H), 2.45 (s, 2H), 1.63 (p, J=3.0 Hz, 4H), 0.98 (s, 6H).

4-[2-({3-[6-({[4-(1-methyl-1H-pyrazol-4-yl)phenyl]methyl}amino)pyrimidin-4-yl]imidazo[1,2-a]pyridin-7-yl}oxy)ethyl]morpholin-3-one ("A92")

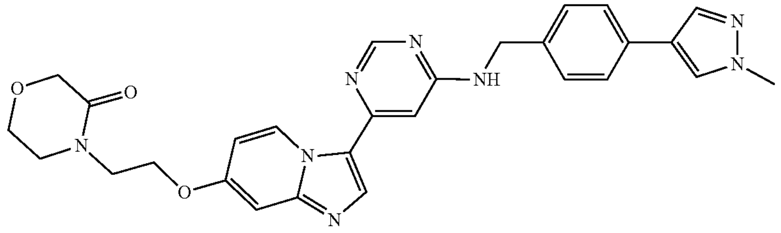 [SMILES: Cn1cc(-c2ccc(CNc3cc(-c4cnc5cc(OCCN6CCOCC6=O)ccn45)ncn3)cc2)cn1]

from G1 and E24; off-white solid; HPLC/MS(A) 1.19 min, $[M+H]^+$ 525.

$^1$H NMR (500 MHz, DMSO-$d_6$) δ 9.69 (d, J=7.7 Hz, 1H), 8.51 (s, 1H), 8.14 (s, 1H), 8.07 (d, J=0.8 Hz, 1H), 7.83 (t, J=6.1 Hz, 1H), 7.80 (d, J=0.8 Hz, 1H), 7.51 (d, J=8.2 Hz, 2H), 7.34 (d, J=7.8 Hz, 2H), 7.13 (d, J=2.6 Hz, 1H), 6.89 (d, J=1.2 Hz, 1H), 6.80 (dd, J=7.7, 2.6 Hz, 1H), 4.54 (d, J=5.7 Hz, 2H), 4.27 (t, J=5.6 Hz, 2H), 4.05 (s, 2H), 3.84 (s, 3H), 3.84-3.81 (m, 2H), 3.75 (t, J=5.6 Hz, 2H), 3.54-3.48 (m, 2H).

1-methyl-4-[2-({3-[6-({[4-(1-methyl-1H-pyrazol-4-yl)phenyl]methyl}amino)pyrimidin-4-yl]imidazo[1,2-a]pyridin-7-yl}oxy)ethyl]piperazin-2-one ("A93")

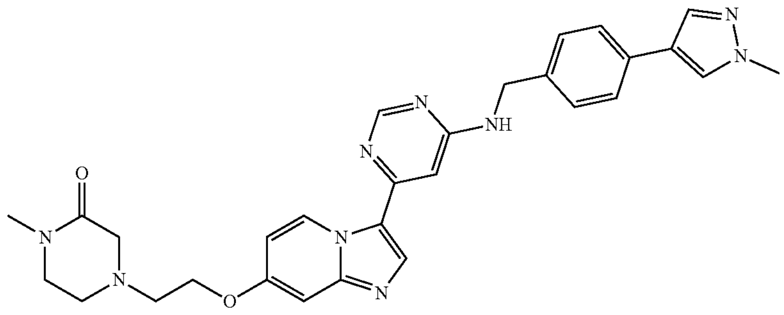

from G1 and E26; pale yellow resin; UPLC/MS 0.424 min, $[M+H]^+$ 538.

$^1$H NMR (500 MHz, DMSO-$d_6$) δ 9.83 (s, 1H), 8.60 (s, 1H), 8.17 (t, J=6.2 Hz, 1H), 8.07 (s, 1H), 7.81 (d, J=0.8 Hz, 1H), 7.58-7.47 (m, 2H), 7.37-7.30 (m, 3H), 7.24-7.14 (m, 1H), 7.01 (s, 1H), 4.57 (s, 2H), 4.50 (t, J=5.0 Hz, 2H), 3.85 (s, 3H), 3.64 (s, 2H), 3.52-3.41 (m, 4H), 3.42-3.19 (m, 4H), 2.87 (s, 3H).

N-{[4-(1-methyl-1H-pyrazol-4-yl)phenyl]methyl}-6-{7-[3-(4-methylpiperazin-1-yl)propoxy]imidazo[1,2-a]pyridin-3-yl}pyrimidin-4-amine ("A94")

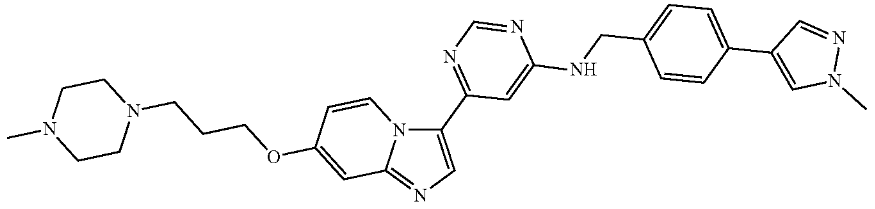

from G1 and E27; yellow resin; UPLC/MS 0.376 min, $[M+H]^+$ 538.

1-[2-({3-[6-({[4-(1-methyl-1H-pyrazol-4-yl)phenyl]methyl}amino)pyrimidin-4-yl]imidazo[1,2-a]pyridin-7-yl}oxy)ethyl]-4-(oxetan-3-yl)piperazin-2-one ("A95")

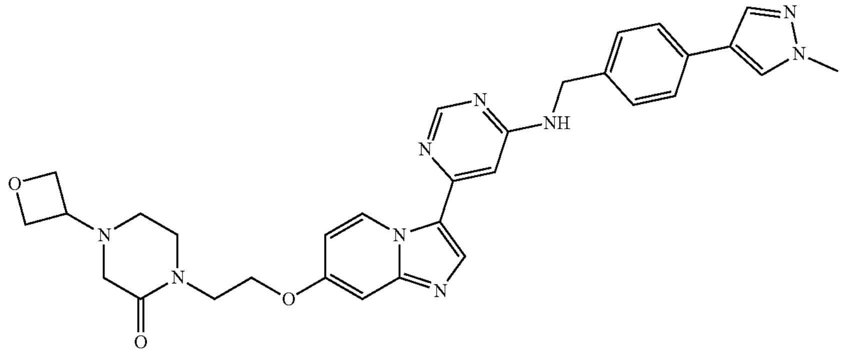 [SMILES: Cn1cc(-c2ccc(CNc3cc(-c4cnc5cc(OCCN6CCN(C7COC7)CC6=O)ccn45)ncn3)cc2)cn1]

from G1 and E28; off-white needles; HPLC/MS(A) 1.16 min, $[M+H]^+$ 580.

$^1H$ NMR (500 MHz, DMSO-$d_6$) δ 9.70 (d, J=7.7 Hz, 1H), 8.51 (s, 1H), 8.14 (s, 1H), 8.07 (d, J=0.8 Hz, 1H), 7.83 (t, J=6.1 Hz, 1H), 7.80 (d, J=0.8 Hz, 1H), 7.51 (d, J=8.2 Hz, 2H), 7.34 (d, J=7.8 Hz, 2H), 7.13 (d, J=2.7 Hz, 1H), 6.89 (d, J=1.2 Hz, 1H), 6.80 (dd, J=7.7, 2.6 Hz, 1H), 4.54 (t, J=6.6 Hz, 2H), 4.44 (t, J=6.1 Hz, 2H), 4.25 (t, J=5.6 Hz, 2H), 3.84 (s, 3H), 3.72 (t, J=5.6 Hz, 2H), 3.52 (p, J=6.2 Hz, 1H), 3.47 (dd, J=6.1, 4.8 Hz, 2H), 2.97 (s, 2H), 2.58 (dd, J=6.2, 4.7 Hz, 2H).

N-{[4-(2-methyl-2H-1,2,3-triazol-4-yl)phenyl]methyl}-6-{7-[3-(4-methylpiperazin-1-yl)propoxy]imidazo[1,2-a]pyridin-3-yl}pyrimidin-4-amine ("A96")

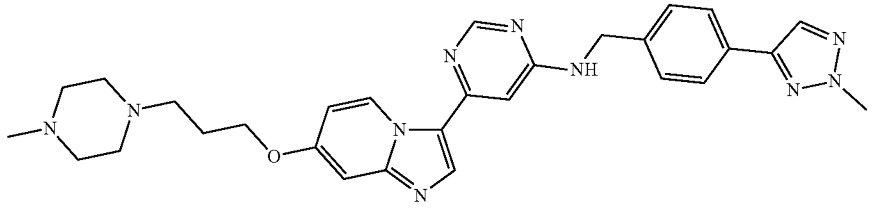

from G3 and E27; pale yellow solid; UPLC/MS 0.367 min, $[M+H]^+$ 539.

5-fluoro-6-{7-methoxyimidazo[1,2-a]pyridin-3-yl}-N-{[4-(1-methyl-1H-pyrazol-4-yl)phenyl]methyl}pyrimidin-4-amine ("A97")

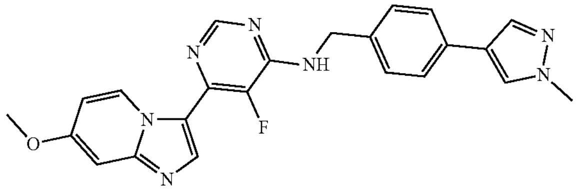

from G5; off-white powder; UPLC/MS 0.519 min, $[M+H]^+$ 430.

$^1$H NMR (500 MHz, DMSO-$d_6$) δ 9.77 (d, J=7.8 Hz, 1H), 8.37 (d, J=2.2 Hz, 1H), 8.28 (t, J=6.2 Hz, 1H), 8.14 (d, J=3.9 Hz, 1H), 8.07 (s, 1H), 7.81 (d, J=0.6 Hz, 1H), 7.51 (d, J=8.2 Hz, 2H), 7.34 (d, J=8.2 Hz, 2H), 7.15 (d, J=2.6 Hz, 1H), 6.85 (dd, J=7.7, 2.7 Hz, 1H), 4.65 (d, J=6.1 Hz, 2H), 3.91 (s, 3H).

(6-{7-[2-(1-methyl-1H-imidazol-2-yl)-ethoxy]-imidazo[1,2-a]pyridin-3-yl}-pyrimidin-4-yl)-[4-(2-methyl-2H-[1,2,3]triazol-4-yl)-benzyl]-amine ("A98")

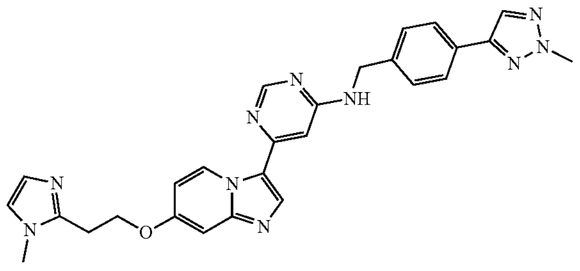 [SMILES: Cn1ncc(-c2ccc(CNc3cc(-c4cnc5cc(OCCc6nccn6C)ccn45)ncn3)cc2)n1]

from G3 and E30; white solid m.p. 240-241° C.; HPLC/MS $[M+H]^+$ 507.

$^1$H NMR (300 MHz, DMSO-$d_6$) δ 9.23 (s, 1H), 8.78 (d, J=19.4 Hz, 2H), 8.18 (s, 1H), 8.12 (s, 2H), 7.79 (d, J=7.9 Hz, 2H), 7.63 (dd, J=17.3, 1.9 Hz, 2H), 7.48 (d, J=2.5 Hz, 3H), 7.40-7.26 (m, 2H), 4.75 (s, 2H), 4.66 (t, J=5.6 Hz, 2H), 4.14 (s, 3H), 3.86 (s, 3H), 3.58 (s, 2H).

6-{7-[2-(azetidin-1-yl)ethoxy]imidazo[1,2-a]pyridin-3-yl}-N-{[4-(1-methyl-1H-pyrazol-4-yl)phenyl]methyl}pyrimidin-4-amine ("A99")

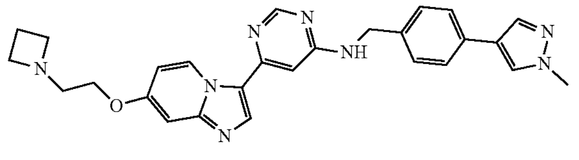 [SMILES: Cn1cc(-c2ccc(CNc3cc(-c4cnc5cc(OCCN6CCC6)ccn45)ncn3)cc2)cn1]

from G1 and E31; white powder; UPLC/MS 0.362 min, $[M+H]^+$ 481.

$^1$H NMR (500 MHz, DMSO-$d_6$) δ 9.69 (d, J=7.7 Hz, 1H), 8.52 (s, 1H), 8.14 (s, 1H), 8.08 (s, 1H), 7.83 (t, J=6.2 Hz, 1H), 7.81 (d, J=0.8 Hz, 1H), 7.52 (d, J=8.3 Hz, 2H), 7.35 (d, J=7.8 Hz, 2H), 7.05 (d, J=2.6 Hz, 1H), 6.89 (d, J=1.3 Hz, 1H), 6.78 (dd, J=7.7, 2.6 Hz, 1H), 4.55 (d, J=6.0 Hz, 2H), 4.03 (t, J=5.5 Hz, 2H), 3.85 (s, 3H), 3.20 (t, J=6.9 Hz, 4H), 2.74 (t, J=5.5 Hz, 2H), 1.98 (p, J=6.9 Hz, 2H).

6-{7-[2-(azetidin-1-yl)ethoxy]imidazo[1,2-a]pyridin-3-yl}-N-{[4-(2-methyl-2H-1,2,3-triazol-4-yl)phenyl]methyl}pyrimidin-4-amine ("A100")

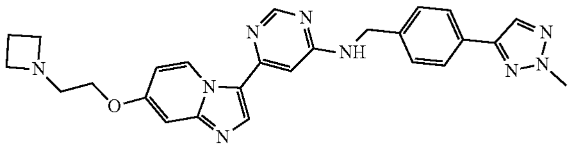 [SMILES: Cn1ncc(-c2ccc(CNc3cc(-c4cnc5cc(OCCN6CCC6)ccn45)ncn3)cc2)n1]

from G3 and E31; off-white powder; UPLC/MS 0.364 min, $[M+H]^+$ 482.

$^1$H NMR (500 MHz, DMSO-$d_6$) δ 9.69 (d, J=7.7 Hz, 1H), 8.52 (s, 1H), 8.17 (s, 1H), 8.15 (s, 1H), 7.89 (t, J=6.2 Hz, 1H), 7.80 (d, J=8.3 Hz, 2H), 7.45 (d, J=7.8 Hz, 2H), 7.05 (d, J=2.6 Hz, 1H), 6.91 (d, J=1.2 Hz, 1H), 6.78 (dd, J=7.7, 2.6 Hz, 1H), 4.60 (d, J=6.0 Hz, 2H), 4.03 (t, J=5.5 Hz, 2H), 3.20 (t, J=6.9 Hz, 4H), 2.75 (t, J=5.5 Hz, 2H), 1.98 (p, J=6.9 Hz, 2H).

6-{7-[3-(3,3-difluoropyrrolidin-1-yl)propoxy]imidazo[1,2-a]pyridin-3-yl}-N-{[4-(1-methyl-1H-pyrazol-4-yl)phenyl]methyl}pyrimidin-4-amine ("A101") trifluoroacetate

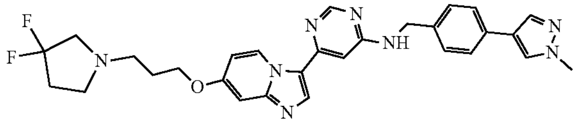 [SMILES: Cn1cc(-c2ccc(CNc3cc(-c4cnc5cc(OCCCN6CCC(F)(F)C6)ccn45)ncn3)cc2)cn1]

from G1 and E32; off-white powder; UPLC/MS 0.408 min, $[M+H]^+$ 545.

$^1$H NMR (500 MHz, DMSO-$d_6$) δ 9.83 (s, 1H), 8.60 (s, 1H), 8.16 (t, J=6.1 Hz, 1H), 8.07 (d, J=0.8 Hz, 1H), 7.81 (d, J=0.8 Hz, 1H), 7.51 (d, J=8.2 Hz, 2H), 7.34 (d, J=7.9 Hz, 2H), 7.28 (d, J=2.6 Hz, 1H), 7.14 (d, J=7.7 Hz, 1H), 7.00 (s, 1H), 4.57 (s, 2H), 4.28 (t, J=6.0 Hz, 2H), 3.85 (s, 3H), 2.15 (p, J=5.9 Hz, 3H), 4.0-3.0 (broad signals).

Example 3

Synthesis of 6-{7-[3-(azetidin-1-yl)propoxy]imidazo[1,2-a]pyridin-3-yl}-N-{[4-(1-methyl-1H-pyrazol-4-yl)phenyl]methyl}pyrimidin-4-amine}pyrimidin-4-amine ("A102")

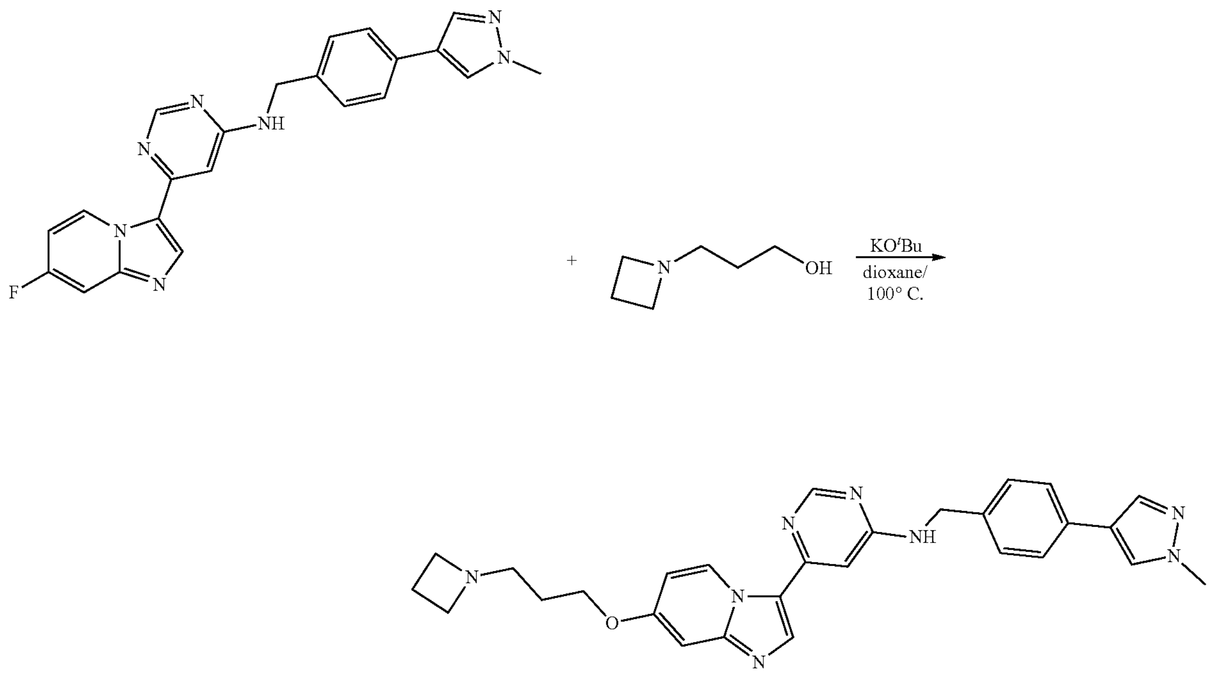

To a suspension of 6-{7-fluoroimidazo[1,2-a]pyridin-3-yl}-N-{[4-(1-methyl-1H-pyrazol-4-yl)phenyl]methyl}pyrimidin-4-amine (H1) in dioxane (48 ml) is added 3-(azetidin-1-yl)propan-1-ol (415 mg, 3.60 mmol) and the mixture is flushed with argon. Potassium tert-butanolate (1.01 g, 9.01 mmol) is added in portions. The mixture is heated to 100° C. and stirred at this temperature for 18 hours. The reaction mixture is allowed to reach room temperature, treated with methanol and evaporated. The residue is taken up in water. The solids are filtered off, washed with water and dried. The residue is chromatographed on a silica gel column with dichloromethane/methanol as eluent to afford 6-{7-[3-(azetidin-1-yl)propoxy]imidazo[1,2-a]pyridin-3-yl}-N-{[4-(1-methyl-1H-pyrazol-4-yl)phenyl]methyl}pyrimidin-4-amine}pyrimidin-4-amine as off-white solid; HPLC/MS(B) 0.639 min, $[M+H]^+$ 495.

$^1$H NMR (500 MHz, DMSO-$d_6$) δ 8.51 (s, 1H), 8.13 (s, 1H), 8.07 (d, J=0.8 Hz, 1H), 7.82 (t, J=6.1 Hz, 1H), 7.80 (d, J=0.8 Hz, 1H), 7.51 (d, J=8.2 Hz, 2H), 7.34 (d, J=7.8 Hz, 2H), 7.03 (d, J=2.5 Hz, 1H), 6.89 (d, J=1.2 Hz, 1H), 6.78 (dd, J=7.7, 2.6 Hz, 1H), 4.54 (d, J=6.0 Hz, 2H), 4.09 (t, J=6.4 Hz, 2H), 3.84 (s, 3H), 3.17 (s, 1H), 3.09 (t, J=6.9 Hz, 4H), 2.46 (t, J=6.9 Hz, 2H), 1.94 (p, J=6.9 Hz, 2H), 1.73 (p, J=6.6 Hz, 2H).

The following compounds are prepared analogously:

[4-(1-methyl-1H-pyrazol-4-yl)-benzyl]-(6-{7-[2-(6-oxa-3-aza-bicyclo[3.1.1]hept-3-yl)-ethoxy]-imidazo[1,2-a]pyridin-3-yl}-pyrimidin-4-yl)-amine ("A103")

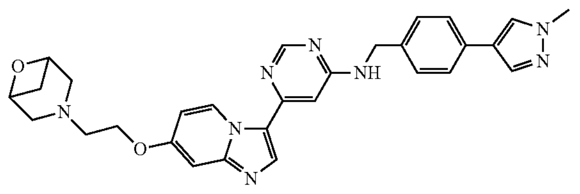 [SMILES: Cn1cc(-c2ccc(CNc3cc(-c4cnc5cc(OCCN6CC7CC(C6)O7)ccn45)ncn3)cc2)cn1]

from H1; white solid; m.p. 185-187° C.; HPLC/MS $[M+H]^+$ 523.

$^1$H NMR (400 MHz, DMSO-$d_6$) δ 9.70 (d, J=7.6 Hz, 1H), 8.52 (s, 1H), 8.22-8.14 (m, 1H), 8.10 (s, 1H), 7.89 (t, J=6.1 Hz, 1H), 7.82 (s, 1H), 7.52 (d, J=8.1 Hz, 2H), 7.39-7.28 (m, 2H), 7.14 (d, J=2.6 Hz, 1H), 6.90 (s, 1H), 6.83 (dd, J=7.7, 2.6 Hz, 1H), 4.58-4.49 (m, 2H), 4.44 (d, J=6.2 Hz, 2H), 4.26 (t, J=5.7 Hz, 2H), 3.85 (s, 3H), 3.17-3.09 (m, 2H), 3.05-2.96 (m, 2H), 2.88-2.82 (m, 1H), 2.81-2.74 (m, 2H), 2.22-2.16 (m, 1H).

{6-[7-(2-amino-2-methyl-propoxy)-imidazo[1,2-a]pyridin-3-yl]-pyrimidin-4-yl}-[4-(1-methyl-1H-pyrazol-4-yl)-benzyl]-amine ("A104")

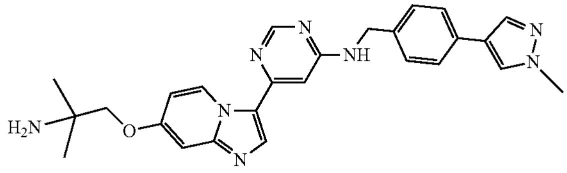 [SMILES: Cn1cc(-c2ccc(CNc3cc(-c4cnc5cc(OCC(C)(C)N)ccn45)ncn3)cc2)cn1]

from H1; white solid; m.p. 224-225° C.; HPLC/MS $[M+H]^+$ 469.

$^1$H NMR (300 MHz, DMSO-$d_6$) δ 9.70 (d, J=7.7 Hz, 1H), 8.51 (s, 1H), 8.15 (s, 1H), 8.09 (s, 1H), 7.88 (t, J=6.1 Hz, 1H), 7.82 (s, 1H), 7.51 (d, J=8.2 Hz, 2H), 7.34 (d, J=7.9 Hz, 2H), 7.03 (d, J=2.6 Hz, 1H), 6.89 (d, J=1.2 Hz, 1H), 6.83 (dd, J=7.7, 2.6 Hz, 1H), 4.54 (s, 2H), 3.84 (s, 3H), 3.77 (s, 2H), 1.23 (s, 2H), 1.12 (s, 6H).

(6-{7-[2-(3,3-difluoro-pyrrolidin-1-yl)-ethoxy]-imidazo[1,2-a]pyridin-3-yl}-pyrimidin-4-yl)-[4-(2-methyl-2H-[1,2,3]triazol-4-yl)-benzyl]-amine ("A105")

from H2; white solid; m.p. 240-241° C.; HPLC/MS $[M+H]^+$ 490.

$^1$H NMR (300 MHz, DMSO-$d_6$) δ 9.72 (d, J=7.7 Hz, 1H), 8.59 (dt, J=4.7, 1.5 Hz, 1H), 8.50 (s, 1H), 8.16 (s, 1H), 7.92 (t, J=6.1 Hz, 1H), 7.85 (td, J=7.7, 1.8 Hz, 1H), 7.78 (d, J=8.2 Hz, 2H), 7.57 (d, J=7.8 Hz, 1H), 7.42 (d, J=8.0 Hz, 2H), 7.36 (ddd, J=7.6, 4.8, 1.2 Hz, 1H), 7.16 (d, J=2.6 Hz, 1H), 6.93-6.88 (m, 2H), 5.28 (s, 2H), 4.58 (d, J=5.8 Hz, 2H), 4.16 (s, 3H).

{6-[7-(2-methyl-2-morpholin-4-yl-propoxy)-imidazo[1,2-a]pyridin-3-yl]-pyrimidin-4-yl}-[4-(1-methyl-1H-pyrazol-4-yl)-benzyl]-amine ("A107")

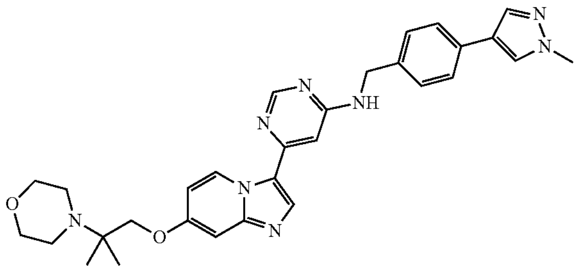

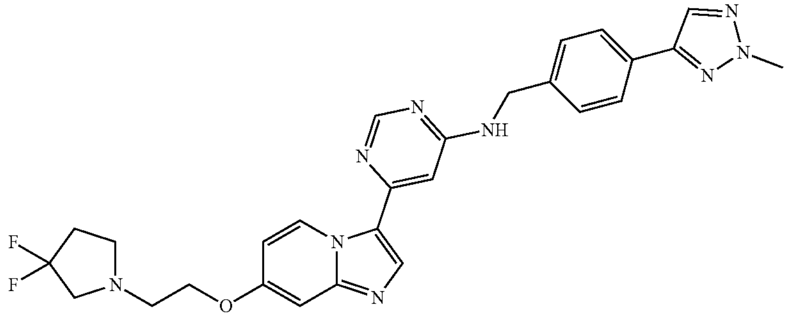 [SMILES: Cn1ncc(-c2ccc(CNc3cc(-c4cnc5cc(OCCN6CCC(F)(F)C6)ccn45)ncn3)cc2)n1]

from H2; white solid; m.p. 257-258° C.; HPLC/MS $[M+H]^+$ 532.

$^1$H NMR (300 MHz, DMSO-$d_6$) δ 9.69 (d, J=7.8 Hz, 1H), 8.50 (s, 1H), 8.17 (s, 1H), 7.93 (t, J=6.1 Hz, 1H), 7.78 (d, J=8.2 Hz, 2H), 7.42 (d, J=7.9 Hz, 2H), 7.10 (s, 1H), 6.89 (s, 1H), 6.81 (dd, J=7.7, 2.3 Hz, 1H), 4.58 (s, 2H), 4.28-3.98 (m, 5H), 2.99 (t, J=13.5 Hz, 2H), 2.86 (t, J=5.3 Hz, 2H), 2.79 (t, J=7.0 Hz, 2H), 2.23 (tt, J=15.2, 6.9 Hz, 2H).

[4-(2-methyl-2H-[1,2,3]triazol-4-yl)-benzyl]-{6-[7-(pyridin-2-ylmethoxy)-imidazo[1,2-a]pyridin-3-yl]-pyrimidin-4-yl}-amine ("A106")

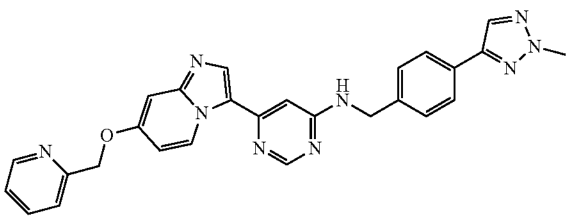 [SMILES: Cn1ncc(-c2ccc(CNc3cc(-c4cnc5cc(OCc6ccccn6)ccn45)ncn3)cc2)n1]

from H1; white solid; m.p. 233-234° C.; HPLC/MS $[M+H]^+$ 539.

$^1$H NMR (300 MHz, DMSO-$d_6$) δ 9.69 (d, J=7.7 Hz, 1H), 8.52 (s, 1H), 8.15 (s, 1H), 8.08 (s, 1H), 7.87 (t, J=6.1 Hz, 1H), 7.81 (d, J=0.8 Hz, 1H), 7.51 (d, J=8.2 Hz, 2H), 7.34 (d, J=7.9 Hz, 2H), 7.13 (d, J=2.6 Hz, 1H), 6.89 (d, J=1.2 Hz, 1H), 6.82 (dd, J=7.7, 2.6 Hz, 1H), 4.53 (d, J=5.9 Hz, 2H), 3.96 (s, 2H), 3.84 (s, 3H), 3.55 (t, J=4.5 Hz, 4H), 2.61 (t, J=4.5 Hz, 4H), 1.12 (s, 6H).

[4-(2-methyl-2H-[1,2,3]triazol-4-yl)-benzyl]-(6-{7-[2-(2-oxa-6-aza-spiro[3.3]hept-6-yl)-ethoxy]-imidazo[1,2-a]pyridin-3-yl}-pyrimidin-4-yl)-amine ("A108")

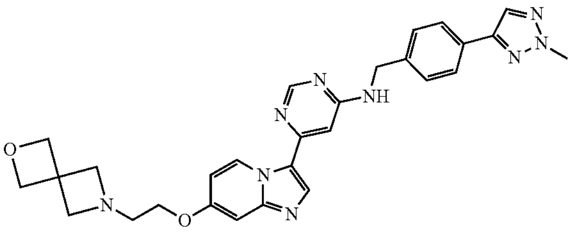 [SMILES: Cn1ncc(-c2ccc(CNc3cc(-c4cnc5cc(OCCN6CC7(COC7)C6)ccn45)ncn3)cc2)n1]

from H2; white solid; m.p. 245-246° C.; HPLC/MS $[M+H]^+$ 524.

$^1H$ NMR (300 MHz, DMSO-$d_6$) δ 9.67 (d, J=7.7 Hz, 1H), 8.50 (s, 1H), 8.16 (s, 1H), 8.14 (s, 1H), 7.91 (t, J=6.1 Hz, 1H), 7.77 (d, J=8.2 Hz, 2H), 7.42 (d, J=7.9 Hz, 2H), 7.03 (d, J=2.6 Hz, 1H), 6.89 (d, J=1.2 Hz, 1H), 6.76 (dd, J=7.7, 2.6 Hz, 1H), 4.62-4.54 (m, 6H), 4.16 (s, 3H), 4.00 (t, J=5.4 Hz, 2H), 3.30 (s, 4H), 2.70 (t, J=5.3 Hz, 2H).

{6-[7-(2-methyl-2-morpholin-4-yl-propoxy)-imidazo[1,2-a]pyridin-3-yl]-pyrimidin-4-yl}-[4-(2-methyl-2H-[1,2,3]triazol-4-yl)-benzyl]-amine ("A109")

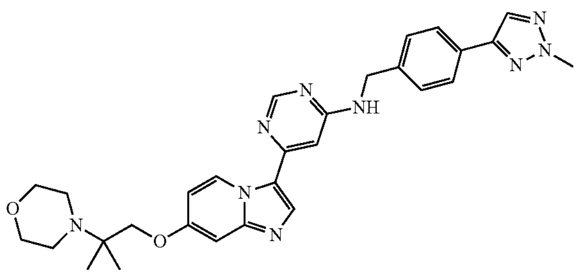 [SMILES: Cn1ncc(-c2ccc(CNc3cc(-c4cnc5cc(OCC(C)(C)N6CCOCC6)ccn45)ncn3)cc2)n1]

from H2; white solid; m.p. 220-221° C.; HPLC/MS $[M+H]^+$ 540.

$^1H$ NMR (300 MHz, DMSO-$d_6$) δ 9.67 (d, J=7.7 Hz, 1H), 8.50 (s, 1H), 8.15 (d, J=6.9 Hz, 2H), 7.91 (t, J=6.2 Hz, 1H), 7.77 (d, J=8.2 Hz, 2H), 7.42 (d, J=7.9 Hz, 2H), 7.12 (d, J=2.6 Hz, 1H), 6.92-6.78 (m, 2H), 4.58 (s, 2H), 4.16 (s, 3H), 3.95 (s, 2H), 3.54 (t, J=4.5 Hz, 4H), 2.60 (d, J=4.9 Hz, 4H), 1.11 (s, 6H).

{6-[7-(1-methyl-1H-imidazol-2-ylmethoxy)-imidazo[1,2-a]pyridin-3-yl]-pyrimidin-4-yl}-[4-(1-methyl-1H-[1,2,3]triazol-4-yl)-benzyl]-amine ("A110")

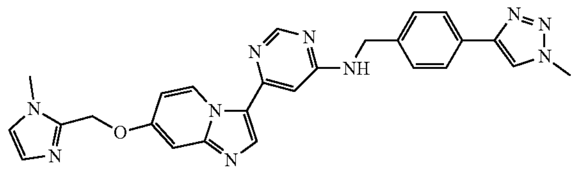 [SMILES: Cn1cc(-c2ccc(CNc3cc(-c4cnc5cc(OCc6nccn6C)ccn45)ncn3)cc2)nn1]

from H3; white solid; m.p. 255-256° C.; HPLC/MS $[M+H]^+$ 493.

$^1H$ NMR (300 MHz, DMSO-$d_6$) δ 9.70 (d, J=7.4 Hz, 1H), 8.48 (d, J=15.2 Hz, 2H), 7.78 (d, J=7.8 Hz, 2H), 7.43 (s, 2H), 7.34 (s, 1H), 7.20 (s, 1H), 6.86 (d, J=21.4 Hz, 3H), 5.25 (s, 2H), 4.06 (s, 3H), 3.68 (s, 3H).

(6-{7-[2-(1-methyl-1H-imidazol-2-yl)-ethoxy]imidazo[1,2-a]pyridin-3-yl}-pyrimidin-4-yl)-[4-(1-methyl-1H-pyrazol-4-yl)-benzyl]-amine ("A111")

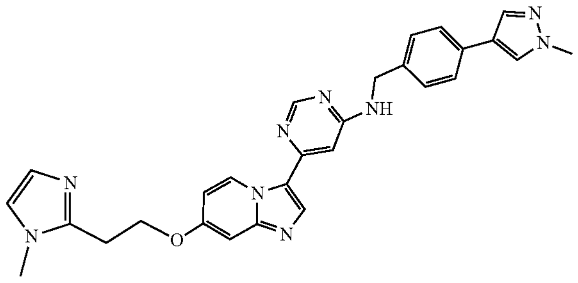 [SMILES: Cn1cc(-c2ccc(CNc3cc(-c4cnc5cc(OCCc6nccn6C)ccn45)ncn3)cc2)cn1]

from H1; white solid; m.p. 215-216° C.; HPLC/MS $[M+H]^+$ 506.

$^1H$ NMR (300 MHz, DMSO-$d_6$) δ 9.69 (d, J=7.8 Hz, 1H), 8.51 (s, 1H), 8.21-8.12 (m, 1H), 8.08 (s, 1H), 7.87 (t, J=6.1 Hz, 1H), 7.81 (s, 1H), 7.51 (d, J=8.1 Hz, 2H), 7.34 (d, J=7.9 Hz, 2H), 7.07 (dd, J=12.6, 1.9 Hz, 2H), 6.89 (d, J=1.3 Hz, 1H), 6.83-6.74 (m, 2H), 4.53 (s, 2H), 4.42 (t, J=6.5 Hz, 2H), 3.84 (s, 3H), 3.63 (s, 3H), 3.15 (t, J=6.5 Hz, 2H).

[4-(2-methyl-2H-[1,2,3]triazol-4-yl)-benzyl]-{6-[7-(pyridin-3-ylmethoxy)-imidazo[1,2-a]pyridin-3-yl]-pyrimidin-4-yl}-amine ("A112")

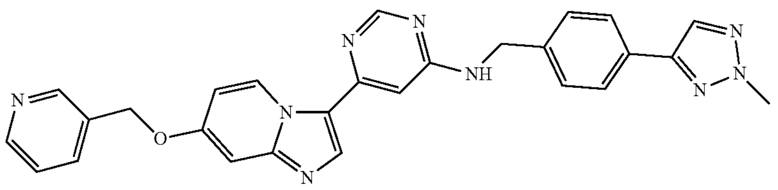 [SMILES: Cn1ncc(-c2ccc(CNc3cc(-c4cnc5cc(OCc6cccnc6)ccn45)ncn3)cc2)n1]

from H2; white solid; m.p. 280-281° C.; HPLC/MS $[M+H]^+$ 490.

$^1H$ NMR (300 MHz, DMSO-$d_6$) δ 9.71 (d, J=7.7 Hz, 1H), 8.71 (d, J=2.2 Hz, 1H), 8.60-8.47 (m, 2H), 8.16 (s, 2H), 7.98-7.85 (m, 2H), 7.78 (d, J=8.2 Hz, 2H), 7.52-7.36 (m, 3H), 7.22 (d, J=2.6 Hz, 1H), 6.93-6.82 (m, 2H), 5.27 (s, 2H), 4.58 (s, 2H), 4.16 (s, 3H).

{6-[7-(1-methyl-1H-imidazol-2-ylmethoxy)-imidazo[1,2-a]pyridin-3-yl]-pyrimidin-4-yl}-[4-(1-methyl-1H-pyrazol-4-yl)-benzyl]-amine ("A113")

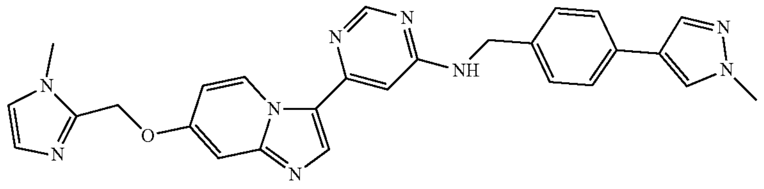 [SMILES: Cn1cc(-c2ccc(CNc3cc(-c4cnc5cc(OCc6nccn6C)ccn45)ncn3)cc2)cn1]

from H1; white solid; m.p. 271-272° C.; HPLC/MS $[M+H]^+$ 492.

$^1H$ NMR (300 MHz, DMSO-$d_6$) δ 9.69 (d, J=7.7 Hz, 1H), 8.49 (s, 1H), 8.23-8.12 (m, 1H), 8.07 (s, 1H), 7.87 (t, J=6.1 Hz, 1H), 7.80 (s, 1H), 7.54-7.46 (m, 2H), 7.42-7.28 (m, 3H), 7.20 (s, 1H), 6.92-6.75 (m, 3H), 5.25 (s, 2H), 4.55-4.49 (m, 2H), 3.83 (s, 3H), 3.68 (s, 3H).

[4-(1-methyl-1H-pyrazol-4-yl)-benzyl]-(6-{7-[2-(2-oxa-6-aza-spiro[3.3]hept-6-yl)-ethoxy]-imidazo[1,2-a]pyridin-3-yl}-pyrimidin-4-yl)-amine ("A114")

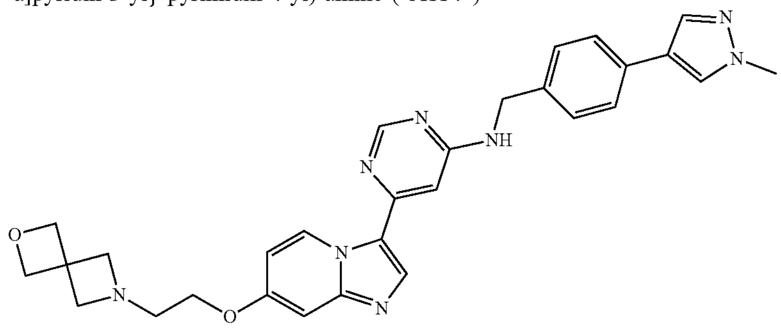

from H1; yellow solid; m.p. 234-235° C.; HPLC/MS $[M+H]^+$ 523.

$^1H$ NMR (300 MHz, DMSO-$d_6$) δ 9.67 (d, J=7.7 Hz, 1H), 8.49 (s, 1H), 8.19-8.10 (m, 1H), 8.07 (s, 1H), 7.86 (t, J=6.1 Hz, 1H), 7.80 (s, 1H), 7.54-7.45 (m, 2H), 7.36-7.25 (m, 2H), 7.03 (d, J=2.6 Hz, 1H), 6.87 (d, J=1.2 Hz, 1H), 6.76 (dd, J=7.7, 2.6 Hz, 1H), 4.58 (s, 4H), 4.55-4.45 (m, 2H), 4.00 (t, J=5.3 Hz, 2H), 3.34 (s, 4H), 2.70 (t, J=5.3 Hz, 2H).

[4-(1-methyl-1H-pyrazol-4-yl)-benzyl]-(6-{7-[2-(1-methyl-pyrrolidin-3-yl)-ethoxy]-imidazo[1,2-a]pyridin-3-yl}-pyrimidin-4-yl)-amine ("A115")

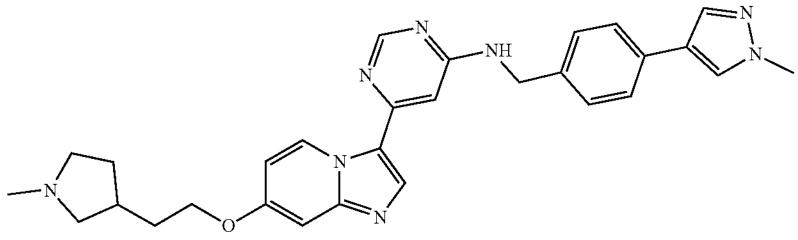

from H1; white solid; m.p. 219-220° C.; HPLC/MS $[M+H]^+$ 509.

$^1H$ NMR (400 MHz, DMSO-$d_6$) δ 9.70 (d, J=7.7 Hz, 1H), 8.52 (s, 1H), 8.25-8.05 (m, 2H), 7.88 (t, J=6.2 Hz, 1H), 7.82 (s, 1H), 7.57-7.49 (m, 2H), 7.35 (d, J=7.8 Hz, 2H), 7.07 (d, J=2.6 Hz, 1H), 6.89 (s, 1H), 6.80 (dd, J=7.7, 2.6 Hz, 1H), 4.62-4.45 (m, 2H), 4.08 (t, J=6.6 Hz, 2H), 3.85 (s, 3H), 3.49-3.31 (m, 1H), 2.68 (t, J=8.9, 7.3 Hz, 1H), 2.45-2.34 (m, 1H), 2.34-2.21 (m, 4H), 2.18-2.09 (m, 1H), 2.04-1.91 (m, 1H), 1.91-1.75 (m, 2H), 1.44 (ddt, J=12.3, 8.3, 6.1 Hz).

(6-{7-[2-(1-methyl-pyrrolidin-3-yl)-ethoxy]-imidazo[1,2-a]pyridin-3-yl}-pyrimidin-4-yl)-[4-(2-methyl-2H-[1,2,3]triazol-4-yl)-benzyl]-amine ("A116")

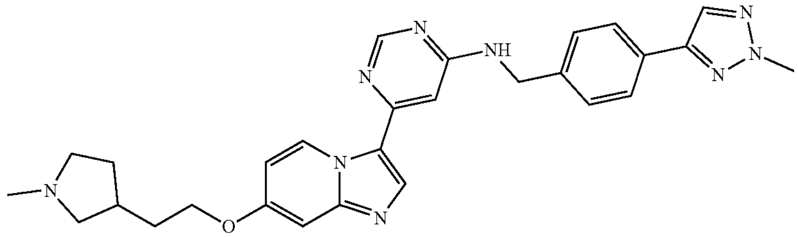

from H2; white solid; m.p. 220-221° C.; HPLC/MS $[M+H]^+$ 510.

$^1H$ NMR (300 MHz, DMSO-$d_6$) δ 9.67 (d, J=7.7 Hz, 1H), 8.50 (s, 1H), 8.15 (d, J=7.5 Hz, 2H), 7.90 (t, J=6.2 Hz, 1H), 7.81-7.74 (m, 2H), 7.42 (d, J=7.9 Hz, 2H), 7.05 (d, J=2.6 Hz, 1H), 6.89 (d, J=1.2 Hz, 1H), 6.77 (dd, J=7.7, 2.6 Hz, 1H), 4.58 (d, J=6.0 Hz, 2H), 4.16 (s, 3H), 4.06 (t, J=6.6 Hz, 2H), 2.64 (dd, J=8.7, 7.3 Hz, 1H), 2.45-2.29 (m, 2H), 2.20 (s, 4H), 2.09 (dd, J=8.8, 6.6 Hz, 1H), 2.01-1.89 (m, 1H), 1.85-1.73 (m, 2H), 1.46-1.34 (m, 1H).

{6-[7-((R)-4-methyl-morpholin-2-ylmethoxy)-imidazo[1,2-a]pyridin-3-yl]-pyrimidin-4-yl}-[4-(1-methyl-1H-pyrazol-4-yl)-benzyl]-amine ("A117")

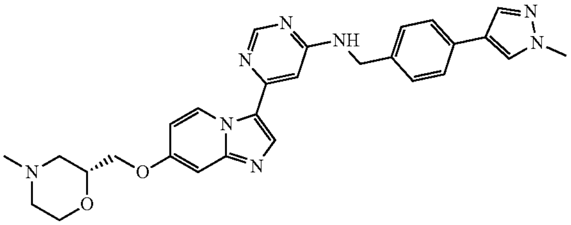

from H1; white solid; m.p. 221-222° C.; HPLC/MS $[M+H]^+$ 511.

$^1H$ NMR (300 MHz, DMSO-$d_6$) δ 9.70 (d, J=7.7 Hz, 1H), 8.51 (s, 1H), 8.25-8.12 (m, 1H), 8.08 (s, 1H), 7.87 (t, J=6.1 Hz, 1H), 7.81 (s, 1H), 7.56-7.47 (m, 2H), 7.38-7.29 (m, 2H), 7.09 (d, J=2.6 Hz, 1H), 6.89 (s, 1H), 6.82 (dd, J=7.7, 2.6 Hz, 1H), 4.64-4.49 (m, 2H), 4.09 (d, J=5.0 Hz, 2H), 3.84 (s, 4H), 3.83-3.78 (m, 1H), 3.60-3.48 (m, 1H), 2.82 (d, J=10.5 Hz, 1H), 2.64 (d, J=11.1 Hz, 1H), 2.29-2.20 (m, 3H), 2.09-1.89 (m, 2H).

{6-[7-((S)-4-methyl-morpholin-2-ylmethoxy)-imidazo[1,2-a]pyridin-3-yl]-pyrimidin-4-yl}-[4-(1-methyl-1H-pyrazol-4-yl)-benzyl]-amine ("A118")

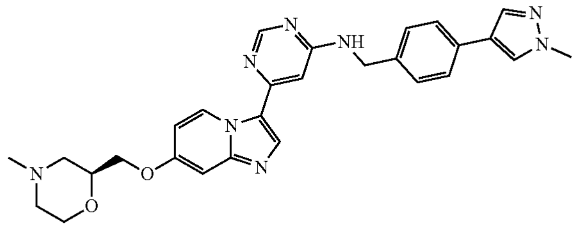

from H1; white solid; m.p. 224-225° C.; HPLC/MS $[M+H]^+$ 511.

$^1$H NMR (300 MHz, DMSO-$d_6$) δ 9.70 (d, J=7.7 Hz, 1H), 8.51 (s, 1H), 8.22-8.12 (m, 1H), 8.08 (s, 1H), 7.87 (t, J=6.2 Hz, 1H), 7.81 (s, 1H), 7.56-7.47 (m, 2H), 7.38-7.29 (m, 2H), 7.09 (d, J=2.6 Hz, 1H), 6.89 (d, J=1.2 Hz, 1H), 6.82 (dd, J=7.7, 2.6 Hz, 1H), 4.60-4.46 (m, 2H), 4.09 (d, J=5.0 Hz, 2H), 3.84 (s, 4H), 3.82-3.78 (m, 1H), 3.62-3.49 (m, 1H), 2.81 (d, J=11.2 Hz, 1H), 2.63 (d, J=11.3 Hz, 1H), 2.29-2.17 (m, 3H), 2.06-1.87 (m, 2H).

[4-(2-methyl-2H-[1,2,3]triazol-4-yl)-benzyl]-(6-{7-[2-(1-oxetan-3-yl-pyrrolidin-3-yl)-ethoxy]-imidazo[1,2-a]pyridin-3-yl}-pyrimidin-4-yl)-amine ("A119")

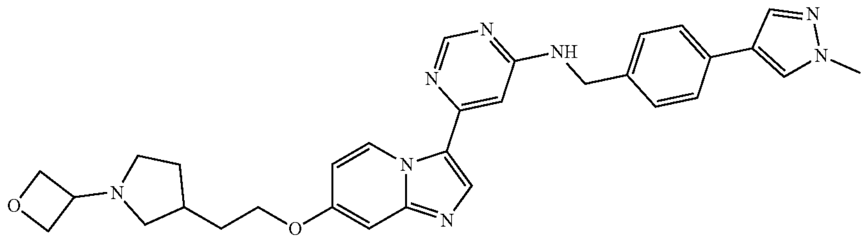 [SMILES: Cn1cc(-c2ccc(CNc3cc(-c4cnc5cc(OCCC6CCN(C7COC7)C6)ccn45)ncn3)cc2)cn1]

from H2; white solid; m.p. 224-225° C.; HPLC/MS $[M+H]^+$ 552.

$^1$H NMR (300 MHz, DMSO-$d_6$) δ 9.67 (d, J=7.7 Hz, 1H), 8.50 (s, 1H), 8.15 (d, J=7.5 Hz, 2H), 7.91 (t, J=6.1 Hz, 1H), 7.82-7.71 (m, 2H), 7.42 (d, J=7.8 Hz, 2H), 7.06 (d, J=2.6 Hz, 1H), 6.89 (d, J=1.2 Hz, 1H), 6.77 (dd, J=7.7, 2.6 Hz, 1H), 4.53 (td, J=6.5, 1.8 Hz, 4H), 4.42 (td, J=6.0, 1.5 Hz, 2H), 4.16 (s, 3H), 4.07 (t, J=6.5 Hz, 2H), 3.53 (t, J=6.2 Hz, 1H), 2.70 (t, J=7.9 Hz, 1H), 2.39 (q, J=8.2 Hz, 1H), 2.25 (q, J=7.8 Hz, 1H), 2.15-2.04 (m, 1H), 2.03-1.08 (m, 1H), 1.81 (q, J=6.7 Hz, 2H), 1.51-1.36 (m, 1H).

{6-[7-(3-azetidin-1-yl-propoxy)-imidazo[1,2-a]pyridin-3-yl]-pyrimidin-4-yl}-[4-(2-methyl-2H-[1,2,3]triazol-4-yl)-benzyl]-amine ("A120")

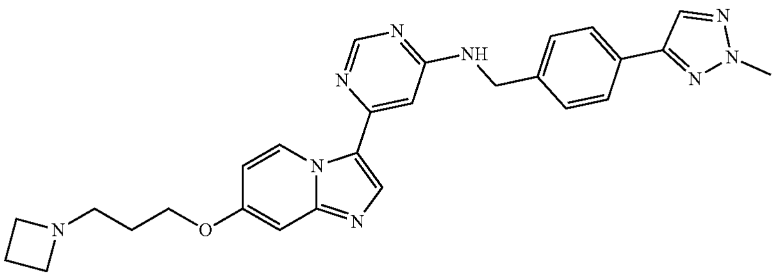 [SMILES: Cn1ncc(-c2ccc(CNc3cc(-c4cnc5cc(OCCCN6CCC6)ccn45)ncn3)cc2)n1]

from H2; white solid; UPLC/MS 0.372 min, $[M+H]^+$ 496. 1H NMR (500 MHz, DMSO-$d_6$) δ 9.69 (d, J=7.7 Hz, 1H), 8.52 (s, 1H), 8.17 (s, 1H), 8.15 (s, 1H), 7.89 (t, J=6.2 Hz, 1H), 7.80 (d, J=8.3 Hz, 2H), 7.45 (d, J=7.8 Hz, 2H), 7.05 (d, J=2.6 Hz, 1H), 6.91 (d, J=1.3 Hz, 1H), 6.79 (dd, J=7.7, 2.6 Hz, 1H), 4.61 (d, J=5.9 Hz, 2H), 4.18 (s, 3H), 4.10 (t, J=6.4 Hz, 2H), 3.10 (t, J=6.9 Hz, 4H), 2.47 (t, J=7.0 Hz, 2H), 1.95 (p, J=6.9 Hz, 2H), 1.74 (p, J=6.7 Hz, 2H).

{6-[7-((R)-4-methyl-morpholin-2-ylmethoxy)-imidazo[1,2-a]pyridin-3-yl]-pyrimidin-4-yl}-[4-(2-methyl-2H-[1,2,3]triazol-4-yl)-benzyl]-amine ("A121")

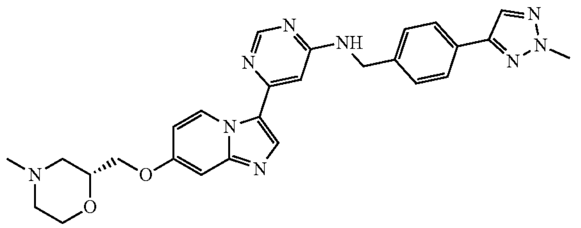

from H2; white solid; m.p. 200-201° C.; HPLC/MS $[M+H]^+$ 512.

$^1$H NMR (300 MHz, DMSO-$d_6$) δ 9.68 (d, J=7.7 Hz, 1H), 8.50 (s, 1H), 8.16 (s, 2H), 7.91 (t, J=6.1 Hz, 1H), 7.82-7.73 (m, 2H), 7.42 (d, J=7.9 Hz, 2H), 7.07 (d, J=2.7 Hz, 1H), 6.89 (d, J=1.3 Hz, 1H), 6.81 (dd, J=7.7, 2.6 Hz, 1H), 4.58 (d, J=6.0 Hz, 2H), 4.16 (s, 3H), 4.07 (d, J=5.0 Hz, 2H), 3.85-3.75 (m, 2H), 3.59-3.47 (m, 1H), 2.77 (d, J=11.0 Hz, 1H), 2.59 (d, J=11.5 Hz, 1H), 2.19 (s, 3H), 1.99 (td, J=11.4, 3.4 Hz, 1H), 1.88 (t, J=10.6 Hz, 1H).

[4-(1-methyl-1H-pyrazol-4-yl)-benzyl]-(6-{7-[2-(1-oxetan-3-yl-pyrrolidin-3-yl)-ethoxy]-imidazo[1,2-a]pyridin-3-yl}-pyrimidin-4-yl)-amine ("A123")

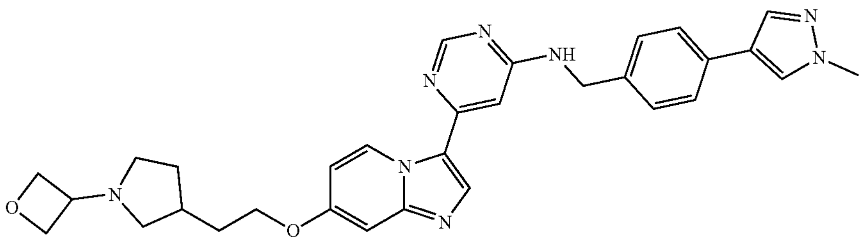

from H2; white solid; m.p. 225-226° C.; HPLC/MS $[M+H]^+$ 512.

$^1$H NMR (300 MHz, DMSO-$d_6$) δ 9.68 (d, J=7.7 Hz, 1H), 8.50 (d, J=1.1 Hz, 1H), 8.16 (s, 2H), 7.91 (t, J=6.1 Hz, 1H), 7.82-7.73 (m, 2H), 7.42 (d, J=7.9 Hz, 2H), 7.07 (d, J=2.6 Hz, 1H), 6.89 (d, J=1.2 Hz, 1H), 6.81 (dd, J=7.7, 2.6 Hz, 1H), 4.58 (d, J=6.1 Hz, 2H), 4.16 (s, 3H), 4.07 (d, J=5.0 Hz, 2H), 3.85-3.75 (m, 2H), 3.53 (td, J=11.2, 2.4 Hz, 1H), 2.77 (d, J=11.2 Hz, 1H), 2.59 (d, J=11.8 Hz, 1H), 2.18 (s, 3H), 2.04-1.81 (m, 2H).

{6-[7-((S)-4-methyl-morpholin-2-ylmethoxy)-imidazo[1,2-a]pyridin-3-yl]-pyrimidin-4-yl}-[4-(2-methyl-2H-[1,2,3]triazol-4-yl)-benzyl]-amine ("A122")

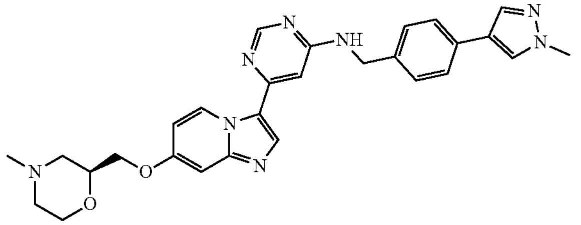

from H1; white solid; m.p. 231-232° C.; HPLC/MS $[M+H]^+$ 551.

$^1$H NMR (400 MHz, DMSO-$d_6$) δ 9.70 (d, J=7.7 Hz, 1H), 8.52 (s, 1H), 8.23-8.13 (m, 1H), 8.09 (s, 1H), 7.88 (t, J=6.2 Hz, 1H), 7.82 (s, 1H), 7.56-7.49 (m, 2H), 7.35 (d, J=7.8 Hz, 2H), 7.08 (d, J=2.6 Hz, 1H), 6.89 (d, J=1.2 Hz, 1H), 6.80 (dd, J=7.7, 2.6 Hz, 1H), 4.56 (td, J=6.4, 2.4 Hz, 4H), 4.45 (td, J=5.9, 1.9 Hz, 2H), 4.10 (t, J=6.6 Hz, 2H), 3.85 (s, 3H), 3.61-3.50 (m, 1H), 2.77-2.68 (m, 1H), 2.57-2.52 (m, 1H), 2.41 (td, J=8.6, 5.5 Hz, 1H), 2.34-2.21 (m, 1H), 2.12 (dd, J=8.8, 7.0 Hz, 1H), 2.05-1.92 (m, 1H), 1.84 (q, J=6.9 Hz, 2H), 1.45 (ddt, J=12.6, 8.3, 6.3 Hz, 1H).

N-{[4-(1-methyl-1H-pyrazol-4-yl)phenyl]methyl}-6-(7-{[(3R)-4-methylmorpholin-3-yl]methoxy}imidazo[1,2-a]pyridin-3-yl)pyrimidin-4-amine ("A124")

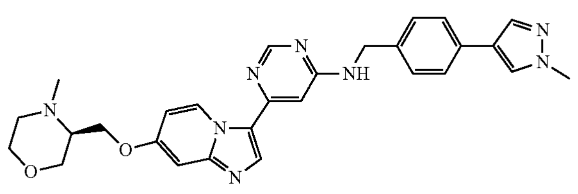 [SMILES: CN1CCOC[C@@H]1COc1ccn2c(-c3cc(NCc4ccc(-c5cnn(C)c5)cc4)ncn3)cnc2c1]

from H1; off-white powder; HPLC/MS(A) 1.034 min, $[M+H]^+$ 511.

$^1$H NMR (500 MHz, DMSO-$d_6$) δ 9.69 (d, J=7.7 Hz, 1H), 8.51 (s, 1H), 8.14 (s, 1H), 8.07 (d, J=0.8 Hz, 1H), 7.83 (t, J=6.1 Hz, 1H), 7.80 (d, J=0.8 Hz, 1H), 7.51 (d, J=8.2 Hz, 2H), 7.34 (d, J=7.8 Hz, 2H), 7.13 (d, J=2.6 Hz, 1H), 6.89 (d, J=1.2 Hz, 1H), 6.80 (dd, J=7.7, 2.6 Hz, 1H), 4.54 (d, J=5.8 Hz, 2H), 4.22 (dd, J=10.4, 4.2 Hz, 1H), 4.02 (dd, J=10.4, 6.0 Hz, 1H), 3.89-3.85 (m, 1H), 3.70 (dt, J=11.0, 3.1 Hz, 1H), 3.56-3.48 (m, 1H), 3.38 (dd, J=11.2, 9.3 Hz, 1H), 2.69 (dt, J=11.8, 2.7 Hz, 1H), 2.50-2.43 (m, 1H), 2.25 (ddd, J=11.8, 10.3, 3.3 Hz, 1H).

N-{[4-(1-methyl-1H-pyrazol-4-yl)phenyl]methyl}-6-(7-{[(3S)-4-methylmorpholin-3-yl]methoxy}imidazo[1,2-a]pyridin-3-yl)pyrimidin-4-amine ("A125")

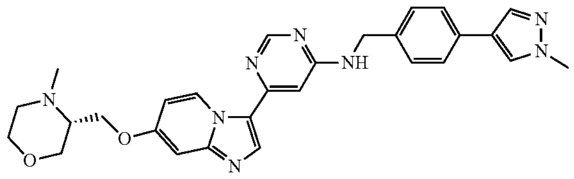 [SMILES: CN1CCOC[C@H]1COc1ccn2c(-c3cc(NCc4ccc(-c5cnn(C)c5)cc4)ncn3)cnc2c1]

(from H1); off-white powder; HPLC/MS(A) 1.034 min, $[M+H]^+$ 511.

$^1$H NMR (500 MHz, DMSO-$d_6$) δ 9.69 (d, J=7.7 Hz, 1H), 8.51 (s, 1H), 8.14 (s, 1H), 8.07 (d, J=0.8 Hz, 1H), 7.83 (t, J=6.1 Hz, 1H), 7.80 (d, J=0.8 Hz, 1H), 7.51 (d, J=8.2 Hz, 2H), 7.34 (d, J=7.8 Hz, 2H), 7.13 (d, J=2.6 Hz, 1H), 6.89 (d, J=1.2 Hz, 1H), 6.80 (dd, J=7.7, 2.6 Hz, 1H), 4.54 (d, J=5.8 Hz, 2H), 4.22 (dd, J=10.4, 4.2 Hz, 1H), 4.02 (dd, J=10.4, 6.0 Hz, 1H), 3.89-3.85 (m, 1H), 3.70 (dt, J=11.0, 3.1 Hz, 1H), 3.56-3.48 (m, 1H), 3.38 (dd, J=11.2, 9.3 Hz, 1H), 2.69 (dt, J=11.8, 2.7 Hz, 1H), 2.50-2.43 (m, 1H), 2.25 (ddd, J=11.8, 10.3, 3.3 Hz, 1H).

[4-(2-methyl-2H-[1,2,3]triazol-4-yl)-benzyl]-{6-[7-(2-pyridin-3-yl-ethoxy)-imidazo[1,2-a]pyridin-3-yl]-pyrimidin-4-yl}-amine ("A126")

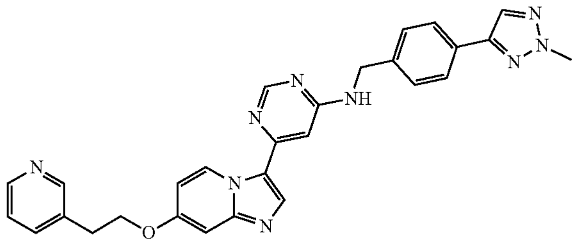 [SMILES: Cn1ncc(-c2ccc(CNc3cc(-c4cnc5cc(OCCc6cccnc6)ccn45)ncn3)cc2)n1]

from H2; HPLC/MS $[M+H]^+$ 504.

(6-{7-[2-(3-aza-bicyclo[3.1.0]hex-3-yl)-ethoxy]-imidazo[1,2-a]pyridin-3-yl}-pyrimidin-4-yl)-[4-(1-methyl-1H-pyrazol-4-yl)-benzyl]-amine ("A127")

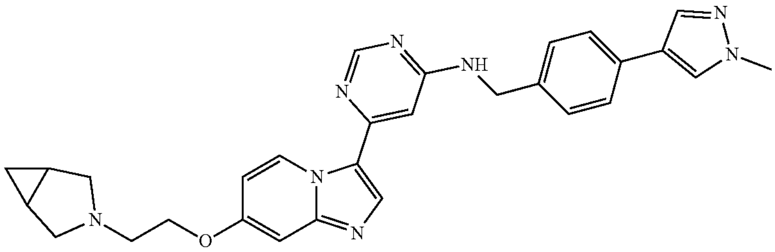 [SMILES: Cn1cc(-c2ccc(CNc3cc(-c4cnc5cc(OCCN6CC7CC7C6)ccn45)ncn3)cc2)cn1]

from H1; white solid; m.p. 219-220° C.; HPLC/MS $[M+H]^+$ 507.

$^1$H NMR (300 MHz, DMSO-$d_6$) δ 9.69 (d, J=7.7 Hz, 1H), 8.51 (s, 1H), 8.22-8.12 (m, 1H), 8.08 (s, 1H), 7.87 (t, J=6.1 Hz, 1H), 7.81 (s, 1H), 7.56-7.47 (m, 2H), 7.38-7.29 (m, 2H), 7.11-7.05 (m, 1H), 6.89 (d, J=1.3 Hz, 1H), 6.79 (dd, J=7.7, 2.6 Hz, 1H), 4.58-4.49 (m, 2H), 4.21-4.07 (m, 2H), 3.84 (s, 3H), 3.01 (d, J=8.6 Hz, 2H), 2.91-2.76 (m, 2H), 2.42-2.33 (m, 2H), 1.42-1.31 (m, 2H), 0.58 (d, J=3.9 Hz, 1H), 0.37-0.24 (m, 1H).

(6-{7-[2-(3-aza-bicyclo[3.1.0]hex-3-yl)-ethoxy]-imidazo[1,2-a]pyridin-3-yl}-pyrimidin-4-yl)-[4-(2-methyl-2H-[1,2,3]triazol-4-yl)-benzyl]-amine ("A128")

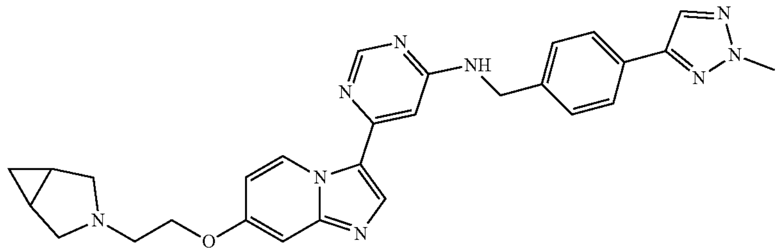 [SMILES: Cn1ncc(-c2ccc(CNc3cc(-c4cnc5cc(OCCN6CC7CC7C6)ccn45)ncn3)cc2)n1]

from H2; white solid; m.p. 220-221° C.; HPLC/MS $[M+H]^+$ 508.

$^1$H NMR (300 MHz, DMSO-$d_6$) δ 9.67 (d, J=7.7 Hz, 1H), 8.50 (s, 1H), 8.16 (s, 2H), 7.94-7.75 (m, 3H), 7.43 (d, J=8.0 Hz, 2H), 7.06 (s, 1H), 6.90-6.75 (m, 2H), 4.58 (s, 2H), 4.13 (d, J=16.6 Hz, 5H), 3.00 (d, J=8.5 Hz, 2H), 2.80 (s, 2H), 2.36 (d, J=8.5 Hz, 2H), 1.34 (s, 2H), 0.57 (s, 1H), 0.28 (s, 1H).

(6-{7-[2-(1-methyl-piperidin-4-yl)-ethoxy]-imidazo[1,2-a]pyridin-3-yl}-pyrimidin-4-yl)-[4-(1-methyl-1H-pyrazol-4-yl)-benzyl]-amine ("A129")

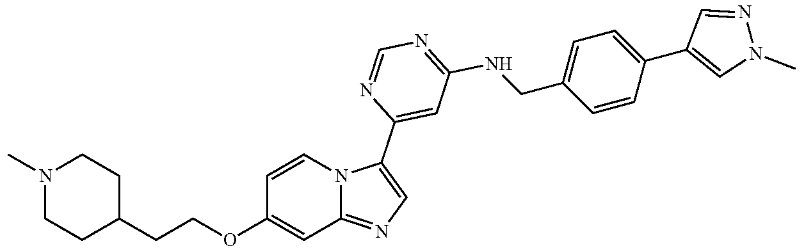

from H1; white solid; m.p. 261-262° C.; HPLC/MS $[M+H]^+$ 523.

(6-{7-[2-(1-methyl-piperidin-4-yl)-ethoxy]-imidazo[1,2-a]pyridin-3-yl}-pyrimidin-4-yl)-[4-(2-methyl-2H-[1,2,3]triazol-4-yl)-benzyl]-amine ("A130")

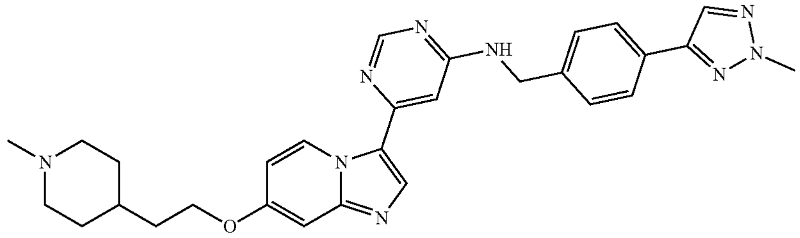

from H2; white solid; m.p. 230-231° C.; HPLC/MS $[M+H]^+$ 524.

$^1$H NMR (300 MHz, DMSO-$d_6$) δ 9.67 (d, J=7.7 Hz, 1H), 8.50 (s, 1H), 8.15 (d, J=8.0 Hz, 2H), 7.91 (t, J=6.1 Hz, 1H), 7.78 (d, J=8.0 Hz, 2H), 7.42 (d, J=7.9 Hz, 2H), 7.07 (d, J=2.6 Hz, 1H), 6.89 (s, 1H), 6.77 (dd, J=7.7, 2.6 Hz, 1H), 4.58 (d, J=6.0 Hz, 2H), 4.16 (s, 3H), 4.10 (t, J=6.6 Hz, 2H), 2.71 (d, J=11.1 Hz, 2H), 2.11 (s, 3H), 1.80 (t, J=11.3 Hz, 2H), 1.72-1.61 (m, 4H), 1.40 (s, 1H), 1.22 (t, J=12.3 Hz, 2H)

3-(3-{6-[4-(1-methyl-1H-pyrazol-4-yl)-benzylamino]-pyrimidin-4-yl}-imidazo[1,2-a]pyridin-7-yloxy)-propan-1-ol ("A131")

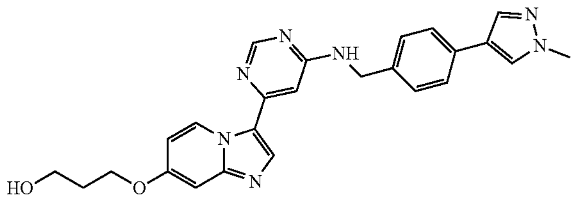 [SMILES: Cn1cc(-c2ccc(CNc3cc(-c4cnc5cc(OCCCO)ccn45)ncn3)cc2)cn1]

from H1; yellow solid; m.p. 216-217° C.; HPLC/MS $[M+H]^+$ 456.

$^1$H NMR (400 MHz, DMSO-$d_6$) δ 9.69 (d, J=7.7 Hz, 1H), 8.51 (s, 1H), 8.14 (s, 1H), 8.08 (s, 1H), 7.86 (t, J=6.2 Hz, 1H), 7.81 (s, 1H), 7.51 (d, J=7.8 Hz, 2H), 7.34 (d, J=7.8 Hz, 2H), 7.06 (d, J=2.7 Hz, 1H), 6.89 (s, 1H), 6.79 (dd, J=7.7, 2.6 Hz, 1H), 4.58 (t, J=5.2 Hz, 1H), 4.56-4.45 (m, 2H), 4.15 (t, J=6.3 Hz, 2H), 3.84 (s, 3H), 3.58 (q, J=5.9 Hz, 2H), 1.91 (p, J=6.3 Hz, 2H).

{6-[7-(3-dimethylamino-propoxy)-imidazo[1,2-a]pyridin-3-yl]-pyrimidin-4-yl}-[4-(1-methyl-1H-pyrazol-4-yl)-benzyl]-amine ("A132")

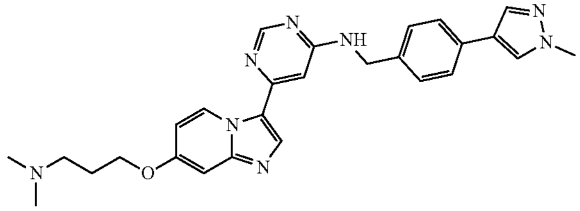

from H1; white solid; m.p. 232-233° C.; HPLC/MS $[M+H]^+$ 483.

$^1$H NMR (400 MHz, DMSO-$d_6$) δ 9.69 (d, J=7.7 Hz, 1H), 8.51 (s, 1H), 8.19-8.10 (m, 1H), 8.08 (s, 1H), 7.86 (t, J=6.1 Hz, 1H), 7.81 (s, 1H), 7.51 (d, J=8.1 Hz, 2H), 7.34 (d, J=7.8 Hz, 2H), 7.05 (d, J=2.6 Hz, 1H), 6.89 (d, J=1.2 Hz, 1H), 6.79 (dd, J=7.7, 2.6 Hz, 1H), 4.60-4.48 (m, 2H), 4.11 (t, J=6.3 Hz, 2H), 3.84 (s, 3H), 2.37 (t, J=7.1 Hz, 2H), 2.15 (s, 6H), 1.89 (p, J=6.7 Hz, 2H).

(6-{7-[2-(1-methyl-pyrrolidin-3-yl)-ethoxy]-imidazo[1,2-a]pyridin-3-yl}-pyrimidin-4-yl)-[4-(2-methyl-2H-[1,2,3]triazol-4-yl)-benzyl]-amine ("A133")

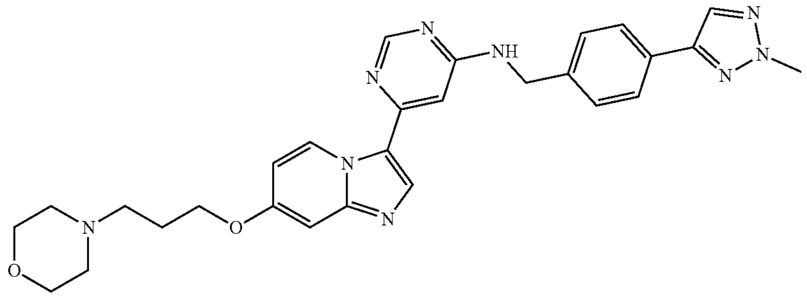 [SMILES: Cn1ncc(-c2ccc(CNc3cc(-c4cnc5cc(OCCCN6CCOCC6)ccn45)ncn3)cc2)n1]

from H2; white solid; HPLC/MS $[M+H]^+$ 526.

3-(3-{6-[4-(2-methyl-2H-[1,2,3]triazol-4-yl)-benzylamino]-pyrimidin-4-yl}-imidazo[1,2-a]pyridin-7-yloxy)-propan-1-ol ("A134")

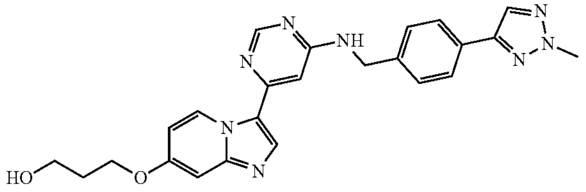 [SMILES: Cn1ncc(-c2ccc(CNc3cc(-c4cnc5cc(OCCCO)ccn45)ncn3)cc2)n1]

from H2; white solid; m.p. 240-241° C.; HPLC/MS $[M+H]^+$ 457.

$^1$H NMR (300 MHz, DMSO-$d_6$) δ 9.68 (d, J=7.8 Hz, 1H), 8.53-8.47 (m, 1H), 8.16 (s, 2H), 7.90 (t, J=6.3 Hz, 1H), 7.82-7.73 (m, 2H), 7.42 (d, J=7.9 Hz, 2H), 7.04 (d, J=2.7 Hz, 1H), 6.89 (d, J=1.3 Hz, 1H), 6.78 (dd, J=7.7, 2.6 Hz, 1H), 4.57 (t, J=5.1 Hz, 3H), 4.15 (d, J=7.7 Hz, 5H), 3.56 (q, J=5.9 Hz, 2H), 1.89 (p, J=6.1 Hz, 2H).

{6-[7-(3-dimethylamino-propoxy)-imidazo[1,2-a]pyridin-3-yl]-pyrimidin-4-yl}-[4-(2-methyl-2H-[1,2,3]triazol-4-yl)-benzyl]-amine ("A135")

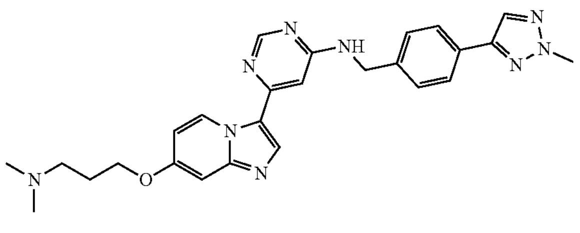

from H2; pale yellow solid; m.p. 250-251° C.; HPLC/MS $[M+H]^+$ 484.

$^1$H NMR (300 MHz, DMSO-$d_6$) δ 9.68 (d, J=7.7 Hz, 1H), 8.50 (s, 1H), 8.15 (d, J=7.2 Hz, 2H), 7.90 (t, J=6.2 Hz, 1H), 7.82-7.73 (m, 2H), 7.42 (d, J=7.9 Hz, 2H), 7.03 (d, J=2.6 Hz, 1H), 6.89 (d, J=1.3 Hz, 1H), 6.78 (dd, J=7.7, 2.6 Hz, 1H), 4.58 (d, J=6.1 Hz, 2H), 4.16 (s, 3H), 4.09 (t, J=6.4 Hz, 2H), 2.35 (t, J=7.2 Hz, 2H), 2.14 (s, 6H), 1.87 (p, J=6.6 Hz, 2H).

6-{7-[2-(3,3-difluoropiperidin-1-yl)ethoxy]imidazo[1,2-a]pyridin-3-yl}-N-{[4-(1-methyl-1H-pyrazol-4-yl)phenyl]methyl}pyrimidin-4-amine ("A136")

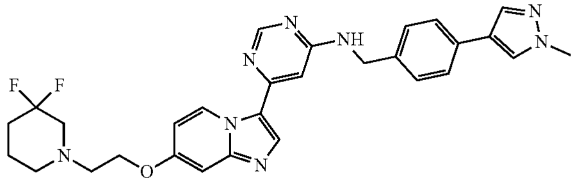 [SMILES: Cn1cc(-c2ccc(CNc3cc(-c4cnc5cc(OCCN6CCCC(F)(F)C6)ccn45)ncn3)cc2)cn1]

from H1; off-white solid; HPLC/MS(B) 0.695 min, $[M+H]^+$ 545.

$^1$H NMR (500 MHz, DMSO-$d_6$) δ 9.69 (d, J=7.7 Hz, 1H), 8.51 (s, 1H), 8.14 (s, 1H), 8.07 (d, J=0.8 Hz, 1H), 7.82 (t, J=6.2 Hz, 1H), 7.80 (d, J=0.8 Hz, 1H), 7.51 (d, J=8.2 Hz, 2H), 7.34 (d, J=7.8 Hz, 2H), 7.13-7.08 (m, 1H), 6.89 (d, J=1.2 Hz, 1H), 6.80 (dd, J=7.7, 2.6 Hz, 1H), 4.54 (d, J=6.0 Hz, 2H), 4.21 (t, J=5.6 Hz, 2H), 3.84 (s, 3H), 2.86 (t, J=5.6 Hz, 2H), 2.79 (t, J=11.7 Hz, 2H), 2.55 (t, J=5.4 Hz, 2H), 1.87 (tt, J=13.9, 6.4 Hz, 2H), 1.71-1.57 (m, 2H).

6-{7-[3-(diethylamino)propoxy]imidazo[1,2-a]pyridin-3-yl}-N-{[4-(1-methyl-1H-pyrazol-4-yl)phenyl]methyl}pyrimidin-4-amine ("A137")

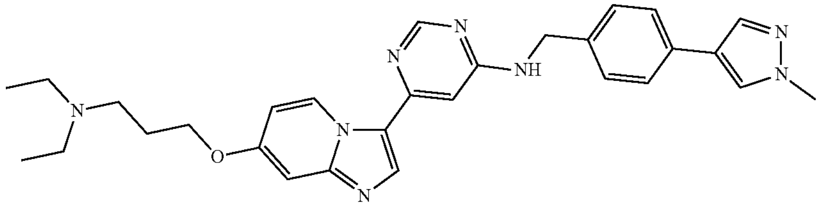 [SMILES: CCN(CC)CCCOc1ccn2c(-c3cc(NCc4ccc(-c5cnn(C)c5)cc4)ncn3)cnc2c1]

from H1; off-white solid; UPLC/MS 0.395 min, $[M+H]^+$ 511.

$^1$H NMR (500 MHz, DMSO-$d_6$) δ 9.68 (d, J=7.7 Hz, 1H), 8.52-8.46 (m, 1H), 8.13 (s, 1H), 8.07 (d, J=0.8 Hz, 1H), 7.82 (t, J=6.2 Hz, 1H), 7.80 (d, J=0.8 Hz, 1H), 7.51 (d, J=8.2 Hz, 2H), 7.34 (d, J=7.8 Hz, 2H), 7.04 (d, J=2.7 Hz, 1H), 6.89 (d, J=1.3 Hz, 1H), 6.78 (dd, J=7.7, 2.6 Hz, 1H), 4.54 (d, J=6.0 Hz, 2H), 4.12 (t, J=6.3 Hz, 2H), 3.84 (s, 3H), 2.53 (t, J=7.0 Hz, 2H), 2.46 (q, J=7.1 Hz, 4H), 1.85 (p, J=6.6 Hz, 2H), 0.95 (t, J=7.1 Hz, 6H).

4-[2-({3-[6-({[4-(1-methyl-1H-pyrazol-4-yl)phenyl]methyl}amino)pyrimidin-4-yl]imidazo[1,2-a]pyridin-7-yl}oxy)ethyl]-1lambda6-thiomorpholine-1,1-dione ("A138")

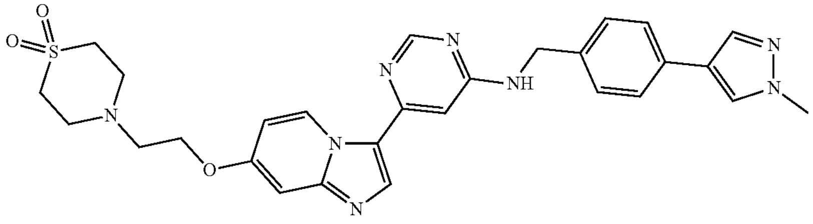 [SMILES: Cn1cc(-c2ccc(CNc3cc(-c4cnc5cc(OCCN6CCS(=O)(=O)CC6)ccn45)ncn3)cc2)cn1]

from H1; off-white solid; UPLC/MS 0.467 min, $[M+H]^+$ 559.

$^1$H NMR (500 MHz, DMSO-$d_6$) δ 9.69 (d, J=7.7 Hz, 1H), 8.51 (s, 1H), 8.14 (s, 1H), 8.07 (d, J=0.8 Hz, 1H), 7.83 (t, J=6.1 Hz, 1H), 7.80 (d, J=0.8 Hz, 1H), 7.51 (d, J=8.2 Hz, 2H), 7.34 (d, J=7.8 Hz, 2H), 7.11 (d, J=2.6 Hz, 1H), 6.89 (d, J=1.2 Hz, 1H), 6.79 (dd, J=7.7, 2.6 Hz, 1H), 4.54 (d, J=6.0 Hz, 2H), 4.21 (t, J=5.5 Hz, 2H), 3.84 (s, 3H), 3.16-3.02 (m, 8H), 2.97 (t, J=5.5 Hz, 2H).

6-{7-[2-(3,3-difluoroazetidin-1-yl)ethoxy]imidazo[1,2-a]pyridin-3-yl}-N-{[4-(1-methyl-1H-pyrazol-4-yl)phenyl]methyl}pyrimidin-4-amine ("A139")

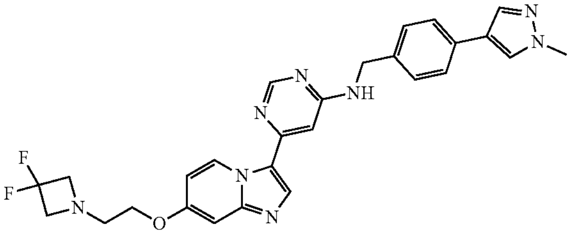 [SMILES: Cn1cc(-c2ccc(CNc3cc(-c4cnc5cc(OCCN6CC(F)(F)C6)ccn45)ncn3)cc2)cn1]

from H1; off-white solid; UPLC/MS 0.443 min, $[M+H]^+$ 517.

$^1$H NMR (500 MHz, DMSO-$d_6$) δ 9.69 (d, J=7.7 Hz, 1H), 8.51 (s, 1H), 8.14 (s, 1H), 8.07 (d, J=0.8 Hz, 1H), 7.83 (t, J=6.1 Hz, 1H), 7.80 (d, J=0.8 Hz, 1H), 7.51 (d, J=8.2 Hz, 2H), 7.34 (d, J=7.8 Hz, 2H), 7.07 (d, J=2.6 Hz, 1H), 6.89 (d, J=1.2 Hz, 1H), 6.80 (dd, J=7.7, 2.6 Hz, 1H), 4.54 (d, J=6.0 Hz, 2H), 4.12 (t, J=5.3 Hz, 2H), 3.84 (s, 3H), 3.69 (t, J=12.4 Hz, 4H), 2.96 (t, J=5.3 Hz, 2H).

6-{7-[2-(3-fluoroazetidin-1-yl)ethoxy]imidazo[1,2-a]pyridin-3-yl}-N-{[4-(1-methyl-1H-pyrazol-4-yl)phenyl]methyl}pyrimidin-4-amine ("A140")

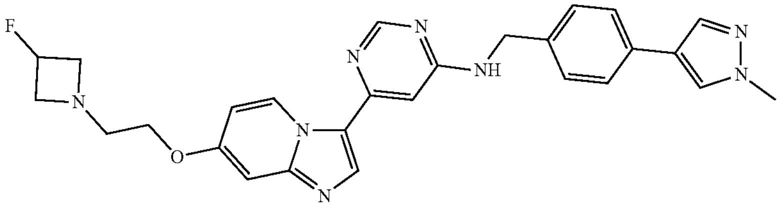 [SMILES: Cn1cc(-c2ccc(CNc3cc(-c4cnc5cc(OCCN6CC(F)C6)ccn45)ncn3)cc2)cn1]

from H1; off-white solid; UPLC/MS 0.372 min, $[M+H]^+$ 499.

$^1$H NMR (500 MHz, DMSO-$d_6$) δ 9.69 (d, J=7.7 Hz, 1H), 8.51 (s, 1H), 8.13 (s, 1H), 8.07 (d, J=0.8 Hz, 1H), 7.83 (t, J=6.2 Hz, 1H), 7.80 (d, J=0.8 Hz, 1H), 7.51 (d, J=8.2 Hz, 2H), 7.34 (d, J=7.8 Hz, 2H), 7.05 (d, J=2.6 Hz, 1H), 6.89 (d, J=1.2 Hz, 1H), 6.78 (dd, J=7.7, 2.6 Hz, 1H), 5.15 (dddd, J=57.9, 10.2, 5.6, 4.6 Hz, 1H), 4.69-4.45 (m, 2H), 4.07 (t, J=5.3 Hz, 2H), 3.84 (s, 3H), 3.64 (dddd, J=15.3, 7.6, 5.6, 2.0 Hz, 2H), 3.21 (dddd, J=23.9, 7.5, 4.6, 2.1 Hz, 2H), 2.86 (t, J=5.3 Hz, 2H).

4-methyl-1-[2-({3-[6-({[4-(1-methyl-1H-pyrazol-4-yl)phenyl]methyl}amino)pyrimidin-4-yl]imidazo[1,2-a]pyridin-7-yl}oxy)ethyl]piperazin-2-one ("A141")

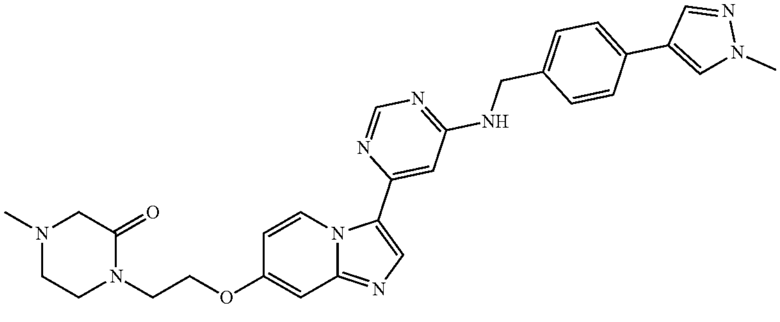

from H1; off-white solid; UPLC/MS 0.380 min, $[M+H]^+$ 538.

$^1H$ NMR (500 MHz, DMSO-$d_6$) δ 9.69 (d, J=7.7 Hz, 1H), 8.51 (s, 1H), 8.14 (s, 1H), 8.07 (d, J=0.7 Hz, 1H), 7.83 (t, J=6.1 Hz, 1H), 7.80 (d, J=0.8 Hz, 1H), 7.51 (d, J=8.2 Hz, 2H), 7.34 (d, J=7.8 Hz, 2H), 7.12 (d, J=2.6 Hz, 1H), 6.89 (d, J=1.3 Hz, 1H), 6.79 (dd, J=7.7, 2.6 Hz, 1H), 4.54 (d, J=6.0 Hz, 2H), 4.24 (t, J=5.7 Hz, 2H), 3.84 (s, 3H), 3.70 (t, J=5.6 Hz, 2H), 3.44 (dd, J=6.1, 4.9 Hz, 2H), 2.94 (s, 2H), 2.68-2.54 (m, 2H), 2.20 (s, 3H).

6-{7-[3-(3,3-difluoroazetidin-1-yl)propoxy]imidazo[1,2-a]pyridin-3-yl}-N-{[4-(1-methyl-1H-pyrazol-4-yl)phenyl]methyl}pyrimidin-4-amine ("A142")

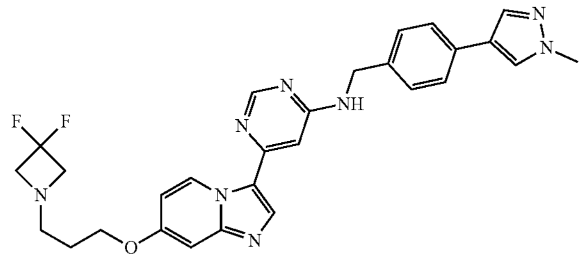 [SMILES: Cn1cc(-c2ccc(CNc3cc(-c4cnc5cc(OCCCN6CC(F)(F)C6)ccn45)ncn3)cc2)cn1]

from H1; off-white solid; UPLC/MS 0.413 min, [M+2H]/2 266.

$^1H$ NMR (500 MHz, DMSO-$d_6$) δ 9.69 (d, J=7.7 Hz, 1H), 8.51 (s, 1H), 8.13 (s, 1H), 8.07 (d, J=0.8 Hz, 1H), 7.82 (t, J=6.2 Hz, 1H), 7.80 (d, J=0.8 Hz, 1H), 7.51 (d, J=8.2 Hz, 2H), 7.34 (d, J=7.8 Hz, 2H), 7.05 (d, J=2.6 Hz, 1H), 6.89 (d, J=1.2 Hz, 1H), 6.78 (dd, J=7.7, 2.6 Hz, 1H), 4.54 (d, J=5.9 Hz, 2H), 4.11 (t, J=6.3 Hz, 2H), 3.84 (s, 3H), 3.58 (t, J=12.5 Hz, 4H), 2.72-2.66 (m, 2H), 1.81 (p, J=6.6 Hz, 2H).

{6-[7-(3-methanesulfonyl-propoxy)-imidazo[1,2-a]pyridin-3-yl]-pyrimidin-4-yl}-[4-(1-methyl-1H-pyrazol-4-yl)-benzyl]-amine ("A143")

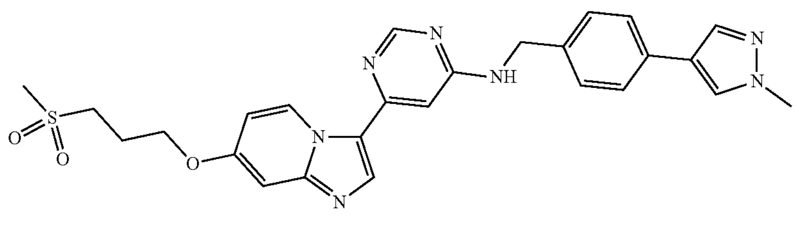 [SMILES: Cn1cc(-c2ccc(CNc3cc(-c4cnc5cc(OCCCS(C)(=O)=O)ccn45)ncn3)cc2)cn1]

from H1; white solid; m.p. 300° C.; HPLC/MS $[M+H]^+$ 518.

$^1H$ NMR (300 MHz, DMSO-$d_6$) δ 9.69 (d, J=7.7 Hz, 1H), 8.50 (s, 1H), 8.10 (d, J=23.3 Hz, 2H), 7.91-7.75 (m, 2H), 7.54-7.45 (m, 2H), 7.32 (d, J=7.8 Hz, 2H), 7.08 (d, J=2.6 Hz, 1H), 6.88 (d, J=1.2 Hz, 1H), 6.80 (dd, J=7.7, 2.6 Hz, 1H), 4.52 (d, J=5.8 Hz, 2H), 4.20 (t, J=6.2 Hz, 2H), 3.83 (s, 3H), 3.30-3.19 (m, 2H), 3.02 (s, 3H), 2.26-2.10 (m, 2H).

N-{[4-(1-methyl-1H-pyrazol-4-yl)phenyl]methyl}-6-{7-[(1-methylazetidin-3-yl)methoxy]imidazo[1,2-a]pyridin-3-yl}pyrimidin-4-amine ("A144")

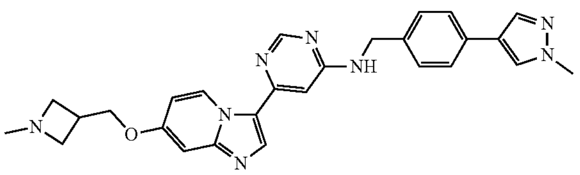

from H1; off-white solid; UPLC/MS 0.365 min, [M+2H]/2 241.

$^1H$ NMR (500 MHz, DMSO-$d_6$) δ 9.70 (d, J=7.7 Hz, 1H), 8.52 (s, 1H), 8.14 (s, 1H), 8.08 (s, 1H), 7.83 (t, J=6.2 Hz, 1H), 7.81 (s, 1H), 7.52 (d, J=8.2 Hz, 2H), 7.35 (d, J=7.8 Hz, 2H), 7.08 (d, J=2.6 Hz, 1H), 6.90 (d, J=1.2 Hz, 1H), 6.80 (dd, J=7.7, 2.6 Hz, 1H), 4.54 (d, J=5.8 Hz, 2H), 4.21 (d, J=6.9 Hz, 2H), 3.85 (s, 3H), 3.32-3.27 (m, 2H), 2.98 (dd, J=7.0, 5.6 Hz, 2H), 2.79 (tt, J=7.4, 5.8 Hz, 1H), 2.22 (s, 3H).

1-[3-({3-[6-({[4-(1-methyl-1H-pyrazol-4-yl)phenyl]methyl}amino)pyrimidin-4-yl]imidazo[1,2-a]pyridin-7-yl}oxy)propyl]pyrrolidin-2-one ("A145")

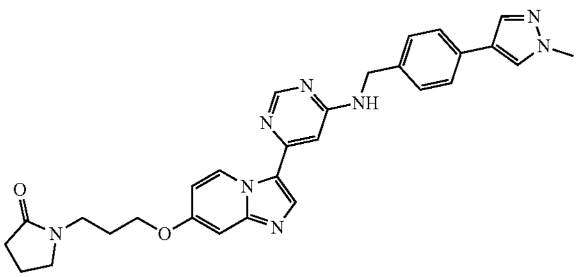 [SMILES: Cn1cc(-c2ccc(CNc3cc(-c4cnc5cc(OCCCN6CCCC6=O)ccn45)ncn3)cc2)cn1]

from H1; off-white solid; HPLC/MS(B) 0.734 min, $[M+H]^+$ 518.

$^1H$ NMR (500 MHz, DMSO-$d_6$) δ 9.69 (d, J=7.7 Hz, 1H), 8.51 (s, 1H), 8.14 (s, 1H), 8.07 (s, 1H), 7.83 (t, J=6.2 Hz, 1H), 7.80 (d, J=0.8 Hz, 1H), 7.51 (d, J=8.2 Hz, 2H), 7.34 (d, J=7.8 Hz, 2H), 7.04 (d, J=2.6 Hz, 1H), 6.89 (d, J=1.2 Hz, 1H), 6.79 (dd, J=7.7, 2.6 Hz, 1H), 4.54 (d, J=5.5 Hz, 2H), 4.08 (t, J=6.2 Hz, 2H), 3.84 (s, 3H), 3.36 (dt, J=9.2, 7.0 Hz, 4H), 2.21 (t, J=8.1 Hz, 2H), 2.04-1.77 (m, 4H).

{6-[7-(3-amino-3-methyl-butoxy)-imidazo[1,2-a]pyridin-3-yl]-pyrimidin-4-yl}-[4-(1-methyl-1H-pyrazol-4-yl)-benzyl]-amine ("A223")

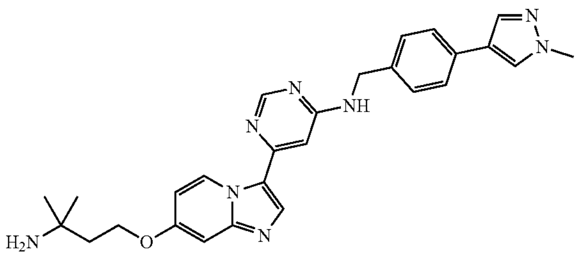 [SMILES: Cn1cc(-c2ccc(CNc3cc(-c4cnc5cc(OCCC(C)(C)N)ccn45)ncn3)cc2)cn1]

from H1; white solid; m.p. 252-253° C.; HPLC/MS $[M+H]^+$ 483.

$^1$H NMR (300 MHz, DMSO-$d_6$) δ 9.67 (d, J=7.7 Hz, 1H), 8.49 (s, 1H), 8.13 (s, 1H), 8.06 (s, 1H), 7.82 (d, J=16.2 Hz, 2H), 7.54-7.45 (m, 2H), 7.32 (d, J=7.8 Hz, 2H), 7.09 (d, J=2.6 Hz, 1H), 6.87 (d, J=1.2 Hz, 1H), 6.75 (dd, J=7.7, 2.6 Hz, 1H), 4.52 (d, J=5.9 Hz, 2H), 4.18 (t, J=7.2 Hz, 2H), 3.83 (s, 3H), 1.80 (t, J=7.2 Hz, 2H), 1.09 (s, 6H)

{6-[7-(2-methanesulfonyl-ethoxy)-imidazo[1,2-a]pyridin-3-yl]-pyrimidin-4-yl}-[4-(1-methyl-1H-pyrazol-4-yl)-benzyl]-amine ("A224")

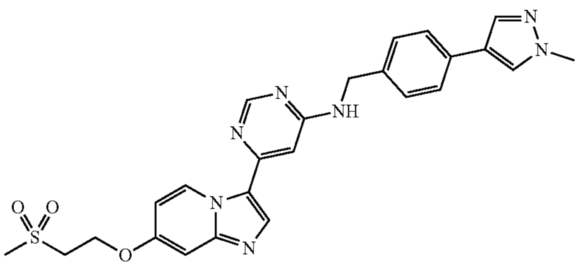

from H1; white solid; HPLC/MS $[M+H]^+$ 504.

$^1$H NMR (300 MHz, DMSO-$d_6$) δ 9.70 (d, J=7.7 Hz, 1H), 8.50 (s, 1H), 8.16 (s, 1H), 8.07 (s, 1H), 7.87 (t, J=6.1 Hz, 1H), 7.80 (d, J=0.8 Hz, 1H), 7.54-7.45 (m, 2H), 7.32 (d, J=7.9 Hz, 2H), 7.19 (d, J=2.6 Hz, 1H), 6.88 (d, J=1.2 Hz, 1H), 6.82 (dd, J=7.7, 2.6 Hz, 1H), 4.49 (dt, J=11.4, 5.6 Hz, 4H), 3.82 (s, 3H), 3.67 (t, J=5.6 Hz, 2H), 3.08 (s, 3H).

{6-[7-(3-methanesulfonyl-propoxy)-imidazo[1,2-a]pyridin-3-yl]-pyrimidin-4-yl}-[4-(2-methyl-2H-[1,2,3]triazol-4-yl)-benzyl]-amine ("A231")

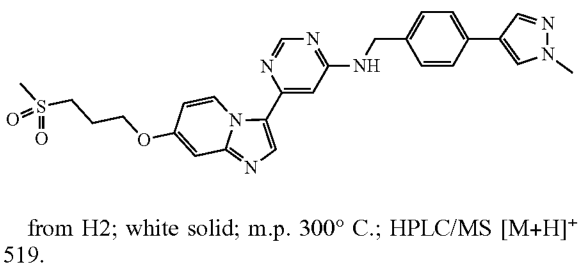

from H2; white solid; m.p. 300° C.; HPLC/MS $[M+H]^+$ 519.

$^1$H NMR (300 MHz, DMSO-$d_6$) δ 9.70 (d, J=7.7 Hz, 1H), 8.50 (s, 1H), 8.16 (s, 2H), 7.91 (t, J=6.2 Hz, 1H), 7.77 (d, J=8.1 Hz, 2H), 7.42 (d, J=7.8 Hz, 2H), 7.08 (d, J=2.6 Hz, 1H), 6.90 (s, 1H), 6.80 (dd, J=7.7, 2.6 Hz, 1H), 4.58 (s, 2H), 4.21 (d, J=6.1 Hz, 2H), 4.16 (s, 3H), 3.26 (s, 2H), 3.02 (s, 3H), 2.18 (t, J=7.9 Hz, 2H).

(6-{7-[2-(3-amino-oxetan-3-yl)-ethoxy]-imidazo[1,2-a]pyridin-3-yl}-pyrimidin-4-yl)-[4-(2-methyl-2H-[1,2,3]triazol-4-yl)-benzyl]-amine ("A233")

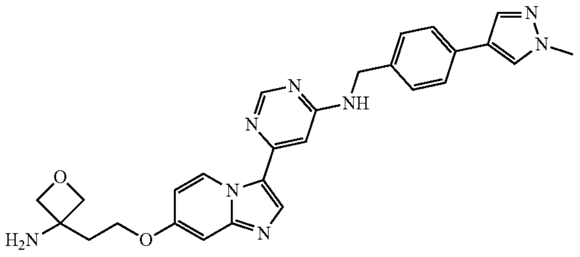 [SMILES: Cn1cc(-c2ccc(CNc3cc(-c4cnc5cc(OCCC6(N)COC6)ccn45)ncn3)cc2)cn1]

from H1; white solid; m.p. 240-241° C.; HPLC/MS $[M+H]^+$ 497.

$^1$H NMR (300 MHz, DMSO-$d_6$) δ 9.73-9.63 (m, 1H), 8.49 (s, 1H), 8.10 (d, J=19.3 Hz, 2H), 7.92-7.82 (m, 1H), 7.80 (s, 1H), 7.50 (d, J=8.0 Hz, 2H), 7.32 (d, J=7.9 Hz, 2H), 7.10-7.02 (m, 1H), 6.91-6.74 (m, 2H), 4.52 (s, 2H), 4.42 (d, J=5.7 Hz, 1H), 4.31 (d, J=5.8 Hz, 1H), 4.21 (t, J=6.6 Hz, 1H), 3.98 (s, 1H), 3.82 (s, 4H), 3.55 (dd, J=79.3, 8.5 Hz, 1H), 2.17 (t, J=6.7 Hz, 2H), 2.00-1.88 (m, 1H), 1.72 (dt, J=11.7, 5.7 Hz, 1H)

2-[2-(3-{6-[4-(1-methyl-1H-pyrazol-4-yl)-benzylamino]-pyrimidin-4-yl}-imidazo[1,2-a]pyridin-7-yloxy)-ethoxy]-ethanol ("A234")

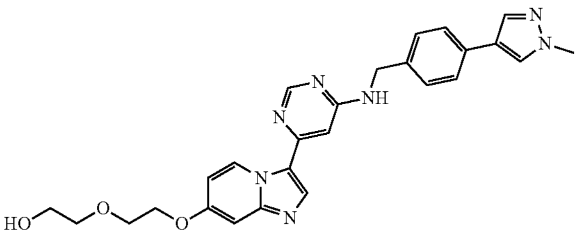 [SMILES: Cn1cc(-c2ccc(CNc3cc(-c4cnc5cc(OCCOCCO)ccn45)ncn3)cc2)cn1]

from H1; white solid; m.p. 240-241° C.; HPLC/MS $[M+H]^+$ 486.

$^1$H NMR (300 MHz, DMSO-$d_6$) 9.68 (d, J=7.7 Hz, 1H), 8.49 (s, 1H), 8.14 (s, 1H), 8.07 (s, 1H), 7.86 (t, J=6.2 Hz, 1H), 7.80 (s, 1H), 7.50 (d, J=8.1 Hz, 2H), 7.32 (d, J=7.9 Hz, 2H), 7.08 (d, J=2.6 Hz, 1H), 6.87 (d, J=1.3 Hz, 1H), 6.81 (dd, J=7.7, 2.6 Hz, 1H), 4.66-4.60 (m, 1H), 4.52 (s, 2H), 4.19 (dd, J=5.9, 3.2 Hz, 2H), 3.82 (s, 3H), 3.77 (dd, J=5.5, 3.4 Hz, 2H), 3.50 (dt, J=8.1, 3.9 Hz, 4H).

2-(3-{6-[4-(2-methyl-oxazol-4-yl)-benzylamino]-pyrimidin-4-yl}-imidazo[1,2-a]pyridin-7-yloxy)-ethanol ("A236")

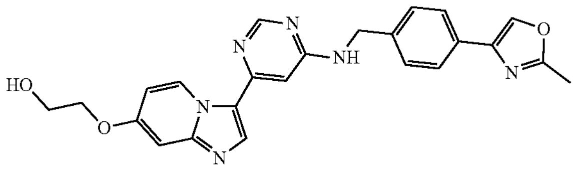 [SMILES: Cc1nc(-c2ccc(CNc3cc(-c4cnc5cc(OCCO)ccn45)ncn3)cc2)co1]

from H4; white solid; m.p. 266-267° C.; HPLC/MS $[M+H]^+$ 443.

$^1$H NMR (400 MHz, DMSO-$d_6$) δ 9.71 (d, J=7.6 Hz, 1H), 8.51 (s, 1H), 8.42 (s, 1H), 8.17-8.13 (m, 1H), 7.93-7.87 (m, 1H), 7.71 (d, J=8.1 Hz, 2H), 7.40 (d, J=7.7 Hz, 2H), 7.08 (d, J=2.6 Hz, 1H), 6.90 (s, 1H), 6.81 (dd, J=7.7, 2.7 Hz, 1H), 4.95 (t, J=5.6 Hz, 1H), 4.63-4.52 (m, 2H), 4.10 (t, J=4.7 Hz, 2H), 3.80-3.72 (m, 2H), 2.45 (s, 3H).

N-{[4-(1-methyl-1H-pyrazol-4-yl)phenyl]methyl}-6-{7-[3-(piperidin-1-yl)propoxy]imidazo[1,2-a]pyridin-3-yl}pyrimidin-4-amine ("A237")

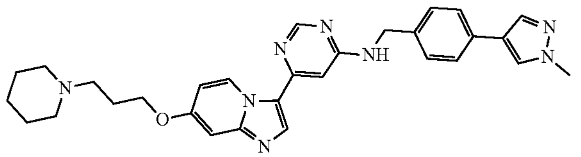 [SMILES: Cn1cc(-c2ccc(CNc3cc(-c4cnc5cc(OCCCN6CCCCC6)ccn45)ncn3)cc2)cn1]

from H1; white solid; UPLC/MS 0.396 min, $[M+H]^+$ 523.

$^1$H NMR (500 MHz, DMSO-$d_6$) δ 9.68 (d, J=7.7 Hz, 1H), 8.51 (s, 1H), 8.13 (s, 1H), 8.07 (d, J=0.7 Hz, 1H), 7.82 (t, J=6.2 Hz, 1H), 7.80 (d, J=0.8 Hz, 1H), 7.51 (d, J=8.2 Hz, 2H), 7.34 (d, J=7.8 Hz, 2H), 7.05 (d, J=2.6 Hz, 1H), 6.88 (d, J=1.3 Hz, 1H), 6.78 (dd, J=7.7, 2.6 Hz, 1H), 4.54 (d, J=5.9 Hz, 2H), 4.11 (t, J=6.4 Hz, 2H), 3.84 (s, 3H), 2.39 (t, J=7.2 Hz, 2H), 2.37-2.31 (m, 4H), 1.90 (p, J=6.7 Hz, 2H), 1.50 (p, J=5.5 Hz, 4H), 1.42-1.33 (m, 2H).

2-{3-[6-(4-oxazol-4-yl-benzylamino)-pyrimidin-4-yl]-imidazo[1,2-a]pyridin-7-yloxy}-ethanol ("A251")

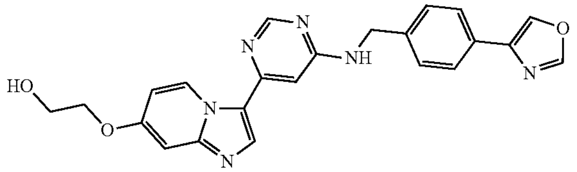 [SMILES: OCCOc1ccn2c(-c3cc(NCc4ccc(-c5cocn5)cc4)ncn3)cnc2c1]

from H6; off-white solid; m.p. 244-245° C.; HPLC/MS $[M+H]^+$ 429.

$^1$H NMR (300 MHz, DMSO-$d_6$) δ 9.69 (d, J=7.7 Hz, 1H), 8.58 (s, 1H), 8.50 (s, 1H), 8.43 (s, 1H), 8.14 (s, 1H), 7.91 (t, J=6.1 Hz, 1H), 7.74 (d, J=8.0 Hz, 2H), 7.41 (d, J=8.0 Hz, 2H), 7.06 (d, J=2.6 Hz, 1H), 6.88 (s, 1H), 6.80 (dd, J=7.8, 2.6 Hz, 1H), 4.94 (t, J=5.4 Hz, 1H), 4.57 (s, 2H), 4.09 (t, J=4.7 Hz, 2H), 3.80-3.71 (m, 2H).

(4-oxazol-4-yl-benzyl)-{6-[7-(3-pyrrolidin-1-yl-propoxy)-imidazo[1,2-a]pyridin-3-yl]-pyrimidin-4-yl}-amine ("A252")

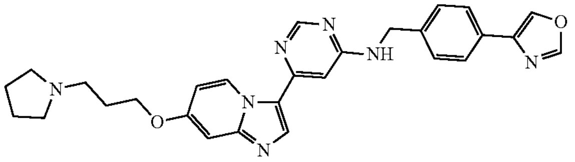 [SMILES: c1nc(NCc2ccc(-c3cocn3)cc2)cc(-c2cnc3cc(OCCCN4CCCC4)ccn23)n1]

white solid; HPLC/MS $[M+H]^+$ 496.

N-{[4-(1-methyl-1H-pyrazol-4-yl)phenyl]methyl}-6-(7-{[1-(2,2,2-trifluoroethyl)azetidin-3-yl]methoxy}imidazo[1,2-a]pyridin-3-yl)pyrimidin-4-amine ("A254")

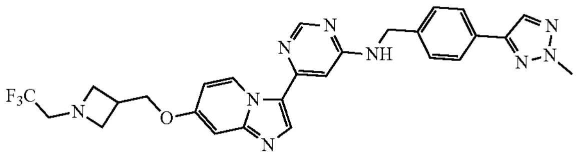 [SMILES: Cn1ncc(-c2ccc(CNc3cc(-c4cnc5cc(OCC6CN(CC(F)(F)F)C6)ccn45)ncn3)cc2)n1]

from H1) white crystalline solid; HPLC/MS(B) 0.717 min, $[M+H]^+$ 549.

$^1$H NMR (500 MHz, DMSO-$d_6$) δ 9.69 (d, J=7.7 Hz, 1H), 8.51 (s, 1H), 8.14 (s, 1H), 8.07 (d, J=0.8 Hz, 1H), 7.83 (t, J=6.2 Hz, 1H), 7.80 (d, J=0.8 Hz, 1H), 7.51 (d, J=8.2 Hz, 2H), 7.34 (d, J=7.8 Hz, 2H), 7.09 (d, J=2.6 Hz, 2H), 6.89 (d, J=1.3 Hz, 1H), 6.81 (dd, J=7.7, 2.6 Hz, 1H), 4.54 (d, J=6.1 Hz, 2H), 4.23 (d, J=6.8 Hz, 2H), 3.84 (s, 3H), 3.53 (t, J=7.4 Hz, 2H), 3.26-3.17 (m, 4H), 2.93 (hept, J=6.9 Hz, 1H).

N-{[4-(1-methyl-1H-pyrazol-4-yl)phenyl]methyl}-6-{7-[2-(1H-pyrazol-1-yl)ethoxy]imidazo[1,2-a]pyridin-3-yl}pyrimidin-4-amine ("A255")

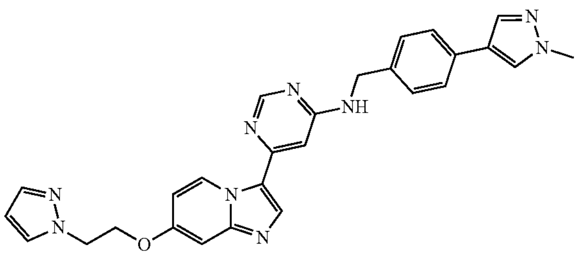 [SMILES: Cn1cc(-c2ccc(CNc3cc(-c4cnc5cc(OCCn6cccn6)ccn45)ncn3)cc2)cn1]

from H1) white crystalline solid; HPLC/MS(B) 1.345 min, $[M+H]^+$ 492.

$^1H$ NMR (400 MHz, DMSO-$d_6$) δ 9.68 (d, J=7.7 Hz, 1H), 8.51 (s, 1H), 8.15 (s, 1H), 8.08 (d, J=0.8 Hz, 1H), 7.88 (t, J=6.1 Hz, 1H), 7.81 (dd, J=3.0, 0.8 Hz, 2H), 7.51 (d, J=8.2 Hz, 2H), 7.47 (dd, J=1.9, 0.7 Hz, 1H), 7.34 (d, J=7.8 Hz, 2H), 7.12 (d, J=2.6 Hz, 1H), 6.89 (d, J=1.3 Hz, 1H), 6.75 (dd, J=7.8, 2.7 Hz, 1H), 6.25 (t, J=2.1 Hz, 1H), 4.64-4.50 (m, 4H), 4.47 (t, J=4.9 Hz, 2H), 3.84 (s, 3H).

6-{7-[(3-fluoro-1-methylazetidin-3-yl)methoxy]imidazo[1,2-a]pyridin-3-yl}-N-{[4-(1-methyl-1H-pyrazol-4-yl)phenyl]methyl}pyrimidin-4-amine ("A256")

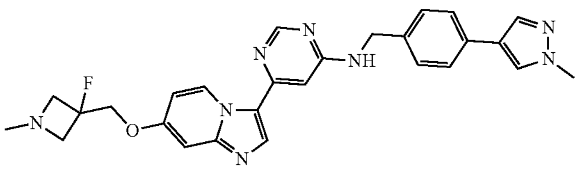

(from H1); off-white powder; UPLC/MS 0.379 min, $[M+H]^+$ 499.

$^1H$ NMR (500 MHz, DMSO-$d_6$) δ 9.71 (d, J=7.7 Hz, 1H), 8.52 (s, 1H), 8.15 (s, 1H), 8.07 (d, J=0.8 Hz, 1H), 7.84 (t, J=6.1 Hz, 1H), 7.80 (d, J=0.8 Hz, 1H), 7.51 (d, J=8.2 Hz, 2H), 7.34 (d, J=7.8 Hz, 2H), 7.17 (d, J=2.6 Hz, 1H), 6.90 (d, J=1.2 Hz, 1H), 6.85 (dd, J=7.7, 2.7 Hz, 1H), 4.54 (d, J=6.0 Hz, 2H), 4.42 (d, J=24.4 Hz, 2H), 3.84 (s, 3H), 3.58-3.51 (m, 2H), 3.17 (dd, J=21.7, 9.5 Hz, 2H), 2.34 (s, 3H).

N-{[4-(1-methyl-1H-pyrazol-4-yl)phenyl]methyl}-6-{7-[3-(1H-pyrazol-1-yl)propoxy]imidazo[1,2-a]pyridin-3-yl}pyrimidin-4-amine ("A257")

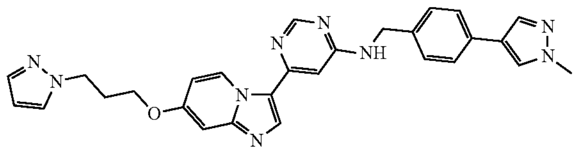 [SMILES: Cn1cc(-c2ccc(CNc3cc(-c4cnc5cc(OCCCn6cccn6)ccn45)ncn3)cc2)cn1]

from H1; off-white powder; UPLC/MS 0.511 min, $[M+H]^+$ 506.

1H NMR (500 MHz, DMSO-$d_6$) δ 9.70 (d, J=7.7 Hz, 1H), 8.51 (s, 1H), 8.13 (s, 1H), 8.07 (d, J=0.8 Hz, 1H), 7.83 (t, J=6.1 Hz, 1H), 7.80 (d, J=0.8 Hz, 1H), 7.74 (dd, J=2.2, 0.7 Hz, 1H), 7.51 (d, J=8.2 Hz, 2H), 7.44 (dd, J=1.8, 0.7 Hz, 1H), 7.34 (d, J=7.8 Hz, 2H), 7.02 (d, J=2.6 Hz, 1H), 6.89 (d, J=1.2 Hz, 1H), 6.80 (dd, J=7.7, 2.6 Hz, 1H), 6.23 (t, J=2.0 Hz, 1H), 4.54 (d, J=6.1 Hz, 2H), 4.30 (t, J=6.9 Hz, 2H), 4.06 (t, J=6.1 Hz, 2H), 3.84 (s, 3H), 2.26 (p, J=6.5 Hz, 2H).

N-{[4-(1-methyl-1H-pyrazol-4-yl)phenyl]methyl}-6-(7-{3-[(oxetan-3-yl)amino]propoxy}imidazo[1,2-a]pyridin-3-yl)pyrimidin-4-amine ("A258")

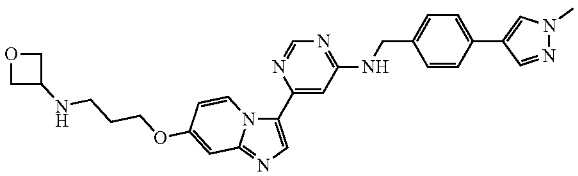 [SMILES: Cn1cc(-c2ccc(CNc3cc(-c4cnc5cc(OCCCNC6COC6)ccn45)ncn3)cc2)cn1]

from H1; white solid; HPLC/MS $[M+H]^+$ 511.

$^1H$ NMR (500 MHz, DMSO-$d_6$) δ 9.69 (d, J=7.7 Hz, 1H), 8.52 (s, 1H), 8.15 (s, 1H), 8.08 (d, J=0.8 Hz, 1H), 7.86 (t, J=6.2 Hz, 1H), 7.82 (d, J=0.8 Hz, 1H), 7.55-7.49 (m, 2H), 7.35 (d, J=7.8 Hz, 2H), 7.07 (d, J=2.7 Hz, 1H), 6.89 (d, J=1.2 Hz, 1H), 6.80 (dd, J=7.7, 2.6 Hz, 1H), 4.67-4.61 (m, 2H), 4.54 (s, 2H), 4.33 (t, J=6.1 Hz, 2H), 4.14 (t, J=6.4 Hz, 2H), 3.91-3.82 (m, 1H), 3.85 (s, 3H), 2.60 (t, J=6.8 Hz, 2H), 1.85 (p, J=6.6 Hz, 2H).

The compound may also be referred to as [4-(1-Methyl-1H-pyrazol-4-yl)-benzyl]-(6-{7-[3-(oxetan-3-ylamino)-propoxy]-imidazo[1,2185yridinedin-3-yl}-pyrimidin-4-yl)-amine.

N-{[4-(2-methyl-2H-1,2,3-triazol-4-yl)phenyl]methyl}-6-(7-{3-[(oxetan-3-yl)amino]propoxy}imidazo[1,2-a]pyridin-3-yl)pyrimidin-4-amine ("A259")

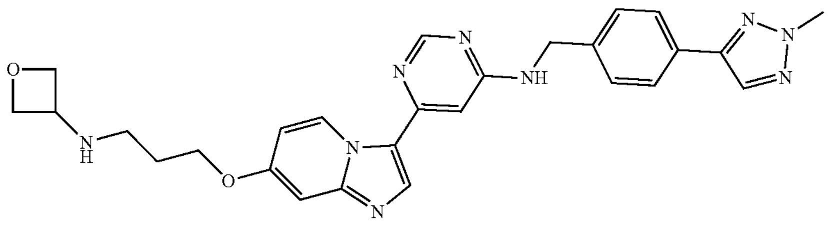 [SMILES: Cn1ncc(-c2ccc(CNc3cc(-c4cnc5cc(OCCCNC6COC6)ccn45)ncn3)cc2)n1]

from H2; white solid; HPLC/MS $[M+H]^+$ 512.

$^1H$ NMR (500 MHz, DMSO-$d_6$) δ 9.70 (d, J=7.7 Hz, 1H), 8.52 (s, 1H), 8.18 (s, 1H), 8.16 (s, 1H), 7.92 (t, J=6.2 Hz, 1H), 7.82-7.78 (m, 2H), 7.44 (d, J=7.5 Hz, 2H), 7.07 (d, J=2.8 Hz, 1H), 6.91 (s, 1H), 6.80 (dd, J=7.7, 2.6 Hz, 1H), 4.63 (t, J=6.6 Hz, 2H), 4.60 (s, 2H), 4.33 (t, J=6.2 Hz, 2H), 4.18 (s, 3H), 4.14 (t, J=6.4 Hz, 2H), 3.86 (p, J=6.7 Hz, 1H), 2.60 (t, J=6.7 Hz, 2H), 1.85 (p, J=6.6 Hz, 2H).

N-{[4-(1-methyl-1H-pyrazol-4-yl)phenyl]methyl}-6-[7-(3-{[(3R)-oxolan-3-yl]amino}propoxy)imidazo[1,2-a]pyridin-3-yl]pyrimidin-4-amine ("A260")

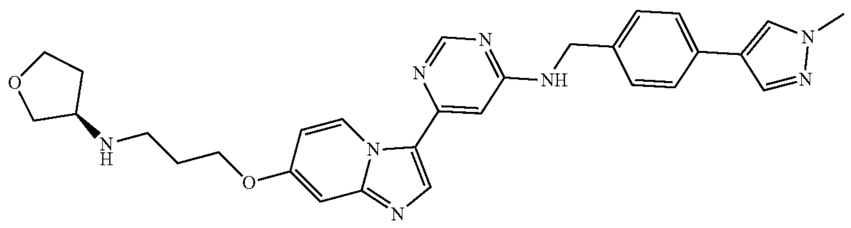 [SMILES: Cn1cc(-c2ccc(CNc3cc(-c4cnc5cc(OCCCN[C@@H]6CCOC6)ccn45)ncn3)cc2)cn1]

from H1; white solid; HPLC/MS $[M+H]^+$ 524.

$^1$H NMR (500 MHz, DMSO-$d_6$) δ 9.72 (d, J=7.7 Hz, 1H), 8.52 (s, 1H), 8.16 (s, 1H), 8.09 (d, J=0.8 Hz, 1H), 7.89 (t, J=6.2 Hz, 1H), 7.82 (d, J=0.8 Hz, 1H), 7.55-7.49 (m, 2H), 7.35 (d, J=7.8 Hz, 2H), 7.11 (d, J=2.6 Hz, 1H), 6.91 (d, J=1.2 Hz, 1H), 6.82 (dd, J=7.7, 2.6 Hz, 1H), 4.54 (s, 2H), 4.21 (t, J=6.2 Hz, 2H), 3.96-3.81 (m, 5H), 3.78 (dd, J=9.6, 5.8 Hz, 1H), 3.67 (td, J=8.2, 6.3 Hz, 1H), 3.07 (q, J=8.6, 6.9 Hz, 2H), 2.21 (dtd, J=13.9, 8.0, 6.0 Hz, 1H), 2.14 (q, J=6.9 Hz, 2H), 2.05-1.96 (m, 1H).

The compound may also be referred to as [4-(1-methyl-1H-pyrazol-4-yl)-benzyl]-[6-(7-{3-[(R)-(tetrahydro-furan-3-yl)amino]-propoxy}-imidazo[1,2186yridinedin-3-yl)-pyrimidin-4-yl]-amine.

4-methyl-1-[2-({3-[6-({[4-(2-methyl-1,3-oxazol-4-yl)phenyl]methyl}amino)pyrimidin-4-yl]imidazo[1,2-a]pyridin-7-yl}oxy)ethyl]-1,4-diazepan-5-one ("A261")

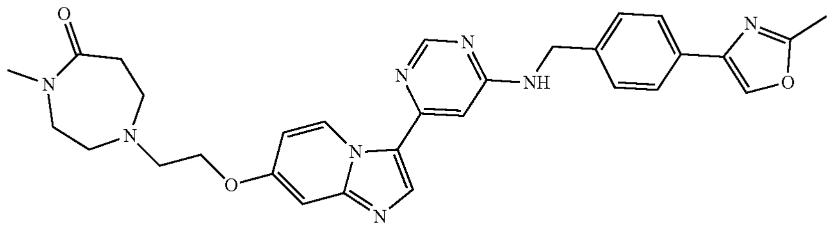

from H4; white solid; HPLC/MS $[M+H]^+$ 553.

$^1$H NMR (500 MHz, DMSO-$d_6$) δ 9.69 (d, J=7.7 Hz, 1H), 8.51 (s, 1H), 8.40 (s, 1H), 8.14 (s, 1H), 7.86 (t, J=6.2 Hz, 1H), 7.70 (d, J=7.9 Hz, 2H), 7.40 (d, J=7.8 Hz, 2H), 7.09 (d, J=2.6 Hz, 1H), 6.89 (s, 1H), 6.79 (dd, J=7.6, 2.6 Hz, 1H), 4.57 (d, J=6.1 Hz, 2H), 4.20 (t, J=5.6 Hz, 2H), 3.45-3.40 (m, 2H), 2.86 (d, J=13.7 Hz, 5H), 2.71-2.61 (m, 4H), 2.56-2.50 (m, 2H), 2.44 (s, 3H).

6-{7-[3-(4-fluoro-4-methylpiperidin-1-yl)propoxy] imidazo[1,2-a]pyridin-3-yl}-N-{[4-(1-methyl-1H-pyrazol-4-yl)phenyl]methyl}pyrimidin-4-amine ("A262")

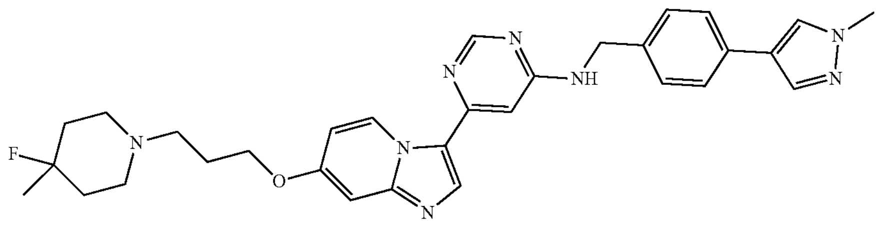 [SMILES: Cn1cc(-c2ccc(CNc3cc(-c4cnc5cc(OCCCN6CCC(C)(F)CC6)ccn45)ncn3)cc2)cn1]

from H1; white solid; HPLC/MS $[M+H]^+$ 555.

$^1$H NMR (500 MHz, DMSO-$d_6$) δ 9.69 (d, J=7.7 Hz, 1H), 8.51 (s, 1H), 8.14 (s, 1H), 8.08 (d, J=0.8 Hz, 1H), 7.86 (t, J=6.1 Hz, 1H), 7.81 (d, J=0.8 Hz, 1H), 7.54-7.48 (m, 2H), 7.34 (d, J=7.7 Hz, 2H), 7.07 (s, 1H), 6.89 (d, J=1.2 Hz, 1H), 6.79 (dd, J=7.7, 2.6 Hz, 1H), 4.54 (s, 2H), 4.13 (s, 2H), 3.84 (s, 3H), 2.60 (s, 1H), 2.49 (s, 2H), 2.23 (s, 2H), 1.93 (s, 2H), 1.73 (s, 4H), 1.32 (d, J=21.5 Hz, 3H).

The compound may also be referred to as (6-{7-[3-(4-Fluoro-4-methyl-piperidin-1-yl)-propoxy]-imidazo[1, 2187yridinedin-3-yl}-pyrimidin-4-yl)-[4-(1-methyl-1H-pyrazol-4-yl)-benzyl]-amine.

6-{7-[3-(4-fluoro-4-methylpiperidin-1-yl)propoxy] imidazo[1,2-a]pyridin-3-yl}-N-{[4-(1,3-oxazol-4-yl) phenyl]methyl}pyrimidin-4-amine ("A263")

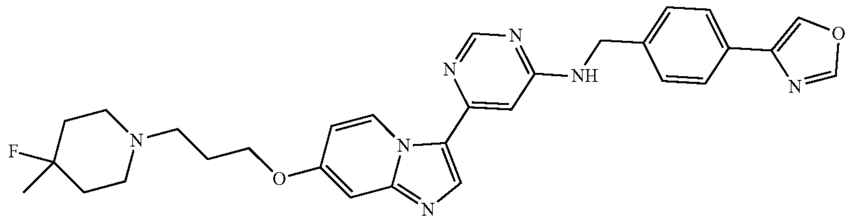 [SMILES: CC1(F)CCN(CCCOc2ccn3c(-c4cc(NCc5ccc(-c6cocn6)cc5)ncn4)cnc3c2)CC1]

from H6; white solid; HPLC/MS $[M+H]^+$ 543.

$^1$H NMR (500 MHz, DMSO-$d_6$) δ 9.69 (d, J=7.7 Hz, 1H), 8.58 (d, J=1.0 Hz, 1H), 8.51 (s, 1H), 8.43 (d, J=1.0 Hz, 1H), 8.15 (s, 1H), 7.89 (t, J=6.2 Hz, 1H), 7.79-7.72 (m, 2H), 7.43 (d, J=7.9 Hz, 2H), 7.06 (d, J=2.6 Hz, 1H), 6.90 (d, J=1.2 Hz, 1H), 6.79 (dd, J=7.7, 2.7 Hz, 1H), 4.58 (s, 2H), 4.12 (t, J=6.3 Hz, 2H), 3.28 (s, 3H), 2.63-2.57 (m, 1H), 2.46 (t, J=7.1 Hz, 2H), 2.22 (t, J=10.6 Hz, 2H), 1.92 (p, J=6.6 Hz, 2H), 1.71 (dd, J=13.5, 9.3 Hz, 2H), 1.69-1.57 (m, 1H), 1.30 (d, J=21.5 Hz, 3H).

N-{[4-(2-methyl-1,3-oxazol-4-yl)phenyl]methyl}-6-[7-(2-{4H,5H,6H,7H-[1,2,3]triazolo[1,5-a]pyrazin-5-yl}ethoxy)imidazo[1,2-a]pyridin-3-yl]pyrimidin-4-amine ("A264")

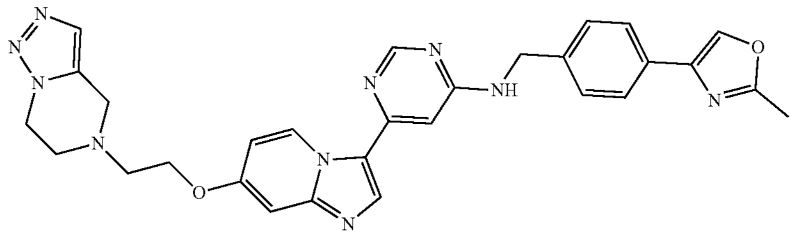 [SMILES: Cc1nc(-c2ccc(CNc3cc(-c4cnc5cc(OCCN6CCn7nncc7C6)ccn45)ncn3)cc2)co1]

from H4; white solid; HPLC/MS [M+H]+ 543.

1H NMR (400 MHz, DMSO-$d_6$) δ 9.70 (d, J=7.7 Hz, 1H), 8.51 (s, 1H), 8.41 (s, 1H), 8.15 (s, 1H), 7.88 (t, J=6.1 Hz, 1H), 7.74-7.67 (m, 2H), 7.53 (s, 1H), 7.40 (d, J=7.9 Hz, 2H), 7.14 (d, J=2.6 Hz, 1H), 6.90 (d, J=1.3 Hz, 1H), 6.82 (dd, J=7.7, 2.6 Hz, 1H), 4.59-4.54 (m, 1H), 4.37 (t, J=5.6 Hz, 2H), 4.30 (t, J=5.5 Hz, 2H), 3.88 (s, 2H), 3.09 (t, J=5.6 Hz, 2H), 3.03 (t, J=5.4 Hz, 2H), 2.45 (s, 3H).

6-[7-(2-{4H,5H,6H,7H-[1,2,3]triazolo[1,5-a]pyrazin-5-yl}ethoxy)imidazo[1,2-a]pyridin-3-yl]-N-{[4-(trifluoromethoxy)phenyl]methyl}pyrimidin-4-amine ("A265")

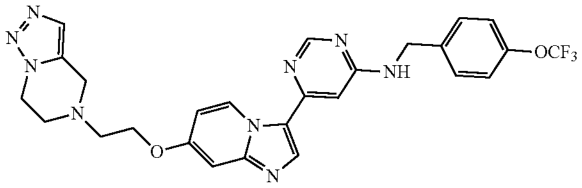 [SMILES: FC(F)(F)Oc1ccc(CNc2cc(-c3cnc4cc(OCCN5CCn6nncc6C5)ccn34)ncn2)cc1]

from H7; white solid; HPLC/MS [M+H]+ 552.

1H NMR (500 MHz, DMSO-$d_6$) δ 9.70 (d, J=7.7 Hz, 1H), 8.52-8.51 (m, 1H), 8.19-8.14 (m, 1H), 7.91 (t, J=6.2 Hz, 1H), 7.54-7.53 (m, 1H), 7.50-7.46 (m, 2H), 7.35-7.31 (m, 2H), 7.15-7.13 (m, 1H), 6.90 (d, J=1.2 Hz, 1H), 6.82 (dd, J=7.7, 2.6 Hz, 1H), 4.62-4.57 (m, 2H), 4.39-4.35 (m, 2H), 4.30 (t, J=5.5 Hz, 2H), 3.89-3.88 (m, 2H), 3.11-3.08 (m, 2H), 3.03 (t, J=5.5 Hz, 2H).

Example 4

Synthesis of 6-{imidazo[1,2-a]pyridin-3-yl}-N-({6-[(3R)-3-methoxypyrrolidin-1-yl]pyridin-3-yl}methyl)pyrimidin-4-amine ("A146")

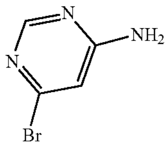

+

-continued

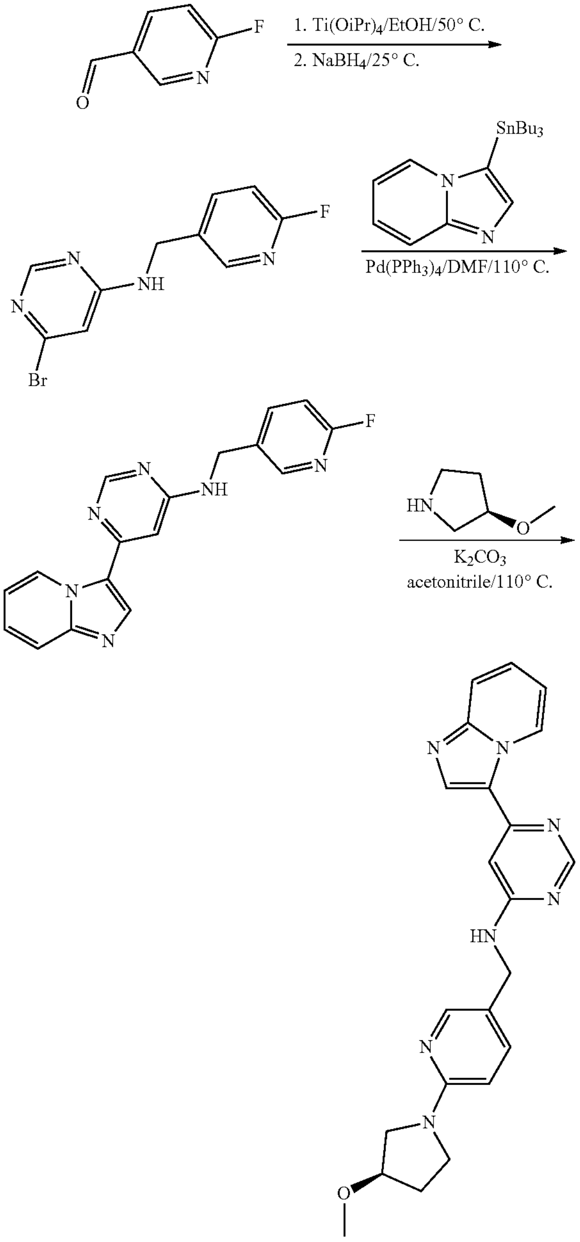

Off-white solid; m.p. 161-163° C.; HPLC/MS $[M+H]^+$ 402.

$^1$H NMR (400 MHz, DMSO-$d_6$) δ 9.85 (d, J=7.1 Hz, 1H), 8.56 (s, 1H), 8.29 (s, 1H), 8.11 (s, 1H), 7.82 (t, J=6.0 Hz, 1H), 7.71 (dt, J=8.9, 1.2 Hz, 1H), 7.56-7.48 (m, 1H), 7.41 (ddd, J=9.2, 6.7, 1.3 Hz, 1H), 7.10 (td, J=6.9, 1.3 Hz, 1H), 6.94 (s, 1H), 6.43 (d, J=8.6 Hz, 1H), 4.40 (s, 2H), 4.08-4.01 (m, 1H), 3.44 (d, J=3.7 Hz, 3H), 3.33-3.29 (m, 1H), 3.24 (s, 3H), 2.03 (td, J=8.1, 4.4 Hz, 2H).

The following compounds are prepared analogously:

(6-imidazo[1,2-a]pyridin-3-yl-pyrimidin-4-yl)-(6-pyrrolidin-1-yl-pyridin-3-ylmethyl)-amine ("A147")

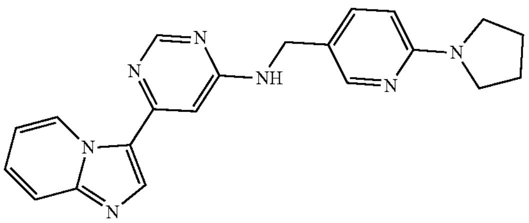 [SMILES: c1ccn2c(-c3cc(NCc4ccc(N5CCCC5)nc4)ncn3)cnc2c1]

yellow solid; m.p. 176-177° C.; HPLC/MS $[M+H]^+$ 372.

$^1$H NMR (400 MHz, DMSO-$d_6$) δ 9.85 (d, J=7.2 Hz, 1H), 8.56 (s, 1H), 8.31 (s, 1H), 8.10 (s, 1H), 7.80 (t, J=6.0 Hz, 1H), 7.71 (dt, J=9.1, 1.2 Hz, 1H), 7.51 (dd, J=8.7, 2.4 Hz, 1H), 7.41 (m, J=9.0, 6.7, 1.3 Hz, 1H), 7.10 (td, J=6.9, 1.3 Hz, 1H), 6.94 (s, 1H), 6.42 (d, J=8.7 Hz, 1H), 4.40 (s, 2H), 3.35-3.32 (m, 4H), 1.94-1.90 (m, 4H).

N-({6-[(3S)-3-fluoropyrrolidin-1-yl]pyridin-3-yl}methyl)-6-{imidazo[1,2-a]pyridin-3-yl}pyrimidin-4-amine ("A148")

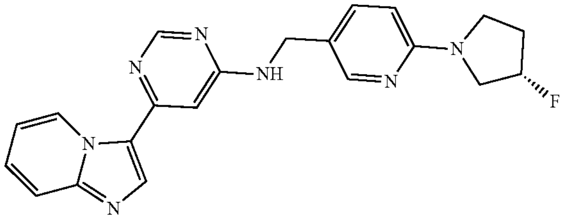 [SMILES: F[C@H]1CCN(c2ccc(CNc3cc(-c4cnc5ccccn45)ncn3)cn2)C1]

off-white solid; m.p. 190-192° C.; HPLC/MS $[M+H]^+$ 390.

$^1$H NMR (400 MHz, DMSO-$d_6$) δ 9.85 (d, J=7.1 Hz, 1H), 8.57 (s, 1H), 8.30 (s, 1H), 8.13 (s, 1H), 7.84 (t, J=6.0 Hz, 1H), 7.71 (dt, J=9.0, 1.2 Hz, 1H), 7.59-7.52 (m, 1H), 7.42 (ddd, J=9.0, 6.8, 1.3 Hz, 1H), 7.10 (td, J=6.9, 1.3 Hz, 1H), 6.95 (s, 1H), 6.49 (dd, J=8.6, 0.8 Hz, 1H), 5.43 (d, J=53.6 Hz, 1H), 4.42 (s, 2H), 3.74-3.48 (m, 3H), 3.44-3.37 (m, 1H), 2.28-2.07 (m, 2H).

[6-(3-aza-bicyclo[3.1.0]hex-3-yl)-pyridin-3-ylmethyl]-(6-imidazo[1,2-a]pyridin-3-yl-pyrimidin-4-yl)-amine ("A149")

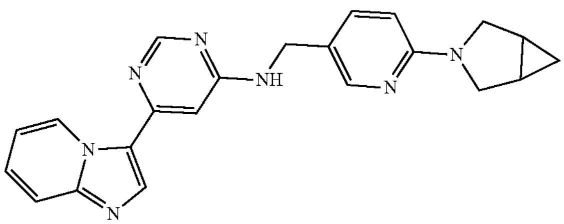 [SMILES: c1ccn2c(-c3cc(NCc4ccc(N5CC6CC6C5)nc4)ncn3)cnc2c1]

white solid; m.p. 185-187° C.; HPLC/MS $[M+H]^+$ 384. $^1$H NMR (400 MHz, DMSO-$d_6$) δ 9.85 (d, J=6.9 Hz, 1H), 8.56 (s, 1H), 8.09 (s, 1H), 7.82 (t, J=6.0 Hz, 1H), 7.71 (dt, J=9.0, 1.2 Hz, 1H), 7.50 (d, J=8.6 Hz, 1H), 7.41 (ddd, J=9.1, 6.8, 1.4 Hz, 1H), 7.10 (td, J=6.9, 1.3 Hz, 1H), 6.93 (s, 1H), 6.42 (d, J=8.6 Hz, 1H), 4.39 (s, 2H), 3.60 (d, J=10.1 Hz, 2H), 3.29 (dt, J=10.1, 1.9 Hz, 2H), 1.69-1.61 (m, 2H), 0.70 (td, J=7.8, 4.4 Hz, 1H), 0.15 (q, J=4.1 Hz, 1H).

[6-(3,3-difluoro-pyrrolidin-1-yl)-pyridin-3-ylmethyl]-(6-imidazo[1,2-a]pyridin-3-yl-pyrimidin-4-yl)-amine ("A150")

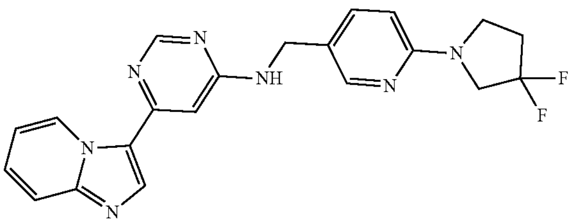 [SMILES: FC1(F)CCN(c2ccc(CNc3cc(-c4cnc5ccccn45)ncn3)cn2)C1]

white solid; m.p. 192-194° C.; HPLC/MS $[M+H]^+$ 408. $^1$H NMR (400 MHz, DMSO-$d_6$) δ 9.85 (d, J=7.0 Hz, 1H), 8.56 (s, 1H), 8.30 (s, 1H), 8.16 (s, 1H), 7.86 (t, J=6.0 Hz, 1H), 7.71 (dt, J=9.0, 1.2 Hz, 1H), 7.60 (d, J=8.5 Hz, 1H), 7.42 (ddd, J=9.0, 6.8, 1.3 Hz, 1H), 7.10 (td, J=6.9, 1.3 Hz, 1H), 6.95 (s, 1H), 6.54 (dd, J=8.6, 0.8 Hz, 1H), 4.44 (s, 2H), 3.80 (t, J=13.4 Hz, 2H), 3.58 (t, J=7.3 Hz, 2H), 2.58-2.52 (m, 1H), 2.47 (d, J=7.3 Hz, 1H).

6-{imidazo[1,2-a]pyridin-3-yl}-N-({6-[(3S)-3-methoxypyrrolidin-1-yl]pyridin-3-yl}methyl)pyrimidin-4-amine ("A151")

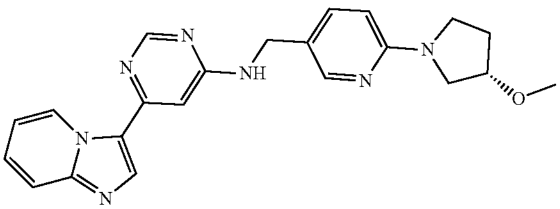 [SMILES: CO[C@H]1CCN(c2ccc(CNc3cc(-c4cnc5ccccn45)ncn3)cn2)C1]

white solid; m.p. 159-161° C.; HPLC/MS $[M+H]^+$ 402. $^1$H NMR (400 MHz, DMSO-$d_6$) δ 9.85 (d, J=7.0 Hz, 1H), 8.56 (s, 1H), 8.28 (s, 1H), 8.11 (s, 1H), 7.83 (t, J=6.0 Hz, 1H), 7.71 (dt, J=9.0, 1.2 Hz, 1H), 7.56-7.48 (m, 1H), 7.41 (ddd, J=9.0, 6.8, 1.3 Hz, 1H), 7.09 (td, J=6.9, 1.3 Hz, 1H), 6.94 (s, 1H), 6.47-6.38 (m, 1H), 4.40 (s, 2H), 4.04 (p, J=3.6 Hz, 1H), 3.47-3.38 (m, 3H), 3.36 (s, 3H), 3.31 (td, J=9.9, 9.4, 7.6 Hz, 1H), 2.02 (td, J=8.6, 8.2, 4.5 Hz, 2H).

(4-fluoro-6-pyrrolidin-1-yl-pyridin-3-ylmethyl)-(6-imidazo[1,2-a]pyridin-3-yl-pyrimidin-4-yl)-amine ("A152")

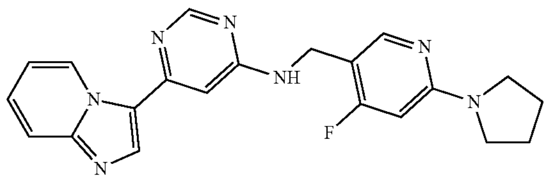 [SMILES: Fc1cc(N2CCCC2)ncc1CNc1cc(-c2cnc3ccccn23)ncn1]

off-white solid; m.p. 239-241° C.; HPLC/MS $[M+H]^+$ 390.

$^1H$ NMR (400 MHz, DMSO-$d_6$) δ 9.85 (d, J=7.1 Hz, 1H), 8.58 (s, 1H), 8.28 (s, 1H), 8.13 (d, J=11.3 Hz, 1H), 7.77 (s, 1H), 7.71 (dt, J=9.0, 1.2 Hz, 1H), 7.42 (ddd, J=9.0, 6.8, 1.3 Hz, 1H), 7.10 (td, J=6.9, 1.3 Hz, 1H), 6.96 (s, 1H), 6.27 (d, J=13.1 Hz, 1H), 4.45 (d, J=5.6 Hz, 2H), 3.35 (d, J=2.7 Hz, 4H), 1.98-1.88 (m, 4H).

N-({6-[(3R)-3-fluoropyrrolidin-1-yl]pyridin-3-yl}methyl)-6-{imidazo[1,2-a]pyridin-3-yl}pyrimidin-4-amine ("A153")

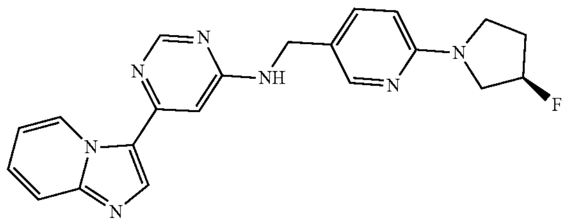 [SMILES: F[C@@H]1CCN(c2ccc(CNc3cc(-c4cnc5ccccn45)ncn3)cn2)C1]

white solid; m.p. 188-190° C.; HPLC/MS $[M+H]^+$ 390. $^1H$ NMR (400 MHz, DMSO-$d_6$) δ 9.85 (d, J=7.0 Hz, 1H), 8.56 (s, 1H), 8.29 (s, 1H), 8.13 (s, 1H), 7.84 (t, J=6.0 Hz, 1H), 7.71 (dt, J=9.0, 1.2 Hz, 1H), 7.62-7.51 (m, 1H), 7.41 (ddd, J=9.0, 6.7, 1.3 Hz, 1H), 7.10 (td, J=6.9, 1.3 Hz, 1H), 6.94 (s, 1H), 6.48 (d, J=8.5 Hz, 1H), 5.52-5.31 (m, 1H), 4.42 (s, 2H), 3.75-3.46 (m, 3H), 3.39 (dd, J=10.4, 6.9 Hz, 1H), 2.28-2.05 (m, 2H).

Example 5

Synthesis of (6-imidazo[1,2-a]pyridin-3-yl-pyrimidin-4-yl)-(4-methyl-6-pyrrolidin-1-yl-pyridin-3-ylmethyl)-amine ("A154")

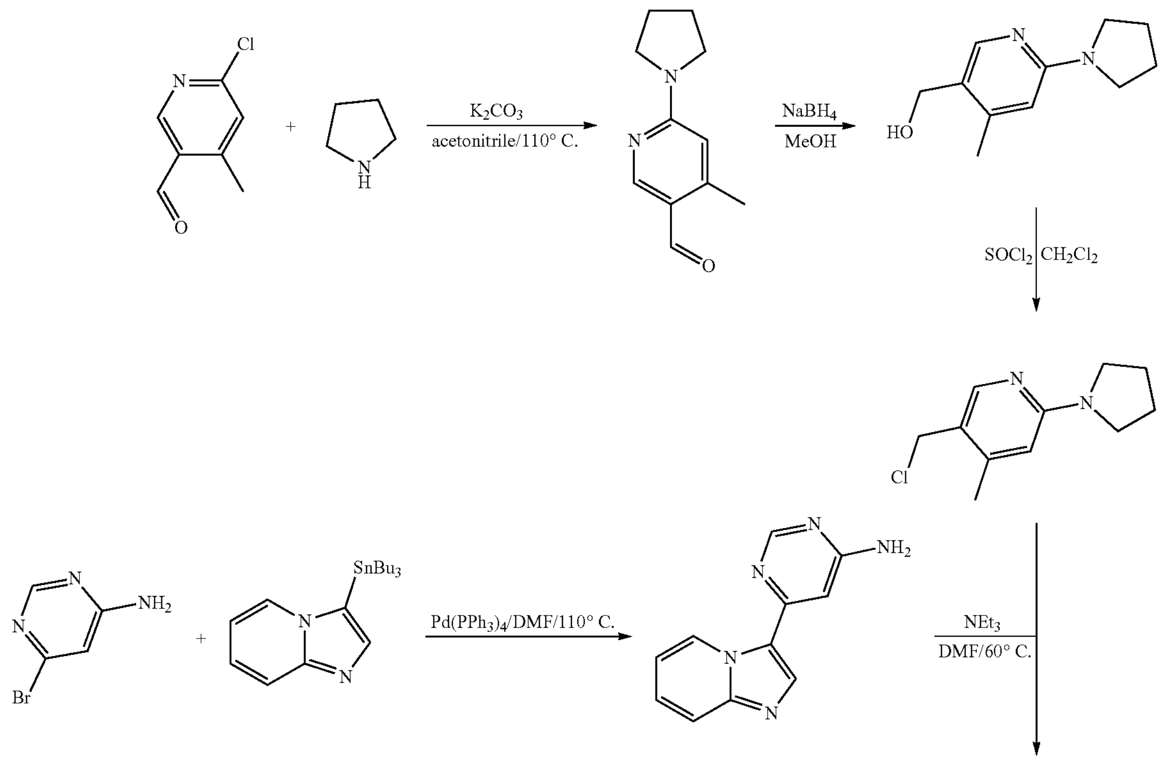

-continued

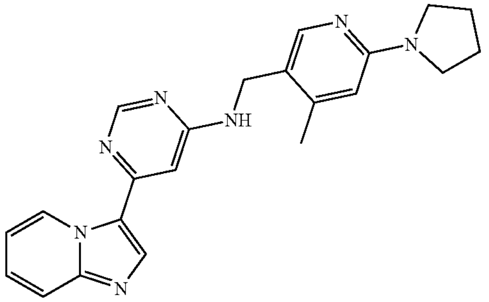

Off-white solid; m.p. 195-197° C.

$^1$H NMR (400 MHz, DMSO-$d_6$) δ 9.85 (d, J=7.0 Hz, 1H), 8.58 (s, 1H), 7.98 (s, 1H), 7.71 (dd, J=9.0, 1.2 Hz, 1H), 7.63 (t, J=5.4 Hz, 1H), 7.46-7.37 (m, 1H), 7.10 (td, J=6.9, 1.3 Hz, 1H), 6.94 (s, 1H), 6.29 (s, 1H), 4.41 (s, 2H), 3.38-3.35 (m, 4H), 2.27 (s, 3H), 1.97-1.87 (m, 4H).

The following compounds are prepared analogously:

[6-((S)-3-fluoro-pyrrolidin-1-yl)-4-methyl-pyridin-3-ylmethyl]-(6-imidazo[1,2-a]pyridin-3-yl-pyrimidin-4-yl)-amine ("A155")

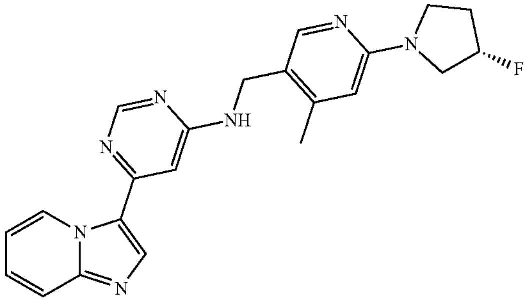 [SMILES: Cc1cc(N2CC[C@H](F)C2)ncc1CNc1cc(-c2cnc3ccccn23)ncn1]

white solid; m.p. 187-190° C.; HPLC/MS $[M+H]^+$ 404.

$^1$H NMR (400 MHz, DMSO-$d_6$) δ 9.85 (d, J=6.9 Hz, 1H), 8.58 (s, 1H), 8.28 (d, J=8.4 Hz, 1H), 8.01 (s, 1H), 7.75-7.67 (m, 1H), 7.65 (t, J=5.5 Hz, 1H), 7.46-7.37 (m, 1H), 7.15-7.06 (m, 1H), 6.95 (s, 1H), 6.37 (s, 1H), 5.42 (d, J=53.8 Hz, 1H), 4.49-4.38 (m, 2H), 3.75-3.47 (m, 4H), 2.29 (s, 3H), 2.24-2.04 (m, 2H).

[6-((R)-3-fluoro-pyrrolidin-1-yl)-4-methyl-pyridin-3-ylmethyl]-(6-imidazo[1,2-a]pyridin-3-yl-pyrimidin-4-yl)-amine ("A156")

white solid; m.p. 184-197° C.; HPLC/MS $[M+H]^+$ 404.

$^1$H NMR (400 MHz, DMSO-$d_6$) δ 9.85 (d, J=7.0 Hz, 1H), 8.58 (s, 1H), 8.35-8.13 (m, 1H), 8.01 (s, 1H), 7.71 (dd, J=9.0, 1.2 Hz, 1H), 7.65 (t, J=5.5 Hz, 1H), 7.45-7.38 (m, 1H), 7.15-7.06 (m, 1H), 6.95 (s, 1H), 6.37 (s, 1H), 5.52-5.32 (m, 1H), 4.44 (s, 2H), 3.75-3.40 (m, 4H), 2.29 (s, 3H), 2.25-2.06 (m, 2H).

Example 6

Synthesis of (6-imidazo[1,2-a]pyridin-3-yl-pyrimidin-4-yl)-[4-(1H-imidazol-2-yl)-benzyl]-amine ("A157")

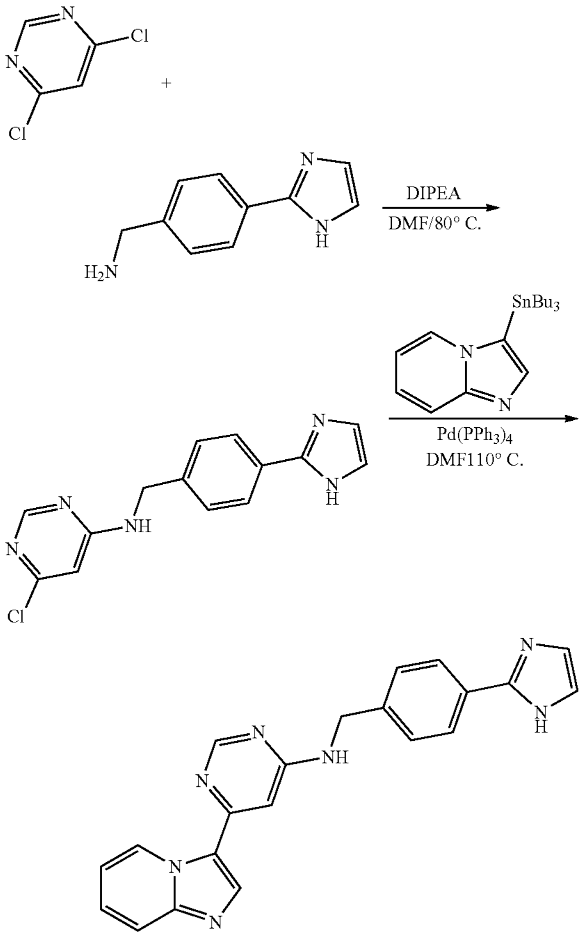

White solid; m.p. 300° C.; HPLC/MS $[M+H]^+$ 368.

$^1$H NMR (400 MHz, DMSO-$d_6$) δ 12.44 (s, 1H), 9.85 (d, J=7.0 Hz, 1H), 8.57 (s, 1H), 8.30 (s, 1H), 7.97 (t, J=6.1 Hz, 1H), 7.92-7.86 (m, 2H), 7.71 (m, 1H), 7.46-7.37 (m, 3H), 7.21 (s, 1H), 7.09 (m, 1H), 6.99 (d, J=1.6 Hz, 2H), 4.61 (s, 2H).

Example 7
Synthesis of 7-methoxy-3-{6-[4-(1-methyl-1H-pyrazol-4-yl)-benzyloxy]-pyrimidin-4-yl}-imidazo[1,2-a]pyridine ("A158")
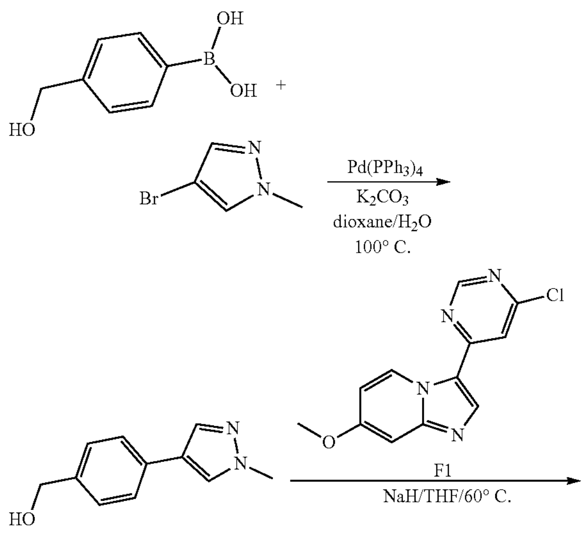
-continued
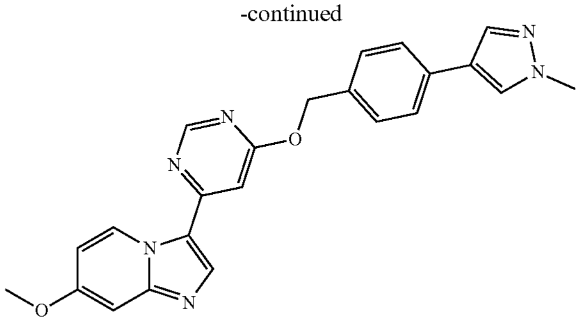
White solid; m.p. 216-218° C.; HPLC/MS $[M+H]^+$ 413. $^1H$ NMR (400 MHz, DMSO-$d_6$) δ 9.77 (d, J=8 Hz, 1H), 8.85 (d, J=1.1 Hz, 1H), 8.50 (s, 1H), 8.15 (s, 1H), 7.87 (d, J=0.8 Hz, 1H), 7.63-7.55 (m, 2H), 7.51-7.43 (m, 3H), 7.15 (d, J=2.4 Hz, 1H), 6.88 (dd, J=7.7, 2.7 Hz, 1H), 5.44 (s, 2H), 3.89-3.83 (m, 6H).
Example 8
Synthesis of N-[(4-{1-[(azetidin-3-yl)methyl]-1H-pyrazol-4-yl}phenyl)methyl]-6-{7-methoxyimidazo[1,2-a]pyridin-3-yl}pyrimidin-4-amine ("A159") trifluoroacetate
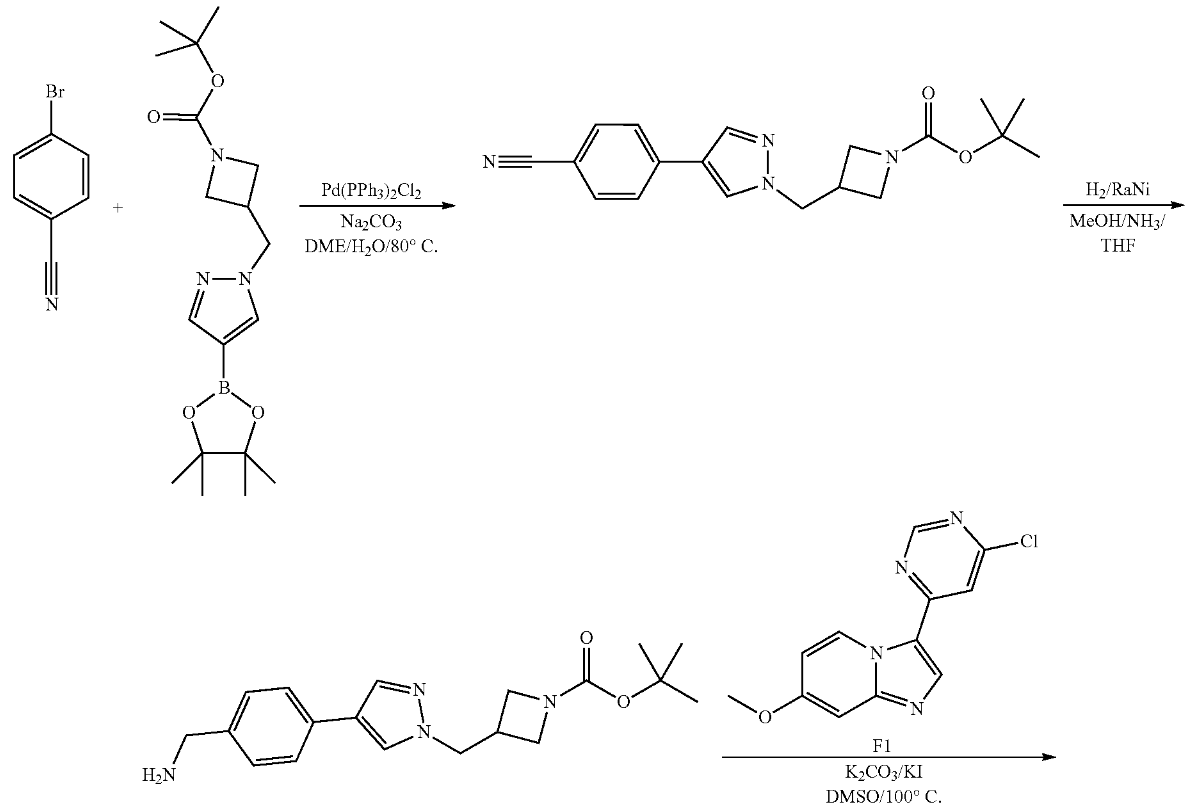

-continued
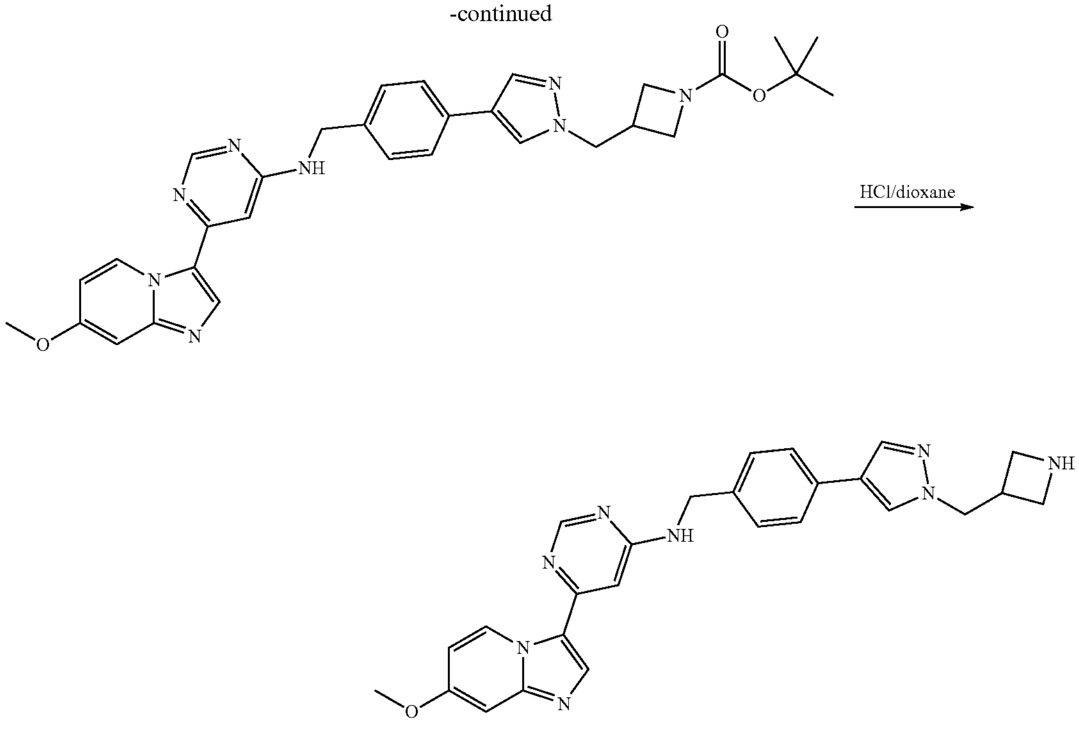
trifluoroacetate
Yellow resin; HPLC/MS(B) 1.017 min, $[M+H]^+$ 467.
Example 9
Synthesis of 3-[6-({[4-(1-methyl-1H-pyrazol-4-yl) phenyl]methyl}amino)pyrimidin-4-yl]imidazo[1,2-a] pyridin-7-ol ("A160")
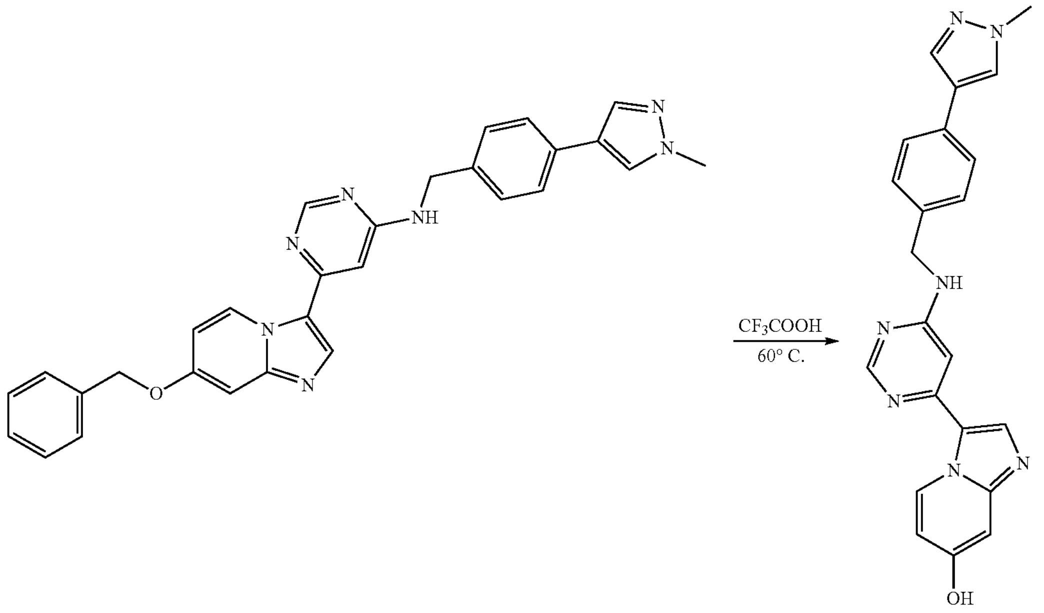 [SMILES: Cn1cc(-c2ccc(CNc3cc(-c4cnc5cc(OCc6ccccc6)ccn45)ncn3)cc2)cn1 ; "CF3COOH" ; Cn1cc(-c2ccc(CNc3cc(-c4cnc5cc(O)ccn45)ncn3)cc2)cn1]

From “A72”; pale brown powder; UPLC/MS 0.450 min, $[M+H]^+$ 398.

$^1$H NMR (400 MHz, DMSO-$d_6$) δ 10.52 (s, 1H), 9.68 (d, J=7.6 Hz, 1H), 8.50 (s, 1H), 8.25-8.02 (m, 3H), 7.84 (t, J=6.3 Hz, 1H), 7.82 (s, 1H), 7.52 (d, J=8.3 Hz, 2H), 7.34 (d, J=7.9 Hz, 2H), 6.86 (d, J=1.3 Hz, 1H), 6.81 (d, J=2.4 Hz, 1H), 6.72 (dd, J=7.6, 2.6 Hz, 1H), 4.53 (s, 2H), 3.84 (s, 3H).

Example 10

Synthesis of [4-(4-{[6-(7-methoxy-imidazo[1,2-a]pyridin-3-yl)-pyrimidin-4-ylamino]-methyl}-phenyl)-2-methyl-2H-pyrazol-3-yl]-methanol (“A161”)

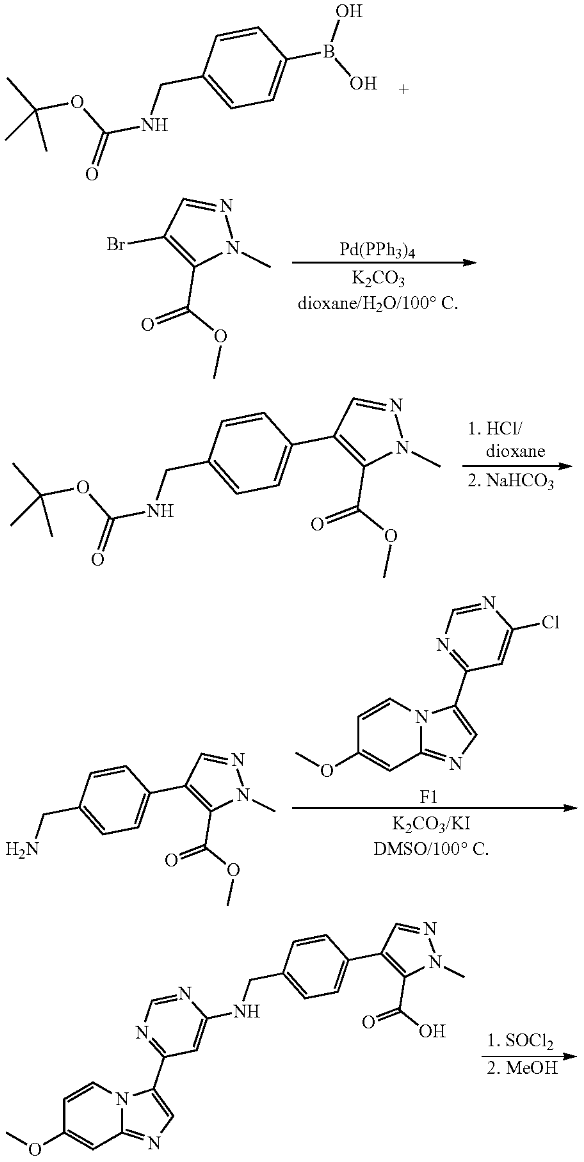

-continued

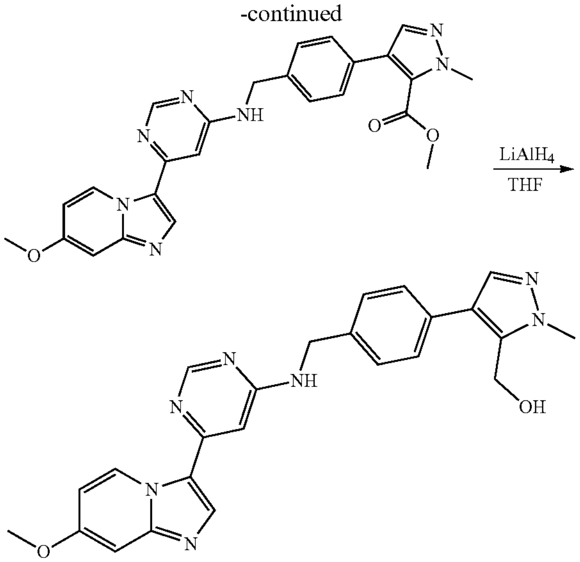

Off-white solid; m.p. 263-264° C.; HPLC/MS $[M+H]^+$ 442.

$^1$H NMR (400 MHz, DMSO-$d_6$) δ 9.70 (d, J=7.7 Hz, 1H), 8.52 (s, 1H), 8.17 (s, 1H), 7.92 (t, J=6.1 Hz, 1H), 7.56 (s, 1H), 7.49-7.33 (m, 5H), 7.09 (d, J=2.6 Hz, 1H), 6.91 (d, J=1.2 Hz, 1H), 6.82 (dd, J=7.9, 2.6 Hz, 1H), 5.36 (t, J=5.2 Hz, 1H), 4.57 (s, 2H), 4.52 (d, J=5.2 Hz, 2H), 3.88 (s, 3H), 3.87 (s, 3H).

Example 11

Synthesis of 6-{7-aminoimidazo[1,2-a]pyridin-3-yl}-N-{[4-(1-methyl-1H-pyrazol-4-yl)phenyl]methyl}pyrimidin-4-amine (“A162”)

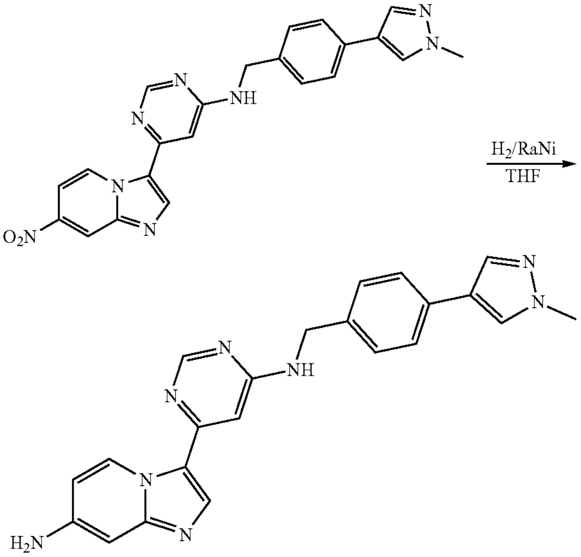

From “A81”; pale brown powder; UPLC/MS 0.446 min, $[M+H]^+$ 397.

$^1$H NMR (400 MHz, DMSO-$d_6$) δ 9.49 (d, J=7.5 Hz, 1H), 8.45 (s, 1H), 8.09 (s, 1H), 7.96 (s, 1H), 7.82 (s, 1H), 7.74 (t, J=6.1 Hz, 1H), 7.51 (d, J=8.2 Hz, 2H), 7.33 (d, J=7.9 Hz, 2H), 6.78 (d, J=1.2 Hz, 1H), 6.52 (dd, J=7.6, 2.3 Hz, 1H), 6.46 (d, J=2.2 Hz, 1H), 5.94 (s, 2H), 4.55-4.48 (m, 2H), 3.84 (s, 3H).

Example 12

Synthesis of 2-methyl-2-(3-{6-[4-(1-methyl-1H-pyrazol-4-yl)-benzylamino]-pyrimidin-4-yl}-imidazo[1,2-a]pyridin-7-ylamino)-propan-1-ol ("A163")

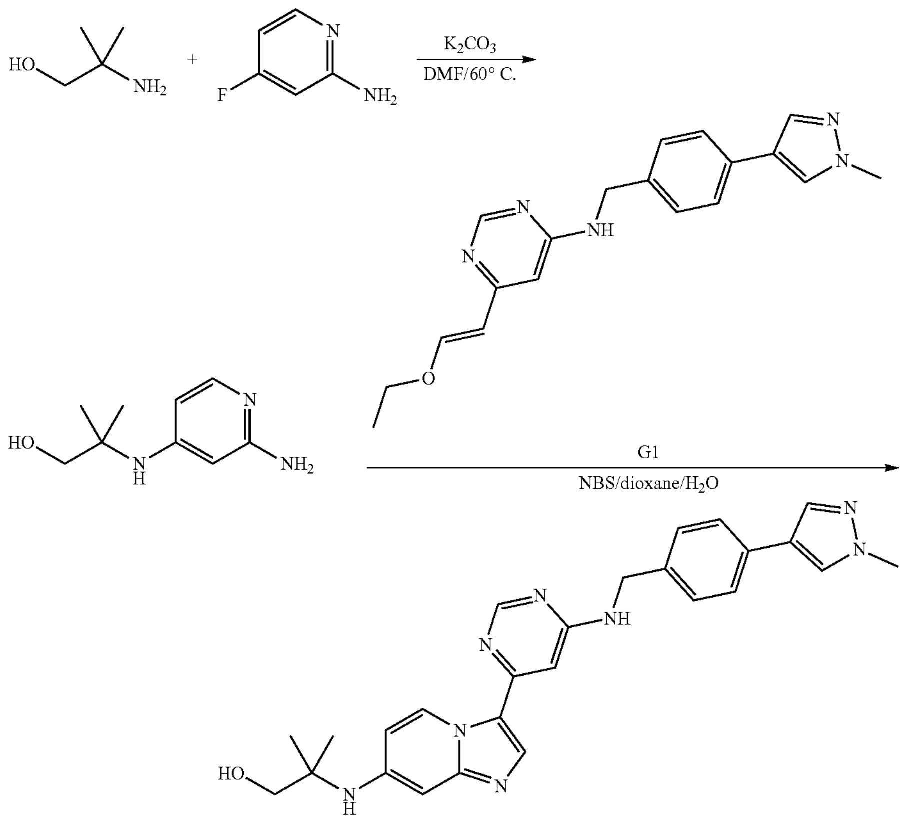

White solid; m.p. 228-229° C.; HPLC/MS $[M+H]^+$ 469. $^1H$ NMR (300 MHz, DMSO-$d_6$) δ 9.42 (d, J=7.7 Hz, 1H), 8.45 (s, 1H), 8.09 (s, 1H), 7.96 (s, 1H), 7.81 (s, 1H), 7.74 (t, J=6.0 Hz, 1H), 7.51 (d, J=8.1 Hz, 2H), 7.33 (d, J=7.9 Hz, 2H), 6.78 (s, 1H), 6.63 (dd, J=7.8, 2.2 Hz, 1H), 6.51 (d, J=2.3 Hz, 1H), 5.94 (s, 1H), 4.91 (t, J=5.7 Hz, 1H), 4.51 (d, J=5.7 Hz, 2H), 3.84 (s, 2H), 3.45 (d, J=5.7 Hz, 2H), 1.29 (s, 6H).

Example 13

Synthesis of N-{[4-(1-methyl-1H-pyrazol-4-yl)phenyl]methyl}-6-[7-(piperidin-4-yloxy)imidazo[1,2-a]pyridin-3-yl]pyrimidin-4-amine ("A164")

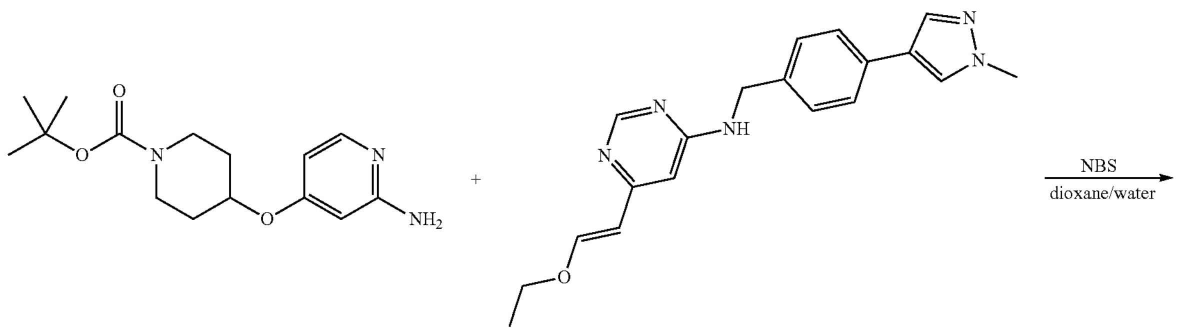

-continued

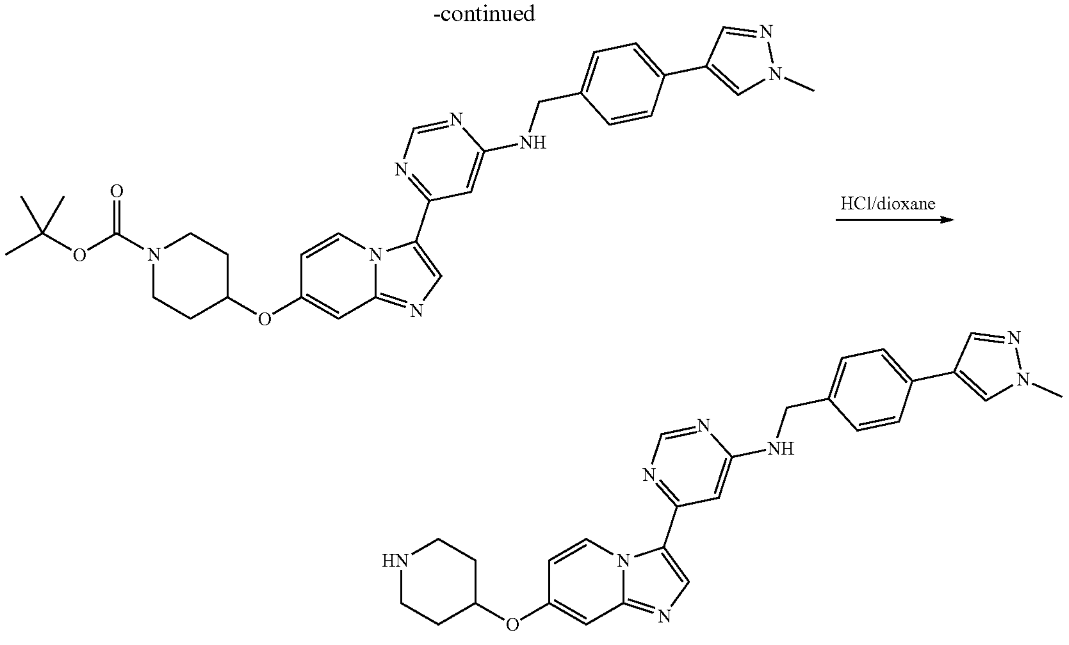

A suspension of 6-[(E)-2-ethoxyethenyl]-N-{[4-(1-methyl-1H-pyrazol-4-yl)phenyl]methyl}pyrimidin-4-amine (G1) (168 mg, 0.50 mmol) in a mixture of 1,4-dioxane (1.5 ml) and water (0.5 ml) is cooled to 0° C. and N-bromosuccinimide (98 mg, 0.55 mmol) is added and the reaction mixture is stirred for 20 minutes at 0° C. tert-Butyl 4-[(2-aminopyridin-4-yl)oxy]piperidine-1-carboxylate (E23) (147 mg, 0.50 mmol) is added. The reaction solution is heated to 60° C. and stirred at this temperature for 5 hours. The reaction mixture is allowed to reach temperature and poured into aqueous 1 N NaOH solution (13 ml). The resultant precipitate is filtered off, washed with water, dried and chromatographed on a silica gel column with dichloromethane/methanol as eluent to afford tert-butyl 4-({3-[6-({[4-(1-methyl-1H-pyrazol-4-yl)phenyl]methyl}amino)pyrimidin-4-yl]imidazo[1,2-a]pyridin-7-yl}oxy)piperidine-1-carboxylate pale beige solid; HPLC/MS(A) 1.50 min, $[M+H]^+$ 581.

$^1H$ NMR (500 MHz, DMSO-$d_6$) δ 9.70 (d, J=7.7 Hz, 1H), 8.51 (s, 1H), 8.14 (s, 1H), 8.07 (d, J=0.8 Hz, 1H), 7.83 (t, J=6.2 Hz, 1H), 7.80 (d, J=0.8 Hz, 1H), 7.51 (d, J=8.2 Hz, 2H), 7.34 (d, J=7.8 Hz, 2H), 7.19 (d, J=2.6 Hz, 1H), 6.88 (d, J=1.2 Hz, 1H), 6.80 (dd, J=7.7, 2.6 Hz, 1H), 4.75 (tt, J=8.0, 3.7 Hz, 1H), 4.54 (d, J=6.0 Hz, 2H), 3.84 (s, 3H), 3.69 (dt, J=13.1, 4.8 Hz, 2H), 3.25-3.18 (m, 2H), 2.04-1.92 (m, 2H), 1.57 (dtd, J=12.9, 8.8, 3.7 Hz, 2H), 1.41 (s, 9H).

A suspension of tert-butyl 4-({3-[6-({[4-(1-methyl-1H-pyrazol-4-yl)phenyl]methyl}amino)pyrimidin-4-yl]imidazo[1,2-a]pyridin-7-yl}oxy)piperidine-1-carboxylate in a 4 N solution of hydrochloric acid in dioxane is stirred at room temperature for 1.5 hours. The reaction mixture is evaporated under reduced pressure and the residue is triturated with tert-butyl methyl ether to afford N-{[4-(1-methyl-1H-pyrazol-4-yl)phenyl]methyl}-6-[7-(piperidin-4-yloxy)imidazo[1,2-a]pyridin-3-yl]pyrimidin-4-amine hydrochloride as beige solid; HPLC/MS(A) 1.06 min, $[M+H]^+$ 481.

$^1H$ NMR (500 MHz, DMSO-$d_6$) δ 9.83 (s, 1H), 9.02 (s, 2H), 8.70 (s, 1H), 8.61 (s, 1H), 8.28 (s, 1H), 8.08 (d, J=0.8 Hz, 1H), 7.81 (d, J=0.9 Hz, 1H), 7.52 (d, J=8.2 Hz, 2H), 7.45 (d, J=2.6 Hz, 1H), 7.34 (d, J=7.8 Hz, 2H), 7.27 (dd, J=7.7, 2.5 Hz, 1H), 7.05 (s, 1H), 5.03 (p, J=3.8 Hz, 1H), 4.58 (s, 2H), 3.85 (s, 3H), 3.40-3.22 (m, 2H), 3.21-3.09 (m, 2H), 2.32-2.08 (m, 2H), 2.04-1.85 (m, 2H).

The following compounds are prepared analogously:

[4-(1-methyl-1H-pyrazol-4-yl)-benzyl]-{6-[7-(piperidin-4-ylmethoxy)-imidazo[1,2-a]pyridin-3-yl]-pyrimidin-4-yl}-amine ("A165")

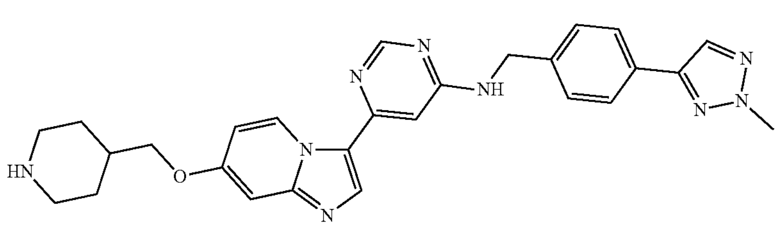 [SMILES: Cn1ncc(-c2ccc(CNc3cc(-c4cnc5cc(OCC6CCNCC6)ccn45)ncn3)cc2)n1]

yellow solid; m.p. 224-225° C.; HPLC/MS $[M+H]^+$ 496.

$^1H$ NMR (400 MHz, DMSO-$d_6$) δ 9.70 (d, J=7.7 Hz, 1H), 8.52 (s, 1H), 8.19 (s, 1H), 8.16 (s, 1H), 7.94 (t, J=6.2 Hz, 1H), 7.80 (d, J=8.2 Hz, 2H), 7.44 (d, J=7.8 Hz, 2H), 7.07 (d, J=2.6 Hz, 1H), 6.91 (d, J=1.2 Hz, 1H), 6.80 (dd, J=7.7, 2.6 Hz, 1H), 4.60 (s, 2H), 4.18 (s, 3H), 3.93 (d, J=6.4 Hz, 2H), 2.99 (d, J=11.9 Hz, 2H), 2.01-1.82 (m, 1H), 1.72 (d, J=11.9 Hz, 2H), 1.32-1.11 (m, 2H).

[4-(1-methyl-1H-pyrazol-4-yl)-benzyl]-{6-[7-(piperidin-4-ylmethoxy)-imidazo[1,2-a]pyridin-3-yl]-pyrimidin-4-yl}-amine ("A166")

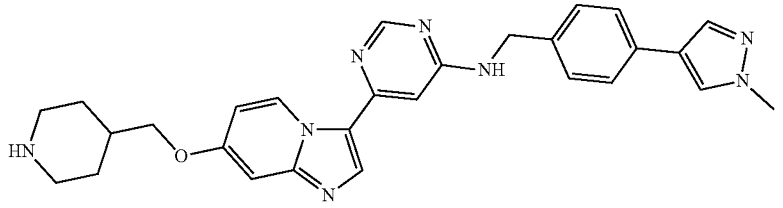 [SMILES: Cn1cc(-c2ccc(CNc3cc(-c4cnc5cc(OCC6CCNCC6)ccn45)ncn3)cc2)cn1]

(from G1 and E16); white solid; m.p. 211-212° C.; HPLC/MS $[M+H]^+$ 495.

$^1$H NMR (400 MHz, DMSO-$d_6$) δ 9.70 (d, J=7.7 Hz, 1H), 8.52 (s, 1H), 8.15 (s, 1H), 8.10 (s, 1H), 7.89 (t, J=6.2 Hz, 1H), 7.82 (s, 1H), 7.52 (d, J=8.1 Hz, 2H), 7.34 (d, J=7.8 Hz, 2H), 7.07 (d, J=2.6 Hz, 1H), 6.89 (d, J=1.2 Hz, 1H), 6.80 (dd, J=7.7, 2.6 Hz, 1H), 4.54 (s, 2H), 3.93 (d, J=6.3 Hz, 2H), 3.85 (s, 3H), 3.00 (d, J=11.9 Hz, 2H), 1.95-1.83 (m, 1H), 1.73 (d, J=12.7 Hz, 2H), 1.33-1.17 (m, 2H).

6-{7-[(azetidin-3-yl)methoxy]imidazo[1,2-a]pyridin-3-yl}-N-{[4-(1-methyl-1H-pyrazol-4-yl)phenyl]methyl}pyrimidin-4-amine ("A167")

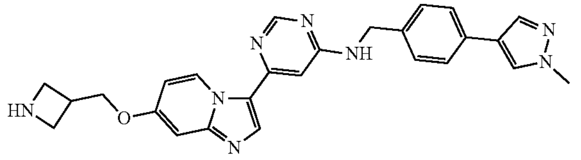 [SMILES: Cn1cc(-c2ccc(CNc3cc(-c4cnc5cc(OCC6CNC6)ccn45)ncn3)cc2)cn1]

(from G1 and E29); off-white powder; UPLC/MS 0.358 min, $[M+H]^+$ 467.

$^1$H NMR (500 MHz, DMSO-$d_6$) δ 9.69 (d, J=7.7 Hz, 1H), 8.51 (s, 1H), 8.14 (s, 1H), 8.07 (s, 1H), 7.86 (t, J=6.1 Hz, 1H), 7.80 (s, 1H), 7.51 (d, J=8.2 Hz, 2H), 7.34 (d, J=7.8 Hz, 2H), 7.09 (d, J=2.6 Hz, 1H), 6.90 (s, 1H), 6.80 (dd, J=7.7, 2.6 Hz, 1H), 4.54 (d, J=6.1 Hz, 2H), 4.32-4.12 (m, 2H), 3.84 (s, 3H), 3.69 (t, J=7.7 Hz, 1H), 3.64-3.51 (m, 1H), 3.46-3.30 (m, 2H), 3.09-2.92 (m, 1H), 2.75-2.66 (m, 1H).

Example 14

Synthesis of [4-(1-methyl-1H-pyrazol-4-yl)-benzyl]-{6-[7-(2-pyrrolidin-1-yl-ethyl)-imidazo[1,2-a]pyridin-3-yl]-pyrimidin-4-yl}-amine ("A168")

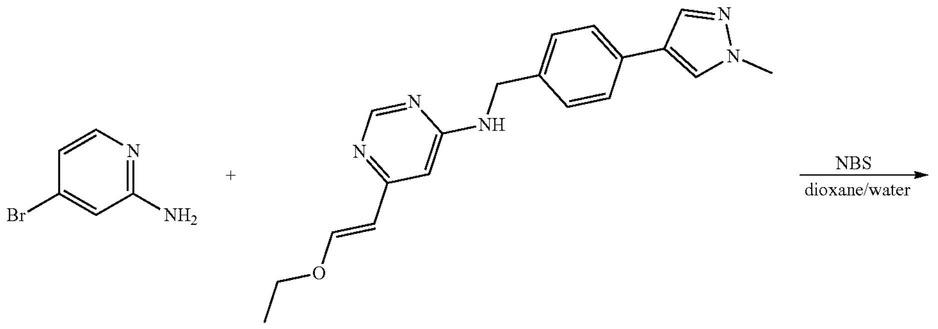

-continued
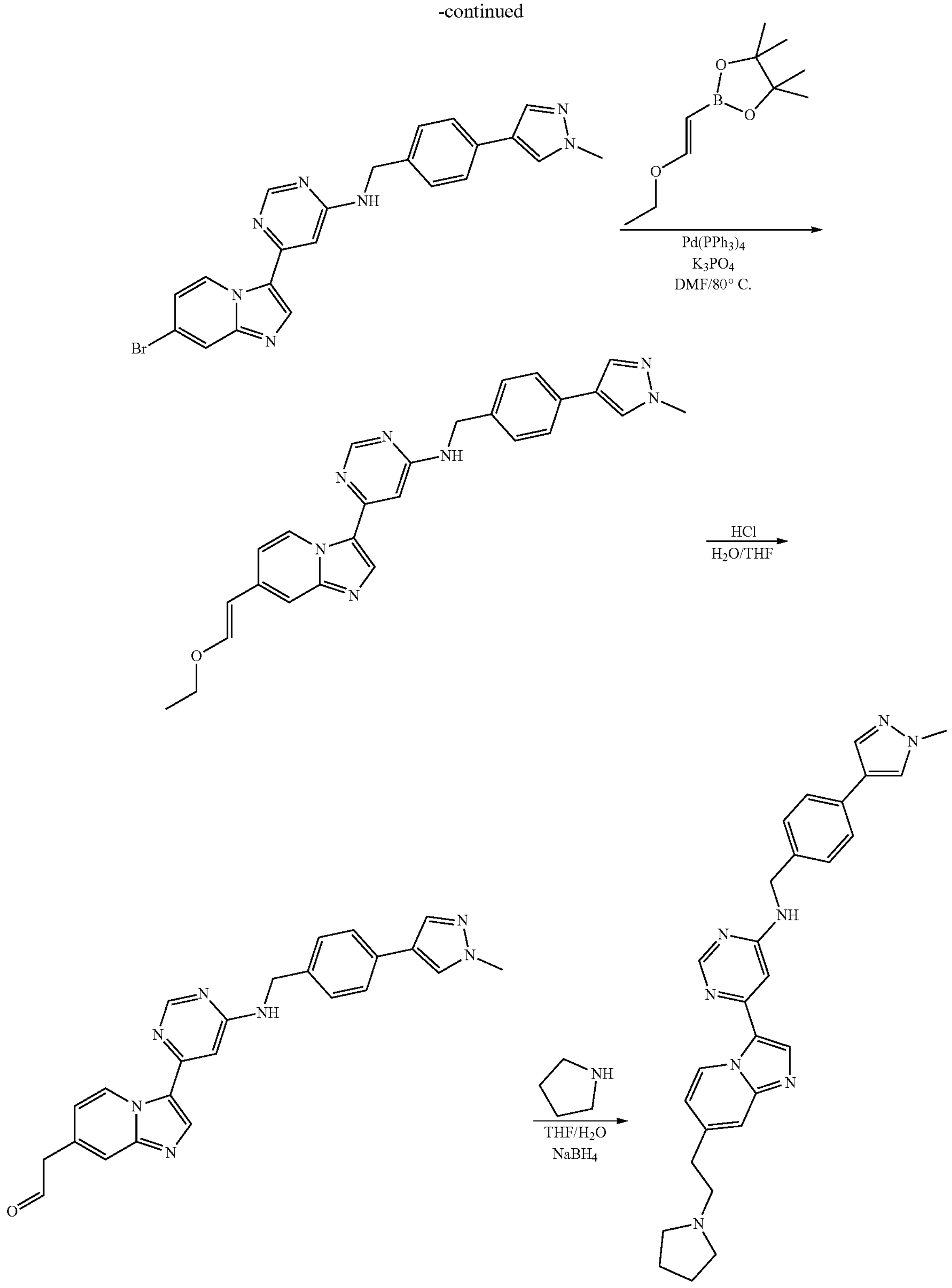
White solid; m.p. 214-215° C.; HPLC/MS $[M+H]^+$ 479. $^1H$ NMR (400 MHz, $CD_3OD$) δ 9.77 (d, J=7.2 Hz, 1H), 8.56 (d, J=1.2 Hz, 1H), 8.15 (s, 1H), 7.95 (s, 1H), 7.81 (d, J=0.8 Hz, 1H), 7.59-7.49 (m, 3H), 7.43-7.36 (m, 2H), 7.03 (dd, J=7.2, 1.7 Hz, 1H), 6.91 (s, 1H), 4.66-4.57 (m, 2H), 3.93 (s, 3H), 3.03-2.96 (m, 2H), 2.92-2.85 (m, 2H), 2.76-2.66 (m, 4H), 1.94-1.80 (m, 4H).

The following compounds are prepared analogously:

(6-{7-[2-(3,3-difluoro-pyrrolidin-1-yl)-ethyl]-imidazo[1,2-a]pyridin-3-yl}-pyrimidin-4-yl)-[4-(1-methyl-1H-pyrazol-4-yl)-benzyl]-amine ("A169")

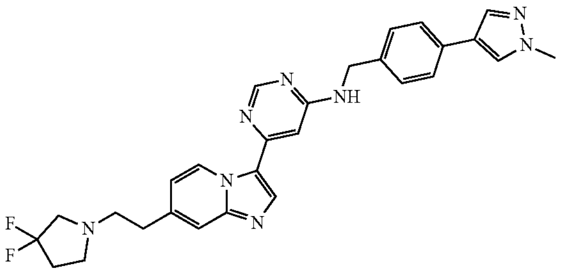 [SMILES: Cn1cc(-c2ccc(CNc3cc(-c4cnc5cc(CCN6CCC(F)(F)C6)ccn45)ncn3)cc2)cn1]

yellow solid; m.p. 205-206° C.; HPLC/MS $[M+H]^+$ 515. $^1H$ NMR (400 MHz, DMSO-$d_6$) δ 9.73 (d, J=7.2 Hz, 1H), 8.55 (s, 1H), 8.24 (s, 1H), 8.09 (s, 1H), 7.91 (t, J=6.2 Hz, 1H), 7.82 (d, J=0.8 Hz, 1H), 7.57 (s, 1H), 7.53 (d, J=8.2 Hz, 2H), 7.35 (d, J=7.9 Hz, 2H), 7.03 (dd, J=7.2, 1.8 Hz, 1H), 6.94 (d, J=1.2 Hz, 1H), 4.56 (s, 2H), 3.85 (s, 3H), 2.96 (t, J=13.5 Hz, 2H), 2.85 (t, J=7.0 Hz, 2H), 2.81-2.71 (m, 4H), 2.23 (tt, J=14.9, 6.9 Hz, 2H).

[4-(1-methyl-1H-pyrazol-4-yl)-benzyl]-(6-{7-[2-(4-oxetan-3-yl-piperazin-1-yl)-ethyl]-imidazo[1,2-a]pyridin-3-yl}-pyrimidin-4-yl)-amine ("A170")

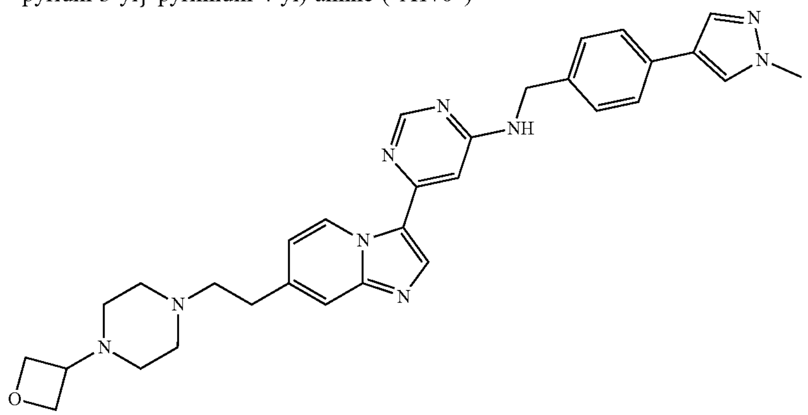

white solid; m.p. 220-221° C.; HPLC/MS $[M+H]^+$ 550. $^1H$ NMR (400 MHz, DMSO-$d_6$) δ 9.72 (d, J=7.2 Hz, 1H), 8.55 (s, 1H), 8.24 (s, 1H), 8.09 (s, 1H), 7.91 (t, J=6.2 Hz, 1H), 7.82 (s, 1H), 7.63-7.46 (m, 3H), 7.35 (d, J=7.9 Hz, 2H), 7.02 (dd, J=7.3, 1.7 Hz, 1H), 6.94 (d, J=1.2 Hz, 1H), 4.62-4.47 (m, 4H), 4.42 (t, J=6.1 Hz, 2H), 3.85 (s, 3H), 2.84 (t, J=7.4 Hz, 2H), 2.62 (t, J=7.4 Hz, 2H), 2.26 (bs, 4H).

Example 15

Synthesis of 7-methoxy-3-(6-{1-[4-(1-methyl-1H-pyrazol-4-yl)-phenyl]-ethoxy}-pyrimidin-4-yl)-imidazo[1,2-a]pyridine ("A171")

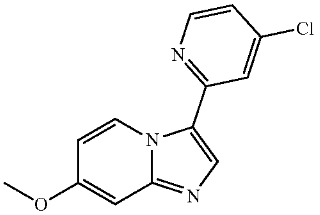

F1

+

-continued

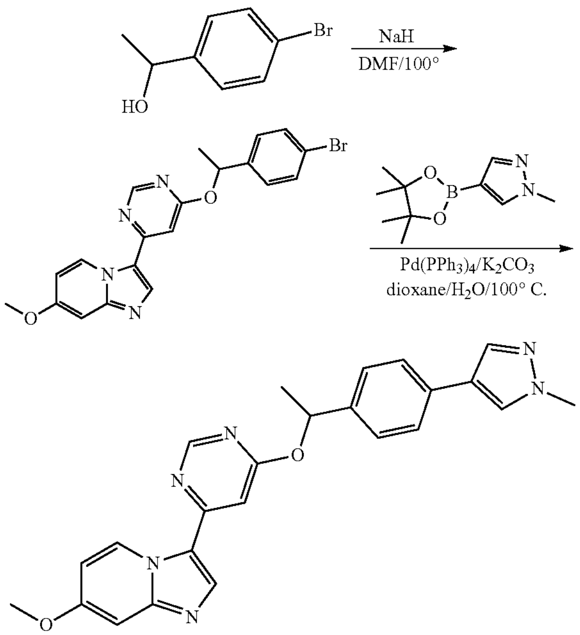

White solid; m.p. 195-196° C.; HPLC/MS $[M+H]^+$ 427. $^1H$ NMR (300 MHz, DMSO-$d_6$) δ 9.73 (d, J=7.7 Hz, 1H), 8.77 (d, J=1.1 Hz, 1H), 8.49 (s, 1H), 8.10 (s, 1H), 7.82 (d, J=0.8 Hz, 1H), 7.54 (d, J=8.3 Hz, 2H), 7.46 (d, J=1.2 Hz, 1H), 7.43 (d, J=8.3 Hz, 2H), 7.14 (d, J=2.6 Hz, 1H), 6.86 (dd, J=7.7, 2.7 Hz, 1H), 6.27 (q, J=6.5 Hz, 1H), 3.88 (s, 3H), 3.85 (s, 3H), 1.63 (d, J=6.5 Hz, 3H).

Example 16

Synthesis of 2-({3-[6-({[4-(1-methyl-1H-pyrazol-4-yl)phenyl]methyl}amino)pyrimidin-4-yl]imidazo[1,2-a]pyridin-7-yl}oxy)ethan-1-ol ("A172")

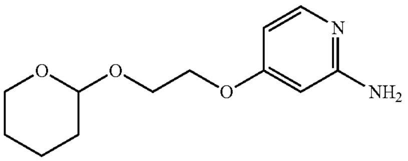

+

-continued

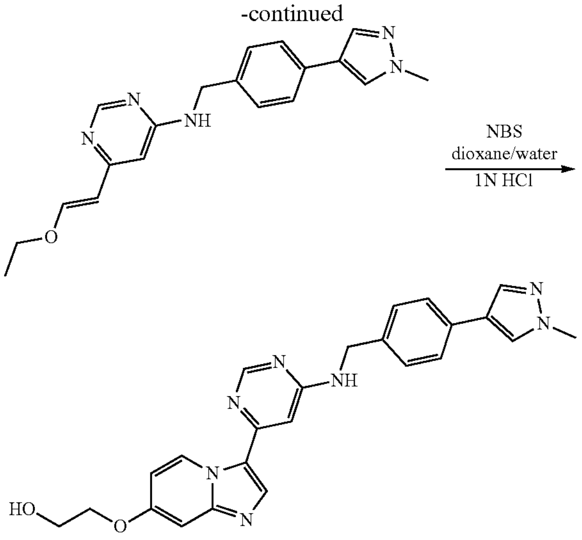

From G1 and E25. The synthesis is carried out analogously to example 2. Before work-up, the reaction mixture is treated with aqueous 1 N hydrochloric acid and stirred for 3 hours at room temperature; white solid; HPLC/MS(B) 0.686 min, $[M+H]^+$ 442.

$^1H$ NMR (500 MHz, DMSO-$d_6$) δ 9.70 (d, J=7.7 Hz, 1H), 8.51 (s, 1H), 8.14 (s, 1H), 8.07 (d, J=0.7 Hz, 1H), 7.83 (t, J=6.1 Hz, 1H), 7.80 (d, J=0.8 Hz, 1H), 7.51 (d, J=8.2 Hz, 2H), 7.34 (d, J=7.8 Hz, 2H), 7.07 (d, J=2.6 Hz, 1H), 6.89 (d, J=1.2 Hz, 1H), 6.81 (dd, J=7.7, 2.6 Hz, 1H), 4.90 (t, J=5.5 Hz, 1H), 4.60-4.51 (m, 2H), 4.11 (t, J=4.8 Hz, 2H), 3.84 (s, 3H), 3.76 (q, J=5.1 Hz, 2H).

The following compound is prepared analogously:

2-({3-[6-({[4-(2-methyl-2H-1,2,3-triazol-4-yl)phenyl]methyl}amino)pyrimidin-4-yl]imidazo[1,2-a]pyridin-7-yl}oxy)ethan-1-ol ("A173")

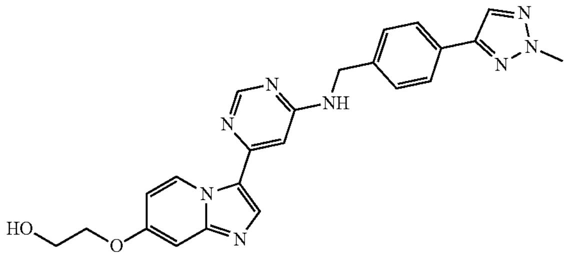 [SMILES: Cn1ncc(-c2ccc(CNc3cc(-c4cnc5cc(OCCO)ccn45)ncn3)cc2)n1]

from G3 and E25; off-white powder; UPLC/MS 0.443 min, $[M+H]^+$ 443.

$^1H$ NMR (500 MHz, DMSO-$d_6$) δ 9.70 (d, J=7.7 Hz, 1H), 8.51 (d, J=1.2 Hz, 1H), 8.16 (s, 1H), 8.15 (s, 1H), 7.88 (t, J=6.2 Hz, 1H), 7.79 (d, J=8.3 Hz, 2H), 7.44 (d, J=7.9 Hz, 2H), 7.07 (d, J=2.6 Hz, 1H), 6.90 (d, J=1.2 Hz, 1H), 6.81 (dd, J=7.7, 2.6 Hz, 1H), 4.90 (t, J=5.4 Hz, 1H), 4.64-4.38 (m, 2H), 4.17 (s, 4H), 4.11 (t, J=4.8 Hz, 2H), 3.76 (q, J=5.0 Hz, 2H).

Example 17

Synthesis of [5-(4-{[6-(7-Methoxy-imidazo[1,2-a]pyridin-3-yl)-pyrimidin-4-ylamino]-methyl}-phenyl)-1-methyl-1H-imidazol-2-yl]-methanol ("A174")

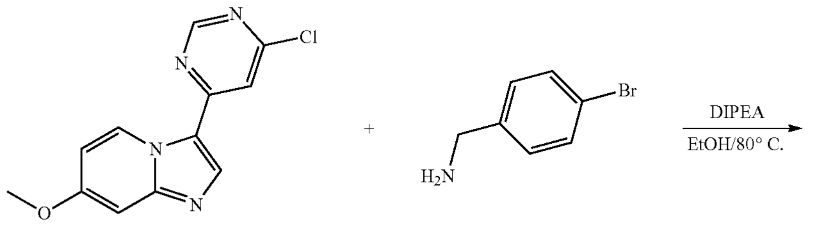

F1

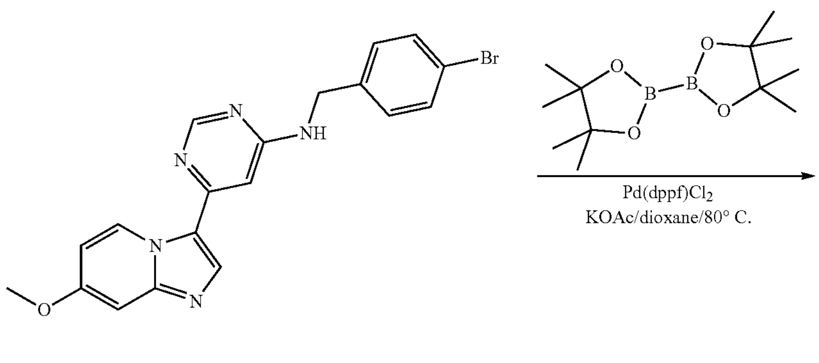

-continued
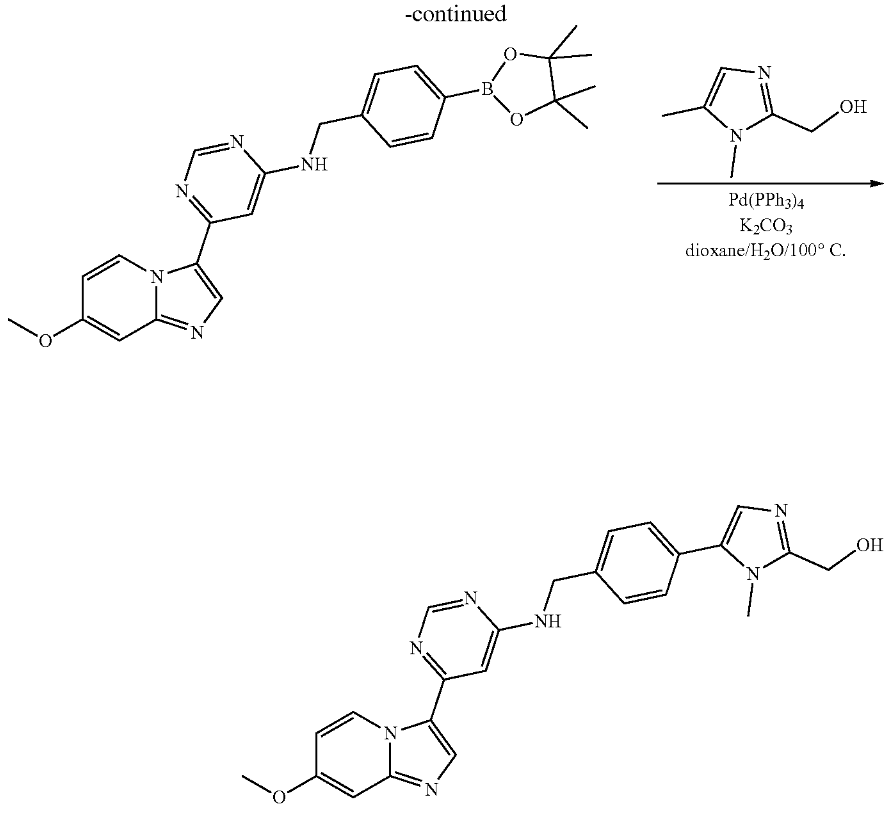
Yellow solid; m.p. 255-256° C.; HPLC/MS $[M+H]^+$ 442. $^1H$ NMR (400 MHz, DMSO-$d_6$) δ 9.71 (d, J=7.7 Hz, 1H), 8.53 (s, 1H), 8.18 (s, 1H), 7.96 (t, J=6.2 Hz, 1H), 7.56-7.38 (m, 4H), 7.10 (d, J=2.6 Hz, 1H), 6.93 (d, J=1.2 Hz, 1H), 6.91 (s, 1H), 6.81 (dd, J=7.7, 2.7 Hz, 1H), 5.32 (t, J=5.5 Hz, 1H), 4.62 (s, 2H), 4.53 (d, J=5.5 Hz, 2H), 3.88 (s, 3H), 3.63 (s, 3H).
Example 18
Synthesis of [4-(1-methyl-1H-pyrazol-4-yl)-benzyl]-{6-[7-(2-pyrrolidin-3-yl-ethoxy)-imidazo[1,2-a]pyridin-3-yl]-pyrimidin-4-yl}-amine ("A175")
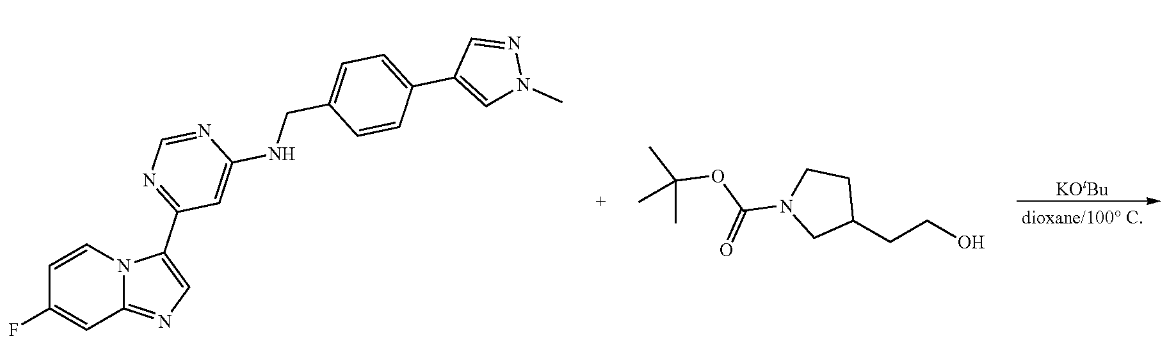
H1

-continued

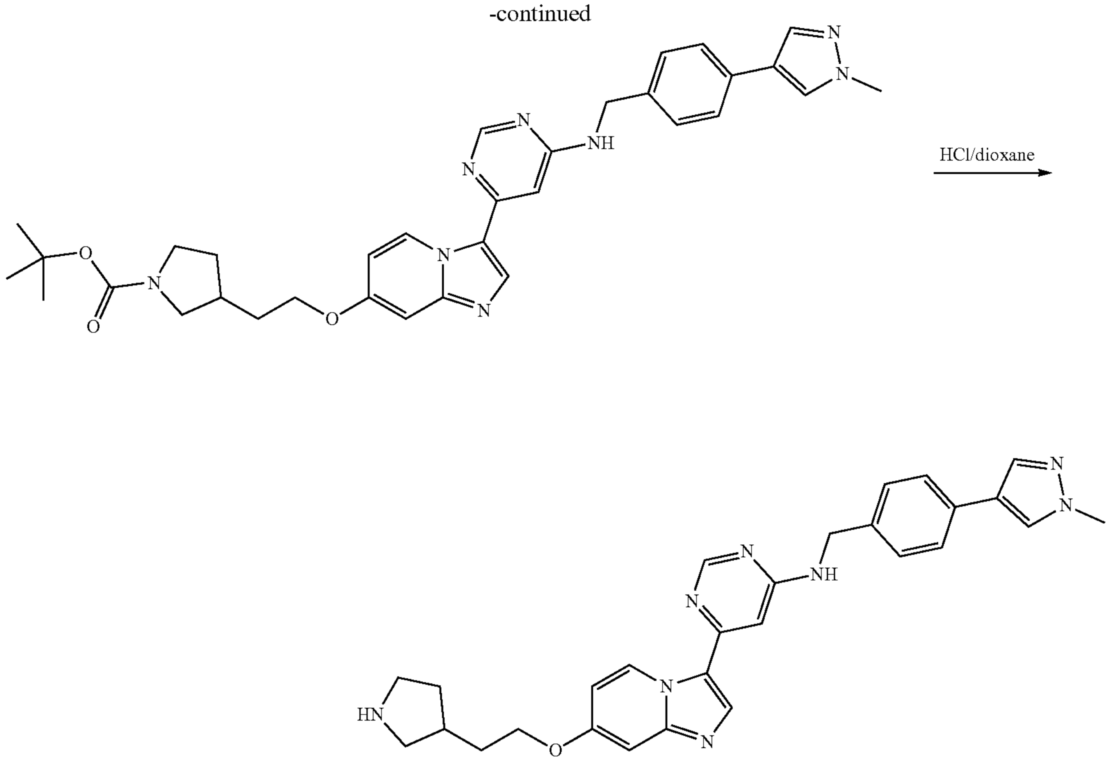

White solid; m.p. 278-279° C.; HPLC/MS $[M+H]^+$ 495.

$^1$H NMR (300 MHz, DMSO-$d_6$) δ 9.70 (d, J=7.7 Hz, 1H), 8.51 (s, 1H), 8.40 (s, 1H), 8.25-8.12 (m, 1H), 8.08 (s, 1H), 7.89 (t, J=6.1 Hz, 1H), 7.81 (s, 1H), 7.58-7.47 (m, 2H), 7.34 (d, J=7.9 Hz, 2H), 7.10 (d, J=2.6 Hz, 1H), 6.89 (d, J=1.3 Hz, 1H), 6.79 (dd, J=7.8, 2.5 Hz, 1H), 4.67-4.48 (m, 2H), 4.13 (t, J=6.4 Hz, 2H), 3.32-3.21 (m, 1H), 3.21-3.08 (m, 1H), 3.08-2.93 (m, 1H), 2.77-2.66 (m, 1H), 2.38-2.23 (m, 1H), 2.11-2.01 (m, 1H), 1.87 (d, J=7.1 Hz, 2H), 1.62-1.43 (m, 1H).

The following compound is prepared analogously:

[4-(2-methyl-2H-[1,2,3]triazol-4-yl)-benzyl]-{6-[7-(2-pyrrolidin-3-yl-ethoxy)-imidazo[1,2-a]pyridin-3-yl]-pyrimidin-4-yl}-amine ("A176")

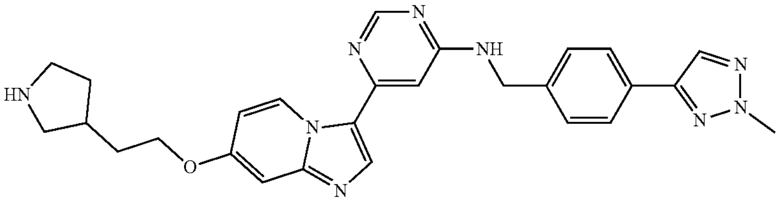 [SMILES: Cn1ncc(-c2ccc(CNc3cc(-c4cnc5cc(OCCC6CCNC6)ccn45)ncn3)cc2)n1]

from H2; white solid; HPLC/MS $[M+H]^+$ 496.

$^1$H NMR (300 MHz, DMSO-$d_6$) δ 9.69 (d, J=7.5 Hz, 1H), 8.50 (s, 1H), 8.17 (s, 2H), 7.96 (s, 1H), 7.78 (d, J=7.9 Hz, 2H), 7.42 (d, J=7.9 Hz, 2H), 7.06-6.75 (m, 3H), 4.58 (s, 2H), 4.14 (d, J=14.5 Hz, 5H), 2.71 (s, 1H), 2.30 (s, 2H), 1.95 (d, J=55.5 Hz, 3H), 1.52 (s, 1H).

Example 19

Synthesis of [4-(1-methyl-1H-pyrazol-4-yl)-benzyl]-[6-(7-pyrrolidin-1-yl-imidazo[1,2-a]pyridin-3-yl)-pyrimidin-4-yl]-amine ("A177")

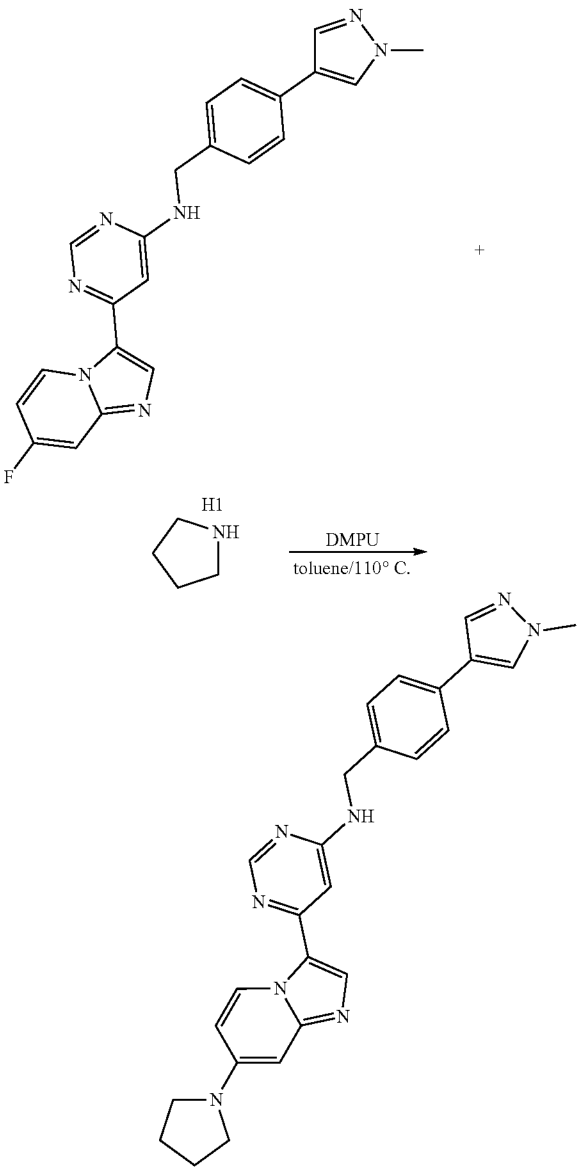

To a suspension of 6-{7-fluoroimidazo[1,2-a]pyridin-3-yl}-N-{[4-(1-methyl-1H-pyrazol-4-yl)phenyl]methyl}pyrimidin-4-amine (H1) (79.9 mg, 0.20 mmol) in toluene (3 ml) is added pyrrolidine (21.3 mg, 0.30 mmol) and 1,3-dimethyl-1,3-diazinan-2-one (dimethyl propylene urea, DMPU, 77 mg, 0.60 mmol) and the reaction mixture is stirred for 16 hours at 110° C. The reaction mixture is allowed to reach room temperature and evaporated under vacuum. The residue is chromatographed on a silica gel column with dichloromethane/methanol as eluent to afford N-{[4-(1-methyl-1H-pyrazol-4-yl)phenyl]methyl}-6-[7-(pyrrolidin-1-yl)imidazo[1,2-a]pyridin-3-yl]pyrimidin-4-amine as yellow solid; m.p. 241-242° C.; HPLC/MS $[M+H]^+$ 451.

$^1$H NMR (400 MHz, DMSO-$d_6$) δ 9.59 (d, J=7.8 Hz, 1H), 8.48 (s, 1H), 8.08 (s, 1H), 7.81 (s, 1H), 7.78 (t, J=6.1 Hz, 1H), 7.51 (d, J=8.2 Hz, 2H), 7.34 (d, J=7.9 Hz, 2H), 6.82 (d, J=1.2 Hz, 1H), 6.71 (dd, J=7.8, 2.5 Hz, 1H), 6.38 (d, J=2.4 Hz, 1H), 4.52 (d, J=5.9 Hz, 2H), 3.84 (s, 3H), 3.42-3.31 (m, 4H), 2.06-1.91 (m, 4H).

The following compounds are prepared analogously:

2-[1-(3-{6-[4-(1-methyl-1H-pyrazol-4-yl)-benzylamino]-pyrimidin-4-yl}-imidazo[1,2-a]pyridin-7-yl)-pyrrolidin-3-yl]-ethanol ("A178")

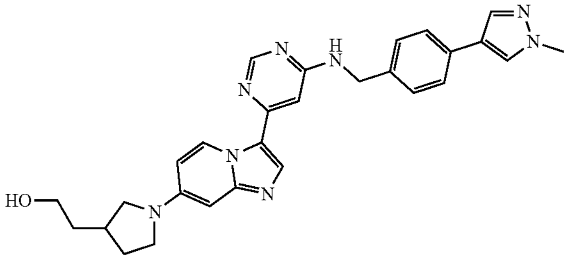 [SMILES: Cn1cc(-c2ccc(CNc3cc(-c4cnc5cc(N6CCC(CCO)C6)ccn45)ncn3)cc2)cn1]

from H1; white solid; m.p. 251-252° C.; HPLC/MS(B) 0.720 min, $[M+H]^+$ 495.

$^1$H NMR (500 MHz, DMSO-$d_6$) δ 9.58 (d, J=7.7 Hz, 1H), 8.46 (d, J=1.1 Hz, 1H), 8.07 (s, 1H), 8.00 (s, 1H), 7.80 (d, J=0.8 Hz, 1H), 7.69 (t, J=6.1 Hz, 1H), 7.51 (d, J=8.2 Hz, 2H), 7.34 (d, J=7.8 Hz, 2H), 6.79 (s, 1H), 6.65 (dd, J=7.8, 2.5 Hz, 1H), 6.35 (d, J=2.4 Hz, 1H), 4.52 (d, J=6.1 Hz, 2H), 4.45 (t, J=5.1 Hz, 1H), 3.84 (s, 3H), 3.59-3.47 (m, 3H), 3.43 (td, J=9.2, 8.3, 3.0 Hz, 1H), 3.32 (dd, J=9.6, 7.4 Hz, 1H), 3.00-2.94 (m, 1H), 2.43-2.32 (m, 1H), 2.23-2.08 (m, 1H), 1.72-1.53 (m, 3H).

2-[1-(3-{6-[4-(2-methyl-2H-[1,2,3]triazol-4-yl)-benzylamino]-pyrimidin-4-yl}-imidazo[1,2-a]pyridin-7-yl)-pyrrolidin-3-yl]-ethanol ("A179")

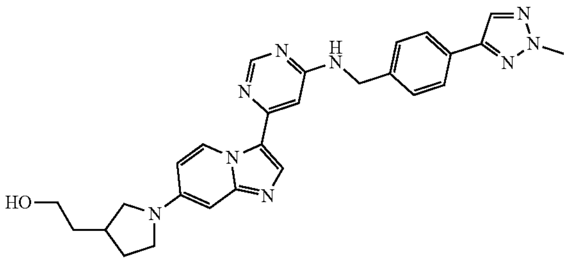 [SMILES: Cn1ncc(-c2ccc(CNc3cc(-c4cnc5cc(N6CCC(CCO)C6)ccn45)ncn3)cc2)n1]

from H2; pale brown solid; m.p. 200-201° C.; HPLC/MS $[M+H]^+$ 496.

$^1$H NMR (300 MHz, DMSO-$d_6$) δ 9.57 (d, J=7.8 Hz, 1H), 8.45 (s, 1H), 8.16 (s, 1H), 8.01 (s, 1H), 7.77 (d, J=8.1 Hz, 3H), 7.42 (d, J=8.1 Hz, 2H), 6.79 (s, 1H), 6.64 (d, J=6.3 Hz, 1H), 6.34 (s, 1H), 4.61-4.44 (m, 3H), 4.16 (s, 3H), 3.48 (q, J=6.7 Hz, 4H), 2.99-2.91 (m, 1H), 1.58 (d, J=6.9 Hz, 3H).

[4-(1-methyl-1H-pyrazol-4-yl)-benzyl]-[6-(7-morpholin-4-yl-imidazo[1,2-a]pyridin-3-yl)-pyrimidin-4-yl]-amine ("A180")

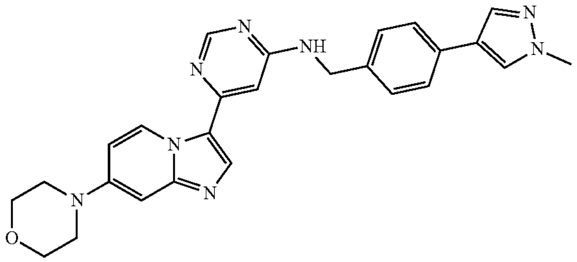 [SMILES: Cn1cc(-c2ccc(CNc3cc(-c4cnc5cc(N6CCOCC6)ccn45)ncn3)cc2)cn1]

from H1; yellow solid; m.p. 241-242° C.; HPLC/MS $[M+H]^+$ 467.

$^1$H NMR (400 MHz, DMSO-$d_6$) δ 9.61 (d, J=7.8 Hz, 1H), 8.49 (s, 1H), 8.12-8.05 (m, 3H), 7.83-7.75 (m, 3H), 7.51 (d, J=8.2 Hz, 2H), 7.34 (d, J=7.9 Hz, 2H), 7.01 (dd, J=7.9, 2.6 Hz, 1H), 6.88-6.80 (m, 2H), 4.53 (s, 2H), 3.84 (s, 3H), 3.76 (t, J=4.8 Hz, 4H), 3.26 (t, J=5.0 Hz, 4H).

{6-[7-(4-methyl-piperazin-1-yl)-imidazo[1,2-a]pyridin-3-yl]-pyrimidin-4-yl}-[4-(1-methyl-1H-pyrazol-4-yl)-benzyl]-amine ("A181")

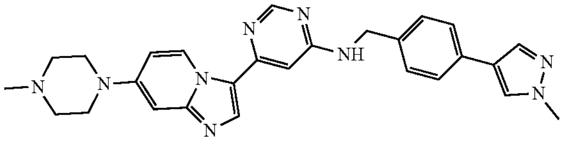

from H1; white solid; m.p. 252-253° C.; HPLC/MS $[M+H]^+$ 480.

$^1$H NMR (400 MHz, DMSO-$d_6$) δ 9.58 (d, J=7.8 Hz, 1H), 8.49 (s, 1H), 8.08 (s, 2H), 7.83-7.75 (m, 2H), 7.51 (d, J=8.1 Hz, 2H), 7.34 (d, J=7.9 Hz, 2H), 7.00 (dd, J=8.0, 2.6 Hz, 1H), 6.86-6.77 (m, 2H), 4.57-4.48 (m, 2H), 3.84 (s, 3H), 3.30-3.25 (m, 4H), 2.48-2.45 (m, 4H), 2.24 (s, 3H).

[4-(1-methyl-1H-pyrazol-4-yl)-benzyl]-{6-[7-(4-oxetan-3-yl-piperazin-1-yl)-imidazo[1,2-a]pyridin-3-yl]-pyrimidin-4-yl}-amine ("A230")

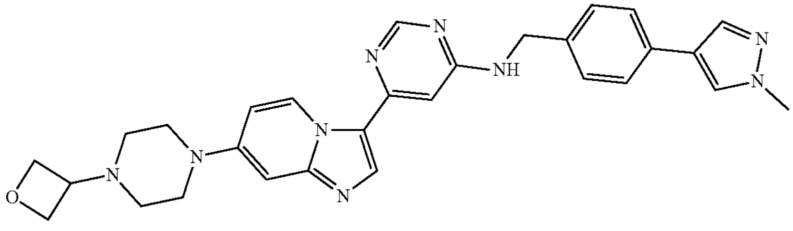 [SMILES: Cn1cc(-c2ccc(CNc3cc(-c4cnc5cc(N6CCN(C7COC7)CC6)ccn45)ncn3)cc2)cn1]

[4-(2-methyl-2H-[1,2,3]triazol-4-yl)-benzyl]-[6-(7-pyrrolidin-1-yl-imidazo[1,2-a]pyridin-3-yl)-pyrimidin-4-yl]-amine ("A232")

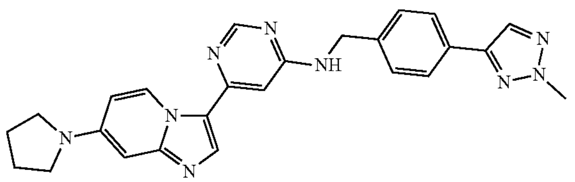 [SMILES: Cn1ncc(-c2ccc(CNc3cc(-c4cnc5cc(N6CCCC6)ccn45)ncn3)cc2)n1]

Example 20

Synthesis of N-{[4-(1-methyl-1H-pyrazol-4-yl)phenyl]methyl}-6-(7-{[1-(oxetan-3-yl)piperidin-4-yl]oxy}imidazo[1,2-a]pyridin-3-yl)pyrimidin-4-amine ("A182")

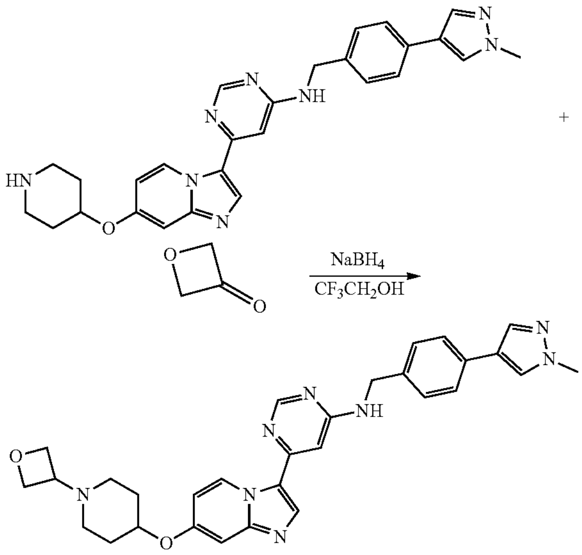

From "A164"; off-white solid; HPLC/MS(B) 0.635 min, $[M+H]^+$ 537.

$^1$H NMR (500 MHz, DMSO-$d_6$) δ 9.69 (d, J=7.7 Hz, 1H), 8.51 (s, 1H), 8.13 (s, 1H), 8.07 (d, J=0.8 Hz, 1H), 7.82 (t, J=6.1 Hz, 1H), 7.80 (d, J=0.8 Hz, 1H), 7.51 (d, J=8.2 Hz, 2H), 7.34 (d, J=7.8 Hz, 2H), 7.13 (d, J=2.6 Hz, 1H), 6.88 (d, J=1.2 Hz, 1H), 6.79 (dd, J=7.7, 2.6 Hz, 1H), 4.60 (tt, J=7.9, 3.9 Hz, 1H), 4.54 (t, J=6.5 Hz, 4H), 4.43 (t, J=6.1 Hz, 2H), 3.84 (s, 3H), 3.43 (p, J=6.4 Hz, 1H), 2.58-2.51 (m, 2H), 2.19-2.12 (m, 2H), 2.06-1.97 (m, 2H), 1.70 (dtt, J=12.3, 8.6, 3.5 Hz, 2H).

The following compound is prepared analogously:

N-{[4-(1-methyl-1H-pyrazol-4-yl)phenyl]methyl}-6-(7-{[1-(oxetan-3-yl)azetidin-3-yl]methoxy}imidazo[1,2-a]pyridin-3-yl)pyrimidin-4-amine ("A183")

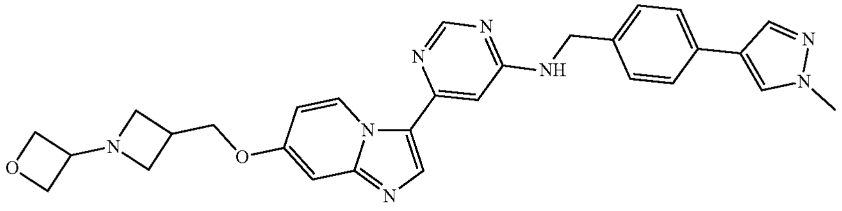 [SMILES: Cn1cc(-c2ccc(CNc3cc(-c4cnc5cc(OCC6CN(C7COC7)C6)ccn45)ncn3)cc2)cn1]

from "A167"; off-white powder; UPLC/MS 0.367 min, $[M+H]^+$ 523.

$^1$H NMR (500 MHz, DMSO-$d_6$) δ 9.70 (d, J=7.7 Hz, 1H), 8.52 (s, 1H), 8.15 (s, 1H), 8.08 (s, 1H), 7.84 (t, J=6.1 Hz, 1H), 7.81 (d, J=0.8 Hz, 1H), 7.52 (d, J=8.2 Hz, 2H), 7.35 (d, J=7.8 Hz, 2H), 7.10 (d, J=2.6 Hz, 1H), 6.90 (d, J=1.3 Hz, 1H), 6.81 (dd, J=7.7, 2.6 Hz, 1H), 4.62-4.51 (m, 5H), 4.39 (dd, J=6.4, 5.3 Hz, 2H), 4.25 (d, J=6.8 Hz, 2H), 3.85 (s, 3H), 3.72 (tt, J=6.8, 5.2 Hz, 1H), 3.39 (t, J=7.4 Hz, 2H), 3.10 (dd, J=7.1, 5.8 Hz, 2H), 2.89 (tt, J=7.6, 6.0 Hz, 1H).

Example 21

Synthesis of [4-(1-methyl-1H-pyrazol-4-yl)-benzyl]-(6-{7-[3-(4-oxetan-3-yl-piperazin-1-yl)-propoxy]-imidazo[1,2-a]pyridin-3-yl}-pyrimidin-4-yl)-amine ("A184")

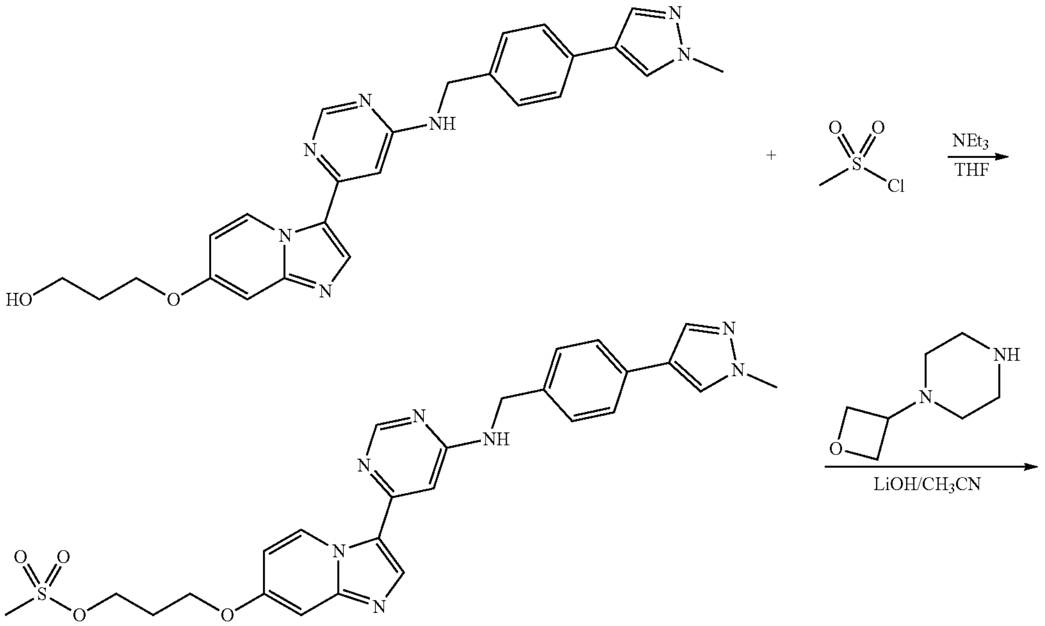

-continued

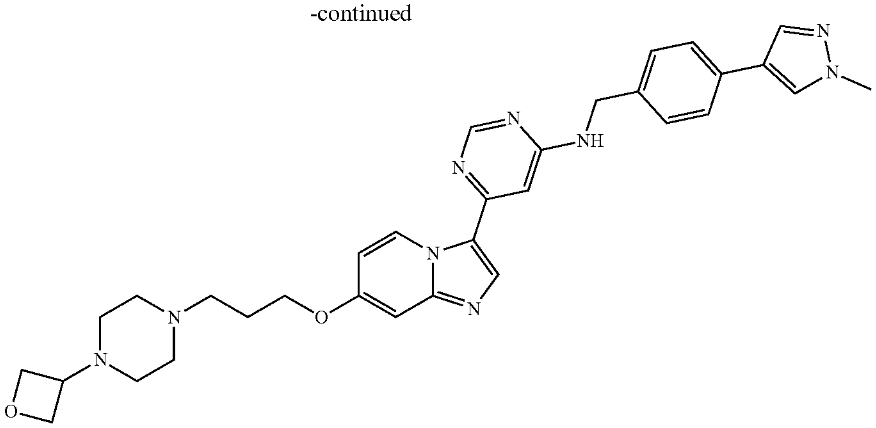

From "A131"; yellow solid; m.p. 300-301° C.; HPLC/MS $[M+H]^+$ 580.

$^1$H NMR (400 MHz, DMSO-$d_6$) δ 9.69 (d, J=7.7 Hz, 1H), 8.51 (s, 1H), 8.14 (s, 1H), 8.08 (s, 1H), 7.85 (t, J=6.1 Hz, 1H), 7.81 (d, J=0.8 Hz, 1H), 7.51 (d, J=8.2 Hz, 2H), 7.34 (d, J=7.9 Hz, 2H), 7.05 (d, J=2.6 Hz, 1H), 6.89 (d, J=1.2 Hz, 1H), 6.79 (dd, J=7.7, 2.6 Hz, 1H), 4.59-4.47 (m, 4H), 4.41 (t, J=6.1 Hz, 2H), 4.12 (t, J=6.3 Hz, 2H), 3.84 (s, 3H), 3.38 (p, J=6.3 Hz, 1H), 2.49-2.39 (m, 6H), 2.27 (bs, 4H), 1.91 (p, J=6.6 Hz, 2H).

The following compound is prepared analogously:

[4-(2-methyl-2H-[1,2,3]triazol-4-yl)-benzyl]-(6-{7-[3-(4-oxetan-3-yl-piperazin-1-yl)-propoxy]-imidazo[1,2-a]pyridin-3-yl}-pyrimidin-4-yl)-amine ("A185")

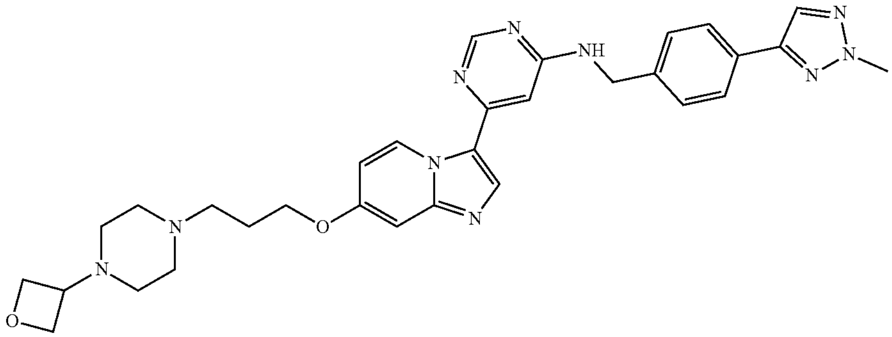 [SMILES: Cn1ncc(-c2ccc(CNc3cc(-c4cnc5cc(OCCCN6CCN(C7COC7)CC6)ccn45)ncn3)cc2)n1]

from "A134"; white solid; m.p. 225-226° C.; HPLC/MS $[M+H]^+$ 581.

$^1$H NMR (300 MHz, DMSO-$d_6$) δ 9.67 (d, J=7.8 Hz, 1H), 8.50 (s, 1H), 8.15 (d, J=7.2 Hz, 2H), 7.89 (t, J=6.2 Hz, 1H), 7.77 (d, J=8.1 Hz, 2H), 7.42 (d, J=8.0 Hz, 2H), 7.04 (d, J=2.7 Hz, 1H), 6.89 (d, J=1.3 Hz, 1H), 6.77 (dd, J=7.7, 2.6 Hz, 1H), 4.58 (d, J=6.2 Hz, 2H), 4.50 (t, J=6.5 Hz, 2H), 4.39 (t, J=6.0 Hz, 2H), 4.16 (s, 3H), 4.10 (t, J=6.3 Hz, 2H), 3.37 (q, J=6.4 Hz, 1H), 2.47-2.38 (m, 6H), 2.25 (s, 4H), 1.89 (t, J=6.7 Hz, 2H).

Example 22

Synthesis of {6-[7-(1-cyclopropyl-piperidin-4-yl-methoxy)-imidazo[1,2-a]pyridin-3-yl]-pyrimidin-4-yl}-[4-(2-methyl-2H-[1,2,3]triazol-4-yl)-benzyl]-amine ("A186")

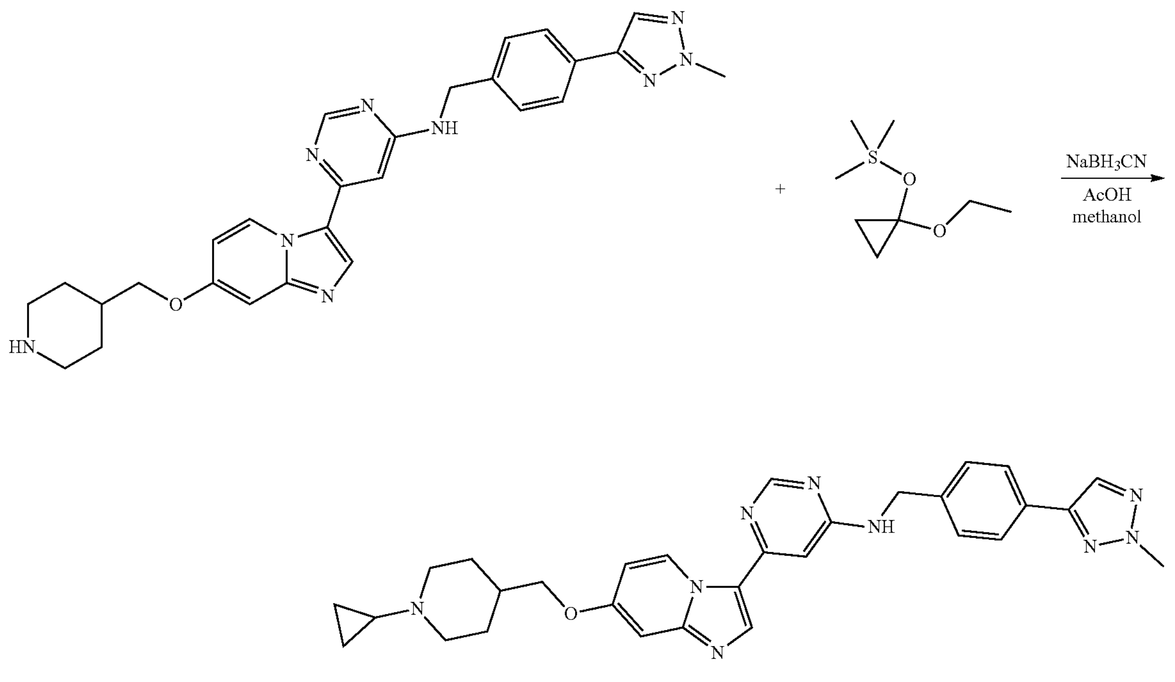

From "A165"; white solid; m.p. 238-240° C.; HPLC/MS $[M+H]^+$ 536.

$^1$H NMR (400 MHz, DMSO-$d_6$ ppm) 9.73-9.63 (m, 1H), 8.51 (s, 1H), 8.20-8.09 (m, 2H), 7.92-7.88 (m, 1H), 7.82-7.75 (m, 2H), 7.47-7.39 (m, 2H), 7.06-7.02 (m, 1H), 6.90 (s, 1H), 6.83-6.75 (m, 1H), 4.63-4.54 (m, 2H), 4.17 (s, 3H), 3.97-3.89 (m, 2H), 3.00-2.90 (m, 2H), 2.22-2.10 (m, 2H), 1.84-1.69 (m, 3H), 1.61-1.55 (m, 1H), 1.26 (s, 1H), 1.24-1.17 (m, 2H), 0.43-0.36 (m, 2H), 0.31-0.24 (m, 2H).

The following compound is prepared similarly:

{6-[7-(1-cyclopropyl-piperidin-4-ylmethoxy)-imidazo[1,2-a]pyridin-3-yl]-pyrimidin-4-yl}-[4-(1-methyl-1H-pyrazol-4-yl)-benzyl]-amine ("A187")

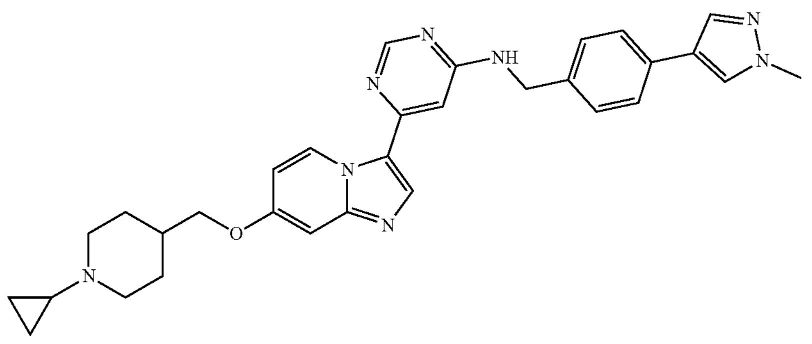 [SMILES: Cn1cc(-c2ccc(CNc3cc(-c4cnc5cc(OCC6CCN(C7CC7)CC6)ccn45)ncn3)cc2)cn1]

from "A166"; white solid; m.p. 236-238° C.; HPLC/MS $[M+H]^+$ 535.

$^1$H NMR (400 MHz, DMSO-$d_6$) δ 9.70-9.66 (m, 1H), 8.51 (s, 1H), 8.17-8.05 (m, 2H), 7.89-7.78 (m, 2H), 7.53-7.45 (m, 2H), 7.38-7.29 (m, 2H), 7.06-7.02 (m, 1H), 6.90-6.85 (m, 1H), 6.83-6.76 (m, 1H), 4.59-4.44 (m, 2H), 3.97-3.89 (m, 2H), 3.84 (s, 3H), 3.00-2.89 (m, 2H), 2.21-2.10 (m, 2H), 1.84-1.70 (m, 3H), 1.61-1.53 (m, 1H), 1.27-1.18 (m, 2H), 0.44-0.36 (m, 2H), 0.29-0.23 (m, 2H).

Example 23

Synthesis of [4-(3-{6-[4-(1methyl-1H-pyrazol-4-yl)-benzylamino]-pyrimidin-4-yl}-imidazo[1,2-a]pyridin-7-yloxymethyl)-piperidin-1-yl]-acetonitrile ("A188")

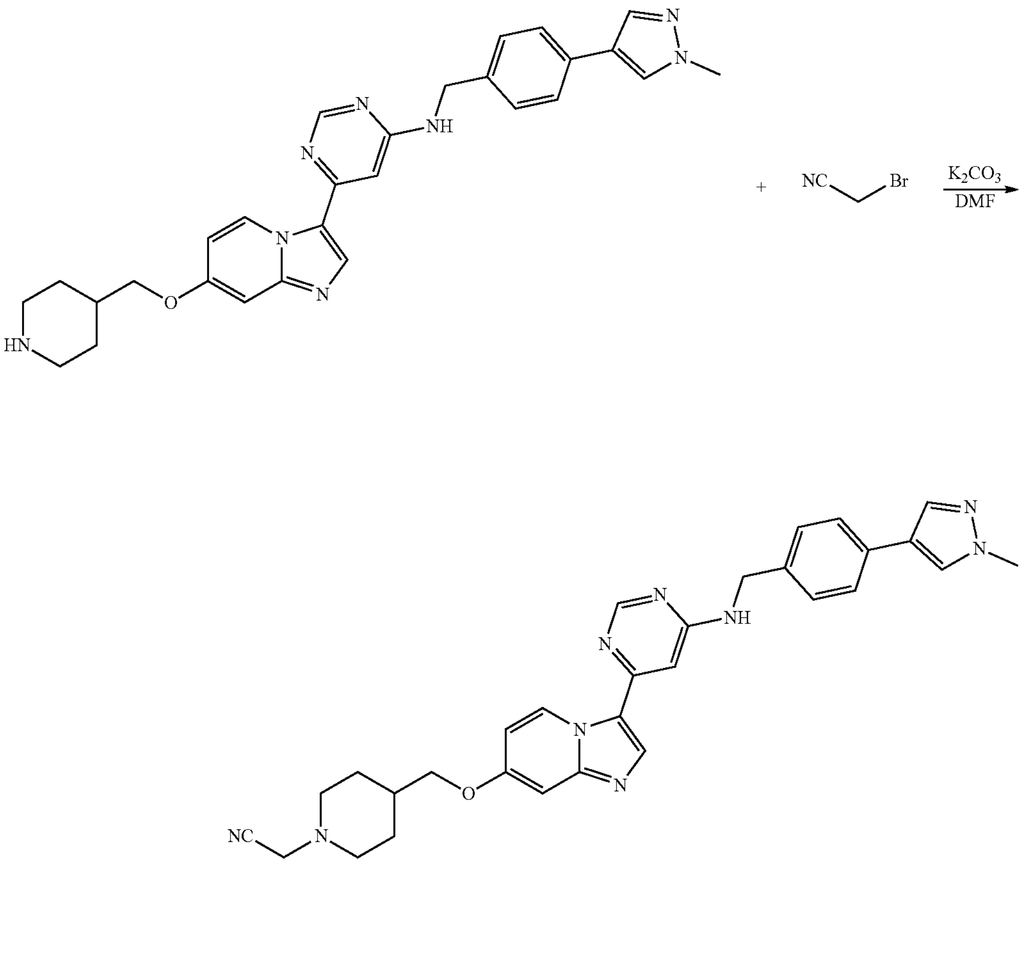

From "A166"; white solid; m.p. 211-212° C.; HPLC/MS $[M+H]^+$ 534.

$^1$H NMR (400 MHz, DMSO-$d_6$) δ 9.69 (d, J=7.7 Hz, 1H), 8.51 (s, 1H), 8.19-8.12 (m, 1H), 8.08 (s, 1H), 7.85 (t, J=6.1 Hz, 1H), 7.81 (s, 1H), 7.51 (d, J=8.1 Hz, 2H), 7.34 (d, J=8.0 Hz, 2H), 7.07 (d, J=2.6 Hz, 1H), 6.89 (s, 1H), 6.80 (dd, J=7.8, 2.6 Hz, 1H), 4.61-4.50 (m, 2H), 3.96 (d, J=5.8 Hz, 2H), 3.84 (s, 3H), 3.71 (s, 2H), 2.83 (d, J=10.8 Hz, 2H), 2.19 (t, J=11.2 Hz, 2H), 1.82 (d, J=12.7 Hz, 3H), 1.36 (d, J=13.0 Hz, 2H).

The following compounds are prepared similarly:

[4-(3-{6-[4-(2-methyl-2H-[1,2,3]triazol-4-yl)-benzylamino]-pyrimidin-4-yl}-imidazo[1,2-a]pyridin-7-yloxymethyl)-piperidin-1-yl]-acetonitrile ("A189")

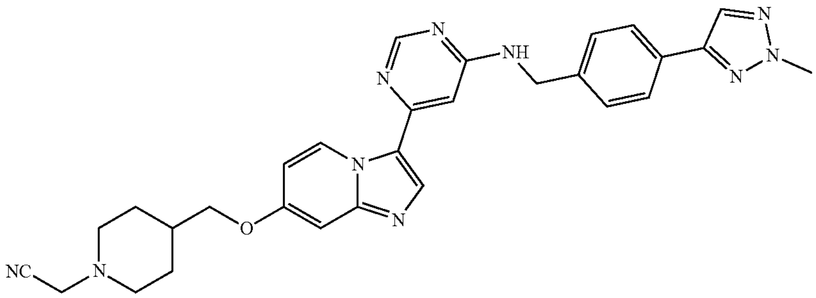 [SMILES: Cn1ncc(-c2ccc(CNc3cc(-c4cnc5cc(OCC6CCN(CC#N)CC6)ccn45)ncn3)cc2)n1]

from "A165"; white solid; m.p. 265-266° C.; HPLC/MS $[M+H]^+$ 535.

$^1$H NMR (300 MHz, DMSO-$d_6$) δ 9.68 (d, J=7.7 Hz, 1H), 8.50 (s, 1H), 8.15 (d, J=6.9 Hz, 2H), 7.90 (t, J=6.1 Hz, 1H), 7.77 (d, J=8.0 Hz, 2H), 7.42 (d, J=7.9 Hz, 2H), 7.05 (d, J=2.6 Hz, 1H), 6.89 (s, 1H), 6.79 (dd, J=7.7, 2.6 Hz, 1H), 4.58 (d, J=6.0 Hz, 2H), 4.16 (s, 3H), 3.94 (d, J=5.7 Hz, 2H), 3.69 (s, 2H), 2.82 (d, J=10.8 Hz, 2H), 2.17 (t, J=11.1 Hz, 2H), 1.80 (d, J=12.3 Hz, 3H), 1.34 (d, J=12.9 Hz, 2H)

[4-(3-{6-[4-(1-methyl-1H-pyrazol-4-yl)-benzylamino]-pyrimidin-4-yl}-imidazo[1,2-a]pyridin-7-yloxymethyl)-piperidin-1-yl]-acetonitrile ("A190")

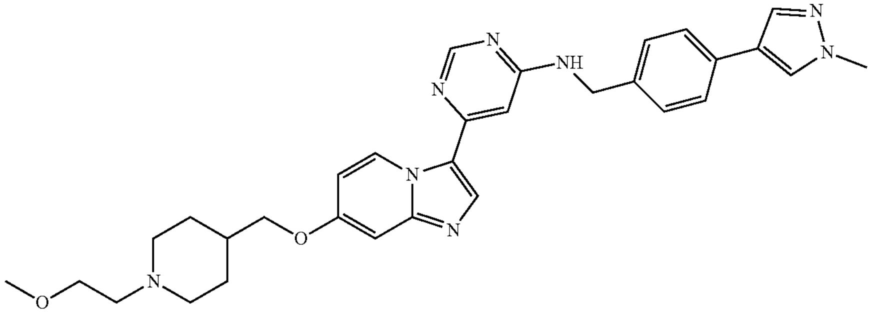

from "A166" and 1-bromo-2-methoxyethane; white solid; m. p. 255-256° C.; HPLC/MS $[M+H]^+$ 553.

$^1$H NMR (400 MHz, DMSO-$d_6$) δ 9.69 (d, J=7.7 Hz, 1H), 8.51 (s, 1H), 8.26-8.11 (m, 1H), 8.08 (s, 1H), 7.85 (t, J=6.1 Hz, 1H), 7.81 (s, 1H), 7.51 (d, J=7.9 Hz, 2H), 7.34 (d, J=7.8 Hz, 2H), 7.05 (d, J=2.6 Hz, 1H), 6.89 (s, 1H), 6.79 (dd, J=7.7, 2.6 Hz, 1H), 4.66-4.48 (m, 2H), 3.94 (d, J=5.9 Hz, 2H), 3.84 (s, 3H), 3.42 (t, J=5.9 Hz, 2H), 2.89 (d, J=11.0 Hz, 2H), 2.45 (t, J=6.0 Hz, 2H), 1.96 (t, J=11.3 Hz, 2H), 1.74 (d, J=11.6 Hz, 3H), 1.41-1.25 (m, 2H).

(6-{7-[1-(2-methoxy-ethyl)-piperidin-4-ylmethoxy]-imidazo[1,2-a]pyridin-3-yl}-pyrimidin-4-yl)-[4-(2-methyl-2H-[1,2,3]triazol-4-yl)-benzyl]-amine ("A191")

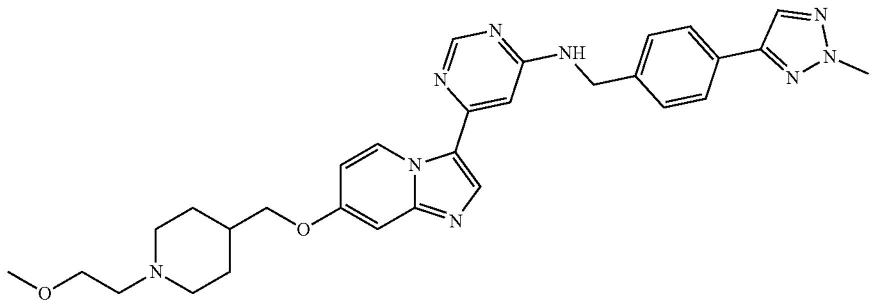

from "A165" and 1-bromo-2-methoxyethane; white solid; m. p. 270-271° C.; HPLC/MS $[M+H]^+$ 554.

$^1$H NMR (300 MHz, DMSO-$d_6$) δ 9.68 (d, J=7.7 Hz, 1H), 8.50 (s, 1H), 8.15 (d, J=7.9 Hz, 2H), 7.89 (t, J=6.1 Hz, 1H), 7.77 (d, J=8.2 Hz, 2H), 7.42 (d, J=7.9 Hz, 2H), 7.04 (d, J=2.6 Hz, 1H), 6.89 (s, 1H), 6.78 (dd, J=7.8, 2.6 Hz, 1H), 4.58 (d, J=5.9 Hz, 2H), 4.16 (s, 3H), 3.93 (d, J=5.9 Hz, 2H), 3.41 (t, J=5.9 Hz, 2H), 2.89 (d, J=10.9 Hz, 2H), 2.45 (s, 2H), 1.97 (t, J=11.6 Hz, 2H), 1.73 (d, J=11.0 Hz, 3H), 1.30 (d, J=11.9 Hz, 2H)

(6-{7-[1-(2,2-difluoro-ethyl)-piperidin-4-ylmethoxy]-imidazo[1,2-a]pyridin-3-yl}-pyrimidin-4-yl)-[4-(1-methyl-1H-pyrazol-4-yl)-benzyl]-amine ("A192")

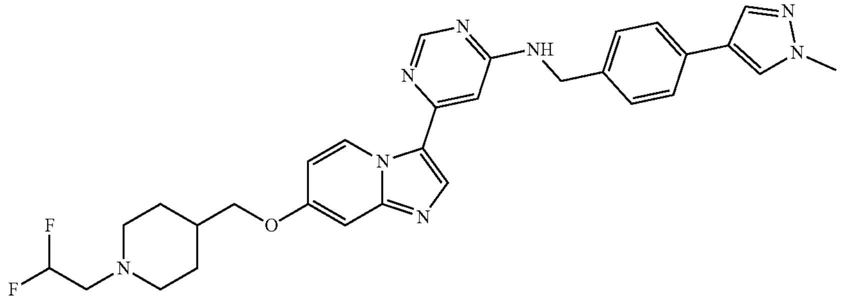 [SMILES: Cn1cc(-c2ccc(CNc3cc(-c4cnc5cc(OCC6CCN(CC(F)F)CC6)ccn45)ncn3)cc2)cn1]

from "A166" and 1,1-difluoro-2-iodoethane; white solid; m. p. 215-216° C.; HPLC/MS $[M+H]^+$ 559.

$^1$H NMR (300 MHz, DMSO-$d_6$) δ 9.67 (d, J=7.7 Hz, 1H), 8.49 (s, 1H), 8.09 (d, J=18.3 Hz, 2H), 7.89-7.76 (m, 2H), 7.50 (d, J=8.1 Hz, 2H), 7.32 (d, J=7.9 Hz, 2H), 7.04 (d, J=2.7 Hz, 1H), 6.87 (d, J=1.3 Hz, 1H), 6.78 (dd, J=7.7, 2.6 Hz, 1H), 6.11 (t, J=4.3 Hz, 1H), 4.52 (s, 2H), 3.93 (d, J=5.9 Hz, 2H), 3.83 (s, 3H), 2.91 (d, J=11.0 Hz, 2H), 2.75-2.62 (m, 2H), 2.15 (t, J=11.4 Hz, 2H), 1.73 (d, J=12.3 Hz, 3H), 1.32 (q, J=11.3 Hz, 2H).-

(6-{7-[1-(2,2-difluoro-ethyl)-piperidin-4-ylmethoxy]-imidazo[1,2-a]pyridin-3-yl}-pyrimidin-4-yl)-[4-(2-methyl-2H-[1,2,3]triazol-4-yl)-benzyl]-amine ("A193")

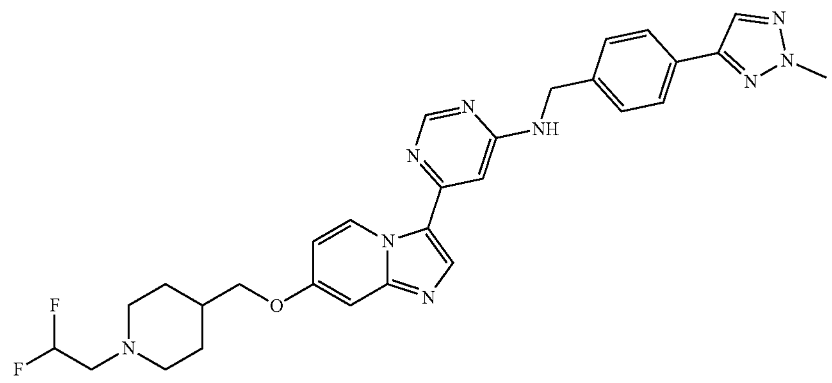 [SMILES: Cn1ncc(-c2ccc(CNc3cc(-c4cnc5cc(OCC6CCN(CC(F)F)CC6)ccn45)ncn3)cc2)n1]

from "A165" and 1,1-difluoro-2-iodoethane; white solid; m. p. 255-256° C.; HPLC/MS $[M+H]^+$ 560.

$^1H$ NMR (300 MHz, DMSO-$d_6$) δ 9.68 (d, J=7.7 Hz, 1H), 8.50 (s, 1H), 8.15 (d, J=7.6 Hz, 2H), 7.90 (t, J=6.2 Hz, 1H), 7.77 (d, J=8.1 Hz, 2H), 7.42 (d, J=7.9 Hz, 2H), 7.04 (d, J=2.6 Hz, 1H), 6.89 (d, J=1.2 Hz, 1H), 6.78 (dd, J=7.7, 2.6 Hz, 1H), 6.14-5.88 (m, 1H), 4.58 (d, J=5.9 Hz, 2H), 4.16 (s, 3H), 3.93 (d, J=5.9 Hz, 2H), 2.91 (d, J=11.0 Hz, 2H), 2.69 (td, J=15.6, 4.3 Hz, 2H), 2.21-2.10 (m, 2H), 1.73 (d, J=11.4 Hz, 3H), 1.40-1.27 (m, 2H)

Example 24

Synthesis of [4-(1-methyl-1H-pyrazol-4-yl)-benzyl]-(6-{7-[2-(1-oxo-1|4-thiomorpholin-4-yl)-ethoxy]-imidazo[1,2-a]pyridin-3-yl}-pyrimidin-4-yl)-amine ("A194")

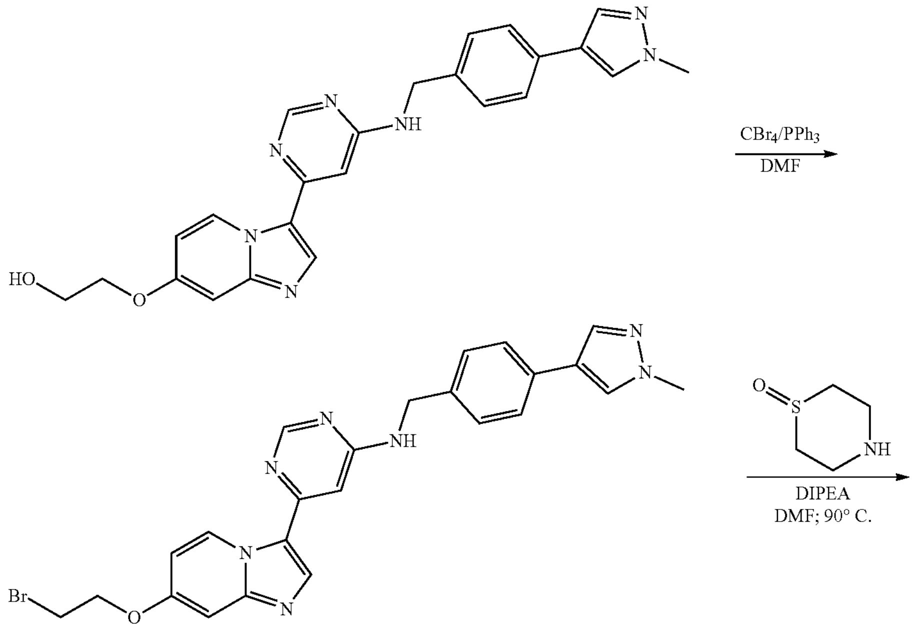

-continued

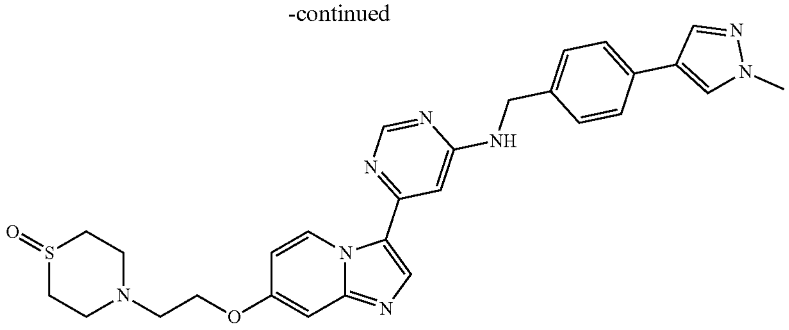

From “A172”; To a suspension of 2-({3-[6-({[4-(1-methyl-1H-pyrazol-4-yl)phenyl]methyl}amino)pyrimidin-4-yl]imidazo[1,2-a]pyridin-7-yl}oxy)ethan-1-ol (10.0 g, 22.6 mmol) in DMF (150 ml) is added triphenylphosphine (8.91 g, 34.0 mmol).

Then carbon tetrabromide (11.27 g, 34.0 mmol) is added portionwise with stirring during 20 min, while cooling the mixture in a cold water bath. The reaction mixture is stirred at room temperature for 18 hours. The solvent is removed under reduced pressure. The residue is triturated with diethyl ether and ethyl acetate. The resultant solid is chromatographed on a silica gel column with methanol/chloroform as eluent to afford 6-[7-(2-bromoethoxy)imidazo[1,2-a]pyridin-3-yl]-N-{[4-(1-methyl-1H-pyrazol-4-yl)phenyl]methyl}pyrimidin-4-amine as white solid.

A reaction vial is charged with 6-[7-(2-bromoethoxy)imidazo[1,2-a]pyridin-3-yl]-N-{[4-(1-methyl-1H-pyrazol-4-yl)phenyl]methyl}pyrimidin-4-amine (50.0 mg, 0.1 mmol), the corresponding amine (0.2 mmol) and DMF (0.3 ml) and the mixture is heated for 18 hours at 90° C. The reaction mixture is allowed to reach room temperature and evaporated. The residue is purified by preparative HPLC with methanol/aqueous ammonia as eluent.

The following compounds are prepared analogously:

(6-{7-[2-(1,3-dihydro-pyrrolo[3,4-c]pyridin-2-yl)-ethoxy]-imidazo[1,2-a]pyridin-3-yl}-pyrimidin-4-yl)-[4-(1-methyl-1H-pyrazol-4-yl)-benzyl]-amine (“A195”)

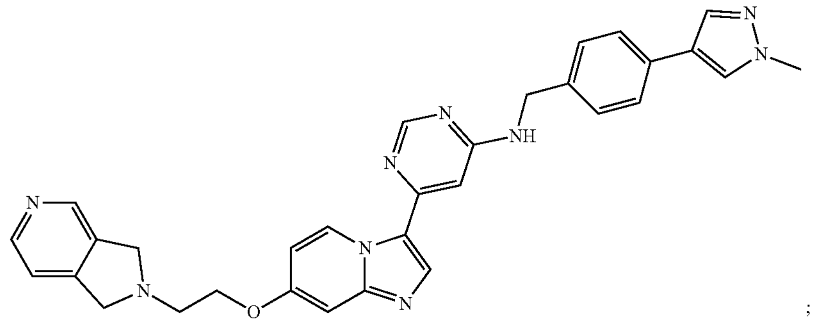 [SMILES: Cn1cc(-c2ccc(CNc3cc(-c4cnc5cc(OCCN6Cc7ccncc7C6)ccn45)ncn3)cc2)cn1]

;

(6-{7-[2-(4-fluoro-4-methyl-piperidin-1-yl)-ethoxy]-imidazo[1,2-a]pyridin-3-yl}-pyrimidin-4-yl)-[4-(1-methyl-1H-pyrazol-4-yl)-benzyl]-amine (“A196”)

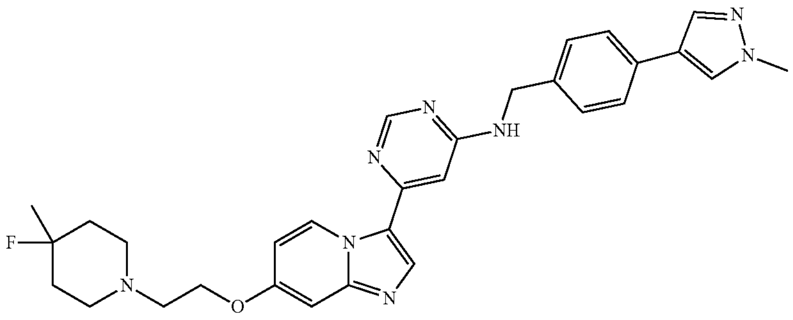

;

(6-{7-[2-(4-cyclopropyl-piperazin-1-yl)-ethoxy]-imidazo[1,2-a]pyridin-3-yl}-pyrimidin-4-yl)-[4-(1-methyl-1H-pyrazol-4-yl)-benzyl]-amine ("A197")
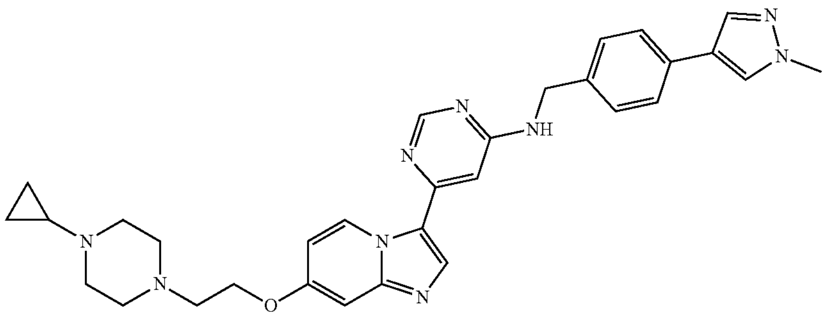 [SMILES: Cn1cc(-c2ccc(CNc3cc(-c4cnc5cc(OCCN6CCN(C7CC7)CC6)ccn45)ncn3)cc2)cn1]
;
(6-{7-[2-(3-methyl-3,8-diaza-bicyclo[3.2.1]oct-8-yl)-ethoxy]-imidazo[1,2-a]pyridin-3-yl}-pyrimidin-4-yl)-[4-(1-methyl-1H-pyrazol-4-yl)-benzyl]-amine ("A198")
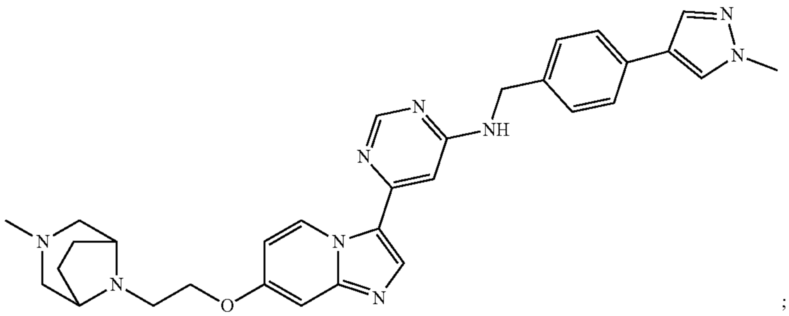
;
[4-(1-methyl-1H-pyrazol-4-yl)-benzyl]-(6-{7-[2-(2-oxo-2l4-thia-5-aza-bicyclo[2.2.1]hept-5-yl)-ethoxy]-imidazo[1,2-a]pyridin-3-yl}-pyrimidin-4-yl)-amine ("A199")
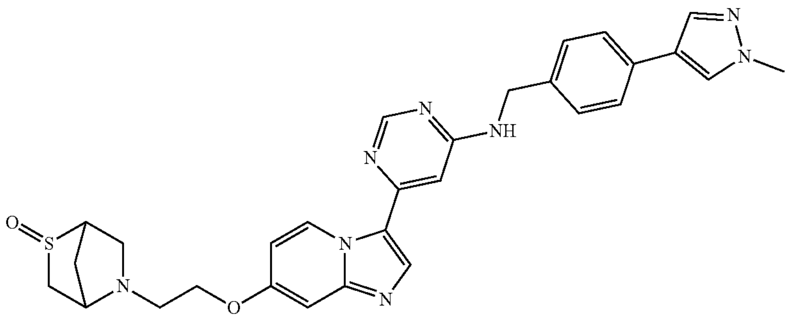 [SMILES: Cn1cc(-c2ccc(CNc3cc(-c4cnc5cc(OCCN6CC7CC6CS7=O)ccn45)ncn3)cc2)cn1]
;

(6-{7-[2-(6,6-difluoro-[1,4]oxazepan-4-yl)-ethoxy]-imidazo[1,2-a]pyridin-3-yl}-pyrimidin-4-yl)-[4-(1-methyl-1H-pyrazol-4-yl)-benzyl]-amine ("A200")
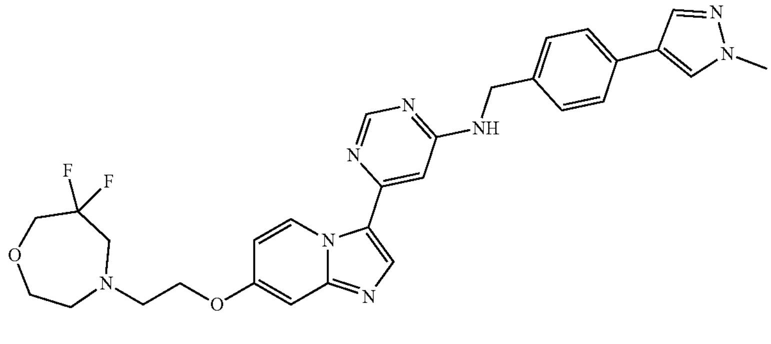 [SMILES: Cn1cc(-c2ccc(CNc3cc(-c4cnc5cc(OCCN6CCOCC(F)(F)C6)ccn45)ncn3)cc2)cn1]
;
(6-{7-[2-(hexahydro-pyrazino[2,1-c][1,4]oxazin-8-yl)-ethoxy]-imidazo[1,2-a]pyridin-3-yl}-pyrimidin-4-yl)-[4-(1-methyl-1H-pyrazol-4-yl)-benzyl]-amine ("A201")
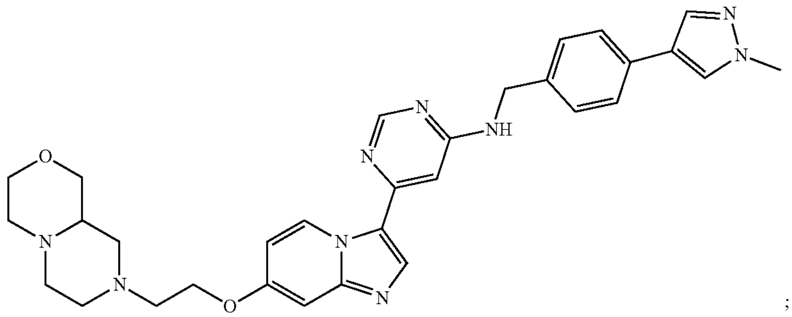 [SMILES: Cn1cc(-c2ccc(CNc3cc(-c4cnc5cc(OCCN6CCN7CCOCC7C6)ccn45)ncn3)cc2)cn1]
;
(6-{7-[2-(4,4-difluoro-piperidin-1-yl)-ethoxy]-imidazo[1,2-a]pyridin-3-yl}-pyrimidin-4-yl)-[4-(1-methyl-1H-pyrazol-4-yl)-benzyl]-amine ("A202")
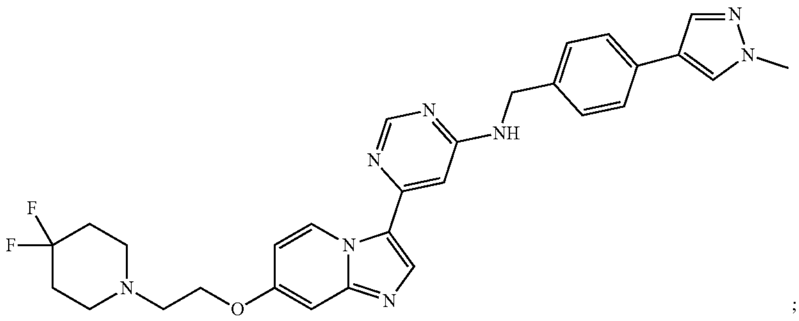 [SMILES: Cn1cc(-c2ccc(CNc3cc(-c4cnc5cc(OCCN6CCC(F)(F)CC6)ccn45)ncn3)cc2)cn1]
;

(6-{7-[2-(5,6-dihydro-8H-[1,2,4]triazolo[4,3-a]pyrazin-7-yl)-ethoxy]-imidazo[1,2-a]pyridin-3-yl}-pyrimidin-4-yl)-[4-(1-methyl-1H-pyrazol-4-yl)-benzyl]-amine ("A203")

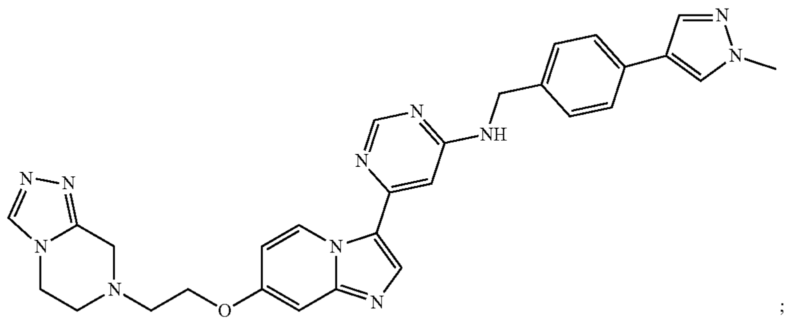 [SMILES: Cn1cc(-c2ccc(CNc3cc(-c4cnc5cc(OCCN6CCn7cnnc7C6)ccn45)ncn3)cc2)cn1]

;

(6-{7-[2-(2-methyl-5,6-dihydro-8H-[1,2,4]triazolo[1,5-a]pyrazin-7-yl)-ethoxy]-imidazo[1,2-a]pyridin-3-yl}-pyrimidin-4-yl)-[4-(1-methyl-1H-pyrazol-4-yl)-benzyl]-amine ("A204")

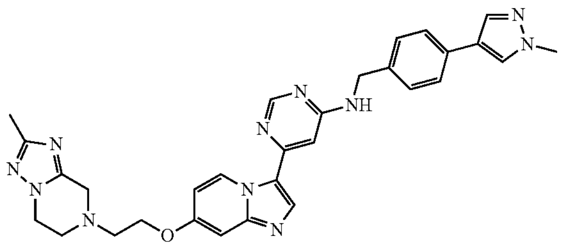

;

{methyl-[2-(3-{6-[4-(1-methyl-1H-pyrazol-4-yl)-benzylamino]-pyrimidin-4-yl}-imidazo[1,2-a]pyridin-7-yloxy)-ethyl]-amino}-acetonitrile ("A205")

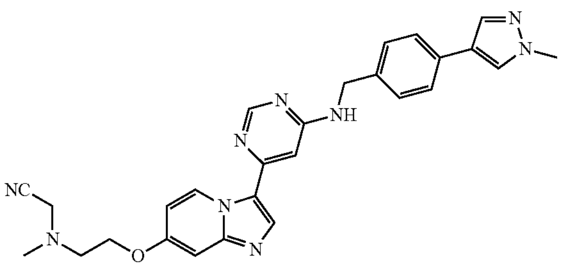

;

[3-methyl-1-[2-(3-{6-[4-(1-methyl-1-pyrazol-4-yl)-benzylamino]-pyrimidin-4-yl}-imidazo[1,2-a]pyridin-7-yloxy)-ethyl]-azetidine-3-carbonitrile ("A206")

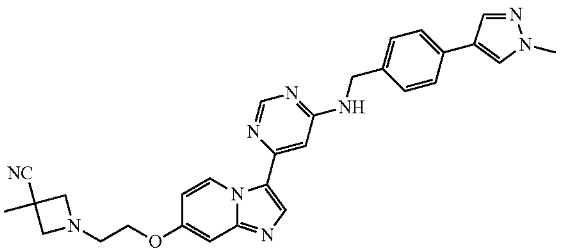

;

[4-(1-methyl-1H-pyrazol-4-yl)-benzyl]-(6-{7-[2-(6-oxa-1-aza-spiro[3.3]hept-1-yl)-ethoxy]-imidazo[1,2-a]pyridin-3-yl}-pyrimidin-4-yl)-amine ("A207")

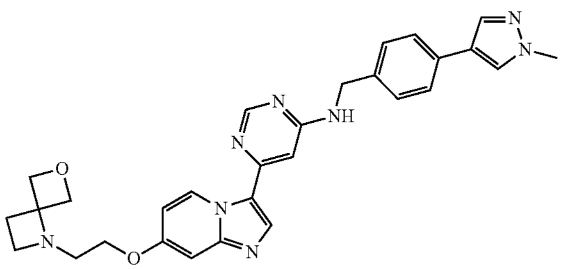

;

[4-(1-methyl-1H-pyrazol-4-yl)-benzyl]-[6-(7-{2-[methyl-(2,2,2-trifluoro-ethyl)-amino]-ethoxy}-imidazo[1,2-a]pyridin-3-yl)-pyrimidin-4-yl]-amine ("A208")

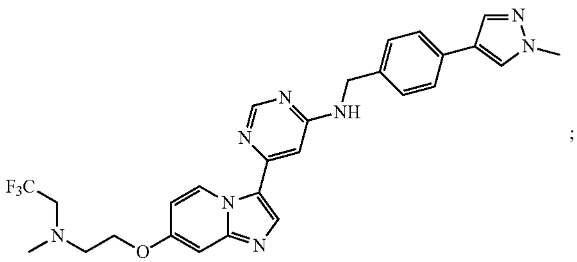 [SMILES: CN(CCOc1ccn2c(-c3cc(NCc4ccc(-c5cnn(C)c5)cc4)ncn3)cnc2c1)CC(F)(F)F]

;

(6-{7-[2-((3S,4R)-3,4-difluoro-pyrrolidin-1-yl)-ethoxy]-imidazo[1,2-a]pyridin-3-yl}-pyrimidin-4-yl)-[4-(1-methyl-1H-pyrazol-4-yl)-benzyl]-amine ("A209")

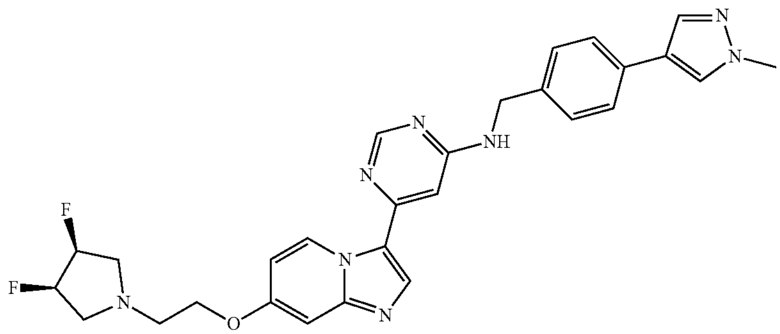

;

(6-{7-[(3aS,7aS)-2-(hexahydro-furo[3,2-b]pyridin-4-yl)-ethoxy]-imidazo[1,2-a]pyridin-3-yl}-pyrimidin-4-yl)-[4-(1-methyl-1H-pyrazol-4-yl)-benzyl]-amine ("A210")

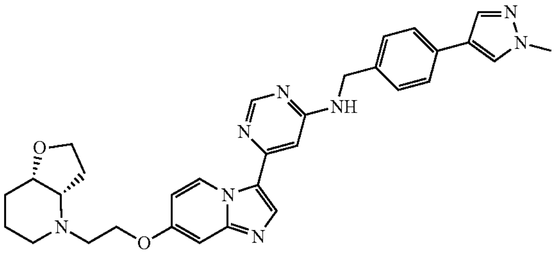

;

(6-{7-[(4aS,8aS)-2-(hexahydro-pyrano[3,4-b][1,4]oxazin-1-yl)-ethoxy]-imidazo[1,2-a]pyridin-3-yl}-pyrimidin-4-yl)-[4-(1-methyl-1H-pyrazol-4-yl)-benzyl]-amine ("A211")

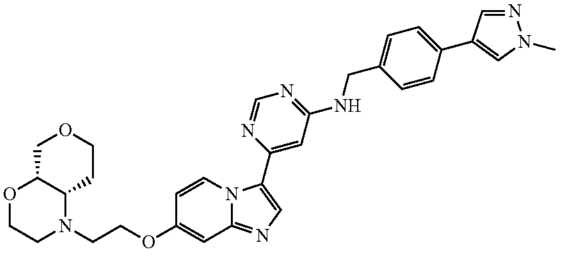

;

(6-{7-[2-(1,4-diaza-bicyclo[3.2.1]oct-4-yl)-ethoxy]-imidazo[1,2-a]pyridin-3-yl}-pyrimidin-4-yl)-[4-(1-methyl-1H-pyrazol-4-yl)-benzyl]-amine ("A212")

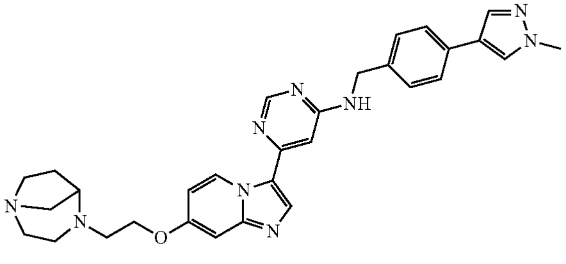

;

[6-(7-{2-[3-(3-methyl-[1,2,4]oxadiazol-5-yl)-azetidin-1-yl]-ethoxy}-imidazo[1,2-a]pyridin-3-yl)-pyrimidin-4-yl]-[4-(1-methyl-1H-pyrazol-4-yl)-benzyl]-amine ("A213")
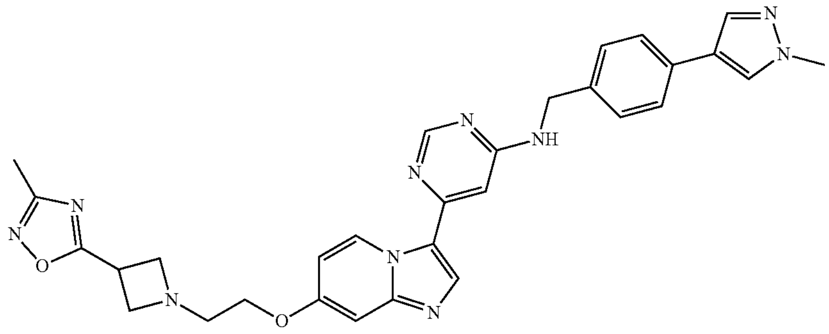
;
(6-{7-[2-(2,2-difluoro-morpholin-4-yl)-ethoxy]-imidazo[1,2-a]pyridin-3-yl}-pyrimidin-4-yl)-[4-(1-methyl-1H-pyrazol-4-yl)-benzyl]-amine ("A214")
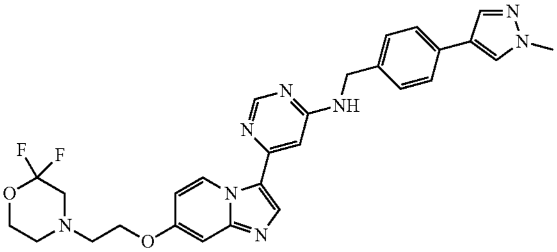
;
(6-{7-[2-(3-methanesulfonyl-azetidin-1-yl)-ethoxy]-imidazo[1,2-a]pyridin-3-yl}-pyrimidin-4-yl)-[4-(1-methyl-1H-pyrazol-4-yl)-benzyl]-amine ("A215")
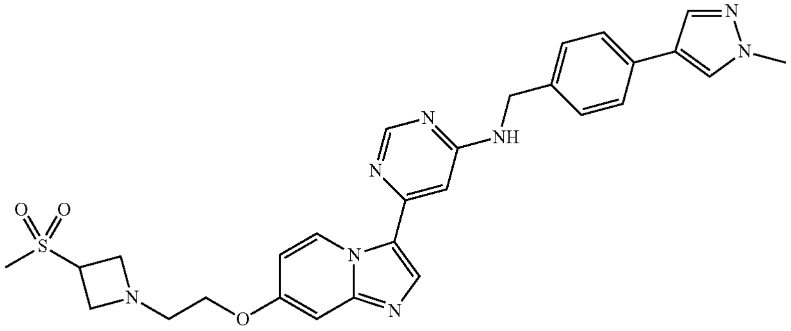
;

(6-{7-[2-(6,7-dihydro-4H-pyrazolo[1,5-a]pyrazin-5-yl)-ethoxy]-imidazo[1,2-a]pyridin-3-yl}-pyrimidin-4-yl)-[4-(1-methyl-1H-pyrazol-4-yl)-benzyl]-amine ("A216")

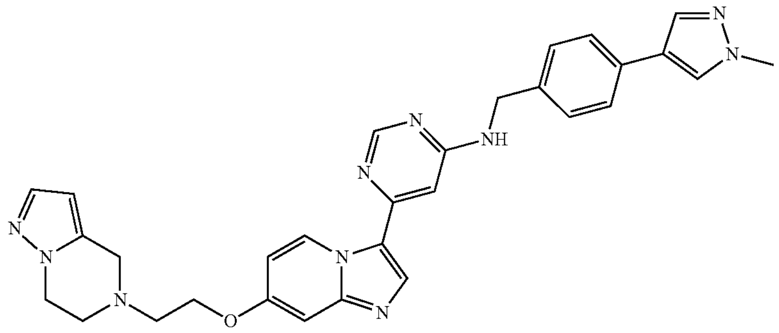

;

(6-{7-[2-(6,7-dihydro-4H-[1,2,3]triazolo[1,5-a]pyrazin-5-yl)-ethoxy]-imidazo[1,2-a]pyridin-3-yl}-pyrimidin-4-yl)-[4-(1-methyl-1H-pyrazol-4-yl)-benzyl]-amine ("A217")

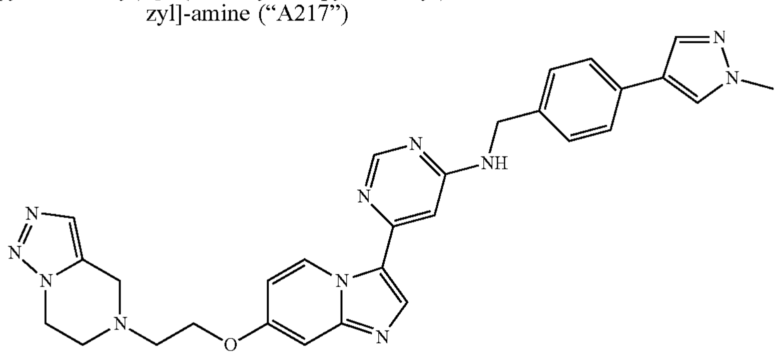

;

light brown solid; HPLC/MS(B): 1.18 min $[M+H]^+=548$. $^1H$ NMR (500 MHz, DMSO-$d_6$) δ 9.73-9.65 (m, 1H), 8.50 (s, 1H), 8.15 (s, 1H), 8.08 (s, 1H), 7.86 (t, J=6.1 Hz, 1H), 7.81 (d, J=0.8 Hz, 1H), 7.56-7.48 (m, 3H), 7.34 (d, J=7.8 Hz, 2H), 7.14 (d, J=2.7 Hz, 1H), 6.92-6.87 (m, 1H), 6.82 (dd, J=7.7, 2.6 Hz, 1H), 4.52 (s, 2H), 4.37 (t, J=5.6 Hz, 2H), 4.30 (t, J=5.5 Hz, 2H), 3.88 (s, 2H), 3.84 (s, 3H), 3.09 (dd, J=6.2, 5.0 Hz, 2H), 3.03 (t, J=5.5 Hz, 2H).

(6-{7-[2-(3,4-dihydro-1H-pyrrolo[1,2-a]pyrazin-2-yl)-ethoxy]-imidazo[1,2-a]pyridin-3-yl}-pyrimidin-4-yl)-[4-(1-methyl-1H-pyrazol-4-yl)-benzyl]-amine ("A218")

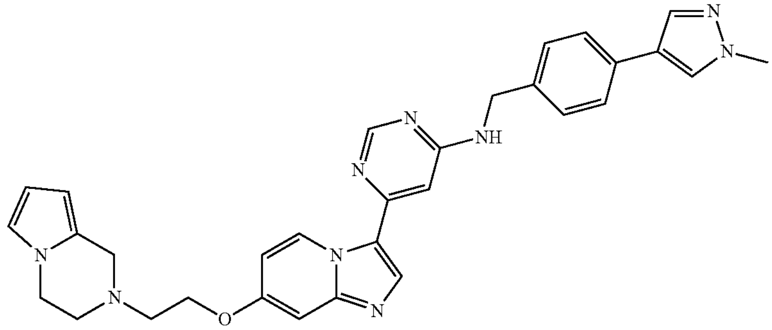

;

4-methyl-1-[2-(3-{6-[4-(1-methyl-1H-pyrazol-4-yl)-benzylamino]-pyrimidin-4-yl}-imidazo[1,2-a]pyridin-7-yloxy)-ethyl]-[1,4]diazepan-5-one ("A219")
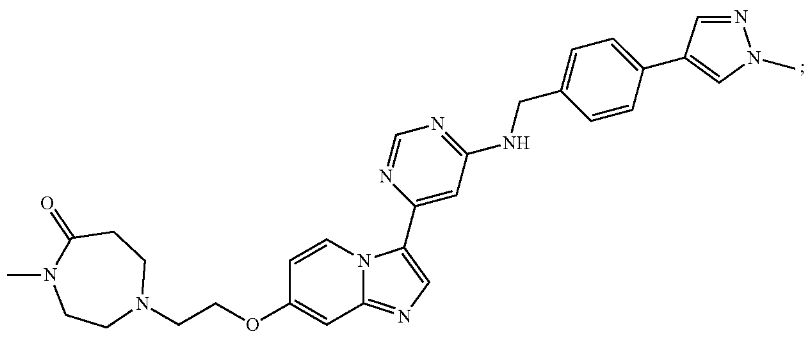
(6-{7-[2-(4-methoxy-4-methyl-piperidin-1-yl)-ethoxy]-imidazo[1,2-a]pyridin-3-yl}-pyrimidin-4-yl)-[4-(1-methyl-1H-pyrazol-4-yl)-benzyl]-amine ("A220")
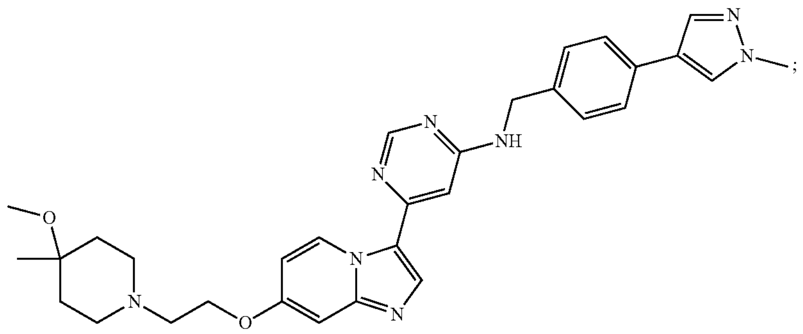
(6-{7-[2-(3-methyl-5,6-dihydro-8H-[1,2,4]triazolo[4,3-a]pyrazin-7-yl)-ethoxy]-imidazo[1,2-a]pyridin-3-yl}-pyrimidin-4-yl)-[4-(1-methyl-1H-pyrazol-4-yl)-benzyl]-amine ("A221")
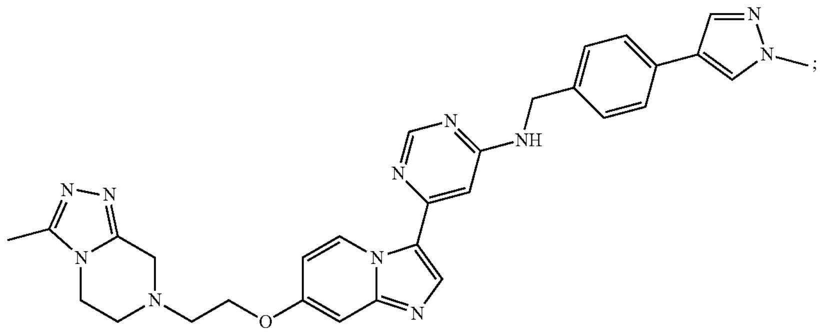

4-methyl-1-[2-(3-{6-[4-(1-methyl-1H-pyrazol-4-yl)-benzylamino]-pyrimidin-4-yl}-imidazo[1,2-a]pyridin-7-yloxy)-ethyl]-piperidine-4-carbonitrile ("A222")
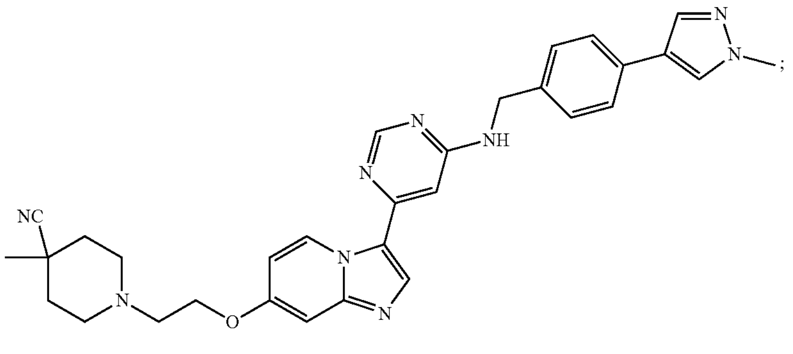
7-methyl-2-[2-(3-{6-[4-(1-methyl-1H-pyrazol-4-yl)-benzylamino]-pyrimidin-4-yl}-imidazo[1,2-a]pyridin-7-yloxy)-ethyl]-5-oxa-2,7-diaza-spiro[3.4]octan-6-one ("A248")
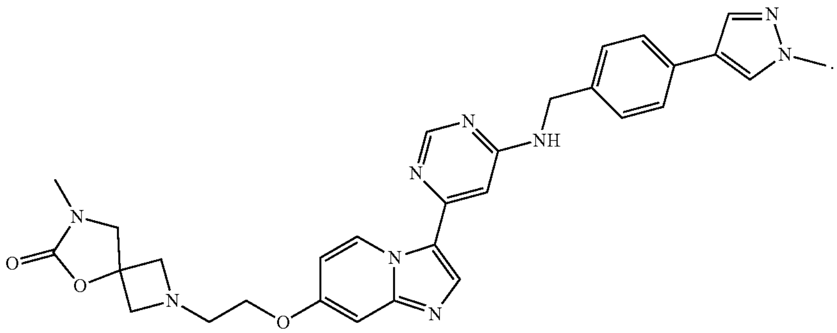 [SMILES: CN1CC2(CN(CCOc3ccn4c(-c5cc(NCc6ccc(-c7cnn(C)c7)cc6)ncn5)cnc4c3)C2)OC1=O]
Example 25
Synthesis of {6-[7-(4-azetidin-1-yl-butoxy)-imidazo[1,2-a]pyridin-3-yl]-pyrimidin-4-yl}-[4-(1-methyl-1H-pyrazol-4-yl)-benzyl]-am amine ("A225")
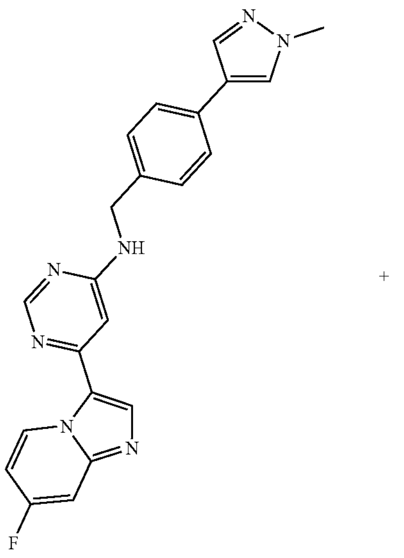
-continued
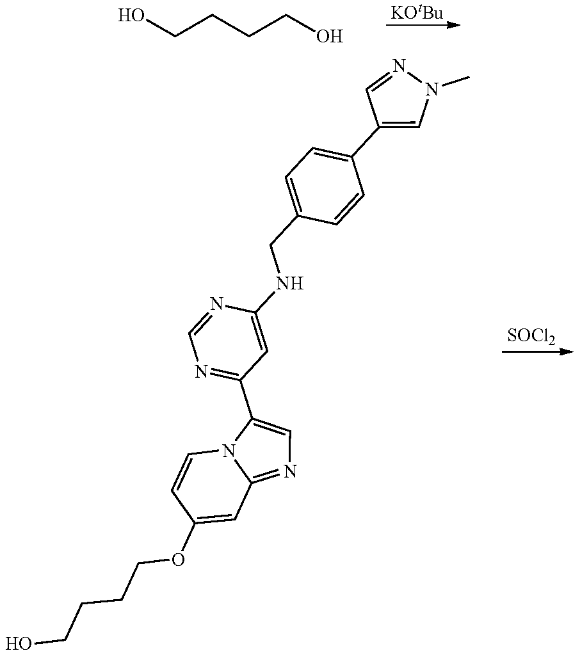

-continued

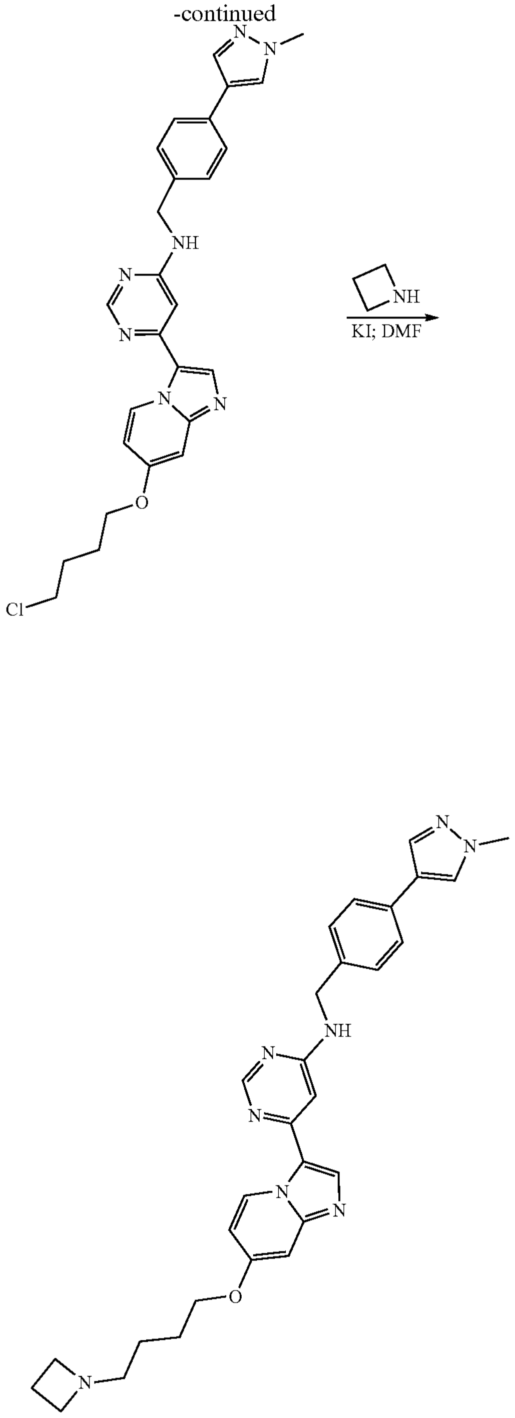

white solid; m.p. 187-195° C.; HPLC/MS $[M+H]^+$ 509. $^1H$ NMR (300 MHz, DMSO-$d_6$) δ 9.67 (d, J=7.7 Hz, 1H), 8.49 (s, 1H), 8.10 (d, J=17.9 Hz, 2H), 7.83 (d, J=19.4 Hz, 2H), 7.50 (d, J=8.0 Hz, 2H), 7.32 (d, J=7.9 Hz, 2H), 7.05 (d, J=2.6 Hz, 1H), 6.87 (s, 1H), 6.77 (dd, J=7.7, 2.6 Hz, 1H), 4.52 (s, 2H), 4.05 (t, J=6.5 Hz, 2H), 3.83 (s, 3H), 3.06 (t, J=6.9 Hz, 4H), 2.36 (t, J=7.1 Hz, 2H), 1.92 (p, J=6.9 Hz, 2H), 1.73 (t, J=7.4 Hz, 2H), 1.40 (q, J=7.3 Hz, 2H).

Example 26

Synthesis of 6-[7-(1-methyl-1H-pyrazol-4-yl)imidazo[1,2-a]pyridin-3-yl]-N-{[4-(1-methyl-1H-pyrazol-4-yl)phenyl]methyl}pyrimidin-4-amine ("A226")

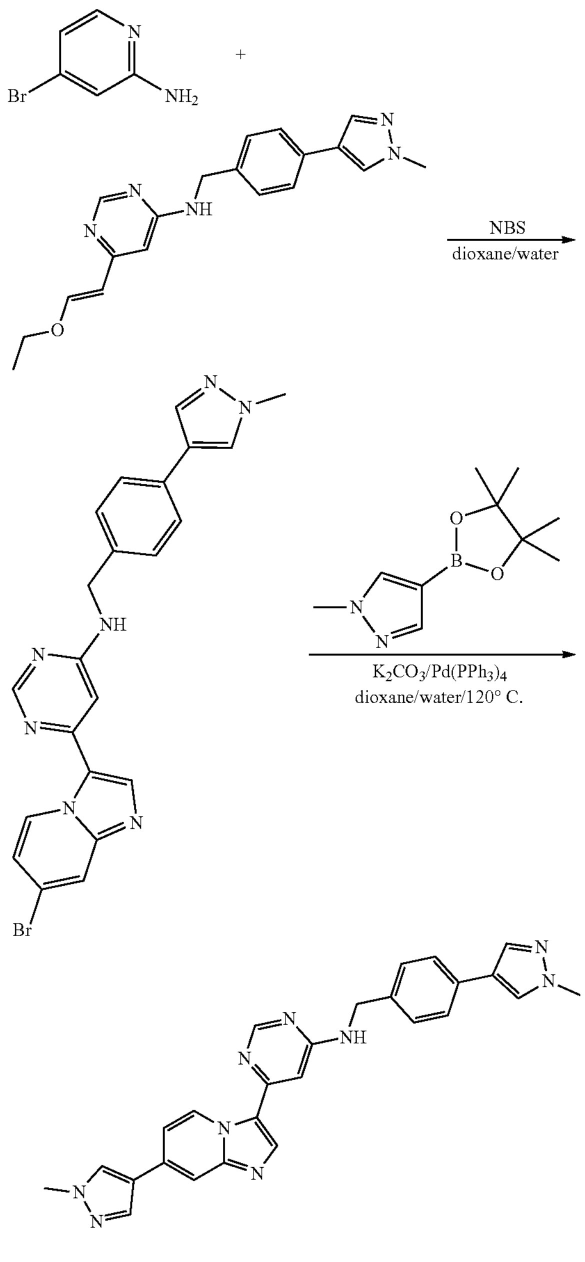

Yellow solid; HPLC/MS(B) 0.741 min, $[M+H]^+$ 462.

$^1H$ NMR (500 MHz, DMSO-$d_6$) δ 9.77 (dd, J=7.3, 0.9 Hz, 1H), 8.55 (s, 1H), 8.35 (s, 1H), 8.24 (s, 1H), 8.07 (d, J=0.8 Hz, 2H), 7.89-7.85 (m, 2H), 7.80 (d, J=0.9 Hz, 1H), 7.55-7.49 (m, 3H), 7.38-7.30 (m, 4H), 6.94 (d, J=1.2 Hz, 1H), 4.55 (d, J=5.9 Hz, 2H), 3.89 (s, 3H), 3.84 (s, 3H).

Example 27
Synthesis of {6-[7-(2-methyl-3-pyrrolidin-1-yl-propoxy)-imidazo[1,2-a]pyridin-3-yl]-pyrimidin-4-yl}-[4-(2-methyl-2H-[1,2,3]triazol-4-yl)-benzyl]-amine ("A227")
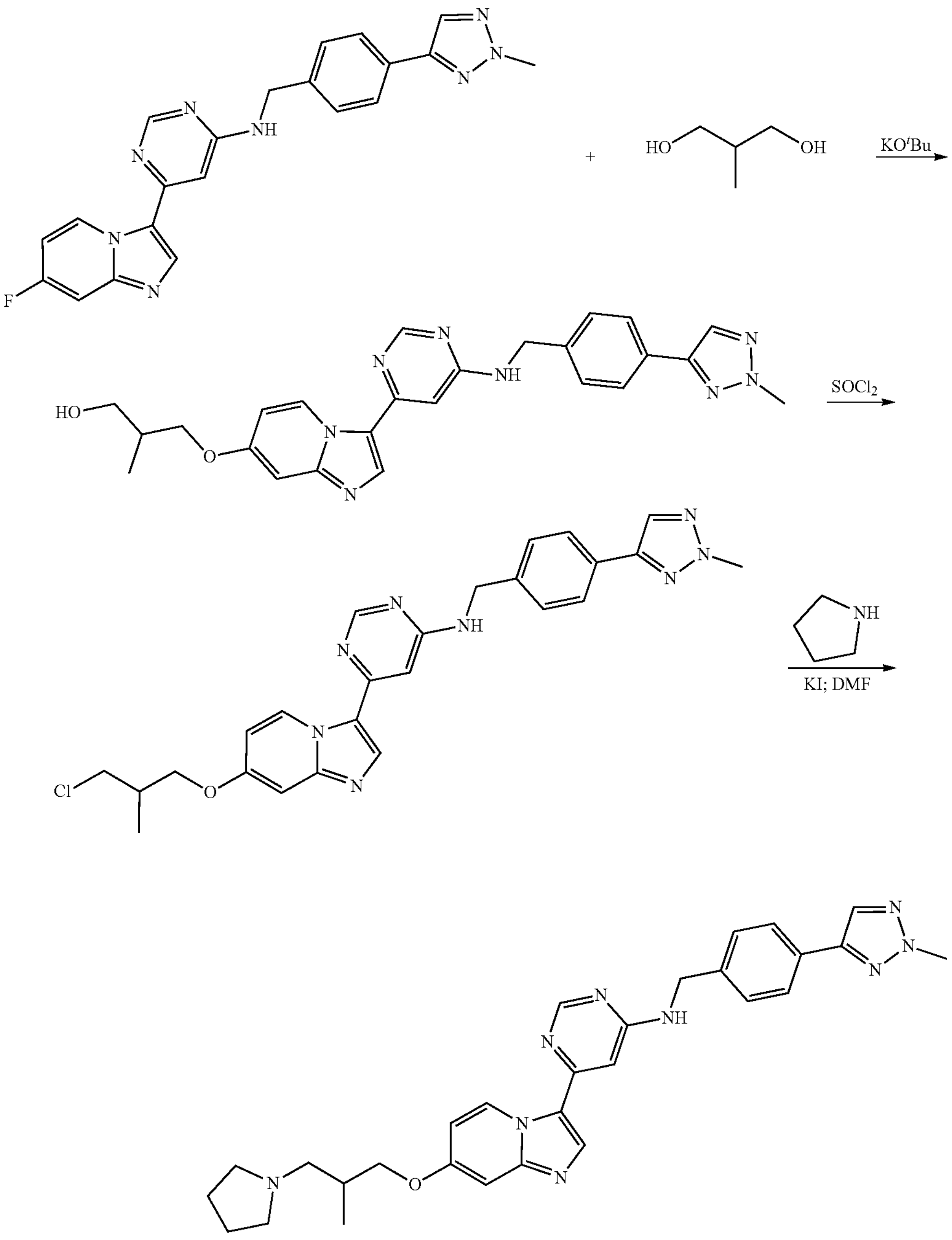
white solid; m.p. 230-231° C.; HPLC/MS $[M+H]^+$ 524. $^{1}$H NMR (300 MHz, DMSO-$d_6$) δ 9.68 (d, J=7.7 Hz, 1H), 8.50 (s, 1H), 8.15 (d, J=7.5 Hz, 2H), 7.90 (t, J=6.2 Hz, 1H), 7.82-7.73 (m, 2H), 7.42 (d, J=7.9 Hz, 2H), 7.04 (d, J=2.6 Hz, 1H), 6.89 (d, J=1.2 Hz, 1H), 6.79 (dd, J=7.7, 2.6 Hz, 1H), 4.58 (d, J=6.0 Hz, 2H), 4.16 (s, 3H), 4.04 (dd, J=9.7, 4.7 Hz, 1H), 3.94 (t, J=7.8 Hz, 1H), 2.13 (s, 1H), 1.69 (s, 4H), 1.02 (d, J=6.6 Hz, 3H).

The following compound is prepared analogously

[4-(1-methyl-1H-pyrazol-4-yl)-benzyl]-{6-[7-(2-methyl-3-pyrrolidin-1-yl-propoxy)-imidazo[1,2-a]pyridin-3-yl]-pyrimidin-4-yl}-amine ("A235")

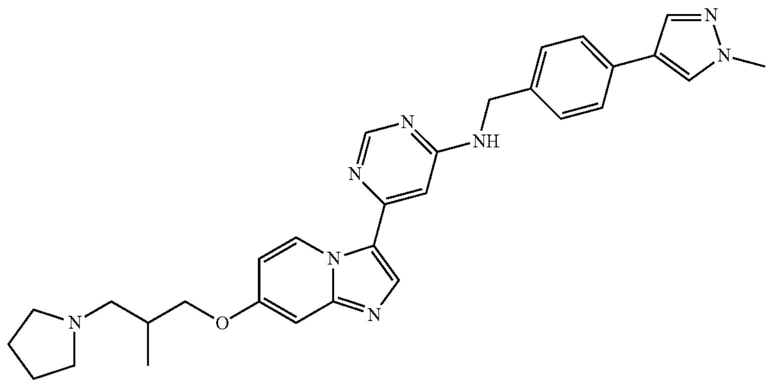 [SMILES: CC(COc1ccn2c(-c3cc(NCc4ccc(-c5cnn(C)c5)cc4)ncn3)cnc2c1)CN1CCCC1]

white solid; m.p. 217-220° C.; HPLC/MS $[M+H]^+$ 523. $^1H$ NMR (300 MHz, DMSO-$d_6$) δ 9.67 (d, J=7.7 Hz, 1H), 8.49 (s, 1H), 8.10 (d, J=19.0 Hz, 2H), 7.82 (d, J=15.6 Hz, 2H), 7.50 (d, J=8.1 Hz, 2H), 7.32 (d, J=7.9 Hz, 2H), 7.03 (d, J=2.5 Hz, 1H), 6.87 (d, J=1.2 Hz, 1H), 6.78 (dd, J=7.7, 2.6 Hz, 1H), 4.52 (d, J=5.9 Hz, 2H), 4.04 (dd, J=9.6, 4.7 Hz, 1H), 3.92 (dd, J=9.6, 6.2 Hz, 1H), 3.83 (s, 3H), 2.53 (s, 1H), 2.43 (s, 4H), 2.29 (dd, J=11.9, 7.3 Hz, 1H), 2.16-2.04 (m, 1H), 1.66 (d, J=6.8 Hz, 4H), 1.01 (d, J=6.6 Hz, 3H).

Example 28

Synthesis of 1-[3-({3-[6-({[4-(1-methyl-1H-pyrazol-4-yl)phenyl]methyl}amino)pyrimidin-4-yl]imidazo[1,2-a]pyridin-7-yl}oxy)propyl]pyrrolidin-1-ium-1-olate ("A228")

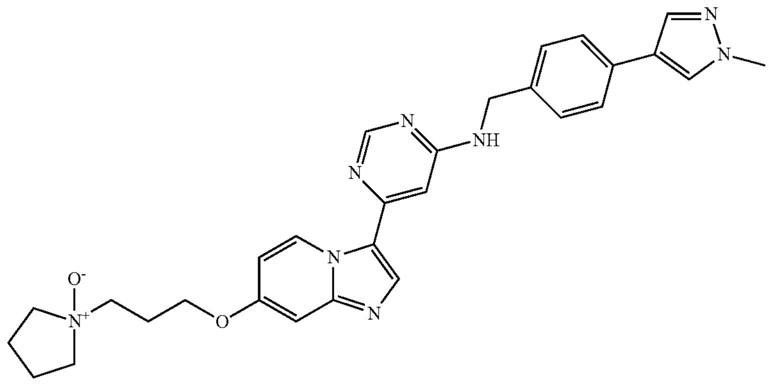 [SMILES: Cn1cc(-c2ccc(CNc3cc(-c4cnc5cc(OCCC[N+]6([O-])CCCC6)ccn45)ncn3)cc2)cn1]

from “A75”
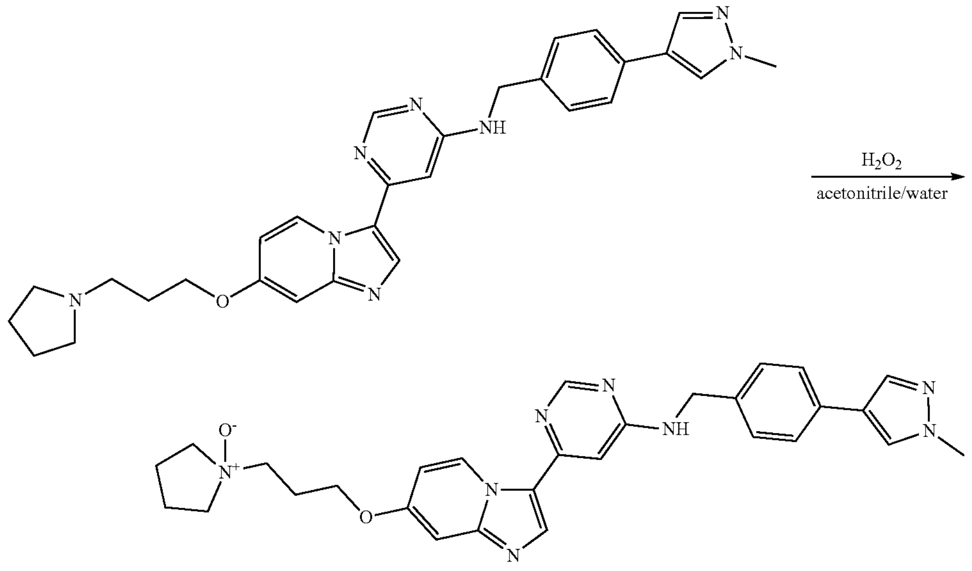
Off-white solid; HPLC/MS(B) 0.651 min, $[M+2H]^{2+}/2$ 263.
$^1$H NMR (500 MHz, DMSO-$d_6$) δ 9.70 (d, J=7.7 Hz, 1H), 8.51 (s, 1H), 8.14 (s, 1H), 8.07 (d, J=0.8 Hz, 1H), 7.85 (t, J=6.1 Hz, 1H), 7.80 (d, J=0.8 Hz, 1H), 7.51 (d, J=8.2 Hz, 2H), 7.34 (d, J=7.7 Hz, 2H), 7.08 (d, J=2.6 Hz, 1H), 6.89 (d, J=1.3 Hz, 1H), 6.79 (dd, J=7.7, 2.6 Hz, 1H), 4.54 (d, J=6.0 Hz, 2H), 4.25 (t, J=6.3 Hz, 2H), 3.84 (s, 3H), 3.39-3.34 (m, 2H), 3.34-3.29 (m, 2H), 3.15-3.07 (m, 2H), 2.41-2.32 (m, 2H), 2.25-2.11 (m, 2H), 1.90-1.78 (m, 2H).
Example 29
Synthesis of 1-[3-amino-4-(4-{[6-(7-methoxy-imidazo[1,2-a]pyridin-3-yl)-pyrimidin-4-ylamino]-methyl}-phenyl)-pyrazol-1-yl]-2-methyl-propan-2-ol (“A229”)
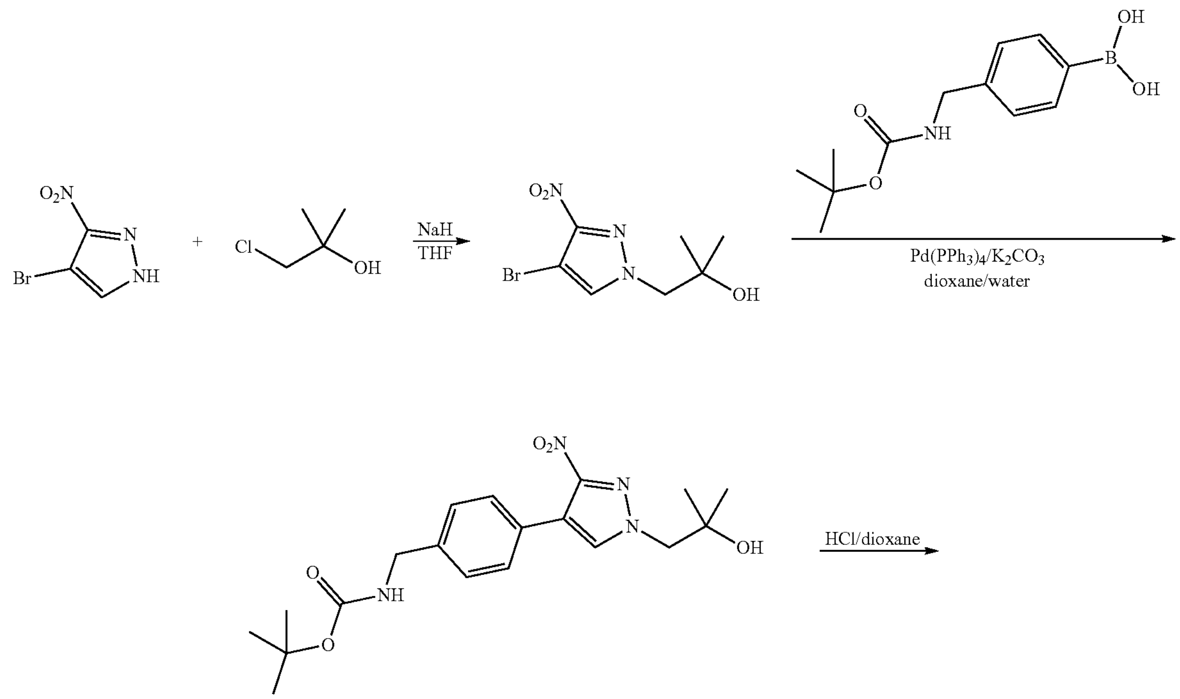

-continued
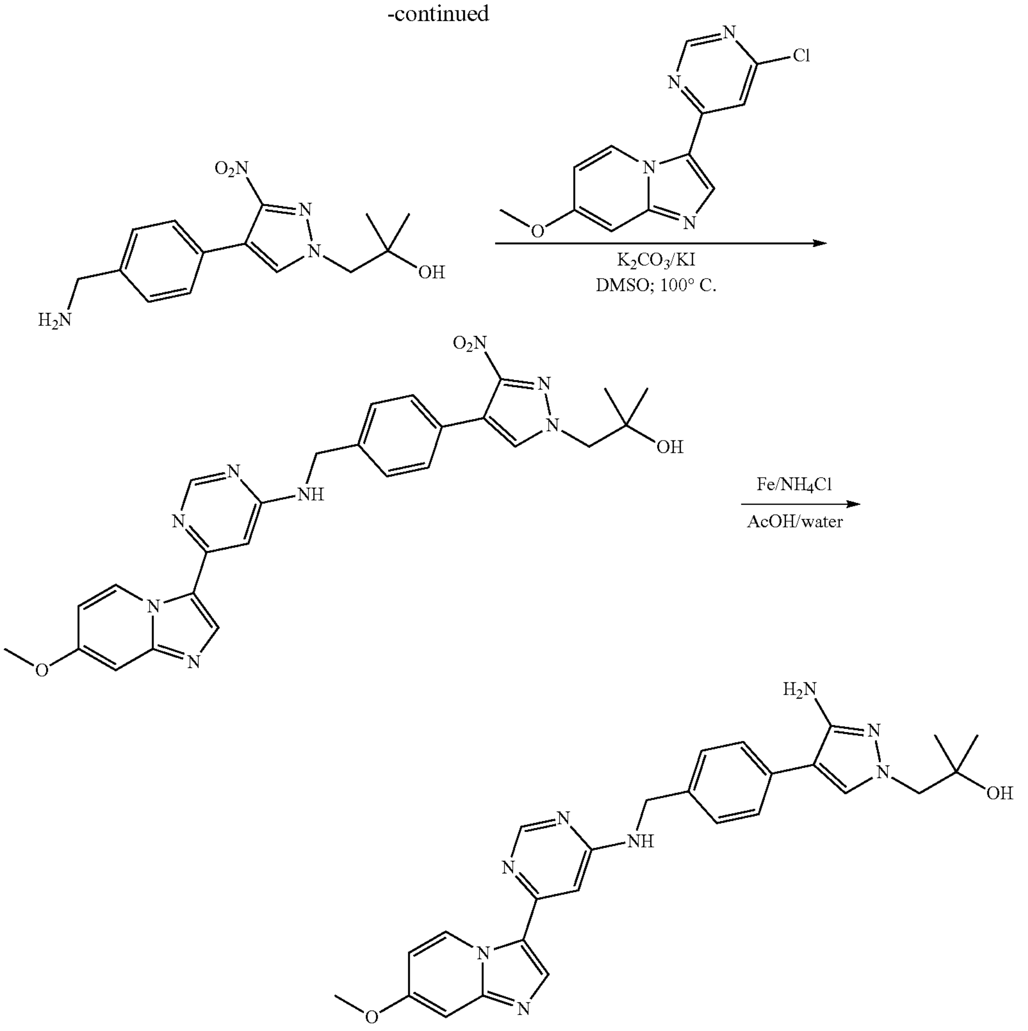
white solid; m.p. 298-299° C.; HPLC/MS $[M+H]^+$ 485. $^1$H NMR (400 MHz, DMSO-d$_6$) δ 9.69 (d, J=7.6 Hz, 1H), 8.51 (s, 1H), 8.16 (s, 1H), 7.90 (t, J=6.1 Hz, 1H), 7.65 (s, 1H), 7.48-7.41 (m, 2H), 7.32 (d, J=7.7 Hz, 2H), 7.09 (d, J=2.7 Hz, 1H), 6.89 (d, J=1.2 Hz, 1H), 6.81 (dd, J=7.7, 2.6 Hz, 1H), 4.70 (s, 1H), 4.66 (s, 2H), 4.53 (s, 2H), 3.87 (s, 3H), 3.77 (s, 2H), 1.14 (s, 1H), 1.06 (s, 6H).
Example 30
Synthesis of [4-(1-methyl-1H-pyrazol-4-yl)-benzyl]-(6-{7-[3-(2-oxa-6-aza-spiro[3.3]hept-6-yl)-propoxy]-imidazo[1,2-a]pyridin-3-yl}-pyrimidin-4-yl)-amine ("A238")
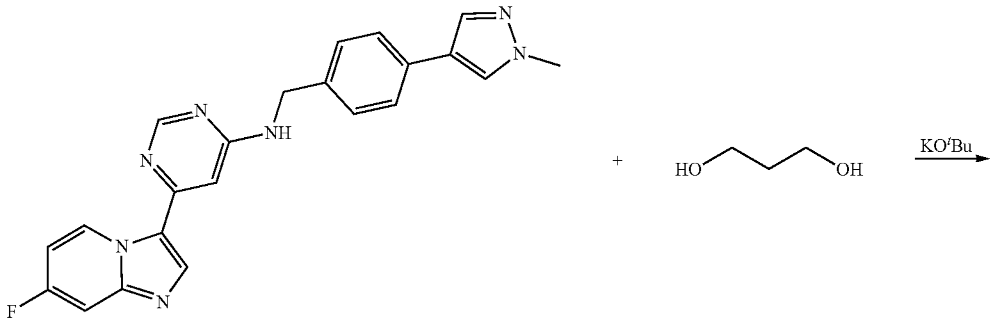

-continued

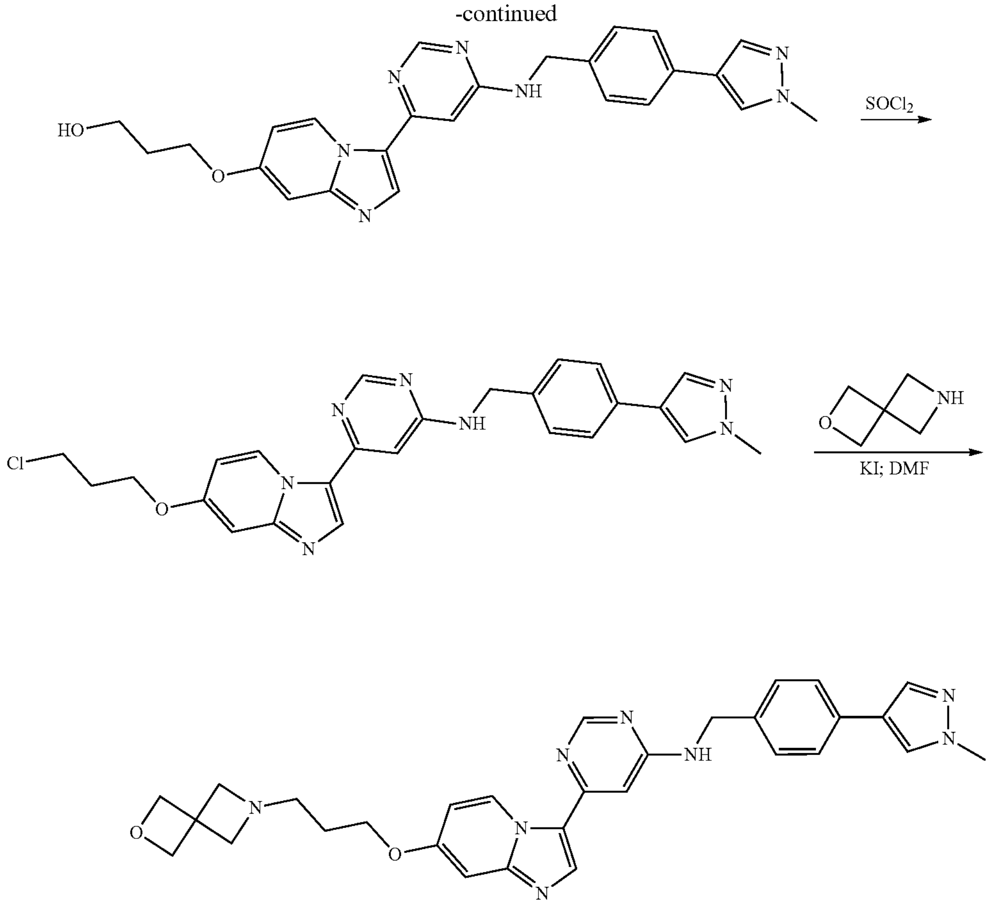

white solid; m.p. 175-180° C.; HPLC/MS $[M+H]^+$ 537. $^1H$ NMR (300 MHz, DMSO-$d_6$) δ 9.67 (d, J=7.7 Hz, 1H), 8.49 (s, 1H), 8.10 (d, J=18.1 Hz, 2H), 7.87 (t, J=6.1 Hz, 1H), 7.80 (s, 1H), 7.50 (d, J=8.1 Hz, 2H), 7.32 (d, J=7.8 Hz, 2H), 7.03 (d, J=2.6 Hz, 1H), 6.87 (d, J=1.2 Hz, 1H), 6.76 (dd, J=7.7, 2.6 Hz, 1H), 4.58 (s, 6H), 4.05 (t, J=6.3 Hz, 2H), 3.83 (s, 3H), 1.72 (t, J=6.6 Hz, 2H).

The following compounds are prepared analogously:

[4-(2-methyl-2H-[1,2,3]triazol-4-yl)-benzyl]-(6-{7-[3-(2-oxa-6-aza-spiro[3.3]hept-6-yl)-propoxy]-imidazo[1,2-a]pyridin-3-yl}-pyrimidin-4-yl)-amine ("A239")

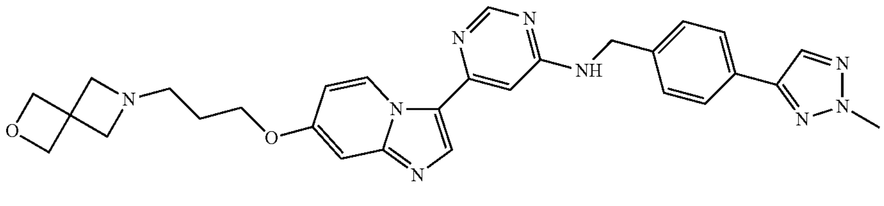 [SMILES: Cn1ncc(-c2ccc(CNc3cc(-c4cnc5cc(OCCCN6CC7(COC7)C6)ccn45)ncn3)cc2)n1]

white solid; m.p. 230-231° C.; HPLC/MS $[M+H]^+$ 538. $^1H$ NMR (300 MHz, DMSO-$d_6$) δ 9.67 (d, J=7.7 Hz, 1H), 8.49 (s, 1H), 8.15 (d, J=8.1 Hz, 2H), 7.90 (t, J=6.1 Hz, 1H), 7.82-7.73 (m, 2H), 7.42 (d, J=7.9 Hz, 2H), 7.02 (d, J=2.6 Hz, 1H), 6.88 (d, J=1.2 Hz, 1H), 6.76 (dd, J=7.7, 2.6 Hz, 1H), 4.57 (s, 6H), 4.16 (s, 3H), 4.05 (t, J=6.3 Hz, 2H), 2.42 (t, J=6.9 Hz, 2H), 1.75-1.63 (m, 2H).

(6-{7-[3-(3-fluoro-azetidin-1-yl)-propoxy]-imidazo[1,2-a]pyridin-3-yl}-pyrimidin-4-yl)-[4-(1-methyl-1H-pyrazol-4-yl)-benzyl]-amine ("A240")

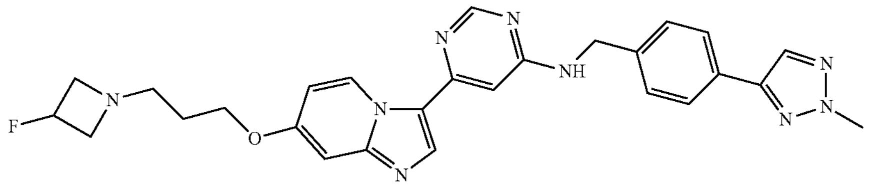 [SMILES: Cn1ncc(-c2ccc(CNc3cc(-c4cnc5cc(OCCCN6CC(F)C6)ccn45)ncn3)cc2)n1]

white solid; m.p. 190-195° C.; HPLC/MS $[M+H]^+$ 513. $^1H$ NMR (300 MHz, DMSO-$d_6$) δ 9.67 (d, J=7.7 Hz, 1H), 8.49 (s, 1H), 8.10 (d, J=18.3 Hz, 2H), 7.91-7.77 (m, 2H), 7.50 (d, J=8.1 Hz, 2H), 7.32 (d, J=7.9 Hz, 2H), 7.03 (d, J=2.6 Hz, 1H), 6.87 (d, J=1.2 Hz, 1H), 6.77 (dd, J=7.7, 2.6 Hz, 1H), 5.22-5.00 (m, 1H), 4.52 (s, 2H), 4.07 (t, J=6.3 Hz, 2H), 3.82 (s, 3H), 3.63-3.47 (m, 2H), 3.14-2.95 (m, 2H), 2.57 (t, J=6.9 Hz, 2H), 1.75 (t, J=6.6 Hz, 2H).

[4-(1-methyl-1H-pyrazol-4-yl)-benzyl]-(6-{7-[3-(1-oxo-1|4-thiomorpholin-4-yl)-propoxy]-imidazo[1,2-a]pyridin-3-yl}-pyrimidin-4-yl)-amine ("A241")

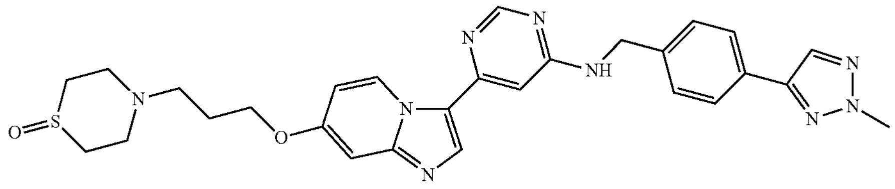 [SMILES: Cn1ncc(-c2ccc(CNc3cc(-c4cnc5cc(OCCCN6CCS(=O)CC6)ccn45)ncn3)cc2)n1]

white solid; m.p. 211-215° C.; HPLC/MS $[M+H]^+$ 557. $^1H$ NMR (300 MHz, DMSO-$d_6$) δ 9.68 (d, J=7.7 Hz, 1H), 8.49 (s, 1H), 8.10 (d, J=19.6 Hz, 2H), 7.87 (t, J=6.2 Hz, 1H), 7.80 (d, J=0.8 Hz, 1H), 7.50 (d, J=8.1 Hz, 2H), 7.32 (d, J=7.8 Hz, 2H), 7.06 (d, J=2.6 Hz, 1H), 6.87 (d, J=1.2 Hz, 1H), 6.78 (dd, J=7.8, 2.6 Hz, 1H), 4.52 (s, 2H), 4.11 (t, J=6.3 Hz, 2H), 3.82 (s, 3H), 2.86 (d, J=9.2 Hz, 4H), 2.76-2.58 (m, 4H), 2.53 (d, J=7.0 Hz, 2H), 1.91 (t, J=6.8 Hz, 2H), 1.21 (s, 1H).

[4-(2-methyl-oxazol-4-yl)-benzyl]-{6-[7-(3-pyrrolidin-1-yl-propoxy)-imidazo[1,2-a]pyridin-3-yl]-pyrimidin-4-yl}-amine ("A242")

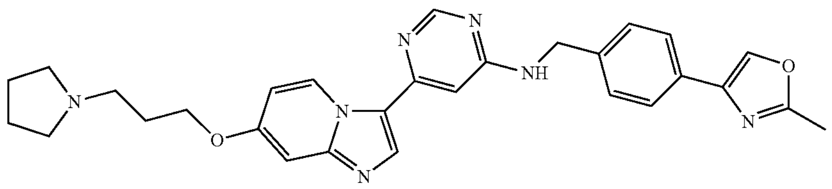 [SMILES: Cc1nc(-c2ccc(CNc3cc(-c4cnc5cc(OCCCN6CCCC6)ccn45)ncn3)cc2)co1]

from intermediate H4; white solid; m.p. 288-289° C.; HPLC/MS $[M+H]^+$ 510.

$^1H$ NMR (400 MHz, DMSO-$d_6$) δ 9.69 (d, J=7.7 Hz, 1H), 8.51 (s, 1H), 8.42 (s, 1H), 8.19-8.10 (m, 1H), 7.90 (t, J=6.2 Hz, 1H), 7.76-7.67 (m, 2H), 7.40 (d, J=7.6 Hz, 2H), 7.06 (d, J=2.7 Hz, 1H), 6.89 (s, 1H), 6.80 (dd, J=7.7, 2.6 Hz, 1H), 4.57 (s, 2H), 4.12 (t, J=6.3 Hz, 2H), 2.58-2.52 (m, 2H), 2.49-2.39 (m, 7H), 1.98-1.88 (m, 2H), 1.74-1.62 (m, 4H).

(6-{7-[3-(4-cyclopropyl-piperazin-1-yl)-propoxy]-imidazo[1,2-a]pyridin-3-yl}-pyrimidin-4-yl)-[4-(1-methyl-1H-pyrazol-4-yl)-benzyl]-amine ("A243")

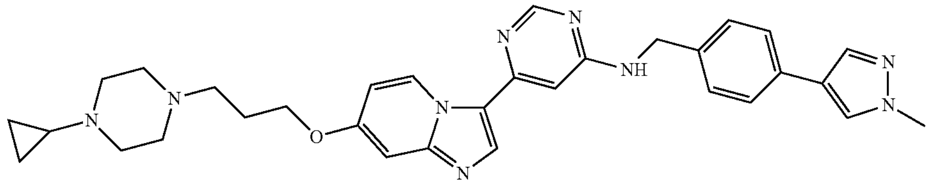 [SMILES: Cn1cc(-c2ccc(CNc3cc(-c4cnc5cc(OCCCN6CCN(C7CC7)CC6)ccn45)ncn3)cc2)cn1]

pale yellow solid; m.p. 215-219° C.; HPLC/MS $[M+H]^+$ 564.

$^1H$ NMR (300 MHz, DMSO-$d_6$) δ 9.67 (d, J=7.7 Hz, 1H), 8.49 (s, 1H), 8.10 (d, J=19.4 Hz, 2H), 7.86 (t, J=6.2 Hz, 1H), 7.80 (d, J=0.8 Hz, 1H), 7.54-7.45 (m, 2H), 7.32 (d, J=7.8 Hz, 2H), 7.04 (d, J=2.6 Hz, 1H), 6.87 (d, J=1.2 Hz, 1H), 6.77 (dd, J=7.7, 2.6 Hz, 1H), 4.52 (d, J=5.8 Hz, 2H), 4.09 (t, J=6.3 Hz, 2H), 3.82 (s, 3H), 2.38 (dd, J=17.6, 10.4 Hz, 6H), 1.89 (q, J=6.7 Hz, 2H), 1.55 (dq, J=6.7, 3.3 Hz, 1H), 0.36 (dt, J=6.0, 2.9 Hz, 2H), 0.28-0.19 (m, 2H).

{6-[7-(3-azetidin-1-yl-propoxy)-imidazo[1,2-a]pyridin-3-yl]-pyrimidin-4-yl}-{1-[4-(1-methyl-1H-pyrazol-4-yl)-phenyl]-ethyl}-amine ("A249")

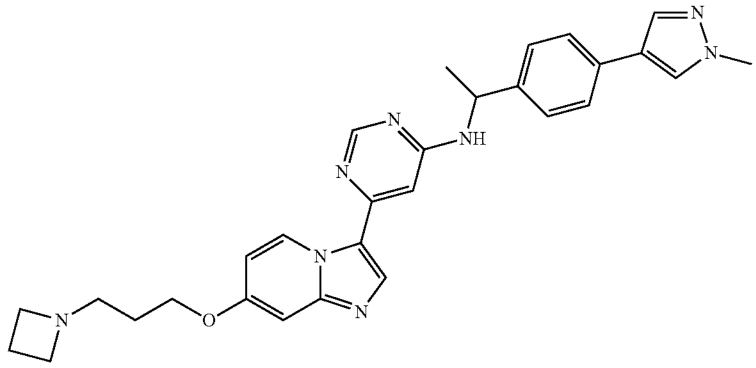 [SMILES: CC(Nc1cc(-c2cnc3cc(OCCCN4CCC4)ccn23)ncn1)c1ccc(-c2cnn(C)c2)cc1]

from H5; white solid; HPLC/MS $[M+H]^+$ 509.

{1-[4-(1-methyl-1H-pyrazol-4-yl)-phenyl]-ethyl}-{6-[7-(3-pyrrolidin-1-yl-propoxy)-imidazo[1,2-a]pyridin-3-yl]-pyrimidin-4-yl}-amine ("A250")

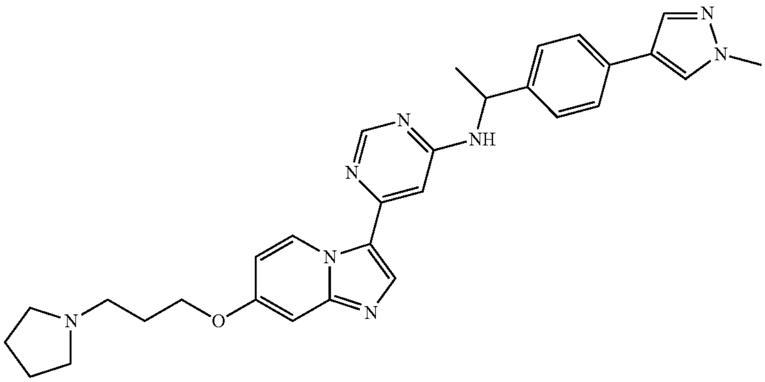 [SMILES: CC(Nc1cc(-c2cnc3cc(OCCCN4CCCC4)ccn23)ncn1)c1ccc(-c2cnn(C)c2)cc1]

from H5; white solid; HPLC/MS $[M+H]^+$ 523.

(6-{7-[3-(4-cyclopropyl-piperazin-1-yl)-propoxy]-imidazo[1,2-a]pyridin-3-yl}-pyrimidin-4-yl)-[4-(2-methyl-2H-[1,2,3]triazol-4-yl)-benzyl]-amine ("A253")

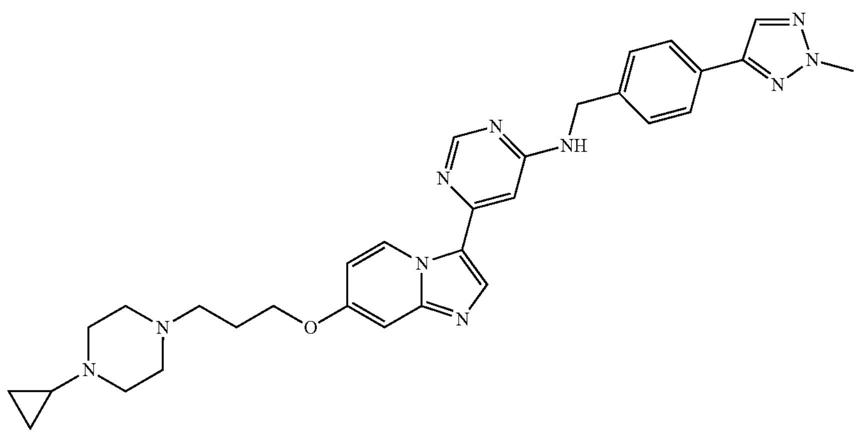 [SMILES: Cn1ncc(-c2ccc(CNc3cc(-c4cnc5cc(OCCCN6CCN(C7CC7)CC6)ccn45)ncn3)cc2)n1]

from H2; pale yellow solid; m.p. 225-226° C.; HPLC/MS $[M+H]^+$ 565.

$^1$H NMR (300 MHz, DMSO-$d_6$) δ 9.67 (d, J=7.7 Hz, 1H), 8.50 (s, 1H), 8.16 (s, 2H), 7.91 (t, J=6.2 Hz, 1H), 7.82-7.73 (m, 2H), 7.42 (d, J=7.8 Hz, 2H), 7.04 (d, J=2.6 Hz, 1H), 6.89 (d, J=1.3 Hz, 1H), 6.77 (dd, J=7.7, 2.6 Hz, 1H), 4.57 (d, J=6.0 Hz, 2H), 4.16 (s, 3H), 4.09 (t, J=6.3 Hz, 2H), 2.38 (dd, J=17.3, 10.2 Hz, 6H), 1.88 (t, J=6.9 Hz, 2H), 1.55 (tt, J=6.5, 3.5 Hz, 1H), 0.36 (dt, J=6.1, 2.8 Hz, 2H), 0.33-0.19 (m, 2H).

Example 31

Synthesis of [4-(2-methyl-2H-[1,2,3]triazol-4-yl)-benzyl]-{6-[7-(4-oxetan-3-yl-piperazin-1-yl)-imidazo[1,2-a]pyridin-3-yl]-pyrimidin-4-yl}-amine ("A244")

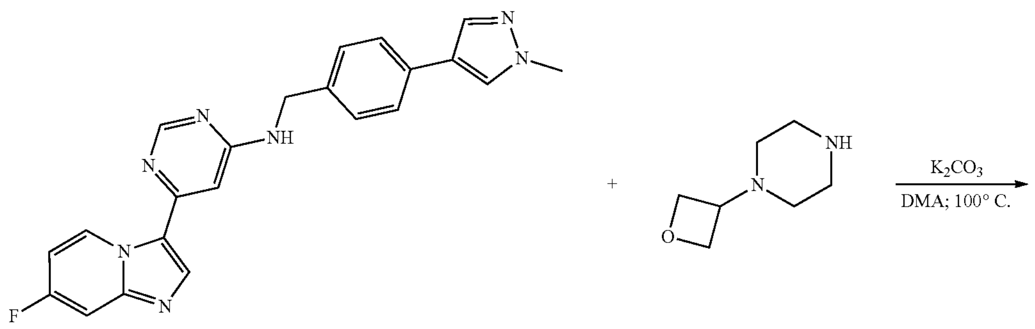

H1

-continued

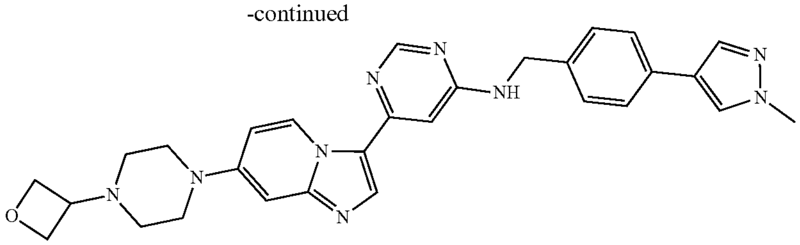

white solid; m.p. 300° C.; HPLC/MS $[M+H]^+$ 523.

$^1H$ NMR (300 MHz, DMSO-$d_6$) δ 9.58 (d, J=7.8 Hz, 1H), 8.48 (s, 1H), 8.16 (s, 1H), 8.08 (s, 1H), 7.85 (t, J=6.1 Hz, 1H), 7.77 (d, J=8.1 Hz, 2H), 7.42 (d, J=7.9 Hz, 2H), 7.00 (dd, J=7.9, 2.5 Hz, 1H), 6.87-6.76 (m, 2H), 4.56 (t, J=6.4 Hz, 4H), 4.46 (t, J=6.0 Hz, 2H), 4.16 (s, 3H), 3.44 (t, J=6.2 Hz, 1H), 2.40 (d, J=5.4 Hz, 4H)

The following compounds are prepared analogously:

1-(3-{6-[4-(1-methyl-1H-pyrazol-4-yl)-benzylamino]-pyrimidin-4-yl}-imidazo[1,2-a]pyridin-7-yl)-pyrrolidin-3-ol ("A245")

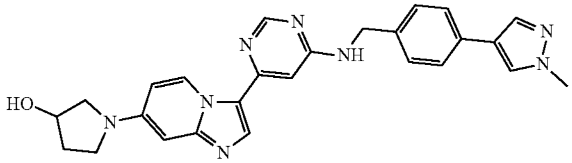 [SMILES: Cn1cc(-c2ccc(CNc3cc(-c4cnc5cc(N6CCC(O)C6)ccn45)ncn3)cc2)cn1]

white solid; m.p. 282-283° C.; HPLC/MS $[M+H]^+$ 467.

$^1H$ NMR (400 MHz, DMSO-$d_6$) δ 9.59 (d, J=7.8 Hz, 1H), 8.46 (s, 1H), 8.08 (s, 1H), 8.05-7.96 (m, 1H), 7.81 (s, 1H), 7.75 (t, J=6.2 Hz, 1H), 7.51 (d, J=8.0 Hz, 2H), 7.33 (d, J=7.8 Hz, 2H), 6.80 (s, 1H), 6.66 (dd, J=7.8, 2.5 Hz, 1H), 6.36 (d, J=2.4 Hz, 1H), 5.04 (d, J=3.7 Hz, 1H), 4.57-4.47 (m, 2H), 4.45-4.40 (m, 1H), 3.84 (s, 3H), 3.49 (dd, J=10.6, 4.7 Hz, 1H), 3.46-3.37 (m, 2H), 3.20 (d, J=10.0 Hz, 1H), 2.13-2.00 (m, 1H), 1.95-1.91 (m, 1H).

[4-(1-methyl-1H-pyrazol-4-yl)-benzyl]-{6-[7-(2-oxa-6-aza-spiro[3.3]hept-6-yl)-imidazo[1,2-a]pyridin-3-yl]-pyrimidin-4-yl}-amine ("A246")

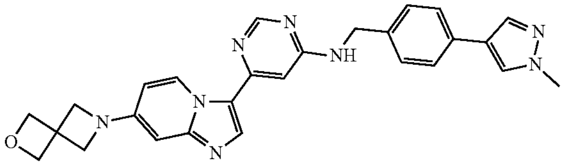 [SMILES: Cn1cc(-c2ccc(CNc3cc(-c4cnc5cc(N6CC7(COC7)C6)ccn45)ncn3)cc2)cn1]

white solid; m.p. 292-293° C.; HPLC/MS $[M+H]^+$ 479.

$^1H$ NMR (400 MHz, DMSO-$d_6$) δ 9.61 (d, J=7.6 Hz, 1H), 8.47 (s, 1H), 8.09-8.02 (m, 2H), 7.83-7.74 (m, 2H), 7.54-7.48 (m, 2H), 7.33 (d, J=7.9 Hz, 2H), 6.81 (s, 1H), 6.47 (dd, J=7.6, 2.4 Hz, 1H), 6.35 (d, J=2.4 Hz, 1H), 4.73 (s, 4H), 4.56-4.47 (m, 2H), 4.12 (s, 4H), 3.84 (s, 3H).

[4-(1-methyl-1H-pyrazol-4-yl)-benzyl]-{6-[7-(2-oxa-6-aza-spiro[3.4]oct-6-yl)-imidazo[1,2-a]pyridin-3-yl]-pyrimidin-4-yl}-amine ("A247")

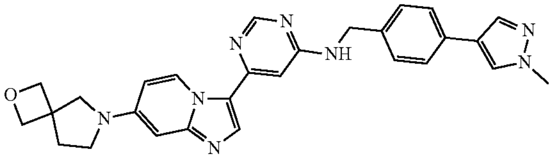 [SMILES: Cn1cc(-c2ccc(CNc3cc(-c4cnc5cc(N6CCC7(COC7)C6)ccn45)ncn3)cc2)cn1]

white solid; m.p. 284-285° C.; HPLC/MS $[M+H]^+$ 493.

$^1H$ NMR (400 MHz, DMSO-$d_6$) δ 9.61 (d, J=7.7 Hz, 1H), 8.48 (s, 1H), 8.09 (s, 1H), 8.07-7.99 (m, 1H), 7.82 (s, 1H), 7.77 (t, J=6.1 Hz, 1H), 7.52 (d, J=8.1 Hz, 2H), 7.39-7.29 (m, 2H), 6.81 (s, 1H), 6.68 (dd, J=7.9, 2.5 Hz, 1H), 6.40 (d, J=2.4 Hz, 1H), 4.61 (d, J=6.0 Hz, 2H), 4.58-4.43 (m, 4H), 3.85 (s, 3H), 3.63 (s, 2H), 3.40-3.35 (m, 2H), 2.30 (t, J=6.9 Hz, 2H).

N-{[4-(1-methyl-1H-pyrazol-4-yl)phenyl]methyl}-6-[7-(1H-1,2,4-triazol-1-yl)imidazo[1,2-a]pyridin-3-yl]pyrimidin-4-amine ("A266")

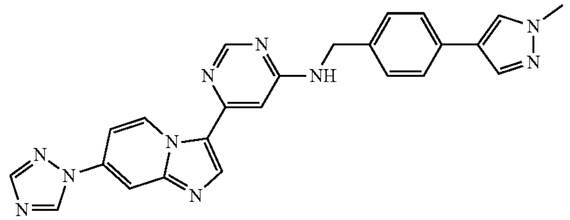 [SMILES: Cn1cc(-c2ccc(CNc3cc(-c4cnc5cc(-n6cncn6)ccn45)ncn3)cc2)cn1]

from H1; white solid; m.p. 272-273° C.; HPLC/MS $[M+H]^+$ 449.

$^1H$ NMR (400 MHz, DMSO-$d_6$) δ 9.93 (d, J=7.7 Hz, 1H), 9.48 (s, 1H), 8.55 (s, 1H), 8.40-8.28 (m, 2H), 8.20 (dd, J=2.3, 0.8 Hz, 1H), 8.05 (s, 1H), 7.95 (t, J=6.1 Hz, 1H), 7.79 (d, J=0.8 Hz, 1H), 7.66 (dd, J=7.7, 2.3 Hz, 1H), 7.53-7.46 (m, 2H), 7.33 (d, J=7.9 Hz, 2H), 6.97 (d, J=1.3 Hz, 1H), 4.53 (s, 2H), 3.82 (s, 3H).

The compound may also be referred to as [4-(1-Methyl-1H-pyrazol-4-yl)-benzyl]-[6-(7-[1,2,4]triazol-1-yl-imidazo[1,2241yridinedin-3-yl)-pyrimidin-4-yl]-amine.

6-[7-(4-methyl-1H-imidazol-1-yl)imidazo[1,2-a]pyridin-3-yl]-N-{[4-(1-methyl-1H-pyrazol-4-yl)phenyl]methyl}pyrimidin-4-amine ("A267")

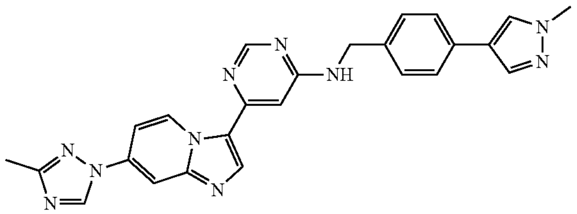

from H1; white solid; m.p. 268-269° C.; HPLC/MS $[M+H]^+$ 462.

$^1$H NMR (400 MHz, DMSO-$d_6$) δ 9.89 (d, J=7.7 Hz, 1H), 8.57 (s, 1H), 8.39 (s, 1H), 8.-5-8.30 (m, 1H), 8.08 (s, 1H), 8.00 (d, J=2.3 Hz, 1H), 7.95 (t, J=6.2 Hz, 1H), 7.82 (s, 1H), 7.67 (s, 1H), 7.-5-7.48 (m, 3H), 7.35 (d, J=7.9 Hz, 2H), 6.97 (s, 1H), 4.56 (s, 2H), 3.85 (s, 3H), 2.19 (s, 3H).

The compound may also be referred to as {6-[7-(4-Methyl-imidazol-1-yl)-imidazo[1,2242yridinedin-3-yl]-pyrimidin-4-yl}-[4-(1-methyl-1H-pyrazol-4-yl)-benzyl]-amine.

N-{[4-(1-methyl-1H-pyrazol-4-yl)phenyl]methyl}-6-{7-[3-(methylamino)azetidin-1-yl]imidazo[1,2-a]pyridin-3-yl}pyrimidin-4-amine ("A268")

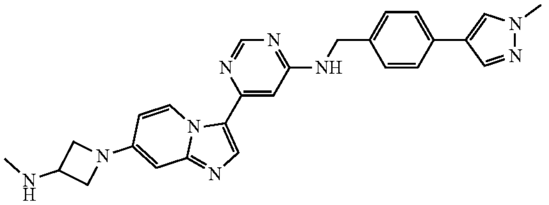

from H1; white solid; m.p. 243-244° C.; HPLC/MS $[M+H]^+$ 466.

$^1$H NMR (400 MHz, DMSO-$d_6$) δ 9.60 (d, J=7.6 Hz, 1H), 8.48 (s, 1H), 8.07 (s, 1H), 8.05-8.02 (m, 1H), 7.81 (s, 1H), 7.77 (t, J=6.1 Hz, 1H), 7.51 (d, J=7.9 Hz, 2H), 7.34 (d, J=7.8 Hz, 2H), 6.82 (s, 1H), 6.45 (dd, J=7.6, 2.3 Hz, 1H), 6.30 (d, J=2.4 Hz, 1H), 4.55-4.50 (m, 2H), 4.13-4.04 (m, 2H), 3.84 (s, 3H), 3.64-3.56 (m, 3H), 2.25 (s, 3H).

The compound may also be referred to as {6-[7-(3-Methylamino-azetidin-1-yl)-imidazo[1,2242yridinedin-3-yl]-pyrimidin-4-yl}-[4-(1-methyl-1H-pyrazol-4-yl)-benzyl]-amine.

Example 32

Salts of "A75": [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine maleate 2-Propanol (2.5 ml) is added to [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine (25 mg, 49 μmol) and the suspension is heated to 50° C. Maleic acid (6.0 mg, 52 μmol) is added to the suspension and the mixture is stirred for 30 min at 50° C. The mixture is slowly cooled to 5° C. Solid/Liquid separation is performed by centrifugation (5 min, 14000 rpm) and the resultant salt is dried at room temperature for 1 day to afford [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine maleate as white powder.

[4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine hydrochloride THF (2 ml) is added to [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine (25 mg, 49 μmol) and the suspension is heated to 50° C. An aqueous solution of hydrochloric acid (53 μl of a 1 M solution, 53 μmol) is added to the suspension and the mixture is stirred for 30 min at 50° C. The mixture is slowly cooled to 5° C. Solid/Liquid separation is performed by centrifugation (5 min, 14000 rpm) and the resultant salt is dried at room temperature for 1 day to afford [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine hydrochloride as white powder.

[4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine phosphate THF (2 ml) is added to [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine (25 mg, 49 μmol) and the suspension is heated to 50° C. An aqueous solution of phosphoric acid (37 μl of a 1.4 M solution, 53 μmol) is added to the suspension and the mixture is stirred for 30 min at 50° C. The mixture is slowly cooled to 5° C. Solid/Liquid separation is performed by centrifugation (5 min, 14000 rpm) and the resultant salt is dried at room temperature for 1 day to afford [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine phosphate as white powder.

A75 hydrochloride:

IC50 [M] c-Kit (V654A)=5.8E-09

IC50 [M] GIST=2.1E-09.

The following examples relate to medicaments:

Example A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound A75 which is [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine of the following formula

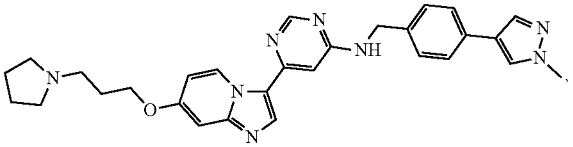 [SMILES: Cn1cc(-c2ccc(CNc3cc(-c4cnc5cc(OCCCN6CCCC6)ccn45)ncn3)cc2)cn1]

and/or a pharmaceutically acceptable salt, tautomer, and/or stereoisomer thereof.

2. A compound A75 which is [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine of the following formula

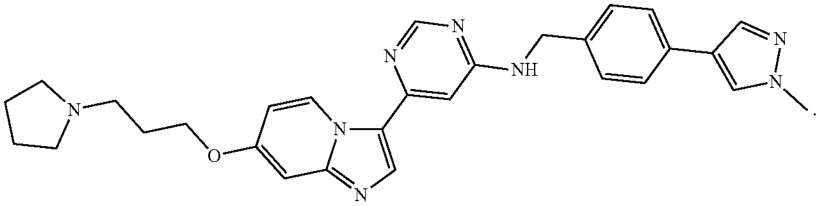 [SMILES: Cn1cc(-c2ccc(CNc3cc(-c4cnc5cc(OCCCN6CCCC6)ccn45)ncn3)cc2)cn1]

3. A pharmaceutically acceptable salt of a compound A75, wherein A75 is [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine of the following formula

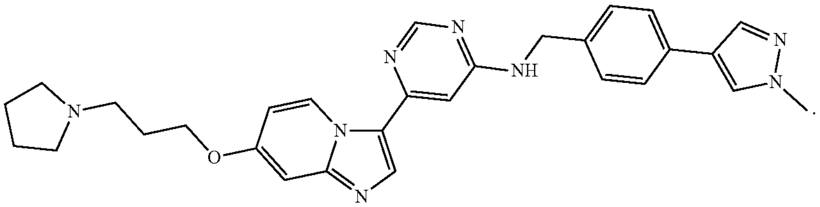 [SMILES: Cn1cc(-c2ccc(CNc3cc(-c4cnc5cc(OCCCN6CCCC6)ccn45)ncn3)cc2)cn1]

4. The pharmaceutically acceptable salt of claim 3, wherein the salt is at least one salt selected from the group consisting of maleate, hydrochloride, and phosphate salts.

5. A medicament, comprising:

at least a compound A75 which is [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine of the following formula 4. The pharmaceutically acceptable salt of claim 3, wherein the salt is at least one salt selected from the group consisting of maleate, hydrochloride, and phosphate salts.

5. A medicament, comprising:

at least a compound A75 which is [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine of the following formula

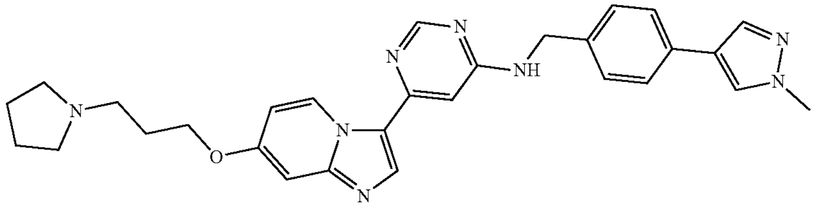 [SMILES: Cn1cc(-c2ccc(CNc3cc(-c4cnc5cc(OCCCN6CCCC6)ccn45)ncn3)cc2)cn1]

and/or a pharmaceutically acceptable salt, tautomer, and/or stereoisomer thereof, and optionally, a pharmaceutically acceptable carrier, excipient, and/or vehicle.

6. A medicament, comprising:

at least a compound A75 which is [4-(1-methyl-1H-pyrazol-4-yl)-benzyl]-{6-[7-(3-pyrrolidin-1-yl-propoxy)-imidazo[1,2-a]pyridin-3-yl]-pyrimidin-4-yl}-amine of the following formula

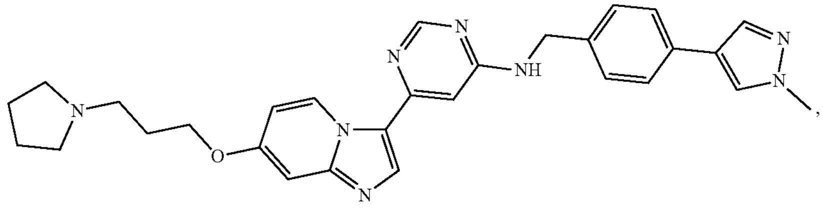 [SMILES: Cn1cc(-c2ccc(CNc3cc(-c4cnc5cc(OCCCN6CCCC6)ccn45)ncn3)cc2)cn1]

and optionally, a pharmaceutically acceptable carrier, excipient, and/or vehicle.

7. The compound of claim 1 and/or the pharmaceutically acceptable salt, tautomer, and/or stereoisomer thereof, which is an isotope-labelled form comprising deuterium.

8. The compound of claim 2, which is an isotope-labelled form comprising deuterium.

* * * * *